United States Patent
McClain et al.

(10) Patent No.: US 9,789,233 B2
(45) Date of Patent: Oct. 17, 2017

(54) STENTS HAVING BIOABSORBABLE LAYERS

(75) Inventors: James B. McClain, Raleigh, NC (US); Douglas Taylor, Franklinton, NC (US)

(73) Assignee: Micell Technologies, Inc., Durham, NC (US)

( * ) Notice: Subject to any disclaimer, the term of this patent is extended or adjusted under 35 U.S.C. 154(b) by 80 days.

(21) Appl. No.: 12/426,198

(22) Filed: Apr. 17, 2009

(65) Prior Publication Data

US 2009/0292351 A1    Nov. 26, 2009

Related U.S. Application Data

(60) Provisional application No. 61/045,928, filed on Apr. 17, 2008, provisional application No. 61/104,669, filed on Oct. 10, 2008.

(51) Int. Cl.
*A61F 2/06* (2013.01)
*A61L 31/14* (2006.01)
*A61L 31/16* (2006.01)

(52) U.S. Cl.
CPC .............. *A61L 31/148* (2013.01); *A61L 31/16* (2013.01); *A61F 2250/0035* (2013.01); *A61F 2250/0067* (2013.01); *A61L 2300/604* (2013.01); *A61L 2300/606* (2013.01); *A61L 2300/63* (2013.01)

(58) Field of Classification Search
USPC .................................. 623/1.1–1.46; 424/423
See application file for complete search history.

(56) References Cited

U.S. PATENT DOCUMENTS

| | | |
|---|---|---|
| 3,087,660 A | 4/1963 | Endicott |
| 3,087,860 A | 4/1963 | Endicott. |
| 3,123,077 A | 3/1964 | Alcamo |
| 3,457,280 A | 7/1969 | Schmitt et al. |
| 3,597,449 A | 8/1971 | Deprospero et al. |
| 3,737,337 A | 6/1973 | Schnoring et al. |
| 3,773,919 A | 11/1973 | Boswell et al. |
| 3,929,992 A | 12/1975 | Sehgal et al. |
| 4,000,137 A | 12/1976 | Dvonch et al. |
| 4,188,373 A | 2/1980 | Krezanoski |
| 4,285,987 A | 8/1981 | Ayer et al. |
| 4,326,532 A | 4/1982 | Hammar |
| 4,336,381 A | 6/1982 | Nagata et al. |

(Continued)

FOREIGN PATENT DOCUMENTS

| CA | 2237466 A1 | 11/1998 |
|---|---|---|
| CA | 2589761 | 12/2004 |

(Continued)

OTHER PUBLICATIONS

PCT/US10/42355 Search Report and Written Opinion dated Sep. 2, 2010.

(Continued)

*Primary Examiner* — Yashita Sharma
(74) *Attorney, Agent, or Firm* — Lerner, David, Littenberg, Krumholz & Mentlik, LLP

(57) ABSTRACT

Provided herein is a device comprising: a. stent; b. a plurality of layers on said stent framework to form said device; wherein at least one of said layers comprises a bioabsorbable polymer and at least one of said layers comprises one or more active agents; wherein at least part of the active agent is in crystalline form.

22 Claims, 22 Drawing Sheets

(56) References Cited

U.S. PATENT DOCUMENTS

| | | |
|---|---|---|
| 4,389,330 A | 6/1983 | Tice et al. |
| 4,474,572 A | 10/1984 | McNaughton et al. |
| 4,474,751 A | 10/1984 | Haslam et al. |
| 4,478,822 A | 10/1984 | Haslam et al. |
| 4,530,840 A | 7/1985 | Tice et al. |
| 4,582,731 A | 4/1986 | Smith |
| 4,606,347 A | 8/1986 | Fogarty et al. |
| 4,617,751 A | 10/1986 | Johansson |
| 4,655,771 A | 4/1987 | Wallsten |
| 4,675,189 A | 6/1987 | Kent et al. |
| 4,733,665 A | 3/1988 | Palmaz |
| 4,734,227 A | 3/1988 | Smith |
| 4,734,451 A | 3/1988 | Smith |
| 4,758,435 A | 7/1988 | Schaaf |
| 4,762,593 A | 8/1988 | Youngner |
| 4,931,037 A | 6/1990 | Wetterman |
| 4,950,239 A | 8/1990 | Gahara |
| 4,985,625 A | 1/1991 | Hurst |
| 5,000,519 A | 3/1991 | Moore |
| 5,090,419 A | 2/1992 | Palestrant |
| 5,096,848 A | 3/1992 | Kawamura |
| 5,102,417 A | 4/1992 | Palmaz |
| 5,104,404 A | 4/1992 | Wolff |
| 5,106,650 A | 4/1992 | Hoy et al. |
| 5,125,570 A | 6/1992 | Jones |
| 5,158,986 A | 10/1992 | Cha et al. |
| 5,185,776 A | 2/1993 | Townsend |
| 5,195,969 A | 3/1993 | Wang et al. |
| 5,243,023 A | 9/1993 | Dezern |
| 5,270,086 A | 12/1993 | Hamlin |
| 5,288,711 A | 2/1994 | Mitchell et al. |
| 5,320,634 A | 6/1994 | Vigil et al. |
| 5,324,049 A | 6/1994 | Mistrater et al. |
| 5,340,614 A | 8/1994 | Perman et al. |
| 5,342,621 A | 8/1994 | Eury |
| 5,350,361 A | 9/1994 | Tsukashima et al. |
| 5,350,627 A | 9/1994 | Nemphos et al. |
| 5,356,433 A | 10/1994 | Rowland et al. |
| 5,360,403 A | 11/1994 | Mische |
| 5,362,718 A | 11/1994 | Skotnicki et al. |
| 5,366,504 A | 11/1994 | Andersen et al. |
| 5,368,045 A | 11/1994 | Clement et al. |
| 5,372,676 A | 12/1994 | Lowe |
| 5,385,776 A | 1/1995 | Maxfield et al. |
| 5,403,347 A | 4/1995 | Roby et al. |
| 5,470,603 A | 11/1995 | Staniforth et al. |
| 5,494,620 A | 2/1996 | Liu et al. |
| 5,500,180 A | 3/1996 | Anderson et al. |
| 5,545,208 A | 8/1996 | Wolff et al. |
| 5,556,383 A | 9/1996 | Wang et al. |
| 5,562,922 A | 10/1996 | Lambert |
| 5,569,463 A | 10/1996 | Helmus et al. |
| 5,570,537 A | 11/1996 | Black et al. |
| 5,578,709 A | 11/1996 | Woiszwillo |
| 5,599,576 A | 2/1997 | Opolski |
| 5,607,442 A | 3/1997 | Fischell et al. |
| 5,609,629 A | 3/1997 | Fearnot et al. |
| 5,626,611 A | 5/1997 | Liu et al. |
| 5,626,862 A | 5/1997 | Brem et al. |
| 5,632,772 A | 5/1997 | Alcime et al. |
| 5,669,932 A | 9/1997 | Fischell et al. |
| 5,674,242 A | 10/1997 | Phan et al. |
| 5,725,570 A | 3/1998 | Heath |
| 5,733,303 A | 3/1998 | Israel et al. |
| 5,766,158 A | 6/1998 | Opolski |
| 5,800,511 A | 9/1998 | Mayer |
| 5,807,404 A | 9/1998 | Richter |
| 5,811,032 A | 9/1998 | Kawai et al. |
| 5,824,049 A | 10/1998 | Ragheb et al. |
| 5,837,313 A | 11/1998 | Ding et al. |
| 5,843,120 A | 12/1998 | Israel et al. |
| 5,871,436 A | 2/1999 | Eury |
| 5,873,904 A | 2/1999 | Ragheb et al. |
| 5,876,426 A | 3/1999 | Kume et al. |
| 5,913,895 A | 6/1999 | Burpee et al. |
| 5,924,631 A | 7/1999 | Rodrigues et al. |
| 5,948,020 A | 9/1999 | Yoon et al. |
| 5,957,975 A | 9/1999 | Lafont et al. |
| 5,981,568 A | 11/1999 | Kunz et al. |
| 5,981,719 A | 11/1999 | Woiszwillo et al. |
| 6,013,855 A | 1/2000 | McPherson et al. |
| 6,036,978 A | 3/2000 | Gombotz et al. |
| 6,039,721 A | 3/2000 | Johnson et al. |
| 6,068,656 A | 5/2000 | Von Oepen |
| 6,071,308 A | 6/2000 | Ballou et al. |
| 6,077,880 A | 6/2000 | Castillo et al. |
| 6,090,925 A | 7/2000 | Woiszwillo et al. |
| 6,129,755 A | 10/2000 | Mathis et al. |
| 6,143,037 A | 11/2000 | Goldsten et al. |
| 6,143,314 A | 11/2000 | Chandrashekar et al. |
| 6,146,356 A | 11/2000 | Wang et al. |
| 6,146,404 A | 11/2000 | Kim et al. |
| 6,153,252 A | 11/2000 | Hossainy et al. |
| 6,171,327 B1 | 1/2001 | Daniel et al. |
| 6,190,699 B1 | 2/2001 | Luzzi et al. |
| 6,193,744 B1 | 2/2001 | Ehr et al. |
| 6,206,914 B1 | 3/2001 | Soykan et al. |
| 6,217,608 B1 | 4/2001 | Penn et al. |
| 6,231,599 B1 | 5/2001 | Ley |
| 6,231,600 B1 | 5/2001 | Zhong et al. |
| 6,245,104 B1 | 6/2001 | Alt |
| 6,248,127 B1 | 6/2001 | Shah et al. |
| 6,248,129 B1 | 6/2001 | Froix |
| 6,251,980 B1 | 6/2001 | Lan et al. |
| 6,268,053 B1 | 7/2001 | Woiszwillo et al. |
| 6,273,913 B1 | 8/2001 | Wright et al. |
| 6,284,758 B1 | 9/2001 | Egi et al. |
| 6,299,635 B1 | 10/2001 | Frantzen |
| 6,309,669 B1 | 10/2001 | Setterstrom et al. |
| 6,319,541 B1 | 11/2001 | Pletcher et al. |
| 6,325,821 B1 | 12/2001 | Gaschino et al. |
| 6,336,934 B1 | 1/2002 | Gilson et al. |
| 6,342,062 B1 | 1/2002 | Suon et al. |
| 6,344,055 B1 | 2/2002 | Shukov |
| 6,355,691 B1 | 3/2002 | Goodman |
| 6,358,556 B1 | 3/2002 | Ding et al. |
| 6,361,819 B1 | 3/2002 | Tedeschi et al. |
| 6,362,718 B1 | 3/2002 | Patrick et al. |
| 6,364,903 B2 | 4/2002 | Tseng et al. |
| 6,368,658 B1 | 4/2002 | Schwarz et al. |
| 6,372,246 B1 | 4/2002 | Wei et al. |
| 6,387,121 B1 | 5/2002 | Alt |
| 6,409,716 B1 | 6/2002 | Sahatjian et al. |
| 6,414,050 B1 | 7/2002 | Howdle et al. |
| 6,416,779 B1 | 7/2002 | D-Augustine et al. |
| 6,448,315 B1 | 9/2002 | Lidgren et al. |
| 6,458,387 B1 | 10/2002 | Scott et al. |
| 6,461,380 B1 | 10/2002 | Cox |
| 6,461,644 B1 | 10/2002 | Jackson et al. |
| 6,488,703 B1 | 12/2002 | Kveen et al. |
| 6,495,163 B1 | 12/2002 | Jordan |
| 6,497,729 B1 | 12/2002 | Moussy et al. |
| 6,506,213 B1 | 1/2003 | Mandel et al. |
| 6,517,860 B1 | 2/2003 | Rosser et al. |
| 6,521,258 B1 | 2/2003 | Mandel et al. |
| 6,524,698 B1 | 2/2003 | Schmoock |
| 6,530,951 B1 | 3/2003 | Bates et al. |
| 6,537,310 B1 | 3/2003 | Palmaz et al. |
| 6,541,033 B1 | 4/2003 | Shah |
| 6,572,813 B1 | 6/2003 | Zhang et al. |
| 6,602,281 B1 | 8/2003 | Klein |
| 6,610,013 B1 | 8/2003 | Fenster et al. |
| 6,627,246 B2 | 9/2003 | Mehta et al. |
| 6,649,627 B1 | 11/2003 | Cecchi et al. |
| 6,660,176 B2 | 12/2003 | Tepper et al. |
| 6,669,785 B2 | 12/2003 | DeYoung et al. |
| 6,669,980 B2 | 12/2003 | Hansen et al. |
| 6,670,407 B2 | 12/2003 | Howdle et al. |
| 6,682,757 B1 | 1/2004 | Wright |
| 6,706,283 B1 | 3/2004 | Appel et al. |
| 6,710,059 B1 | 3/2004 | Labrie et al. |
| 6,720,003 B2 | 4/2004 | Cheng et al. |
| 6,726,712 B1 | 4/2004 | Raeder-Devens et al. |
| 6,736,996 B1 | 5/2004 | Carbonell et al. |

(56) References Cited

U.S. PATENT DOCUMENTS

| | | |
|---|---|---|
| 6,743,505 B2 | 6/2004 | Antall et al. |
| 6,749,902 B2 | 6/2004 | Yonker et al. |
| 6,755,871 B2 | 6/2004 | Damaso et al. |
| 6,756,084 B2 | 6/2004 | Fulton et al. |
| 6,767,558 B2 | 7/2004 | Wang et al. |
| 6,780,475 B2 | 8/2004 | Fulton et al. |
| 6,794,902 B2 | 9/2004 | Becker et al. |
| 6,800,663 B2 | 10/2004 | Asgarzadeh et al. |
| 6,815,218 B1 | 11/2004 | Jacobson et al. |
| 6,821,549 B2 | 11/2004 | Jayaraman |
| 6,837,611 B2 | 1/2005 | Kuo et al. |
| 6,838,089 B1 | 1/2005 | Carlsson et al. |
| 6,838,528 B2 | 1/2005 | Zhou |
| 6,858,598 B1 | 2/2005 | McKearn et al. |
| 6,860,123 B1 | 3/2005 | Uhlin |
| 6,884,377 B1 | 4/2005 | Burnham et al. |
| 6,884,823 B1 | 4/2005 | Pierick et al. |
| 6,897,205 B2 | 5/2005 | Beckert et al. |
| 6,905,555 B2 | 6/2005 | DeYoung et al. |
| 6,908,624 B2 | 6/2005 | Hossainy et al. |
| 6,916,800 B2 | 7/2005 | McKearn et al. |
| 6,923,979 B2 | 8/2005 | Fotland et al. |
| 6,936,270 B2 | 8/2005 | Watson et al. |
| 6,939,569 B1 | 9/2005 | Green et al. |
| 6,973,718 B2 | 12/2005 | Sheppard et al. |
| 7,056,591 B1 | 6/2006 | Pacetti et al. |
| 7,094,256 B1 | 8/2006 | Shah et al. |
| 7,148,201 B2 | 12/2006 | Stern et al. |
| 7,152,452 B2 | 12/2006 | Kokish |
| 7,160,592 B2 | 1/2007 | Rypacek et al. |
| 7,163,715 B1 | 1/2007 | Kramer |
| 7,169,404 B2 | 1/2007 | Hossainy et al. |
| 7,171,255 B2 | 1/2007 | Holupka et al. |
| 7,201,750 B1 | 4/2007 | Eggers et al. |
| 7,201,940 B1 | 4/2007 | Kramer |
| 7,229,837 B2 | 6/2007 | Chen |
| 7,278,174 B2 | 10/2007 | Villalobos |
| 7,279,174 B2 | 10/2007 | Pacetti et al. |
| 7,282,020 B2 | 10/2007 | Kaplan |
| 7,308,748 B2 | 12/2007 | Kokish |
| 7,323,454 B2 | 1/2008 | De Nijs et al. |
| 7,326,734 B2 | 2/2008 | Zi et al. |
| 7,329,383 B2 | 2/2008 | Stinson |
| 7,378,105 B2 | 5/2008 | Burke et al. |
| 7,419,696 B2 | 9/2008 | Berg et al. |
| 7,429,378 B2 | 9/2008 | Serhan et al. |
| 7,444,162 B2 | 10/2008 | Hassan |
| 7,455,688 B2 | 11/2008 | Furst et al. |
| 7,456,151 B2 | 11/2008 | Li et al. |
| 7,462,593 B2 | 12/2008 | Cuttitta et al. |
| 7,485,113 B2 | 2/2009 | Varner et al. |
| 7,498,042 B2 | 3/2009 | Igaki et al. |
| 7,524,865 B2 | 4/2009 | D'Amato et al. |
| 7,537,610 B2 | 5/2009 | Reiss |
| 7,537,785 B2 | 5/2009 | Loscalzo et al. |
| 7,553,827 B2 | 6/2009 | Attawia et al. |
| 7,713,538 B2 | 5/2010 | Lewis et al. |
| 7,727,275 B2 | 6/2010 | Betts et al. |
| 7,745,566 B2 | 6/2010 | Chattopadhyay et al. |
| 7,763,277 B1 | 7/2010 | Canham et al. |
| 7,771,468 B2 | 8/2010 | Whitbourne et al. |
| 7,837,726 B2 | 11/2010 | Von Oepen et al. |
| 7,842,312 B2 | 11/2010 | Burgermeister et al. |
| 7,919,108 B2 | 4/2011 | Rees et al. |
| 7,955,383 B2 | 6/2011 | Krivoruchko et al. |
| 7,967,855 B2 | 6/2011 | Furst et al. |
| 7,972,661 B2 | 7/2011 | Pui et al. |
| 8,070,796 B2 | 12/2011 | Furst et al. |
| 8,295,565 B2 | 10/2012 | Gu et al. |
| 8,298,565 B2 | 10/2012 | Taylor et al. |
| 8,377,356 B2 | 2/2013 | Huang et al. |
| 8,535,372 B1 | 9/2013 | Fox et al. |
| 8,709,071 B1 | 4/2014 | Huang et al. |
| 8,753,659 B2 | 6/2014 | Lewis et al. |
| 8,753,709 B2 | 6/2014 | Hossainy et al. |
| 8,758,429 B2 | 6/2014 | Taylor et al. |
| 8,795,762 B2 | 8/2014 | Fulton et al. |
| 8,834,913 B2 | 9/2014 | Shaw et al. |
| 8,852,625 B2 | 10/2014 | DeYoung et al. |
| 8,900,651 B2 | 12/2014 | McClain et al. |
| 9,433,516 B2 | 9/2016 | McClain et al. |
| 2001/0026804 A1 | 10/2001 | Boutignon |
| 2001/0034336 A1 | 10/2001 | Shah et al. |
| 2001/0044629 A1 | 11/2001 | Stinson |
| 2001/0049551 A1 | 12/2001 | Tseng et al. |
| 2002/0007209 A1 | 1/2002 | Scheerder et al. |
| 2002/0051845 A1 | 5/2002 | Mehta et al. |
| 2002/0082680 A1 | 6/2002 | Shanley et al. |
| 2002/0091433 A1 | 7/2002 | Ding et al. |
| 2002/0099332 A1 | 7/2002 | Slepian et al. |
| 2002/0125860 A1 | 9/2002 | Schworm et al. |
| 2002/0133072 A1 | 9/2002 | Wang et al. |
| 2002/0144757 A1 | 10/2002 | Craig et al. |
| 2003/0001830 A1 | 1/2003 | Wampler et al. |
| 2003/0004563 A1 | 1/2003 | Jackson et al. |
| 2003/0031699 A1 | 2/2003 | Van Antwerp |
| 2003/0077200 A1 | 4/2003 | Craig et al. |
| 2003/0088307 A1 | 5/2003 | Shulze et al. |
| 2003/0125800 A1 | 7/2003 | Shulze et al. |
| 2003/0143315 A1 | 7/2003 | Pui et al. |
| 2003/0170305 A1 | 9/2003 | O'Neil et al. |
| 2003/0180376 A1 | 9/2003 | Dalal et al. |
| 2003/0185964 A1 | 10/2003 | Weber et al. |
| 2003/0204238 A1 | 10/2003 | Tedeschi |
| 2003/0222017 A1 | 12/2003 | Fulton et al. |
| 2003/0222018 A1 | 12/2003 | Yonker et al. |
| 2003/0232014 A1 | 12/2003 | Burke et al. |
| 2004/0013792 A1 | 1/2004 | Epstein et al. |
| 2004/0018228 A1 | 1/2004 | Fischell et al. |
| 2004/0022400 A1 | 2/2004 | Magrath |
| 2004/0022853 A1 | 2/2004 | Ashton et al. |
| 2004/0044397 A1 | 3/2004 | Stinson |
| 2004/0059290 A1 | 3/2004 | Palasis et al. |
| 2004/0106982 A1 | 6/2004 | Jalisi |
| 2004/0122205 A1 | 6/2004 | Nathan |
| 2004/0126542 A1 | 7/2004 | Fujiwara et al. |
| 2004/0143317 A1 | 7/2004 | Stinson et al. |
| 2004/0144317 A1 | 7/2004 | Chuman et al. |
| 2004/0147904 A1 | 7/2004 | Hung et al. |
| 2004/0157789 A1 | 8/2004 | Geall |
| 2004/0170685 A1 | 9/2004 | Carpenter et al. |
| 2004/0193177 A1 | 9/2004 | Houghton et al. |
| 2004/0193262 A1 | 9/2004 | Shadduck |
| 2004/0220660 A1 | 11/2004 | Shanley et al. |
| 2004/0224001 A1 | 11/2004 | Pacetti et al. |
| 2004/0236416 A1 | 11/2004 | Falotico |
| 2004/0260000 A1 | 12/2004 | Chaiko |
| 2005/0003074 A1 | 1/2005 | Brown et al. |
| 2005/0004661 A1* | 1/2005 | Lewis et al. ............. 623/1.42 |
| 2005/0010275 A1 | 1/2005 | Sahatjian et al. |
| 2005/0015046 A1 | 1/2005 | Weber et al. |
| 2005/0019747 A1 | 1/2005 | Anderson et al. |
| 2005/0038498 A1 | 2/2005 | Dubrow et al. |
| 2005/0048121 A1 | 3/2005 | East et al. |
| 2005/0049694 A1 | 3/2005 | Neary |
| 2005/0060028 A1 | 3/2005 | Horres et al. |
| 2005/0069630 A1 | 3/2005 | Fox et al. |
| 2005/0070989 A1 | 3/2005 | Lye et al. |
| 2005/0070990 A1 | 3/2005 | Stinson |
| 2005/0074479 A1 | 4/2005 | Weber et al. |
| 2005/0075714 A1 | 4/2005 | Cheng et al. |
| 2005/0079199 A1 | 4/2005 | Heruth et al. |
| 2005/0079274 A1 | 4/2005 | Palasis et al. |
| 2005/0084533 A1 | 4/2005 | Howdle et al. |
| 2005/0131513 A1 | 6/2005 | Myers et al. |
| 2005/0147734 A1 | 7/2005 | Seppala et al. |
| 2005/0159704 A1 | 7/2005 | Scott et al. |
| 2005/0166841 A1 | 8/2005 | Robida |
| 2005/0175772 A1 | 8/2005 | Worsham et al. |
| 2005/0177223 A1 | 8/2005 | Palmaz |
| 2005/0191491 A1 | 9/2005 | Wang et al. |
| 2005/0196424 A1 | 9/2005 | Chappa |
| 2005/0208102 A1 | 9/2005 | Schultz |
| 2005/0209244 A1 | 9/2005 | Prescott et al. |

(56) References Cited

U.S. PATENT DOCUMENTS

| | | |
|---|---|---|
| 2005/0216075 A1 | 9/2005 | Wang et al. |
| 2005/0238829 A1 | 10/2005 | Motherwell et al. |
| 2005/0245637 A1 | 11/2005 | Hossainy et al. |
| 2005/0255327 A1 | 11/2005 | Chaney |
| 2005/0260186 A1 | 11/2005 | Bookbinder et al. |
| 2005/0268573 A1 | 12/2005 | Yan |
| 2005/0288481 A1 | 12/2005 | Desnoyer et al. |
| 2005/0288629 A1 | 12/2005 | Kunis |
| 2006/0001011 A1 | 1/2006 | Wilson et al. |
| 2006/0002974 A1 | 1/2006 | Pacetti et al. |
| 2006/0020325 A1 | 1/2006 | Burgermeister et al. |
| 2006/0030652 A1 | 2/2006 | Adams et al. |
| 2006/0045901 A1 | 3/2006 | Weber et al. |
| 2006/0073329 A1 | 4/2006 | Boyce et al. |
| 2006/0089705 A1 | 4/2006 | Ding et al. |
| 2006/0093771 A1 | 5/2006 | Rypacek et al. |
| 2006/0094744 A1 | 5/2006 | Maryanoff et al. |
| 2006/0106455 A1 | 5/2006 | Furst et al. |
| 2006/0116755 A1 | 6/2006 | Stinson |
| 2006/0121080 A1* | 6/2006 | Lye et al. .................. 424/423 |
| 2006/0121089 A1 | 6/2006 | Michal et al. |
| 2006/0134168 A1 | 6/2006 | Chappa et al. |
| 2006/0134211 A1 | 6/2006 | Lien et al. |
| 2006/0136041 A1 | 6/2006 | Schmid et al. |
| 2006/0147698 A1 | 7/2006 | Carroll et al. |
| 2006/0153729 A1 | 7/2006 | Stinson et al. |
| 2006/0160455 A1 | 7/2006 | Sugyo et al. |
| 2006/0188547 A1 | 8/2006 | Bezwada |
| 2006/0193886 A1 | 8/2006 | Owens et al. |
| 2006/0193890 A1 | 8/2006 | Owens et al. |
| 2006/0198868 A1 | 9/2006 | DeWitt et al. |
| 2006/0210638 A1 | 9/2006 | Liversidge et al. |
| 2006/0216324 A1 | 9/2006 | Stucke et al. |
| 2006/0222756 A1 | 10/2006 | Davila et al. |
| 2006/0228415 A1 | 10/2006 | Oberegger et al. |
| 2006/0228453 A1 | 10/2006 | Cromack et al. |
| 2006/0235506 A1 | 10/2006 | Ta et al. |
| 2006/0276877 A1 | 12/2006 | Owens et al. |
| 2006/0287611 A1 | 12/2006 | Fleming |
| 2007/0009564 A1 | 1/2007 | McClain et al. |
| 2007/0009664 A1 | 1/2007 | Fallais et al. |
| 2007/0026042 A1 | 2/2007 | Narayanan |
| 2007/0032864 A1 | 2/2007 | Furst et al. |
| 2007/0038227 A1 | 2/2007 | Massicotte et al. |
| 2007/0038289 A1 | 2/2007 | Nishide et al. |
| 2007/0043434 A1 | 2/2007 | Meerkin et al. |
| 2007/0059350 A1 | 3/2007 | Kennedy et al. |
| 2007/0065478 A1 | 3/2007 | Hossainy |
| 2007/0110888 A1 | 5/2007 | Radhakrishnan et al. |
| 2007/0123973 A1 | 5/2007 | Roth et al. |
| 2007/0123977 A1* | 5/2007 | Cottone et al. .............. 623/1.42 |
| 2007/0128274 A1 | 6/2007 | Zhu et al. |
| 2007/0148251 A1 | 6/2007 | Hossainy et al. |
| 2007/0154513 A1 | 7/2007 | Atanasoska et al. |
| 2007/0154554 A1 | 7/2007 | Burgermeister et al. |
| 2007/0196242 A1 | 8/2007 | Boozer et al. |
| 2007/0196423 A1 | 8/2007 | Ruane et al. |
| 2007/0198081 A1 | 8/2007 | Castro et al. |
| 2007/0200268 A1 | 8/2007 | Dave |
| 2007/0203569 A1 | 8/2007 | Burgermeister et al. |
| 2007/0219579 A1 | 9/2007 | Paul |
| 2007/0225795 A1 | 9/2007 | Granada et al. |
| 2007/0259017 A1 | 11/2007 | Francis |
| 2007/0280992 A1 | 12/2007 | Margaron et al. |
| 2008/0030066 A1 | 2/2008 | Mercier et al. |
| 2008/0051866 A1 | 2/2008 | Chen et al. |
| 2008/0065192 A1 | 3/2008 | Berglund |
| 2008/0071347 A1 | 3/2008 | Cambronne |
| 2008/0071358 A1 | 3/2008 | Weber et al. |
| 2008/0071359 A1 | 3/2008 | Thornton et al. |
| 2008/0075753 A1 | 3/2008 | Chappa |
| 2008/0077232 A1 | 3/2008 | Nishide |
| 2008/0085880 A1 | 4/2008 | Viswanath et al. |
| 2008/0095919 A1 | 4/2008 | McClain et al. |
| 2008/0097575 A1 | 4/2008 | Cottone |
| 2008/0097591 A1 | 4/2008 | Savage et al. |
| 2008/0098178 A1 | 4/2008 | Veazey et al. |
| 2008/0107702 A1 | 5/2008 | Jennissen |
| 2008/0118543 A1 | 5/2008 | Pacetti et al. |
| 2008/0124372 A1 | 5/2008 | Hossainy et al. |
| 2008/0138375 A1 | 6/2008 | Yan et al. |
| 2008/0206304 A1 | 8/2008 | Lindquist et al. |
| 2008/0213464 A1 | 9/2008 | O'Connor |
| 2008/0233267 A1 | 9/2008 | Berglund |
| 2008/0255510 A1 | 10/2008 | Wang |
| 2008/0269449 A1 | 10/2008 | Chattopadhyay et al. |
| 2008/0286325 A1 | 11/2008 | Reyes et al. |
| 2008/0292776 A1 | 11/2008 | Dias et al. |
| 2008/0300669 A1 | 12/2008 | Hossainy |
| 2009/0043379 A1 | 2/2009 | Prescott |
| 2009/0062909 A1 | 3/2009 | Taylor et al. |
| 2009/0068266 A1 | 3/2009 | Raheja et al. |
| 2009/0076446 A1 | 3/2009 | Dubuclet et al. |
| 2009/0082855 A1 | 3/2009 | Borges et al. |
| 2009/0098178 A1 | 4/2009 | Hofmann et al. |
| 2009/0105687 A1 | 4/2009 | Deckman et al. |
| 2009/0105809 A1 | 4/2009 | Lee et al. |
| 2009/0110711 A1 | 4/2009 | Trollsas et al. |
| 2009/0111787 A1 | 4/2009 | Lim et al. |
| 2009/0123515 A1 | 5/2009 | Taylor et al. |
| 2009/0186069 A1 | 7/2009 | DeYoung et al. |
| 2009/0202609 A1 | 8/2009 | Keough et al. |
| 2009/0216317 A1 | 8/2009 | Cromack et al. |
| 2009/0227949 A1 | 9/2009 | Knapp et al. |
| 2009/0231578 A1 | 9/2009 | Ling et al. |
| 2009/0263460 A1 | 10/2009 | McDonald |
| 2009/0285974 A1 | 11/2009 | Kerrigan |
| 2009/0292351 A1 | 11/2009 | McClain et al. |
| 2009/0297578 A1 | 12/2009 | Trollsas et al. |
| 2010/0000328 A1 | 1/2010 | Mahmoud |
| 2010/0006358 A1 | 1/2010 | Ishikawa |
| 2010/0015200 A1 | 1/2010 | McClain et al. |
| 2010/0030261 A1 | 2/2010 | McClain et al. |
| 2010/0042206 A1 | 2/2010 | Yadav et al. |
| 2010/0055145 A1 | 3/2010 | Betts et al. |
| 2010/0055294 A1 | 3/2010 | Wang et al. |
| 2010/0063570 A1 | 3/2010 | Pacetti et al. |
| 2010/0063580 A1 | 3/2010 | McClain et al. |
| 2010/0074934 A1 | 3/2010 | Hunter |
| 2010/0131044 A1 | 5/2010 | Patel |
| 2010/0155496 A1 | 6/2010 | Stark et al. |
| 2010/0166869 A1 | 7/2010 | Desai et al. |
| 2010/0196482 A1 | 8/2010 | Radovic-Moreno et al. |
| 2010/0198330 A1 | 8/2010 | Hossainy et al. |
| 2010/0198331 A1 | 8/2010 | Rapoza et al. |
| 2010/0211164 A1 | 8/2010 | McClain et al. |
| 2010/0228348 A1 | 9/2010 | McClain et al. |
| 2010/0233332 A1 | 9/2010 | Xing et al. |
| 2010/0239635 A1 | 9/2010 | McClain et al. |
| 2010/0241220 A1 | 9/2010 | McClain et al. |
| 2010/0256746 A1 | 10/2010 | Taylor et al. |
| 2010/0256748 A1 | 10/2010 | Taylor et al. |
| 2010/0262224 A1 | 10/2010 | Kleiner |
| 2010/0272775 A1 | 10/2010 | Cleek et al. |
| 2010/0272778 A1 | 10/2010 | McClain et al. |
| 2010/0298928 A1 | 11/2010 | McClain et al. |
| 2010/0305689 A1 | 12/2010 | Venkatraman et al. |
| 2011/0009953 A1 | 1/2011 | Luk et al. |
| 2011/0034422 A1 | 2/2011 | Kannan et al. |
| 2011/0159069 A1 | 6/2011 | Shaw et al. |
| 2011/0160751 A1 | 6/2011 | Granja |
| 2011/0172763 A1 | 7/2011 | Ndondo-Lay |
| 2011/0190864 A1 | 8/2011 | McClain et al. |
| 2011/0223212 A1 | 9/2011 | Taton et al. |
| 2011/0238161 A1 | 9/2011 | Fulton et al. |
| 2011/0257732 A1 | 10/2011 | McClain et al. |
| 2011/0264190 A1 | 10/2011 | McClain et al. |
| 2011/0301697 A1 | 12/2011 | Hoffmann et al. |
| 2012/0064124 A1 | 3/2012 | McClain et al. |
| 2012/0064143 A1 | 3/2012 | Sharp et al. |
| 2012/0065723 A1 | 3/2012 | Drasler et al. |
| 2012/0101566 A1 | 4/2012 | Mews et al. |
| 2012/0150275 A1 | 6/2012 | Shaw-Klein |
| 2012/0160408 A1 | 6/2012 | Clerc et al. |

(56) References Cited

U.S. PATENT DOCUMENTS

| | | |
|---|---|---|
| 2012/0172787 A1 | 7/2012 | McClain et al. |
| 2012/0177742 A1 | 7/2012 | McClain et al. |
| 2012/0231037 A1 | 9/2012 | Levi et al. |
| 2012/0271396 A1 | 10/2012 | Zheng et al. |
| 2012/0280432 A1 | 11/2012 | Chen et al. |
| 2012/0290075 A1 | 11/2012 | Mortisen et al. |
| 2012/0323311 A1 | 12/2012 | McClain et al. |
| 2013/0006351 A1 | 1/2013 | Taylor et al. |
| 2013/0087270 A1 | 4/2013 | Hossainy et al. |
| 2013/0172853 A1 | 7/2013 | McClain et al. |
| 2014/0343667 A1 | 11/2014 | McClain |
| 2014/0350522 A1 | 11/2014 | McClain et al. |
| 2014/0371717 A1 | 12/2014 | McClain et al. |
| 2015/0024116 A1 | 1/2015 | Matson et al. |
| 2015/0025620 A1 | 1/2015 | Taylor et al. |
| 2016/0095726 A1 | 4/2016 | McClain et al. |

FOREIGN PATENT DOCUMENTS

| | | |
|---|---|---|
| CA | 2615452 A1 | 1/2007 |
| CA | 2679712 A1 | 7/2008 |
| CA | 2684482 A1 | 10/2008 |
| CA | 2721832 A1 | 12/2009 |
| CN | 2423899 Y | 3/2001 |
| CN | 1465410 | 1/2004 |
| CN | 1575860 A | 2/2005 |
| CN | 1649551 | 8/2005 |
| CN | 1684641 A | 10/2005 |
| CN | 101161300 A | 4/2008 |
| CN | 102481195 A | 5/2012 |
| DE | 4336209 A1 | 3/1995 |
| DE | 29702671 U1 | 4/1997 |
| DE | 29716476 U1 | 12/1997 |
| DE | 19633901 A1 | 2/1998 |
| DE | 29716467 U1 | 2/1998 |
| DE | 19740506 A1 | 3/1998 |
| DE | 19754870 A1 | 8/1998 |
| DE | 19822157 A1 | 11/1999 |
| DE | 69611186 T2 | 5/2001 |
| EP | 0335341 | 10/1989 |
| EP | 0604022 | 6/1994 |
| EP | 800801 A1 | 10/1997 |
| EP | 0876806 A1 | 11/1998 |
| EP | 0982041 | 3/2000 |
| EP | 1195822 A2 | 4/2002 |
| EP | 1327422 A1 | 7/2003 |
| EP | 1454677 | 9/2004 |
| EP | 1502655 A2 | 2/2005 |
| EP | 1909973 A2 | 4/2008 |
| EP | 2197070 A1 | 6/2010 |
| EP | 2293357 A1 | 3/2011 |
| EP | 2293366 A1 | 3/2011 |
| FR | 2758253 A1 | 7/1998 |
| JP | 1994-098902 | 4/1994 |
| JP | H06218063 A | 8/1994 |
| JP | H08206223 A | 8/1996 |
| JP | H09-056807 | 3/1997 |
| JP | H1029524 A | 2/1998 |
| JP | H10151207 A | 6/1998 |
| JP | H10314313 A | 12/1998 |
| JP | H1157018 A | 3/1999 |
| JP | 2000316981 A | 11/2000 |
| JP | 2001521503 A | 11/2001 |
| JP | 2003533493 | 11/2001 |
| JP | 2003-205037 | 7/2003 |
| JP | 2003-533286 | 11/2003 |
| JP | 2003533492 | 11/2003 |
| JP | 2004512059 A | 4/2004 |
| JP | 2004/173770 | 6/2004 |
| JP | 2004-518458 | 6/2004 |
| JP | 2004-529674 | 9/2004 |
| JP | 2004528060 A | 9/2004 |
| JP | 2005-505318 | 2/2005 |
| JP | 2005519080 A | 6/2005 |
| JP | 2005-523119 | 8/2005 |
| JP | 2005-523332 | 8/2005 |
| JP | 2005-296690 | 10/2005 |
| JP | 2006506191 A | 2/2006 |
| JP | 2006512175 A | 4/2006 |
| JP | 2007502281 A | 2/2007 |
| JP | 2009-501566 | 1/2009 |
| JP | 2010052503 A | 3/2010 |
| KR | 1020040034064 | 4/2004 |
| WO | 9409010 A1 | 4/1994 |
| WO | WO-95/06487 | 3/1995 |
| WO | 9616691 A1 | 6/1996 |
| WO | WO 96/20698 | 7/1996 |
| WO | 9632907 A1 | 10/1996 |
| WO | 9641807 A1 | 12/1996 |
| WO | WO 97/45502 | 12/1997 |
| WO | 9802441 A2 | 1/1998 |
| WO | 9908729 A1 | 2/1999 |
| WO | 9915530 A1 | 4/1999 |
| WO | 9916388 A1 | 4/1999 |
| WO | 9917680 A1 | 4/1999 |
| WO | 0006051 A1 | 2/2000 |
| WO | 0025702 A1 | 5/2000 |
| WO | 0032238 A1 | 6/2000 |
| WO | 0114387 A1 | 3/2001 |
| WO | WO-01/54662 | 8/2001 |
| WO | WO-01-87371 | 11/2001 |
| WO | WO-01/87372 | 11/2001 |
| WO | WO-02/40702 | 5/2002 |
| WO | WO-02/43799 | 6/2002 |
| WO | 02055122 A1 | 7/2002 |
| WO | 02074194 A2 | 9/2002 |
| WO | WO-02/090085 | 11/2002 |
| WO | WO-03/039553 | 5/2003 |
| WO | 03082368 A1 | 10/2003 |
| WO | 03090684 A2 | 11/2003 |
| WO | WO-03/101624 A1 | 12/2003 |
| WO | 2004009145 A1 | 1/2004 |
| WO | 2004028406 A1 | 4/2004 |
| WO | WO-2004/028589 | 4/2004 |
| WO | WO-2004/043506 | 5/2004 |
| WO | WO-2004/045450 | 6/2004 |
| WO | WO-2004/098574 | 11/2004 |
| WO | WO-2005-042623 A1 | 5/2005 |
| WO | WO-2005/063319 | 7/2005 |
| WO | WO-2005/069889 | 8/2005 |
| WO | WO-2005-117942 A2 | 12/2005 |
| WO | WO-2006/014534 | 2/2006 |
| WO | WO-2006/052575 | 5/2006 |
| WO | 2006063430 A1 | 6/2006 |
| WO | WO-2006/065685 | 6/2006 |
| WO | WO-2006-083796 A2 | 8/2006 |
| WO | WO-2006-099276 A2 | 9/2006 |
| WO | 2007017707 A2 | 1/2007 |
| WO | 2007017708 A3 | 1/2007 |
| WO | WO-2007-002238 | 1/2007 |
| WO | WO-2007-011707 A2 | 1/2007 |
| WO | WO-2007-011707 A3 | 1/2007 |
| WO | WO-2007-011708 A2 | 1/2007 |
| WO | WO-2007-011708 A3 | 1/2007 |
| WO | WO-2007-127363 A2 | 1/2007 |
| WO | WO-2007/092179 | 8/2007 |
| WO | WO 2007/143609 | 12/2007 |
| WO | WO-2008/042909 | 4/2008 |
| WO | WO-2008-046641 A2 | 4/2008 |
| WO | WO-2008-046642 A1 | 4/2008 |
| WO | WO-2008/052000 | 5/2008 |
| WO | WO-2008/070996 | 6/2008 |
| WO | WO 2008/086369 | 7/2008 |
| WO | WO-2008-131131 A1 | 10/2008 |
| WO | WO-2008/148013 | 12/2008 |
| WO | 2009039553 A1 | 4/2009 |
| WO | 2009051614 A1 | 4/2009 |
| WO | WO-2009/051780 | 4/2009 |
| WO | WO-2009/146209 | 12/2009 |
| WO | WO 2010/009335 | 1/2010 |
| WO | WO-2010/075590 | 7/2010 |
| WO | WO-2010-111196 A2 | 9/2010 |
| WO | WO-2010-111196 A3 | 9/2010 |
| WO | WO-2010-111232 A3 | 9/2010 |

(56) References Cited

FOREIGN PATENT DOCUMENTS

| | | |
|---|---|---|
| WO | WO-2010-111232 A9 | 9/2010 |
| WO | WO-2010-111238 A2 | 9/2010 |
| WO | WO-2010-111238 A3 | 9/2010 |
| WO | WO-2010-120552 A2 | 10/2010 |
| WO | WO-2010-120552 A3 | 10/2010 |
| WO | WO-2010-121187 A2 | 10/2010 |
| WO | WO-2010-121187 A3 | 10/2010 |
| WO | 2010136604 A1 | 12/2010 |
| WO | WO-2011-009096 A1 | 1/2011 |
| WO | WO-2011/097103 | 8/2011 |
| WO | 2011119159 A1 | 9/2011 |
| WO | WO-2011/119762 | 9/2011 |
| WO | WO-2011/130448 | 10/2011 |
| WO | WO-2011/133655 | 10/2011 |
| WO | 2012009684 A2 | 1/2012 |
| WO | WO-2012/009684 | 1/2012 |
| WO | WO-2012/034079 | 3/2012 |
| WO | 2012078955 A1 | 6/2012 |
| WO | WO-2012/082502 | 6/2012 |
| WO | WO-2012/092504 | 7/2012 |
| WO | WO-2012/142319 | 10/2012 |
| WO | WO-2012/166819 | 12/2012 |
| WO | WO-2013/012689 | 1/2013 |
| WO | WO-2013/025535 | 2/2013 |
| WO | WO-2013/059509 | 4/2013 |
| WO | WO-2013/173657 | 11/2013 |
| WO | WO-2013/177211 | 11/2013 |
| WO | WO-2014/063111 | 4/2014 |
| WO | 2014165264 A1 | 10/2014 |
| WO | 2014186532 A1 | 11/2014 |

OTHER PUBLICATIONS

Domingo, C. et al., "Precipication of ultrafine organic crystals from the rapid expansion of supercritical solutions over a capillary and a frit nozzle," J. Supercritical Fluids 10:39-55 (1997).
Mario et al., "Drug-Eluting Bioabsorbable Magnesium Stent," J. Inverventional Cardiology 16(6):391=395 (2004).
McAlpine, J.B. et al., "Revised NMR Assignments for Rapamycine," J. Antibiotics 44:688-690 (1991).
Ong and Serruys, "Technology Insight: an overview of research in drug-eluting stents," Nat. Clin. Parct. Cardiovas. Med. 2(12):647-658 (2005).
PCT/US06/24221 Search Report mailed Jan. 29, 2007.
PCT/US06/27321 Search Report mailed Oct. 16, 2007.
PCT/US06/27322 Search Report mailed Apr. 25, 2007.
PCT/US07/10227 Search Report mailed Aug. 8, 2008.
PCT/US07/80213 Search Report dated Apr. 16, 2008.
PCT/US07/82275 Search Report dated Apr. 18, 2008.
PCT/US08/11852 Search Report dated Dec. 19, 2008.
PCT/US08/50536 Search Report dated Jun. 2, 2008.
PCT/US08/60671 Search Report dated Sep. 5, 2008.
PCT/US08/64732 Search Report dated Sep. 4, 2008.
PCT/US09/41045 Search Report dated Aug. 11, 2009.
Schreiber, S.L. et al., "Atomic Structure of the Rapamycin Human Immunophilin FKBP-12 Complex," J. Am. Chem. Soc. 113:7433-7435 (1991).
PCT/US09/50883 Search Report dated Nov. 17, 2009.
Serruys, Patrick et al., Comparison of Coronary-Artery Bypass Surgery and Stenting for the Treatment of Multivessel Disease, N. Engl. J. Med., 2001, vol. 344, No. 15, pp. 1117-1124.
PCT/US2011/032371, International Search Report dated Jul. 7, 2011.
Latella et al., "Nanoindentation hardness. Young's modulus, and creep behavior of organic-inorganic silica-based sol-gel thin films on copper," J Mater Res 23(9): 2357-2365 (2008).
Schmidt et al., "A Comparison of the Mechanical Performance Characteristics of Seven Drug-Eluting Stent Systems," Catheterization and Cardiovascular Interventions 73:350-360 (2009).
Schmidt et al., "Trackability, Crossability, and Pushability of Coronary Stent Systems—An Experimental Approach," Biomed Techn 47 (2002), Erg. 1, S. 124-126.
Schmidt et al., "In vitro measurement of quality parameters of stent-catheter systems," Biomed Techn 50(S1):1505-1506 (2005).
Schmidt et al., "New aspects of in vitro testing of arterial stents based on the new European standard," EN 14299, [online] (2009), [retrieved on Mar. 10, 2001] http://www.lib0ev.de/pl/pdf/EN14299.pdf (2009).
Szabadits et al., "Flexibility and trackability of laser cut coronary stent systems," Acta of Bioengineering and Biomechanics 11(3):11-18 (2009).
PCT/US10/42355 Search Report mailed Sep. 2, 2010.
PCT/US10/28253 Search Report and Written Opinion mailed Dec. 6, 2010.
PCT/US10/28265 Search Report and Written Opinion mailed Dec. 13, 2010.
PCT/US10/28195 Search Report and Written Opinion mailed Jan. 21, 2011.
PCT/US10/31470 Search Report and Written Opinion mailed Jan. 28, 2011.
PCT/US10/29494 Search Report and Written Opinion mailed Feb. 7, 2011.
PCT/US11/22623 Search Report and Written Opinion mailed Mar. 28, 2011.
U.S. Appl. No. 11/995,685 Office Action Mailed Aug. 20, 2010.
U.S. Appl. No. 11/995,685 Office Action Mailed Nov. 24, 2009.
U.S. Appl. No. 11/158,724 Office Action Mailed Sep. 8, 2008.
U.S. Appl. No. 11/158,724 Office Action Mailed Sep. 17, 2009.
Akoh et al., "One-Stage Synthesis of Raffinose Fatty Acid Polyesters. "Journal Food Science (1987) 52:1570.
Albert et al., "Antibiotics for preventing recurrent urinary tract infection in non-pregnant women,"Cochrane Database System Rev. 3, CD001209 (2004).
Au et al., "Methods to improve efficacy of intravesical mitomycin C: Results of a randomized phase III trial," Journal of the National Cancer Institute, 93(8), 597-604 (2001).
AU2006270221 Exam Report dated Apr. 6, 2010.
AU2011232760 Exam Report dated Apr. 10, 2013.
AU2012203203 Exam Report dated Apr. 12, 2013.
AU2007243268 Exam Report dated May 15, 2013.
AU2007243268 Exam Report dated Aug. 31, 2011.
AU2009251504 Exam Report dated Dec. 8, 2011.
AU2009270849 Exam Report dated Feb. 14, 2012.
AU2012203577 Exam Report dated Jun. 7, 2013.
AU2011256902 Exam Report dated Jun. 13, 2013.
Balss et al., "Quantitative spatial distribution of sirolumus and polymers in drug-eluting stents using confocal Raman microscopy," J. of Biomedical Materials Research Part A, 258-270 (2007).
Belu et al., "Three-Dimensional Compositional Analysis of Drug Eluting Stent Coatings Using Cluster Secondary Ioan Mass Spectroscopy," Anal. Chem. 80:624-632 (2008).
Belu, et al., "Chemical imaging of drug eluting coatings: Combining surface analysis and confocal Rama microscopy" J. Controlled Release 126: 111-121 (2008).
Boneff, "Topical Treatment of Chronic Prostatitis and Premature Ejaculation," International Urology and Nephrology 4(2):183-186 (1971).
Bookbinder et al., "A recombinant human enzyme for enhanced interstitial transport of therapeutics," Journal of Controlled Release 114:230-241 (2006).
Borchert et al., "Prevention and treatement of urinary tract infection with probiotics: Review and research perspective," Indian Journal Urol. 24(2):139-144 (2008).
Brunstein et al., "Histamine, a vasoactive agent with vascular disrupting potential improves tumour response by enhancing local drug delivery," British Journal of Cancer 95:1663-1669 (2006).
Bugay et al., "Raman Analysis of Pharmaceuticals," in "Applications of Vibrational Spectroscopy in Pharmaceutical Research and Development," Ed. Pivonka, D.E., Chalmers, J.M., Griffiths, P.R. (2007) Wiley and Sons.
CA 2615452 Office Action dated Dec. 19, 2012.
CA 2684482 Office Action Jul. 11, 2012.

(56) References Cited

OTHER PUBLICATIONS

CA 2684482 Office Action dated Nov. 10, 2011.
CA 2688314 Office Action dated Jun. 6, 2012.
CA 2730995 Office Action dated Sep. 26, 2012.
CA 2757276 Office Action dated Feb. 15, 2013.
CA 2756307 Office action dated Feb. 18, 2013.
CA 2756386 Office action dated Mar. 15, 2013.
CA 2759015 Office action dated Apr. 8, 2013.
CA 2756388 Office Action dated Apr. 11, 2013.
CA 2613280 Office Action dated Oct. 2, 2012.
CA 2730995 Office action dated May 29, 2013.
Cadieux et al., "Use of triclosan-eluting ureteral stents in patients with long-term stents," J. Endourol (Epub) (Jun. 19, 2009).
Channon et al., "Nitric Oxide Synthase in Atherosclerosis and Vascular Injury: Insights from Experimental Gene Therapy," Arteriosclerosis, Thrombosis and Vascular Biology, 20(8):1873-1881 (2000).
Chen et al. Immobilization of heparin on a silicone surface through a heterobifunctional PEG spacer. Biomaterials. Dec. 2005;26(35):7418-24.
Chopek et al. "The influence of carbon fibres on the resorption time and mechanical properties of the lactide-glycolide co-polymer." J. Biomater. Sci. Polymer Edn, vol. 18, No. 11, pp. 1355-1368 (2007).
Clair and Burks, "Thermoplastic/Melt-Processable Polyimides," NASA Conf. Pub. #2334 (1984), pp. 337-355.
CN 2006800258093 Office Action dated May 30, 2012.
CN 200880007308.1 Office Action dated Nov. 23, 2011.
CN 200880007308.1 Office Action dated Oct. 18, 2012.
CN 200880020515 Office Action dated Oct. 9, 2012.
CN 200880100102.3 Office Action dated Jun. 1, 2012.
CN 200980122691 Office Action dated Oct. 10, 2012.
CN 200780047425.6 Office action dated Aug. 3, 2012.
CN 200780047425.6 Office action dated Feb. 28, 2013.
CN 200980136432.2 Office action dated Jan. 14, 2013.
CN 200880100102.3 Office Action dated Apr. 11, 2013.
Cohen, et al. "Sintering Technique for the Preparation of Polymer Matrices fro the Controlled Release of Macromolecules." Journal of Pharamceutical Sciences, vol. 73, No. 8, 1984, p. 1034-1037.
CRC Handbook of chemistry and physics. 71st ed. David R. Lide, Editor-in-Chief. Boca Raton, FL, CRC Press; 1990; 6-140.
Cyrus et al., "Intramural delivery of rapamycin with alphavbeta3-targeted paramagnetic nanoparticles inhibits stenosis after balloon injury," Arterioscler Thromb Vasc Biol 2008;28:820-826.
Derwent-Acc-No. 2004-108578 Abstracting 2004003077; Jan. 8, 2004; 3 pages.
DiStasi et al., "Percutaneous sequential bacillus Calmette-Guerin and mitomycin C for panurothelial carcinomatosis," Can. J. Urol. 12(6):2895-2898 (2005).
Domb and Langer, "Polyanhydrides. I. Preparation of High Molecular Weight Polyanhydrides. "J. Polym Sci. 25:3373-3386 (1987).
Dzik-Jurasz, "Molecular imaging in vivo: an introduction," The British Journal of Radiology, 76:S98-S109 (2003).
EA 201001497 Office Action dated Feb. 11, 2013.
EA 200901254/28 Office Action dated Jul. 18, 2012.
Electrostatic Process, Wiley Encyclopedia of Electrical and Electronics Engineering, John Wiley & Sons, Inc. 1999; 7:15-39.
Eltze et al., "Imidazoquinolinon, imidazopyridine, and isoquinolindione derivatives as novel and potent inhibitors of the poly (ADP-ribose) polymerase (PARP): a comparison with standard PARP inhibitors," Mol. Pharmacol 74(6):1587-1598 (2008).
EP06773731.2 Search Report dated Oct. 2, 2012.
EP06787258.0 Search Report dated Feb. 6, 2012.
EP07756094.4 Search Report dated Aug. 31, 2012.
EP08733210.2 Search Report dated Oct. 23, 2012.
EP08756215.3 Search Report dated Oct. 5, 2011.
EP08756215.3 Search Report dated Jan. 28, 2013.
EP09805981.9 Office Action dated Feb. 13, 2013.
EP06787258.0 Office Action dated Mar. 15, 2013.
EP09755571.8 Search Report dated Apr. 9, 2013.
EP08705772.5 Search Report dated Feb. 20, 2013.
EP07756094.4 Office action dated May 29, 2013.
EP08733210.2 Office action dated Jul. 16, 2013.
Ettmayer et al. Lessons learned from marketed and investigational prodrugs. J Med Chem. May 6 2004;47(10):2393-404.
Fibbi et al., "Chronic inflammation in the pathogenesis of benign prostatic hyperplasia," Int J Androl. Jun. 1, 2010;33(3):475-88.
Fleischmann et al., "High Expression of Gastrin-Releasing Peptide Receptors in the Vascular bed of Urinary Tract Cancers: Promising Candidates for Vascular Targeting Applications." Jun. 2009, Endocr. Relat. Cancer 16(2):623-33.
Froehlich et al., "Conscious sedation for gastroscopy: patient tolerance and cardiorespiratory parameters," Gastroenterology 108(3):697-704 (1995).
Fujiwara et al., "Insulin-like growth factor 1 treatment via hydrogels rescues cochlear hair cells from ischemic injury," Oct. 29, 2008, NeuroReport 19(16):1585-1588.
Fulton et al. Thin Fluoropolymer films and nanoparticle coatings from the rapid expansion of supercritical carbon dioxide solutions with electrostatic collection, Polymer Communication. 2003; 2627-3632.
Green et al., "Simple conjugated polymer nanoparticles as biological labels," Proc Roy Soc A. published online Jun. 24, 2009 doi:10.1098/rspa.2009.0181.
Griebenow et al., "On Protein Denaturation in Aqueous-Organic Mixtures but not in Pure Organic Solvents," J. Am Chem Soc., vol. 118. No. 47, 11695-11700 (1996).
Hamilos et al., "Differential effects of Drug-Eluting Stents on Local Endothelium-Dependent Coronary Vasomotion." JACC vol. 51, No. 22, 2008, Endothelium and DES Jun. 3, 2008:2123-9.
Hartmann et al., "Tubo-ovarian abscess in virginal adolescents: exposure of the underlying etiology," J. Pediatr Adolesc Gynecol, 22(3):313-16 (2009).
Hasegawa et al., "Nylong 6/Na-montmorillonite nanocomposites prepared by compounding Nylon 6 with Na-montmorillonite slurry," Polymer 44 (2003) 2933-2937.
Hinds, WC. Aerosol Technology, Properties, Behavior and Measurement of Airborne Particles, Department of Environmental Health Sciences, Harvard University School of Public Health, Boston, Massachusetts. 1982; 283-314.
Hladik et al., "Can a topical microbicide prevent rectal HIV transmission?" PLoS Med. 5(8):e167 (2008).
Iconomidou et al., "Secondary Structure of Chorion Proteins of the Teleosatan Fish Dentex dentex by ATR FR-IR and FT-Raman Spectroscopy," J. of Structural Biology, 132, 112-122 (2000).
IN-368/DELNP/2008 Exam Report dated Oct. 17, 2011.
IL-208648 Official Notification dated Feb. 9, 2012.
Jackson et al., "Characterization of perivascular poly(lactic-co-glycolic acid) films containing paclitaxel" Int. J. Of Pharmaceutics, 283:97-109 (2004), incorporated in its entirety herein by reference.
Jensen et al., Neointimal hyperplasia after sirollmus-eluting and paclitaxel-eluting stend implantation in diabetic patients: the randomized diabetes and drug eluting stent (DiabeDES) intravascular ultrasound trial. European heart journal (29), pp. 2733-2741. Oct. 2, 2008. Retrieved from the Internet. Retrieved on [Jul. 17, 2012]. URL:<http://eurheartj.oxfordjournals.org/content/29/22/2733.full.pdf> entire document.
Jewell, et al., "Release of Plasmid DNA from Intravascular Stents Coated with Ultrathin Multilayered Polyelectrolyte Films" Biomacromolecules. 7: 2483-2491 (2006).
Johns, H.E, J.R.Cunningham, Thomas, Charles C., Publisher, "The Physics of Radiology, "1983, Springfield, IL, pp. 133-143.
Joner et al. "Site-specific targeting of nanoparticle prednisolone reduces in-stent restenosis in a rabbit model of established atheroma," Arterioscler Thromb Vasc Biol. 2008;28:1960-1966.
Mei et al., "Local Delivery of Modified Paclitaxel-Loaded Poly(ε-caprolactone)/Pluronic F68 Nanoparticles for Long-Term Inhibition of Hyperplasia,"Journal of Pharmaceutical Sciences, Vol. 98, No. 6, Jun. 2009.
Jovanovic et al. "Stabilization of Proteins in Dry Powder Formulations Using Supercritical Fluid Technology," Pharm. Res. 2004; 21(11).
JP 2008-521633 Office Action dated Oct. 12, 2012.
JP2008-521633 Office Action dated Dec. 28, 2011.

(56) References Cited

OTHER PUBLICATIONS

JP-2009-534823 Office Action dated Sep. 20, 2012.
JP-2009-534823 Office Action dated Feb. 21, 2012.
JP-2009-545647 Office Action dated Jun. 5, 2012.
JP-2010-504253 Office Action dated Dec. 12, 2011.
JP-2010-504253 Office Action dated Dec. 7, 2012.
JP-2011-518920 Office action dated Dec. 17, 2012.
JP-2009-534823 Office Action dated Apr. 23, 2013.
JP-2012-503677 Office action dated Jan. 18, 2013.
JP-2011-505248 Office action dated Jun. 4, 2013.
JP-2010-510441 Office action dated May 7, 2013.
Kazemi et al., "The effect of betamethasone gel in reducing sore throat, cough, and hoarseness after laryngo-tracheal intubation," Middle East J. Anesthesiol. 19(1):197-204 (2007).
Kehinde et al., "Bacteriology of urinary tract infection associated with indwelling J ureteral stents," J. Endourol. 18(9):891-896 (2004).
Kelly et al., "Double-balloon trapping technique for embolization of a large wide-necked superior cerebellar artery aneurysm: case report," Neurosurgery 63(4 Suppl 2):291-292 (2008).
Khan et al., "Cyclic Acetals of 4,1',6'-Trichloro-4,1',6',-Trideoxy-Trideoxy-galacto-Sucrose and their Conversion into Methyl Ether Derivatives." . Carb. Res. (1990) 198:275-283.
Khan et al., "Chemistry and the new uses of Sucrose: How Important?" Pur and Appl. Chem (1984) 56:833-844.
Khan et al., "Enzymic Regioselective Hydrolysis of Peracetylated Reducing Disaccharides, Specifically at the Anomeric Centre: Intermediates for the Synthesis of Oligosaccharides." Tetrahedron Letters (1933) 34:7767.
Khayankarn et al., "Adhesion and Permeability of Polyimide-Clay Nanocomposite Films for Protective Coatings," Journal of Applied Polymer Science, vol. 89, 2875-2881 (2003).
Koh et al. "A novel nanostructured poly(lactic-co-glycolic-acid)—multi-walled carbon nanotube composite for blood-contacting applications: Thrombogenicity studies."
KR10-2008-7003756 Office Action dated Oct. 30, 2012.
Kurt et al., "Tandem oral, rectal and nasal administrations of Ankaferd Blood Stopper to control profuse bleeding leading to hemodynamic instability," Am J. Emerg. Med. 27(5):631, el-2 (2009).
Labhasetwar et al., "Arterial uptake of biodegradable nanoparticles: effect of surface modifications," Journal of Pharmaceutical Sciences, vol. 87, No. 10, Oct. 1998; 1229-1234.
Lamm et al., "Bladder Cancer: Current Optimal Intravesical Treatment: Pharmacologic Treatment," Urologic Nursing 25(5):323-6, 331-2 (Oct. 26, 2005).
Lawrence et al., "Rectal tacrolimus in the treatment of resistant ulcerative proctitis," Aliment. Pharmacol Ther. 28(10):1214-20 (2008).
Lee et al., "Novel therapy for hearing loss: delivery of insulin-like growth factor 1 to the cochlea using gelatin hydrogel, "Otol. Neurotol. 28(7):976-81 (2007).
Lehmann et al, "Drug treatment of nonviral sexually transmitted diseases: specific issues in adolescents," Pediatr Drugs 3(7):481-494 (2001.
Mahoney et al., "Three-Dimensional Compositional Analysis of Drug Eluting Stent Coatings Using Cluster Secondary Ion mass Spectrometry," Anal. Chem. , 80, 624-632 (2008).
Mehik et al., "Alfuzosin treatment for chronic prostatitis/chronic pelvic pain syndrome: a prospecitve, randomized, double-blind, placebo-controlled, pilot study,"Urology 62(3):425-429 (2003).
Melonakos et al., Treatment of low-grade bulbar transitional cell carcinoma with urethral instillation of mitomycin C, Oct. 28, 2008, Adv. Urol., 173694 Epub.
Merrett et al., "Interaction of corneal cells with transforming growth factor beta2-modified poly dimethyl siloxane surfaces," Journal of Biomedical Materials Research, Part A, vol. 67A, No. 3, pp. 981-993 (2003).
Middleton and Tipton, Synthetic biodegradable polymers as orthopedic devises. Biomaterials 2000; 21:2335-46.

Minchin, "Nanomedicine: sizing up targets with nanoparticles," Nature Nanotechnology, vol. 33, Jan. 12-13, 2008.
Minoque et al., "Laryngotracheal topicalization with lidocaine before intubation decreases the incidence of coughing on emergence from general anesthesia," Anesth. Analg. 99(4):1253-1257 (2004).
Mishima et al. "Microencapsulation of Proteins by Rapid Expansion of Supercritical Solution with a Nonsolvent," AIChE J. 2000;46(4):857-65.
Mocco et al., "Pharos neurovascular intracranail stent: Elective use for a symptomatic stenosis refractory to medical therapy," Catheter Cardiovasc. Interv. (epub) (Mar. 2009).
Mollen et al., "Prevalence of tubo-ovarian abcess in adolescents diagnosed with pelvice inflammatory disease in a pediatric emergency department," Pediatr. Emerg. Care, 22(9): 621-625 (2006).
Moroni et al., "Post-ischemic brain damage:targeting PARP-1 within the ischemic neurovaschular units as a realistic avenue to stroke treatment," FEBS J. 276(1):36-45 (2009).
Muhlen et al., "Magnetic Resonance Imaging Contrast Agent Targeted Toward Activated Platelets Allows in Vivo Detection of Thrombosis and Monitoring of Thrombolysis Circulation," 118:258-267 (2008).
Murphy et al., "Chronic prostatitis: management strategies," Drugs 69(1): 71-84 (2009).
NZ 588549 Examination Report dated Mar. 28, 2011.
NZ 600814 Examination Report dated Jun. 29, 2012.
O'Neil et al., "Extracellular matrix binding mixed micelles for drug delivery applications," Journal of Controlled Release 137 (2009) 146-151.
O'Donnell et al., "Salvage intravesical therapy with interferon-alpha 2b plus low dose bacillus Calmette-Guerin alone perviously failed," Journ. Urology, 166(4):1300-1304 (2001).
Olbert et al., "In vitro and in vivo effects of CpG-Oligodeoxynucleotides (CpG-ODN) on murine transitional cell carcinoma and on the native murine urinary bladder wall," Anti-cancer Res. 29(6):2067-2076 (2009).
PCT/US09/50883 International Search Report mailed Nov. 17, 2009.
PCT/US12/46545 International Search Report mailed Nov. 20, 2012.
PCT/US12/50408 International Search Report mailed Oct. 19, 2012.
PCT/US2012/040040 International Search Report mailed Sep. 7, 2012.
Perry et al., Chemical Engineer's Handbook, 5th Edition, McGraw-Hill, New York, 1973; 20-106.
Torchlin, "Micellar Nanocarriers: Pharmaecutial Perspectives," Pharmaceutical Research, vol. 24, No. 1, Jan. 2007.
Plas et al., "Tubers and tumors: rapamycin therapy for benign and malignant tumors", Curr Opin Cell Bio 21: 230-236, (2009).
Poling et al., The Properties of Gases and Liquids. McGraw-Hill. 2001; 9:1-9.97.
Pontari, "Chronic prostatitis/chronic pelvic pain syndrome in elderly men: toward better understanding and treatment," Drugs Aging 20(15):1111-1115 (2003).
Pontari, "Inflammation and anti-inflammatory therapy in chronic prostatits," Urology 60(6Suppl1):29-33 (2002).
Raganath et al., "Hydrogel matrix entrapping PLGA-paclitaxel microspheres: drug delivery with near zero-order release and implantability advantages for malignant brain tumour," Pharm Res (Epub) Jun. 20, 2009).
Ranade et al., "Physical characterization of controlled release of paclitaxel from the TAXUS Express2 drug-eluting stent," J. Biomed Mater. Res. 71(4):625-634 (2004).
Reddy et al., "Inhibition of apoptosis through localized delivery of rapamycin-loaded nanoparticles prevented neointimal hyperplasia and reendothelialized injured artery," Circ Cardiovasc Interv 2008;1;209-216.
Ristikankare et al., "Sedation, topical pharnygeal anesthesia and cardiorespiratory safety during gastroscopy," J. Clin Gastorenterol. 40(1):899-905 (2006).
Sahajanand Medical Technologies (Supralimus Core; Jul. 6, 2008).

(56) References Cited

OTHER PUBLICATIONS

Salo et al., "Biofilm formation by *Escherichia coli* isolated from patients with urinary tract infections," Clin Nephrol. 71(5):501-507 (2009).
Saxena et al., "Haemodialysis catheter-related bloodstream infections: current treatment options and strategies for prevention," Swiss Med Wkly 135:127-138 (2005).
Schetsky, L. McDonald, "Shape Memory Alloys", Encyclopedia of Chemical Technology (3d Ed), John Wiley & Sons 1982, vol. 20 pp. 726-736.
Scheuffler et al., "Crystal Structure of Human Bone Morphogenetic Protein-2 at 2.7 Angstrom resolution," Journal of Molecular Biology, vol. 287, Issue 1, Mar. 1999, retrieved online at http://www.sciencedirect.com/science/article/pii/S002283699925901:.
Sen et al., "Topical heparin: A promising agent for the prevention of tracheal stenosis in airway surgery," J. Surg. Res (Epub ahead of print) Feb. 21, 2009.
SG201007602-4 Written Opinion dated Jun. 20, 2012.
SG201007602-4 Examination Report dated Feb. 13, 2013.
Shekunov et al. "Crystallization Processes in Pharmaceutical Technology and Drug Delivery Design." Journal of Crystal Growth 211 (2000), pp. 122-136.
Simpson et al., "Hyaluronan and hyaluronidase in genitourinary tumors." Front Biosci. 13:5664-5680.
Smith et al., "Mitomycin C and the endoscopic treatment of laryngotracheal stenosis: are two applications better than one?" Laryngoscope 119(2):272-283 (2009).
Sumathi et al., "Controlled comparison between betamethasone gel and lidocaine jelly applied over tracheal tube to reduce postoperative sore throat, cough, and hoarseness of voice," Br. J. Anaesth. 100(2):215-218 (2008.
Testa, B. Prodrug research: futile or fertile? Biochem Pharmacol. Dec. 1, 2004;68(11):2097-106.
Thalmann et al., "Long-term experience with bacillus Calmette-Guerin therapy of upper urinary tract transitional cell carcinoma in patients not eligible for surgery," J Urol. 168(4 Pt 1):1381-1385 (2002).
Merriam-Webster Online Dictionary, obtained onlie at: http://www.merriam-webster.com/dictionary/derivative, downloaded 07 Jul. 5, 2008.
U.S. Appl. No. 11/158,724 Office Action Mailed Sep. 26, 2012.
U.S. Appl. No. 11/877,591 Office Action Mailed Feb. 29, 2012.
U.S. Appl. No. 11/877,591 Office Action Mailed Sep. 21, 2012.
U.S. Appl. No. 11/995,687 Office Action Mailed Apr. 6, 2012.
U.S. Appl. No. 11/995,687 Office Action Mailed Sep. 28, 2011.
U.S. Appl. No. 12/298,459 Office Action Mailed Aug. 10, 2011.
U.S. Appl. No. 12/298,459 Office Action Mailed Apr. 6, 2012.
U.S. Appl. No. 12/443,959 Office Action Mailed Dec. 13, 2012.
U.S. Appl. No. 12/443,959 Office Action mailed Feb. 15, 2012.
U.S. Appl. No. 12/504,597 Final Office Action Mailed Oct. 3, 2012.
U.S. Appl. No. 12/504,597 Office Action Mailed Dec. 5, 2011.
U.S. Appl. No. 12/522,379 Office Action Mailed Dec. 26, 2012.
U.S. Appl. No. 12/595,848 Office Action Mailed Jan. 13, 2012.
U.S. Appl. No. 12/601,101 Office Action Mailed Dec. 27, 2012.
U.S. Appl. No. 12/601,101 Office Action Mailed Mar. 27, 2012.
U.S. Appl. No. 12/648,106 Final Office Action Mailed Sep. 25, 2012.
U.S. Appl. No. 12/648,106 Office Action Mailed Jan. 30, 2012.
U.S. Appl. No. 12/729,156 Final Office Action Mailed Oct. 16, 2012.
U.S. Appl. No. 12/729,156 Office Action Mailed Feb. 1, 2012.
U.S. Appl. No. 12/729,580 Office Action Mailed Apr. 10, 2012.
U.S. Appl. No. 12/729,580 Office Action Mailed Jan. 22, 2013.
U.S. Appl. No. 12/729,603 Final Office Action Mailed Oct. 10, 2012.
U.S. Appl. No. 12/729,603 Office Action Mailed Mar. 27, 2012.
U.S. Appl. No. 12/751,902 Office Action Mailed Jul. 13, 2012.
U.S. Appl. No. 12/595,848 Office Action Mailed Mar. 15, 2013.
U.S. Appl. No. 12/738,411 Final Office action Mailed Apr. 11, 2013.
U.S. Appl. No. 13/605,904 Office Action Mailed Nov. 27, 2012.
U.S. Appl. No. 12/762,007 Office action Mailed Feb. 11, 2013.
U.S. Appl. No. 13/384,216 Office action Mailed Apr. 24, 2013.
U.S. Appl. No. 13/340,472 Office action Mailed Apr. 26, 2013.
U.S. Appl. No. 12/729,156 Office action Mailed May 8, 2013.
U.S. Appl. No. 13/014,632 Office action Mailed May 8, 2013.
U.S. Appl. No. 13/086,335 Office action Mailed May 22, 2013.
U.S. Appl. No. 11/158,724 Office action Mailed May 23, 2013.
U.S. Appl. No. 12/601,101 Office action Mailed May 22, 2013.
U.S. Appl. No. 12,298,459 Office Action Mailed May 31, 2013.
U.S. Appl. No. 13/229,473 Office Action Mailed Jun. 17, 2013.
U.S. Appl. No. 13/605,904 Office Action Mailed Jun. 28, 2013.
U.S. Appl. No. 11/877,591 Office Action Mailed Jul. 1, 2013.
U.S. Appl. No. 12/748,134 Office Action Mailed Jul. 18, 2013.
Unger et al., "Poly(ethylene carbonate): A thermoelastic and biodegradable biomaterial for drug eluting stent coatings?" Journal fo Controlled Release, vol. 117, Issue 3, 312-321 (2007).
Verma et al., "Effect of surface properties on nanoparticle-cell interactions," *Small* 2010, 6, No. 1, 12-21.
Wagenlehner et al., "A pollen extract (Cernilton) in patients with inflammatory chronic prostatitis/chronic pelvic pain syndrome: a multicentre, randomized, prospective, double-blind, placebo-controlled phase 3 study," Eur Urol 9 (Epub) (Jun. 3, 2009).
Wang et al. Controlled release of sirolimus from a multilayered PLGA stent matrix. Biomaterials 2000; 27:5588-95.
Wang et al., "Treatment with melagatran alone or in combination with thrombolytic therapy reduced ischemic brain injury," Exp. Neurol 213(1):171-175 (2008).
Warner et al., "Mitomycin C and airway surgery: how well does it work?" Ontolaryngol Head Neck Surg. 138(6):700-709 (2008).
Wermuth, CG Similarity in drugs: reflections on analogue design. Drug Discov Today. Apr. 2006;11(7-8):348-54.
Witjes et al., "Intravesical pharmacotherapy for non-muscle-invasive bladder cancer: a critical analysis of currently available drugs, treatment schedules, and long-term results," Eur. Urol. 53(1):45-52.
Wu et al., "Study on the preparation and characterization of biodegradable polylactide/multi-walled carbon nanotubes nanocomposites." Polymer 48 (2007) 4449-4458.
Xue et al., "Spray-as-you-go airway topical anesthesia in patients with a difficult airway: a randomized, double-blind comparison of 2% and 4% lidocaine," Anesth. Analg. 108(2): 536-543 (2009).
Yepes et al., "Tissue-type plasminogen activator in the ischemic brain: more than a thrombolytic," Trends Neurosci. 32(1):48-55 (2009).
Yousof et al., "Reveratrol exerts its neuroprotective effect by modulating mitochondrial dysfunction and associated cell death during cerebral ischemia," Brain Res. 1250:242-253 (2009).
Zhou et al. Synthesis and Characterization of Biodegradable Low Molecular Weight Aliphatic Polyesters and Their Use in Protein-Delivery Systems. J Appl Polym Sci 2004; 91:1848-56.
PCT/US2011/044263 International Search Report, International Preliminary Report on Patentability and Written Opinion dated Feb. 9, 2012.
PCT/US2007/82775 International Preliminary Report on Patentablity dated Apr. 28, 2009.
PCT/US09/69603 International Search Report mailed Nov. 5, 2010.
PCT/US10/28253 International Preliminary Report on Patentability dated Sep. 27, 2011.
PCT/US12/33367 International Search Report mailed Aug. 1, 2012.
PCT/US10/28195 International Preliminary Report on Patentability dated Oct. 6, 2011.
PCT/US2011/051092 International Preliminary Report on Patentability dated Mar. 21, 2013.
PCT/US10/42355 International Preliminary Report on Patentability dated Jan. 17, 2012.
PCT/US2011/67921 Search Report and Written Opinion mailed Jun. 22, 2012.
PCT/US2011/67921 International Preliminary Report on Patentability dated Jul. 11, 2013.
Abreu Filho et al., "Influence of metal alloy and the profile of coronary stents in patients with multivessel coronary disease," CLINICS 2011:66(6):985-989.
CA 2615452 Office Action dated Oct. 8, 2013.

(56) References Cited

OTHER PUBLICATIONS

CA 2650590 Office action dated Jul. 23, 2013.
CA 2613280 Office action dated Dec. 10, 2013.
CA 2756386 Office action dated Oct. 24, 2013.
CN 200880007308.1 Office Action dated Jul. 3, 2013.
CN 200880020515 Office Action dated Jul. 22, 2013.
CN 200880100102.3 Office Action dated Dec. 11, 2013.
CN 200980136432.2 Office action dated Nov. 4, 2013.
Colombo et al. "Selection of Coronary Stents," Journal of the American College of Cardiology, vol. 40, No. 6, 2002, p. 1021-1033.
EA 200901254 Office Action dated Jul. 29, 2013.
EA 201001497 Office Action dated Jul. 29, 2013.
EP08705772.5 Office Action dated Oct. 30, 2013.
EP09755571.8 Office Action dated Dec. 13, 2013.
EP09798764.8 Search Report dated Sep. 30, 2013.
EP10756696.0 Search Report dated Oct. 10, 2013.
EP10764884.2 Search Report dated Oct. 28, 2013.
EP10765295.0 Search Report dated Oct. 17, 2013.
EP11769546.0 Search Report dated Sep. 19, 2013.
IL-201550 Official Notification dated Dec. 8, 2013.
IN-6884DEFNP2009 Office Action dated Oct. 31, 2013.
JP-2009-545647 Office Action dated May 14, 2013.
JP-2012-503677 Office action dated Nov. 1, 2003.
JP-2012-151964 Office Action dated Dec. 10, 2013.
KR10-2008-7003756 Office Action dated Sep. 23, 2013.
PCT/US09/41045 International Preliminary Report on Patentability dated Oct. 19, 2010.
PCT/US09/69603 International Preliminary Report on Patentability dated Jun. 29, 2011.
PCT/US10/28265 International Report on Patentability dated Sep. 27, 2011.
PCT/US10/29494 International Preliminary Report on Patentability dated Oct. 4, 2011.
PCT/US10/31470 International Preliminary Report on Patentability dated Oct. 18, 2011.
PCT/US11/032371 International Report on Patentability dated Oct. 16, 2012.
PCT/US11/051092 International Search Report dated Apr. 2, 2012.
PCT/US11/051092 Written Opinion dated Mar. 9, 2013.
PCT/US11/22623 International Preliminary Report on Patentability dated Aug. 7, 2012.
PCT/US11/29667 International Search Report and Written Opinion mailed Jun. 1, 2011.
PCT/US12/33367 International Preliminary Report on Patentability dated Oct. 15, 2013.
U.S. Appl. No. 11/158,724 Office action Mailed Dec. 31, 2013.
U.S. Appl. No. 11/877,591 Final Action dated Nov. 4, 2013.
U.S. Appl. No. 12/522,379 Final Office Action Mailed Aug. 28, 2013.
U.S. Appl. No. 12/595,848 Office Action Mailed Oct. 22, 2013.
U.S. Appl. No. 12/648,106 Office Action Mailed Sep. 18, 2013.
U.S. Appl. No. 12/729,580 Final Action dated Nov. 14, 2013.
U.S. Appl. No. 12/738,411 Office action Mailed Aug. 21, 2013.
U.S. Appl. No. 12/751,902 Office Action Mailed Dec. 19, 2013.
U.S. Appl. No. 12/762,007 Final Office action Mailed Oct. 22, 2013.
U.S. Appl. No. 13/340,472 Office action Mailed Jan. 15, 2014.
U.S. Appl. No. 13/384,216 Final Action dated Nov. 6, 2013.
U.S. Appl. No. 13/014,632 Office action Mailed Jan. 10, 2014.
Zilberman et al., Drug-Bluting bioresorbable stents for various applications, Annu Rev Biomed Eng., 2006;8:158-180.
CA 2757276 Office Action dated Feb. 5, 2014.
CA 2794704 Office action dated Feb. 7, 2014.
CA 2667228 Office action dated Jan. 22, 2014.
CA 2679712 Office action dated Feb. 24, 2014.
CA 2667228 office action dated May 7, 2013.
CA 2730995 Office Action dated Feb. 20, 2014.
CA 2756307 Office Action dated Mar. 24, 2014.
CA 2756388 Office Action dated Apr. 14, 2014.
CA 2756386 Office action dated May 16, 2014.
CA 2805631 Office Action dated Jan. 17, 2014.
CA 2823355 Office action dated Apr. 14, 2014.
CN 200880007308.1 Office Action dated Jan. 2, 2014.
CN 200880020515 Office Action dated Apr. 15, 2014.
CN 200980136432.2 Office action dated Jul. 3, 2014.
CN 201080024973.9 Office action dated Dec. 20, 2013.
EP07756094.4 Office Action dated Jan. 21, 2014.
EP10756676.2 Search Report dated Jan. 31, 2014.
EP10800642.0 Search Report dated Mar. 19, 2014.
EP11772624.0 Search Report dated Jun. 5, 2014.
EP09798764.8 Office action dated Jun. 30, 2014.
ID-W00201003529 Office action dated Apr. 28, 2014.
JP-2009-545647 Office Action dated Apr. 22, 2014.
JP-2011-518920 Office action dated Oct. 23, 2013.
JP-2013-024508 Office Action dated Apr. 24, 2014.
KR10-2013-7031237 Office action dated Mar. 17, 2014.
Matsumoto, D, et al. Neointimal Coverage of Sirolimus-Eluting Stents at 6-month Follow-up: Evaluated by Optical Coherence Tomography, European Heart Journal, Nov. 29, 2006; 28:961-967.
MX/a/2010/01148 Office action dated Feb. 11, 2014.
PCT/US06/24221 International Preliminary Report on Patentability dated Dec. 24, 2007.
PCT/US06/27321 International Preliminary Report on Patentability dated Jan. 16, 2008.
PCT/US06/27322 International Preliminary Report on Patentability dated Jan. 16, 2008.
PCT/US07/10227 International Preliminary Report on Patentability dated Oct. 28, 2008.
PCT/US07/80213 International Preliminary Report on Patentability dated Apr. 7, 2009.
PCT/US08/11852 International Preliminary Report on Patentability dated Apr. 20, 2010.
PCT/US08/50536 International Preliminary Report on Patentability dated Jul. 14, 2009.
PCT/US08/60671 International Preliminary Report on Patentability dated Oct. 20, 2009.
PCT/US08/64732 International Preliminary Report on Patentability dated Dec. 1, 2009.
PCT/US13/41466 International Search Report and Written Opinion dated Oct. 17, 2013.
PCT/US13/42093 International Search Report and Written Opinion dated Oct. 24, 2013.
PCT/US2011/033225 International Search Report and Written Opinion dated Jul. 7, 2011.
PCT/US2012/60896 International Search Report and Written Opinion dated Dec. 28, 2012.
PCT/US2013/065777 International Search Report and Written Opinion dated Jan. 29, 2014.
PCT/US2014/025017 International Search Report and Written Opinion dated Jul. 7, 2014.
Putkisto, K. et al. "Polymer Coating of Paper Using Dry Surface Treatment —Coating Structure and Performance", ePlace newsletter, 2004 (Apr. 12), vol. 1, No. 8, pp. 1-20.
U.S. Appl. No. 11/158,724 Office Action Mailed Jun. 25, 2014.
U.S. Appl. No. 11/877,591 Office Action Mailed May 7, 2014.
U.S. Appl. No. 12/504,597 Office Action Mailed Apr. 1, 2014.
U.S. Appl. No. 12/522,379 Office Action Mailed Apr. 8, 2014.
U.S. Appl. No. 12/601,101 Office Action mailed Feb. 13, 2014.
U.S. Appl. No. 12/729,156 Office Action Mailed Feb. 13, 2014.
U.S. Appl. No. 12/729,603 Office Action Mailed Jun. 25, 2014.
U.S. Appl. No. 12/738,411 Office Action mailed Feb. 6, 2014.
U.S. Appl. No. 12/738,411 Office Action mailed May 30, 2014.
U.S. Appl. No. 12/762,007 Final Office action Mailed Apr. 30, 2014.
U.S. Appl. No. 13/086,335 Office action Mailed Apr. 4, 2014.
U.S. Appl. No. 13/445,723 Office action mailed Mar. 14, 2014.
U.S. Appl. No. 13/090,525 Office action mailed Apr. 11, 2014.
U.S. Appl. No. 11/995,685 Office Action Mailed Jun. 18, 2014.
Handschumacher, R.E. et al., Purine and Pyrimidine Antimetabolites, Chemotherapeutic Agents, pp. 712-732, Ch. XV1-2, 3rd Edition, Edited by J. Holland, et al., Lea and Febigol, publishers.

(56) References Cited

OTHER PUBLICATIONS

Higuchi, Rate of Release of Medicaments from Ointment Bases Containing Drugs in Suspension, Journal of Pharmaceutical Sciences, vol. 50, No. 10, p. 874, Oct. 1961.
Ji, et al., "96-Wellliquid-liquid extraction liquid chromatographytandem mass spectrometry method for the quantitative determination of ABT-578 in human blood samples" Journal of Chromatography B. 805:67-75 (2004).
Levit, et al., "Supercritical C02 Assisted Electrospinning" J. of Supercritical Fluids, 329-333, vol. 31, Issue 3, (Nov. 2004).
David Grant, Crystallization Impact on the Nature and Properties of the Crystalline Product, 2003, SSCI, http://www.ssci-inc.com/Information/RecentPublications/ApplicationNotes/CrystallizationImpact/tabid/138/Default.aspx.
Analytical Ultracentrifugation of Polymers and Nanoparticles, W. Machtle and L. Borger, (Springer) 2006, p. 41.
Chalmers, et al. (2007) Wiley and Sons.
European International Search Report of PCT/EP01/05736 dated Oct. 24, 2001.
Finn et al. Differential Response of Delayed Healing . . . Circulation vol. 112 (2005) 270-8.
Greco et al. (Journal of Thermal Analysis and Calorimetry, vol. 72 (2003) 1167-1174.).
Han, et al., "Studies of a Novel Human Thrombomodulin Immobilized Substrate: Surface Characterization and Anticoagulation Activity Evaluation." J. Biomater. Sci. Polymer Edn, 2001, 12 (10), 1075-1089.
Ju et al., J. Pharm. Sci. vol. 84, No. 12, 1455-1463.
Lewis, D. H., "Controlled Release of Bioactive Agents from Lactides/Glycolide Polymers" in Biodegradable Polymers as Drug Delivery Systems, Chasin, M. and Langer, R., eds., Marcel Decker (1990).
Luzzi, L.A., J. Phann. Psy. 59:1367 (1970).
Park et al., Pharm. Res. (1987) 4(6):457-464.
PCT/EP01/05736 International Preliminary Examination Report dated Jan. 14, 2002.
PCT/EP2000/004658 International Search Report from dated Sep. 15, 2000.
PCT/US06/27321 Written Opinion dated Oct. 16, 2007.
PCT/US09/50883 International Preliminary Report on Patentability dated Jan. 18, 2011.
PCT/US11/33225 International Search Report and Written Opinion dated Jul. 7, 2011.
PCT/US11/51092 Written Opinion dated Mar. 27, 2012.
PCT/US12/50408 International Search Report mailed Oct. 16, 2012.
PCT/US13/41466 International Preliminary Report on Patentability dated Nov. 18, 2014.
PCT/US13/42093 International Preliminary Report on Patentability dated Nov. 25, 2014.
PCT/US14/38117 International Search Report and Written Opinion dated Oct. 7, 2014.
Wang et al. "Synthesis, characterization, biodegradation, and drug delivery application of biodegradable lactic/glycolic acid polymers: I. Synthesis and characterization" J. Biomater. Sci. Polymer Edn. 11(3):301-318 (2000).
Xu et al., "Biodegradation of poly(L-lactide-co-glycolide) tube stents in bile", Polymer Degradation and Stability. 93:811-817(2008).
Extended European Search Report for Application No. 14797966.0 dated Dec. 19, 2016.

\* cited by examiner

STENTS HAVING BIOABSORBABLE LAYERS

CROSS REFERENCE

This application claims the benefit of U.S. Provisional Application No. 61/045,928, filed Apr. 17, 2008, and U.S. Provisional Application No. 61/104,669 filed Oct. 10, 2008. The contents of the applications are incorporated herein by reference in their entirety.

This application relates to U.S. Provisional Application No. 60/912,408, filed Apr. 17, 2007, U.S. Provisional Application No. 60/912,394, filed Apr. 17, 2007, U.S. Provisional Application No. 60/981,445, filed Oct. 19, 2007 and U.S. Provisional Application entitled Stents Having Bioabsorbable U.S. Provisional Application No. 61/212,964, filed Apr. 17, 2009. The contents of the applications are incorporated herein by reference in their entirety.

BACKGROUND OF THE INVENTION

Drug-eluting stents are used to address the drawbacks of bare stents, namely to treat restenosis and to promote healing of the vessel after opening the blockage by PCI/stenting. Some current drug eluting stents can have physical, chemical and therapeutic legacy in the vessel over time. Others may have less legacy, bur are not optimized for thickness, deployment flexibility, access to difficult lesions, and minimization of vessel wall intrusion.

SUMMARY OF THE INVENTION

The present invention relates to methods for forming stents comprising a bioabsorbable polymer and a pharmaceutical or biological agent in powder form onto a substrate.

It is desirable to have a drug-eluting stent with minimal physical, chemical and therapeutic legacy in the vessel after a proscribed period of time. This period of time is based on the effective healing of the vessel after opening the blockage by PCI/stenting (currently believed by leading clinicians to be 6-18 months).

It is also desirable to have drug-eluting stents of minimal cross-sectional thickness for (a) flexibility of deployment (b) access to small vessels (c) minimized intrusion into the vessel wall and blood.

Provided herein is a device comprising a stent; and a plurality of layers that form a laminate coating on said stent; wherein at least one of said layers comprises a bioabsorbable polymer and at least one of said layers comprises one or more active agents; wherein at least a portion of the active agent is in crystalline form.

Provided herein is a device comprising a stent; and a plurality of layers that form a laminate coating on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof, wherein at least a portion of the pharmaceutical agent is in crystalline form.

In some embodiments, the device has at least one pharmaceutical agent layer defined by a three-dimensional physical space occupied by crystal particles of said pharmaceutical agent and said three dimensional physical space is free of polymer. In some embodiments, at least some of the crystal particles in said three dimensional physical space defining said at least one pharmaceutical agent layer are in contact with polymer particles present in a polymer layer adjacent to said at least one pharmaceutical agent layer defined by said three-dimensional space free of polymer.

In some embodiments, the plurality of layers comprises a first polymer layer comprising a first bioabsorbable polymer and a second polymer layer comprising a second bioabsorbable polymer, wherein said at least one layer comprising said pharmaceutical agent is between said first polymer layer and said second polymer layer. In some embodiments, first and second bioabsorbable polymers are the same polymer. In some embodiments, the first and second bioabsorbable polymers are different. In some embodiments, the second polymer layer has at least one contact point with at least one particle of said pharmaceutical agent in said pharmaceutical agent layer and said second polymer layer has at least one contact point with said first polymer layer.

In some embodiments, the stent has a stent longitudinal axis; and said second polymer layer has a second polymer layer portion along said stent longitudinal wherein said second layer portion is free of contact with particles of said pharmaceutical agent. In some embodiments, the device has at least one pharmaceutical agent layer defined by a three-dimensional physical space occupied by crystal particles of said pharmaceutical agent and said three dimensional physical space is free of polymer.

In some embodiments, the stent comprises at least one strut having a strut length along said stent longitudinal axis, wherein said second layer portion extends substantially along said strut length. In some embodiments, the stent has a stent length along said stent longitudinal axis and said second layer portion extends substantially along said stent length.

In some embodiments, the stent comprises at least five struts, each strut having a strut length along said stent longitudinal axis, wherein said second layer portion extends substantially along substantially the strut length of at least two struts. In some embodiments, the stent comprises at least five struts, each strut having a strut length along said stent longitudinal axis, wherein said second layer portion extends substantially along substantially the strut length of at least three struts. In some embodiments, the stent comprises at least five struts, each strut having a strut length along said stent longitudinal axis, wherein said second layer portion extends substantially along substantially the strut length of least four struts. In some embodiments, the stent comprises at least five struts, each strut having a strut length along said stent longitudinal axis, wherein said second layer portion extends substantially along substantially the strut length of all said at least five struts. In some embodiments, the stent has a stent length along said stent longitudinal axis and said second layer portion extends substantially along said stent length.

In some embodiments, the stent has a stent length along said stent longitudinal axis and said second layer portion extends along at least 50% of said stent length. In some embodiments, the stent has a stent length along said stent longitudinal axis and said second layer portion extends along at least 75% of said stent length. In some embodiments, the stent has a stent length along said stent longitudinal axis and said second layer portion extends along at least 85% of said stent length. In some embodiments, the stent has a stent length along said stent longitudinal axis and said second layer portion extends along at least 90% of said stent length. In some embodiments, the stent has a stent length along said stent longitudinal axis and said second layer portion extends along at least 99% of said stent length.

In some embodiments, the laminate coating has a total thickness and said second polymer layer portion has a thickness of from about 0.01% to about 10% of the total thickness of said laminate coating. In some embodiments, the laminate coating has a total thickness and said horizontal second polymer layer portion has a thickness of from about 1% to about 5% of the total thickness of said laminate coating. In some embodiments, the laminate coating has a total thickness of from about 5 µm to about 50 µm and said horizontal second polymer layer portion has a thickness of from about 0.001 µm to about 5 µm. In some embodiments, the laminate coating has a total thickness of from about 10 µm to about 20 µm and said second polymer layer portion has a thickness of from about 0.01 µm to about 5 µm.

In some embodiments, the laminate coating is at least 25% by volume pharmaceutical agent. In some embodiments, the laminate coating is at least 35% by volume pharmaceutical agent. In some embodiments, the laminate coating is about 50% by volume pharmaceutical agent.

In some embodiments, at least a portion of the pharmaceutical agent is present in a phase separate from one or more phases formed by said polymer.

In some embodiments, the pharmaceutical agent is at least 50% crystalline. In some embodiments, the pharmaceutical agent is at least 75% crystalline. In some embodiments, the pharmaceutical agent is at least 90% crystalline. In some embodiments, the pharmaceutical agent is at least 95% crystalline. In some embodiments, the pharmaceutical agent is at least 99% crystalline.

In some embodiments, the stent has a stent longitudinal length and the coating has a coating outer surface along said stent longitudinal length, wherein said coating comprises pharmaceutical agent in crystalline form present in the coating below said coating outer surface. In some embodiments, the stent has a stent longitudinal length and the coating has a coating outer surface along said stent longitudinal length, wherein said coating comprises pharmaceutical agent in crystalline form present in the coating up to at least 1 µm below said coating outer surface. In some embodiments, the stent has a stent longitudinal length and the coating has a coating outer surface along said stent longitudinal length, wherein said coating comprises pharmaceutical agent in crystalline form present in the coating up to at least 5 µm below said coating outer surface.

In some embodiments, the coating exhibits an X-ray spectrum showing the presence of said pharmaceutical agent in crystalline form. In some embodiments, the coating exhibits a Raman spectrum showing the presence of said pharmaceutical agent in crystalline form. In some embodiments, the coating exhibits a Differential Scanning Calorimetry (DSC) curve showing the presence of said pharmaceutical agent in crystalline form. The device of claims 36-38, wherein said coating exhibits Wide Angle X-ray Scattering (WAXS) spectrum showing the presence of said pharmaceutical agent in crystalline form. In some embodiments, the coating exhibits a wide angle radiation scattering spectrum showing the presence of said pharmaceutical agent in crystalline form. In some embodiments, the coating exhibits an Infra Red (IR) spectrum showing the presence of said pharmaceutical agent in crystalline form.

In some embodiments, the stent has a stent longitudinal axis and a stent length along said stent longitudinal axis, wherein said coating is conformal to the stent along substantially said stent length.

In some embodiments, the stent has a stent longitudinal axis and a stent length along said stent longitudinal axis, wherein said coating is conformal to the stent along at least 75% of said stent length. In some embodiments, the stent has a stent longitudinal axis and a stent length along said stent longitudinal axis, wherein said coating is conformal to the stent along at least 85% of said stent length. In some embodiments, the stent has a stent longitudinal axis and a stent length along said stent longitudinal axis, wherein said coating is conformal to the stent along at least 90% of said stent length. In some embodiments, the stent has a stent longitudinal axis and a stent length along said stent longitudinal axis, wherein said coating is conformal to the stent along at least 95% of said stent length. In some embodiments, the stent has a stent longitudinal axis and a stent length along said stent longitudinal axis, wherein said coating is conformal to the stent along at least 99% of said stent length.

In some embodiments, the stent has a stent longitudinal axis and a plurality of struts along said stent longitudinal axis, wherein said coating is conformal to at least 50% of said struts. In some embodiments, the stent has a stent longitudinal axis and a plurality of struts along said stent longitudinal axis, wherein said coating is conformal to at least 75% of said struts. In some embodiments, the stent has a stent longitudinal axis and a plurality of struts along said stent longitudinal axis, wherein said coating is conformal to at least 90% of said struts. In some embodiments, the stent has a stent longitudinal axis and a plurality of struts along said stent longitudinal axis, wherein said coating is conformal to at least 99% of said struts. In some embodiments, the stent has a stent longitudinal axis and a stent length along said stent longitudinal axis, wherein an electron microscopy examination of the device shows said coating is conformal to said stent along at least 90% of said stent length.

In some embodiments, the stent has a stent longitudinal axis and a stent length along said stent longitudinal axis, wherein said coating has a substantially uniform thickness along substantially said stent length.

In some embodiments, the stent has a stent longitudinal axis and a stent length along said stent longitudinal axis, wherein said coating has a substantially uniform thickness along at least 75% of said stent length. In some embodiments, the stent has a stent longitudinal axis and a stent length along said stent longitudinal axis, wherein said coating has a substantially uniform thickness along at least 95% of said stent length.

In some embodiments, the stent has a stent longitudinal axis and a stent length along said stent longitudinal axis, wherein said coating has an average thickness determined by an average calculated from coating thickness values measured at a plurality of points along said stent longitudinal axis; wherein a thickness of the coating measured at any point along stent longitudinal axis is from about 75% to about 125% of said average thickness. In some embodiments, the stent has a stent longitudinal axis and a stent length along said stent longitudinal axis, wherein said coating has an average thickness determined by an average calculated from coating thickness values measured at a plurality of points along said stent longitudinal axis; wherein a thickness of the coating measured at any point along stent longitudinal axis is from about 95% to about 105% of said average thickness.

Provided herein is a device comprising: a stent; and a plurality of layers that form a laminate coating on said stent, wherein a first layer comprises a first bioabsorbable polymer, a second layer comprises a pharmaceutical agent, a third layer comprises a second bioabsorbable polymer, a fourth layer comprises the pharmaceutical agent, and a fifth layer comprises a third bioabsorbable polymer, wherein the pharmaceutical agent is selected from rapamycin, a prodrug, a derivative, an analog, a hydrate, an ester, and a salt thereof, and wherein at least a portion of the pharmaceutical agent is in crystalline form.

In some embodiments, at least two of said first bioabsorbable polymer, said second bioabsorbable polymer and said third bioabsorbable polymer are the same polymer. In some embodiments, the first bioabsorbable polymer, the second bioabsorbable polymer and the third bioabsorbable polymer are the same polymer. In some embodiments, at least two of said first bioabsorbable polymer, said second bioabsorbable polymer and said third bioabsorbable polymer are different polymers. In some embodiments, the first bioabsorbable polymer, said second bioabsorbable polymer and said third bioabsorbable polymer are different polymers.

In some embodiments, the third layer has at least one contact point with particles of said pharmaceutical agent in said second layer; and said third layer has at least one contact point with said first layer.

In some embodiments, at least two of the first polymer, the second polymer, and the third polymer are the same polymer, and wherein said same polymer comprises a PLGA copolymer. In some embodiments, the third polymer has an in vitro dissolution rate higher than the in vitro dissolution rate of the first polymer. In some embodiments, the third polymer is PLGA copolymer with a ratio of about 40:60 to about 60:40 and the first polymer is a PLGA copolymer with a ratio of about 70:30 to about 90:10. In some embodiments, the third polymer is PLGA copolymer having a molecular weight of about 10 kD and the second polymer is a PLGA copolymer having a molecular weight of about 19 kD.

In some embodiments, measuring the in vitro dissolution rate of said polymers comprises contacting the device with elution media and determining polymer weight loss at one or more selected time points. In some embodiments, measuring the in vitro dissolution rate of said polymers comprises contacting the device with elution media and determining polymer weight loss at one or more selected time points.

Provided herein is a device, comprising: a stent; and a coating on said stent comprising a first bioabsorbable polymer, a second bioabsorbable polymer; and pharmaceutical agent selected from rapamycin, a prodrug, a derivative, an analog, a hydrate, an ester, and a salt thereof wherein at least a portion of the pharmaceutical agent is in crystalline form, and wherein the first polymer has an in vitro dissolution rate higher than the in vitro dissolution rate of the second polymer.

In some embodiments, the first polymer is PLGA copolymer with a ratio of about 40:60 to about 60:40 and the second polymer is a PLGA copolymer with a ratio of about 70:30 to about 90:10. In some embodiments, the first polymer is PLGA copolymer having a molecular weight of about 10 kD and the second polymer is a PLGA copolymer having a molecular weight of about 19 kD. In some embodiments, measuring the in vitro dissolution rate of said polymers comprises contacting the device with elution media and determining polymer weight loss at one or more selected time points.

Provided herein is a device comprising a stent; and a plurality of layers that form a laminate coating on said stent; wherein at least one of said layers comprises a first bioabsorbable polymer, at least one of said layers comprises a second bioabsorbable polymer, and at least one of said layers comprises one or more active agents; wherein at least a portion of the active agent is in crystalline form, and wherein the first polymer has an in vitro dissolution rate higher than the in vitro dissolution rate of the second polymer.

Provided herein is a device comprising a stent; and a plurality of layers that form a laminate coating on said stent; wherein at least one of said layers comprises a first bioabsorbable polymer, at least one of said layers comprises a second bioabsorbable polymer, and at least one of said layers comprises a pharmaceutical agent selected from rapamycin, a prodrug, a derivative, an analog, a hydrate, an ester, and a salt thereof, wherein at least a portion of the pharmaceutical agent is in crystalline form and wherein the first polymer has an in vitro dissolution rate higher than the in vitro dissolution rate of the second polymer.

In some embodiments, the first polymer is PLGA copolymer with a ratio of about 40:60 to about 60:40 and the second polymer is a PLGA copolymer with a ratio of about 70:30 to about 90:10. In some embodiments, the first polymer is PLGA copolymer having a molecular weight of about 10 kD and the second polymer is a PLGA copolymer having a molecular weight of about 19 kD. In some embodiments, measuring the in vitro dissolution rate comprises contacting the device with elution media and determining polymer weight loss at one or more selected time points.

Provided herein is a device comprising a stent; and a plurality of layers that form a laminate coating on said stent; wherein at least one of said layers comprises a bioabsorbable polymer, at least one of said layers comprises a first active agent and at least one of said layers comprises a second active agent; wherein at least a portion of first and/or second active agents is in crystalline form.

In some embodiments, the bioabsorbable polymer is selected from the group PLGA, PGA poly(glycolide), LPLA poly(1-lactide), DLPLA poly(dl-lactide), PCL poly(ε-caprolactone) PDO, poly(dioxolane) PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid). In some embodiments, the polymer comprises an intimate mixture of two or more polymers.

In some embodiments, the first and second active agents are independently selected from pharmaceutical agents and active biological agents.

In some embodiments, the stent is formed of stainless steel material. In some embodiments, the stent is formed of a material comprising a cobalt chromium alloy. In some embodiments, the stent is formed from a material comprising the following percentages by weight: about 0.05 to about 0.15 C, about 1.00 to about 2.00 Mn, about 0.04 Si, about 0.03 P, about 0.3 S, about 19.0 to about 21.0 Cr, about 9.0 to about 11.0 Ni, about 14.0 to about 16.00 W, about 3.0 Fe, and Bal. Co. In some embodiments, the stent is formed from a material comprising at most the following percentages by weight: about 0.025 C, about 0.15 Mn, about 0.15 Si, about 0.015 P, about 0.01 S, about 19.0 to about 21.0 Cr, about 33 to about 37 Ni, about 9.0 to about 10.5 Mo, about 1.0 Fe, about 1.0 Ti, and Bal. Co. In some embodiments, the stent is formed from a material comprising L605 alloy.

In some embodiments, the stent has a thickness of from about 50% to about 90% of a total thickness of said device. In some embodiments, the device has a thickness of from about 20 µm to about 500 µm. In some embodiments, the device has a thickness of about 90 µm or less. In some embodiments, the laminate coating has a thickness of from about 5 µm to about 50 µm. In some embodiments, the laminate coating has a thickness of from about 10 µm to about 20 µm. In some embodiments, the stent has a thickness of from about 50 µm to about 80 µm.

Provided herein is a device comprising: a stent, wherein the stent is formed from a material comprising the following percentages by weight: 0.05-0.15 C, 1.00-2.00 Mn, 0.040 Si, 0.030 P, 0.3 S, 19.00-21.00 Cr, 9.00-11.00 Ni, 14.00-16.00 W, 3.00 Fe, and Bal. Co; and a plurality of layers that form a laminate coating on said stent, wherein a first layer comprises a first bioabsorbable polymer, a second layer comprises a pharmaceutical agent, a third layer comprises a second bioabsorbable polymer, a fourth layer comprises the pharmaceutical agent, and a fifth layer comprises a third bioabsorbable polymer, wherein the pharmaceutical agent is selected from rapamycin, a prodrug, a derivative, an analog, a hydrate, an ester, and a salt thereof, wherein at least a portion of the pharmaceutical agent is in crystalline form, and wherein at least one of said first polymer, second polymer and third polymer comprises a PLGA copolymer.

In some embodiments, the device has a pharmaceutical agent content of from about 0.5 µg/mm to about 20 µg/mm. In some embodiments, the device has a pharmaceutical agent content of from about 8 µg/mm to about 12 µg/mm. In some embodiments, the device has a pharmaceutical agent content of from about 5 µg to about 500 µg. In some embodiments, the device has a pharmaceutical agent content of from about 100 µg to about 160 µg. In some embodiments, the device has a pharmaceutical agent content of from about 100 µg to about 160 µg.

Provided herein is a method of preparing a device comprising a stent and a plurality of layers that form a laminate coating on said stent; said method comprising: (a) providing a stent; (b) forming a plurality of layers on said stent to form said laminate coating on said stent; wherein at least one of said layers comprises a bioabsorbable polymer and at least one of said layers comprises one or more active agents; wherein at least a portion of the active agent is in crystalline form.

Provided herein is a method of preparing a device comprising a stent and a plurality of layers that form a laminate coating on said stent; said method comprising: (a) providing a stent; (b) forming a plurality of layers to form said laminate coating on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof, wherein at least a portion of the pharmaceutical agent is in crystalline form.

Provided herein is a method of preparing a device comprising a stent and a plurality of layers that form a laminate coating on said stent; said method comprising: (a) providing a stent; (b) forming a plurality of layers to form said laminate coating on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof, wherein at least a portion of the pharmaceutical agent is in crystalline form, wherein said method comprises forming at least one pharmaceutical agent layer defined by a three-dimensional physical space occupied by crystal particles of said pharmaceutical agent and said three dimensional physical space is free of polymer.

Provided herein is a method of preparing a device comprising a stent and a plurality of layers that form a laminate coating on said stent; said method comprising: (a) providing a stent; (b) discharging at least one pharmaceutical agent and/or at least one active biological agent in dry powder form through a first orifice; (c) forming a supercritical or near supercritical fluid solution comprising at least one supercritical fluid solvent and at least one polymer and discharging said supercritical or near supercritical fluid solution through a second orifice under conditions sufficient to form solid particles of the polymer; (d) depositing the polymer and pharmaceutical agent and/or active biological agent particles onto said substrate, wherein an electrical potential is maintained between the substrate and the polymer and pharmaceutical agent and/or active biological agent particles, thereby forming said coating; and (e) sintering said polymer under conditions that do not substantially modify a morphology of said pharmaceutical agent and/or activity of said biological agent.

In some embodiments, step (b) comprises discharging a pharmaceutical agent selected from rapamycin, a prodrug, a derivative, an analog, a hydrate, an ester, and a salt thereof, wherein at least a portion of the pharmaceutical agent is in crystalline form. In some embodiments, step (c) comprises forming solid particles of a bioabsorbable polymer.

In some embodiments, step (e) comprises forming a polymer layer having a length along a horizontal axis of said device wherein said polymer layer has a layer portion along said length, wherein said layer portion is free of pharmaceutical agent.

In some embodiments, step (e) comprises contacting said polymer with a densified fluid. In some embodiments, step (e) comprises contacting said polymer with a densified fluid for a period of time at a temperature of from about 5° C. and 150° C. and a pressure of from about 10 psi to about 500 psi. In some embodiments, step (e) comprises contacting said polymer with a densified fluid for a period of time at a temperature of from about 25° C. and 95° C. and a pressure of from about 25 psi to about 100 psi. In some embodiments, step (e) comprises contacting said polymer with a densified fluid for a period of time at a temperature of from about 50° C. and 85° C. and a pressure of from about 35 psi to about 65 psi.

Provided herein is a method of preparing a device comprising a stent and a plurality of layers that form a laminate coating on said stent; said method comprising: (a) providing a stent; (b) forming a supercritical or near supercritical fluid solution comprising at least one supercritical fluid solvent and a first polymer, discharging said supercritical or near supercritical fluid solution under conditions sufficient to form solid particles of said first polymer, depositing said first polymer particles onto said stent, wherein an electrical potential is maintained between the stent and the first polymer, and sintering said first polymer; (c) depositing pharmaceutical agent particles in dry powder form onto said stent, wherein an electrical potential is maintained between the stent and said pharmaceutical agent particles; and (d) forming a supercritical or near supercritical fluid solution comprising at least one supercritical fluid solvent and a second polymer and discharging said supercritical or near supercritical fluid solution under conditions sufficient to form solid particles of said second polymer, wherein an electrical potential is maintained between the stent and the second polymer, and sintering said second polymer.

In some embodiments, step (c) and step (d) are repeated at least once. In some embodiments, steps (c) and step (d) are repeated 2 to 20 times.

In some embodiments, the pharmaceutical agent is selected from rapamycin, a prodrug, a derivative, an analog, a hydrate, an ester, and a salt thereof, wherein at least a portion of the pharmaceutical agent is in crystalline form. In some embodiments, the first and second polymers are bioabsorbable.

In some embodiments, step (d) comprises forming a polymer layer having a length along a horizontal axis of said device wherein said polymer layer has a layer portion along said length, wherein said layer portion is free of pharmaceutical agent.

In some embodiments, sintering said first and/or sintering said second polymer comprises contacting said first and/or second polymer with a densified fluid.

In some embodiments, the contacting step is carried out for a period of from about 1 minute to about 60 minutes. In some embodiments, the contacting step is carried out for a period of from about 10 minutes to about 30 minutes.

In some embodiments, maintaining said electrical potential between said polymer particles and or pharmaceutical agent particles and said stent comprises maintaining a voltage of from about 5 kvolts to about 100 kvolts. In some embodiments, maintaining said electrical potential between said polymer particles and or pharmaceutical agent particles and said stent comprises maintaining a voltage of from about 20 kvolts to about 30 kvolts.

Provided herein is a device prepared by a process comprising a method as described herein.

Provided herein is method of treating a subject comprising delivering a device as described herein in a body lumen of the subject.

Provided herein is a method of treating a subject comprising delivering in the body of the subject a device comprising: a stent, wherein the stent is formed from a material comprising the following percentages by weight: 0.05-0.15 C, 1.00-2.00 Mn, 0.040 Si, 0.030 P, 0.3 S, 19.00-21.00 Cr, 9.00-11.00 Ni, 14.00-16.00 W, 3.00 Fe, and Bal. Co; and a plurality of layers that form a laminate coating on said stent, wherein a first layer comprises a first bioabsorbable polymer, a second layer comprises a pharmaceutical agent, a third layer comprises a second bioabsorbable polymer, a fourth layer comprises the pharmaceutical agent, and a fifth layer comprises a third bioabsorbable polymer, wherein the pharmaceutical agent is selected from rapamycin, a prodrug, a derivative, an analog, a hydrate, an ester, and a salt thereof, wherein at least a portion of the pharmaceutical agent is in crystalline form, and wherein at least one of said first polymer, second polymer and third polymer comprises a PLGA copolymer.

In some embodiments, the device has a pharmaceutical agent content of from about 0.5 µg/mm to about 20 µg/mm. In some embodiments, the device has a pharmaceutical agent content of from about 8 µg/mm to about 12 µg/mm. In some embodiments, the device has a pharmaceutical agent content of from about 100 µg to about 160 µg. In some embodiments, the device has a pharmaceutical agent content of from about 120 µg to about 150 µg.

In some embodiments, the device has an initial pharmaceutical agent amount and the amount of pharmaceutical agent delivered by said device to vessel wall tissue of said subject is higher than the amount of pharmaceutical agent delivered by a conventional drug eluting stent having the same initial pharmaceutical agent content as the initial pharmaceutical agent content of said device. In some embodiments, the amount of pharmaceutical agent delivered by said device to vessel wall tissue of said subject is at least 25% more that the amount of pharmaceutical agent delivered to vessel wall tissue of said subject by said conventional drug eluting stent. In some embodiments, the method comprises treating restenosis in a blood vessel of said the subject. In some embodiments, the subject is selected from a pig, a rabbit and a human.

Provided herein is a device comprising: a stent; and a plurality of layers on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof, wherein said device provides an in vitro pharmaceutical agent elution profile wherein said elution profile shows about 5% to about 25% of pharmaceutical agent is eluted one day after the device is contacted with elution media; 15% to about 45% of pharmaceutical agent is eluted 7 days after the device is contacted with elution media; about 25% to about 60% of pharmaceutical agent is eluted 14 days after the device is contacted with elution media; about 35% to about 70% of pharmaceutical agent is eluted 21 days after the device is contacted with elution media; and about 40% to about 100% of pharmaceutical agent is eluted 28 days after the device is contacted with elution media.

Provided herein is a device comprising a stent; and a plurality of layers on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof, wherein said device provides an in vitro pharmaceutical agent elution profile wherein said elution profile shows about 7% to about 15% of pharmaceutical agent is eluted one day after the device is contacted with elution media; 25% to about 35% of pharmaceutical agent is eluted 7 days after the device is contacted with elution media; about 35% to about 55% of pharmaceutical agent is eluted 14 days after the device is contacted with elution media; about 45% to about 60% of pharmaceutical agent is eluted 21 days after the device is contacted with elution media; and about 50% to about 70% of pharmaceutical agent is eluted 28 days after the device is contacted with elution media.

Provided herein is a device comprising a stent; and a plurality of layers on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof, wherein said device provides an in vitro pharmaceutical agent elution profile wherein said elution profile shows at least 5% of pharmaceutical agent is eluted one day after the device is contacted with elution media; at least 15% of pharmaceutical agent is eluted 7 days after the device is contacted with elution media; at least 25% of pharmaceutical agent is eluted 14 days after the device is contacted with elution media; at least 30% of pharmaceutical agent is eluted 21 days after the device is contacted with elution media; at least 40% of pharmaceutical agent is eluted 28 days after the device is contacted with elution media.

Provided herein is a device comprising a stent; and a plurality of layers on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof, wherein said device provides an in vitro pharmaceutical agent elution profile wherein said elution profile shows about 10% of pharmaceutical agent is eluted one day after the device is contacted with elution media; about 30% of pharmaceutical agent is eluted 7 days after the device is contacted with elution media; about 45% of pharmaceutical agent is eluted 14 days after the device is contacted with elution media; about 50% of pharmaceutical agent is eluted 21 days after the device is contacted with elution media; about 60% of pharmaceutical agent is eluted 28 days after the device is contacted with elution media.

Provided herein is a device comprising a stent; and a plurality of layers on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof, wherein said device provides an in vitro pharmaceutical agent elution profile wherein said elution profile shows about 10% to about 75% of pharmaceutical agent is eluted at week 1 after the device is contacted with elution media, about 25% to about 85% of pharmaceutical agent is eluted at week 2 and about 50% to about 100% of pharmaceutical agent is eluted at week 10.

Provided herein is a device comprising: a stent; and a plurality of layers on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof, wherein said device provides an in vitro pharmaceutical agent elution profile shown in FIG. 5.

In some embodiments, the in vitro pharmaceutical agent elution profile is determined by a procedure comprising: (i) contacting the device with an elution media comprising 5% ethanol by volume wherein the pH of the media is about 7.4 and wherein the device is contacted with the elution media at a temperature of about 37° C.; (ii) optionally agitating the elution media during the contacting step in (i); (iii) removing the elution media at designated time points; and (iv) assaying the removed elution media to determine pharmaceutical agent content.

In some embodiments, the in vitro pharmaceutical agent elution profile is determined by a procedure comprising: (i) contacting the device with an elution media comprising 5% ethanol by volume, wherein the pH of the media is about 7.4 and wherein the device is contacted with the elution media at a temperature of about 37° C.; (ii) optionally agitating the elution media during the contacting step in (i); (iii) removing said device from the elution media at designated time points; and (iv) assaying the elution media to determine pharmaceutical agent content.

In some embodiments, the in vitro pharmaceutical agent elution profile is determined in the absence of agitation.

In some embodiments, the procedure further comprises: (v) determining polymer weight loss by comparing the weight of the device before and after the contacting step and adjusting for the amount of pharmaceutical agent eluted into the elution media as determined in step (iv). In some embodiments, step (v) shows at least 50% of polymer is released into the media after the device is contacted with the media for 90 days or more. In some embodiments, step (v) shows at least 75% of polymer is released into the media after the device is contacted with the media for 90 days or more.

In some embodiments, step (v) shows at least 85% of polymer is released into the media after the device is contacted with the media for 90 days or more. In some embodiments, step (v) shows at least 50% of polymer is released into the media after the device is contacted with the media for about 90 days. In some embodiments, step (v) shows at least 75% of polymer is released into the media after the device is contacted with the media for about 90 days. In some embodiments, step (v) shows at least 85% of polymer is released into the media after the device is contacted with the media for about 90 days. In some embodiments, step (v) shows at least 95% of polymer is released into the media after the device is contacted with the media for about 90 days. In some embodiments, step (v) shows up to 100% of polymer is released into the media after the device is contacted with the media for about 90 days.

Provided herein is a device comprising: a stent; and a plurality of layers on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof, wherein said device provides an in vitro pharmaceutical agent elution profile wherein said elution profile shows about 1% to about 35% of pharmaceutical agent is eluted one hour after the device is contacted with elution media; 5% to about 45% of pharmaceutical agent is eluted 3 hours after the device is contacted with elution media; about 30% to about 70% of pharmaceutical agent is eluted 1 day after the device is contacted with elution media; about 40% to about 80% of pharmaceutical agent is eluted 3 days after the device is contacted with elution media; about 50% to about 90% of pharmaceutical agent is eluted 10 days after the device is contacted with elution media about 55% to about 95% of pharmaceutical agent is eluted 15 days after the device is contacted with elution media; and about 60% to about 100% of pharmaceutical agent is eluted 20 days after the device is contacted with elution media.

Provided herein is a device comprising: a stent; and a plurality of layers on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof, wherein said device provides an in vitro pharmaceutical agent elution profile wherein said elution profile shows about 5% to about 25% of pharmaceutical agent is eluted one hour after the device is contacted with elution media; 5% to about 35% of pharmaceutical agent is eluted 3 hours after the device is contacted with elution media; about 30% to about 65% of pharmaceutical agent is eluted 1 day after the device is contacted with elution media; about 45% to about 70% of pharmaceutical agent is eluted 3 days after the device is contacted with elution media; about 55% to about 85% of pharmaceutical agent is eluted 10 days after the device is contacted with elution media about 65% to about 85% of pharmaceutical agent is eluted 15 days after the device is contacted with elution media; and about 75% to about 100% of pharmaceutical agent is eluted 20 days after the device is contacted with elution media.

Provided herein is a device comprising: a stent; and a plurality of layers on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof, wherein said device provides an in vitro pharmaceutical agent elution profile shown in FIG. 9.

In some embodiments, the in vitro pharmaceutical agent elution profile is determined by a procedure comprising: (i) contacting the device with an elution media comprising ethanol and phosphate buffered saline wherein the pH of the media is about 7.4 and wherein the device is contacted with the elution media at a temperature of about 37° C.; (ii) optionally agitating the elution media during the contacting step in (i); (iii) removing the elution media at designated time points; and (iv) assaying the removed elution media to determine pharmaceutical agent content.

In some embodiments, the in vitro pharmaceutical agent elution profile is determined by a procedure comprising: (i) contacting the device with an elution media comprising ethanol and phosphate buffered saline wherein the pH of the media is about 7.4 and wherein the device is contacted with the elution media at a temperature of about 37° C.; (ii) optionally agitating the elution media during the contacting step in (i); (iii) removing said device from the elution media at designated time points; and (iv) assaying the elution media to determine pharmaceutical agent content.

In some embodiments, the in vitro pharmaceutical agent elution profile is determined in the absence of agitation.

In some embodiments, the procedure further comprises: (v) determining polymer weight loss by comparing the weight of the device before and after the contacting step and adjusting for the amount of pharmaceutical agent eluted into the elution media as determined in step iv. The device of claim 160 wherein step v shows at least 50% of polymer is released into the media after the device is contacted with the media for 90 days or more.

In some embodiments, step (v) shows at least 75% of polymer is released into the media after the device is contacted with the media for 90 days or more. In some embodiments, step (v) shows at least 85% of polymer is released into the media after the device is contacted with the media for 90 days or more. In some embodiments, step (v) shows at least 50% of polymer is released into the media after the device is contacted with the media for about 90 days. In some embodiments, step (v) shows at least 75% of polymer is released into the media after the device is contacted with the media for about 90 days. In some embodiments, step (v) shows at least 85% of polymer is released into the media after the device is contacted with the media for about 90 days. In some embodiments, step (v) shows at least 95% of polymer is released into the media after the device is contacted with the media for about 90 days.

Provided herein is a device comprising: a stent; and a coating comprising a pharmaceutical agent selected from rapamycin, a prodrug, a derivative, ester and a salt thereof and a polymer wherein the coating has an initial pharmaceutical agent amount; wherein when said device is delivered in a body lumen of a subject the pharmaceutical agent is delivered in vessel wall tissue of the subject as follows: from about 0.1% to about 35% of the initial pharmaceutical agent amount is delivered in the subject's vessel wall tissue one week after the device is delivered in the subject's body; and from about 0.5% to about 50% of the initial pharmaceutical agent amount is delivered in the subject's vessel wall tissue two weeks after the device is delivered in the subject's body.

In some embodiments, the amount delivered to the subject's lumen is obtained by adding pharmaceutical agent present alone in said subject's vessel wall tissue and pharmaceutical agent delivered together with said polymer. In some embodiments, the subject is a human.

In some embodiments, subject is a pig and the amount of pharmaceutical agent delivered in the subject's vessel wall tissue is determined as follows: delivering the device in the pig's blood vessel lumen; euthanizing the pig at predetermined period of time after the device is delivered in the pig's blood vessel lumen and explanting the device; measuring the amount of pharmaceutical agent delivered in the vessel wall tissue.

Provided herein, a device comprising: a stent; and a coating comprising a pharmaceutical agent selected from rapamycin, a prodrug, a derivative, an analog, a hydrate, an ester, and a salt thereof and a bioabsorbable polymer wherein the coating has an initial pharmaceutical agent content of about 1 µg/mm to about 15 µg/mm; wherein said device provides an area under a curve (AUC) for content of pharmaceutical agent delivered in the vessel wall tissue of a subject over time as follows: from about 0.05 (µg/mm)*day to about 1 (µg/mm)*day when AUC is calculated from the time the device is delivered in a subject's body to one day after the device is delivered in the subject's body; from about 5 (µg/mm)*day to about 10 (µg/mm)*day when AUC is calculated starting after the first week the device is delivered in the subject's body through the second week after the device is delivered in the subject's body; from about 10 (µg/mm)*day to about 20 (µg/mm)*day when AUC is calculated starting after the second week the device is delivered in the subject's body through the fourth week after the device is delivered in the subject's body; and an AUC last of from about 40 (µg/mm)*day to about 60 (µg/mm)*day.

Provided herein is a device comprising: a stent; and a coating comprising a pharmaceutical agent selected from rapamycin, a prodrug, a derivative, an analog, a hydrate, an ester, and a salt thereof and a bioabsorbable polymer wherein the coating has an initial polymer amount; wherein when said device is delivered in a body lumen of a subject about 75% of polymer is released from the device 90 days or more after the device is delivered in the body lumen of the subject.

Provided herein is a device comprising: a stent; and a coating comprising a pharmaceutical agent selected from rapamycin, a prodrug, a derivative, an analog, a hydrate, an ester, and a salt thereof and a bioabsorbable polymer wherein the coating has an initial polymer amount; wherein when said device is delivered in a body lumen of a subject about 85% of polymer is released from the device about 90 days after the device is delivered in the body lumen of the subject.

Provided herein is a device comprising: a stent; and a coating comprising a pharmaceutical agent selected from rapamycin, a prodrug, a derivative, an analog, a hydrate, an ester, and a salt thereof and a bioabsorbable polymer wherein the coating has an initial polymer amount; wherein when said device is delivered in a body lumen of a subject at least about 75% of polymer is released from the device about 90 days after the device is delivered in the body lumen of the subject.

Provided herein is a device comprising: a stent; and a coating comprising a pharmaceutical agent selected from rapamycin, a prodrug, a derivative, an analog, a hydrate, an ester, and a salt thereof and a bioabsorbable polymer wherein the coating has an initial polymer amount; wherein when said device is delivered in a body lumen of a subject about 100% of polymer is released from the device about 90 days after the device is delivered in the body lumen of the subject.

In some embodiments, the subject is a human. In some embodiments, the subject is a pig and the amount of polymer released from the device is determined as follows: delivering the device in the pig's blood vessel lumen; euthanizing the pig at predetermined period of time after the device is delivered in the pig's blood vessel lumen and explanting the device; and measuring the amount of polymer released from the device.

In some embodiments, measuring the amount of polymer released from the device comprises LC/MS/MS measurements. In some embodiments, measuring the amount released from the device comprises weight loss measurement. In some embodiments, weight loss measurement comprises measuring an amount of polymer remaining in the device and subtracting said remaining amount from the initial amount present in the device prior to delivering the device to the pig's blood vessel lumen.

Provided herein is a device comprising a stent; and a plurality of layers on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof, wherein the device has an initial pharmaceutical agent content of about 1 µg/mm to about 15 µg/mm; wherein when said device is delivered in a body lumen of a subject said device provides a blood concentration within 60 minutes from delivery of said device to the subject's body lumen that is from about 1% to about 50% of the blood concentration provided by a conventional drug eluting stent delivered to the subject under similar conditions.

Provided herein is a device comprising a stent; and a plurality of layers on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof, wherein the device has an initial pharmaceutical agent content of about 1 µg/mm to about 15 µg/mm; wherein when said device is delivered in a body lumen of a subject said device provides a blood concentration within 60 minutes from delivery of said device to the subject's body lumen that is from about 11% to about 20% of the blood concentration provided by a conventional drug eluting stent delivered to the subject under similar conditions.

Provided herein is a device comprising a stent; and coating on said stent; wherein said coating comprises a bioabsorbable polymer and a pharmaceutical agent selected from rapamycin, a prodrug, a derivative, an analog, a hydrate, an ester, and a salt thereof, wherein the device has an initial pharmaceutical agent content of about 1 µg/mm to about 15 µg/mm; wherein when said device is delivered in a body lumen of a subject said device provides about the same blood concentration over the first 72 hours from delivery of said device to the subject's body lumen.

In some embodiments, the blood concentration during the first 72 hours from delivery of said device to the subject's body lumen remains between 75% and 125% of an average blood concentration calculated over the first 72 hours from delivery of said device to the subject's body lumen. In some embodiments, the average blood concentration is from about 0.05 ng/mL to about 0.5 ng/mL. In some embodiments, the device provides an AUC for blood concentration over a period of 72 hours after the device is delivered to the subject's body lumen of from about 2 (ng/mL)*hour to about 20 (ng/mL)*hour.

In some embodiments, the device provides an AUC for blood concentration over a period of 72 hours after the device is delivered to the subject's body lumen of from about 4 (ng/mL)*hour to about 10 (ng/mL)*hour. In some embodiments, at least part of pharmaceutical agent is in crystalline form. In some embodiments, the pharmaceutical agent is provided at a reduced dose compared to a conventional drug eluting stent. In some embodiments, at least one of said layers comprises a PLGA bioabsorbable polymer.

In some embodiments, the pharmaceutical agent in said device has a shelf stability of at least 12 months.

In some embodiments, the device provides an in vitro pharmaceutical agent elution profile comparable to first order kinetics.

In some embodiments, the device provides pharmaceutical agent tissue concentration of at least twice the tissue concentration provided by a conventional stent. In some embodiments, the device provides a pharmaceutical agent tissue concentration of at least 5 times greater than the tissue concentration provided by a conventional stent. In some embodiments, the device provides a pharmaceutical agent tissue concentration of at least 25 times greater than the tissue concentration provided by a conventional stent. In some embodiments, the device provides a pharmaceutical agent tissue concentration of at least 100 times greater than the tissue concentration provided by a conventional stent.

In some embodiments, about 50% of said polymer is resorbed within 45-90 days after an angioplasty procedure wherein said device is delivered in a subject's body. In some embodiments, about 75% of said polymer is resorbed within 45-90 days after an angioplasty procedure wherein said device is delivered in a subject's body. In some embodiments, about 95% of said polymer is resorbed within 45-90 days after an angioplasty procedure wherein said device is delivered in a subject's body.

In some embodiments, 99% of said polymer is resorbed within 45-90 days after an angioplasty procedure wherein said device is delivered in a subject's body.

In some embodiments, the device provides reduced inflammation over the course of polymer resorbtion compared to a conventional stent.

Provided herein is a method of treating a subject comprising delivering a device as described herein in a body lumen.

Provided herein, is a method of treating a subject comprising delivering in the body of the subject a device comprising: a stent; and a coating comprising a pharmaceutical agent selected from rapamycin, a prodrug, a derivative, an analog, a hydrate, an ester, and a salt thereof and a polymer wherein the coating has an initial pharmaceutical agent amount; wherein said device is delivered in a body lumen of the subject and the pharmaceutical agent is delivered in vessel wall tissue of the subject as follows: i. from about 0.05% to about 35% of the initial pharmaceutical agent amount is delivered in the subject's vessel wall tissue one week after the device is delivered in the subject's body; and ii. from about 0.5% to about 50% of the initial pharmaceutical agent amount is delivered in the subject's vessel wall tissue two weeks after the device is delivered in the subject's body.

In some embodiments, the device provides reduced inflammation over the course of polymer resorbtion.

In some embodiments, the presence of crystallinity is shown by at least one of XRD, Raman Spectroscopy, Infrared analytical methods, and DSC.

In some embodiments, the coating on an abluminal surface of said stent has a greater thickness than coating on a luminal surface of said stent. In some embodiments, the ratio of coating on the abluminal surface to coating on the luminal surface of the device is 80:20. In some embodiments, the ratio of coating on the abluminal surface to coating on the luminal surface of the device is 75:25. In some embodiments, the ratio of coating on the abluminal surface to coating on the luminal surface of the device is 70:30. In some embodiments, the ratio of coating on the abluminal surface to coating on the luminal surface of the device is 60:40.

In some embodiments, the stent is a coronary stent, a vascular stent, a peripheral stent, billiarty stent, and intercranial stent.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6 depicts AS1 and AS2 as having statistically different elution profiles; AS2 and AS2b have stastically different profiles; AS1 and AS1b are not statistically different; and AS2 and AS1(213) begin to converge at 35 days. FIG. 6 suggests that the coating thickness does not affect elution rates form 3095 polymer, but does affect elution rates from the 213 polymer.

FIG. 7 depicts that agitation in elution media increases the rate of elution for AS2 stents, but is not statistically significantly different for AS1 stents. The profiles are based on two stent samples.

FIG. 8 depicts that agitating the stent in elution media increases the elution rate in phosphate buffered saline, but the error is much greater.

DETAILED DESCRIPTION

Figure 1:
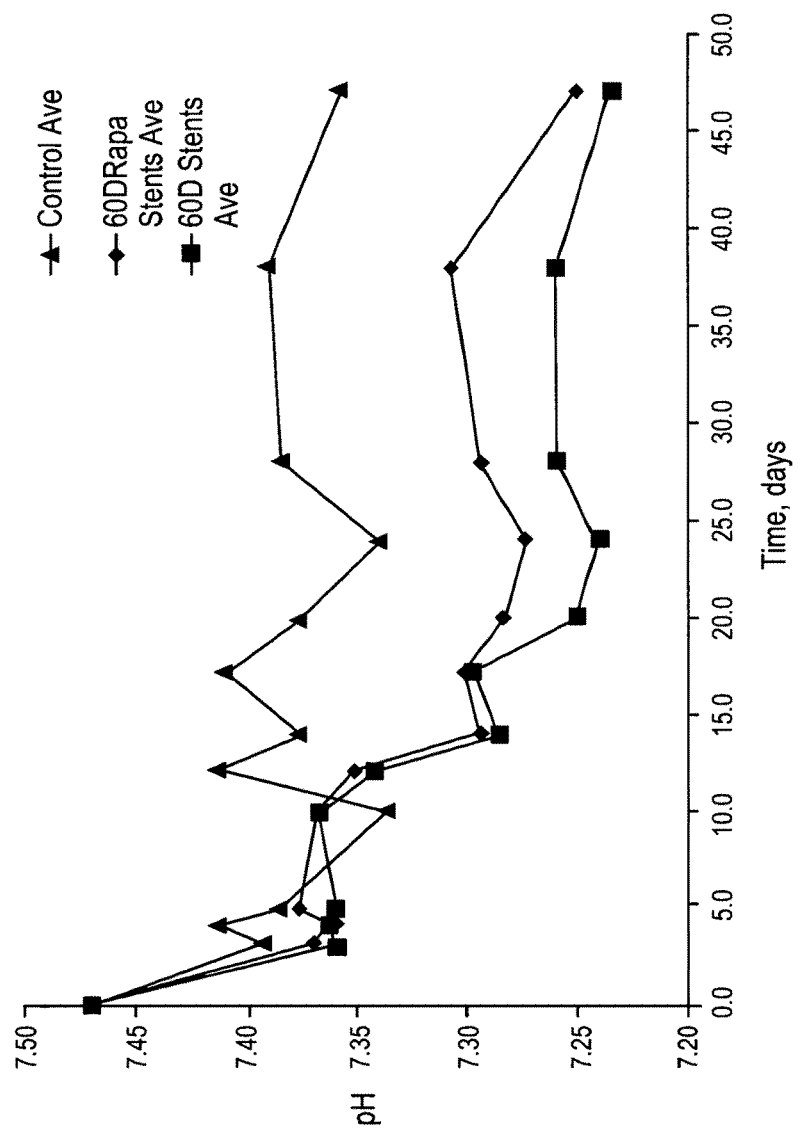
FIG. 1: Bioabsorbability testing of 50:50 PLGA-ester end group (MW ~19 kD) polymer coating formulations on stents by determination of pH Changes with Polymer Film Degradation in 20% Ethanol/Phosphate Buffered Saline as set forth in Example 3 described herein.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments contemplated herein will be apparent to those skilled in the art in light of the instant disclosure, which do not depart from the instant invention. Hence, the following specification is intended to illustrate selected embodiments of the invention, and not to exhaustively specify all permutations, combinations and variations thereof.

Definitions

As used in the present specification, the following words and phrases are generally intended to have the meanings as set forth below, except to the extent that the context in which they are used indicates otherwise.

"Substrate" as used herein, refers to any surface upon which it is desirable to deposit a coating comprising a polymer and a pharmaceutical or biological agent, wherein the coating process does not substantially modify the morphology of the pharmaceutical agent or the activity of the biological agent. Biomedical implants are of particular interest for the present invention; however the present invention is not intended to be restricted to this class of substrates. Those of skill in the art will appreciate alternate substrates that could benefit from the coating process described herein, such as pharmaceutical tablet cores, as part of an assay apparatus or as components in a diagnostic kit (e.g. a test strip).

"Biomedical implant" as used herein refers to any implant for insertion into the body of a human or animal subject, including but not limited to stents (e.g., coronary stents, vascular stents including peripheral stents and graft stents, urinary tract stents, urethral/prostatic stents, rectal stent, oesophageal stent, biliary stent, pancreatic stent), electrodes, catheters, leads, implantable pacemaker, cardioverter or defibrillator housings, joints, screws, rods, ophthalmic implants, femoral pins, bone plates, grafts, anastomotic devices, perivascular wraps, sutures, staples, shunts for hydrocephalus, dialysis grafts, colostomy bag attachment devices, ear drainage tubes, leads for pace makers and implantable cardioverters and defibrillators, vertebral disks, bone pins, suture anchors, hemostatic barriers, clamps, screws, plates, clips, vascular implants, tissue adhesives and sealants, tissue scaffolds, various types of dressings (e.g., wound dressings), bone substitutes, intraluminal devices, vascular supports, etc.

The implants may be formed from any suitable material, including but not limited to polymers (including stable or inert polymers, organic polymers, organic-inorganic copolymers, inorganic polymers, and biodegradable polymers), metals, metal alloys, inorganic materials such as silicon, and composites thereof, including layered structures with a core of one material and one or more coatings of a different material. Substrates made of a conducting material facilitate electrostatic capture. However, the invention contemplates the use of electrostatic capture, as described below, in conjunction with substrate having low conductivity or which are non-conductive. To enhance electrostatic capture when a non-conductive substrate is employed, the substrate is processed for example while maintaining a strong electrical field in the vicinity of the substrate.

Subjects into which biomedical implants of the invention may be applied or inserted include both human subjects (including male and female subjects and infant, juvenile, adolescent, adult and geriatric subjects) as well as animal subjects (including but not limited to pig, rabbit, mouse, dog, cat, horse, monkey, etc.) for veterinary purposes and/or medical research.

In a preferred embodiment the biomedical implant is an expandable intraluminal vascular graft or stent (e.g., comprising a wire mesh tube) that can be expanded within a blood vessel by an angioplasty balloon associated with a catheter to dilate and expand the lumen of a blood vessel, such as described in U.S. Pat. No. 4,733,665 to Palmaz.

"Pharmaceutical agent" as used herein refers to any of a variety of drugs or pharmaceutical compounds that can be used as active agents to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). It is possible that the pharmaceutical agents of the invention may also comprise two or more drugs or pharmaceutical compounds. Pharmaceutical agents, include but are not limited to antirestenotic agents, antidiabetics, analgesics, antiinflammatory agents, antirheumatics, antihypotensive agents, antihypertensive agents, psychoactive drugs, tranquillizers, antiemetics, muscle relaxants, glucocorticoids, agents for treating ulcerative colitis or Crohn's disease, antiallergics, antibiotics, antiepileptics, anticoagulants, antimycotics, antitussives, arteriosclerosis remedies, diuretics, proteins, peptides, enzymes, enzyme inhibitors, gout remedies, hormones and inhibitors thereof, cardiac glycosides, immunotherapeutic agents and cytokines, laxatives, lipid-lowering agents, migraine remedies, mineral products, otologicals, anti parkinson agents, thyroid therapeutic agents, spasmolytics, platelet aggregation inhibitors, vitamins, cytostatics and metastasis inhibitors, phytopharmaceuticals, chemotherapeutic agents and amino acids. Examples of suitable active ingredients are acarbose, antigens, beta-receptor blockers, non-steroidal antiinflammatory drugs [NSAIDs], cardiac glycosides, acetylsalicylic acid, virustatics, aclarubicin, acyclovir, cisplatin, actinomycin, alpha- and beta-sympatomimetics, (dmeprazole, allopurinol, alprostadil, prostaglandins, amantadine, ambroxol, amlodipine, methotrexate, S-aminosalicylic acid, amitriptyline, amoxicillin, anastrozole, atenolol, azathioprine, balsalazide, beclomethasone, betahistine, bezafibrate, bicalutamide, diazepam and diazepam derivatives, budesonide, bufexamac, buprenorphine, methadone, calcium salts, potassium salts, magnesium salts, candesartan, carbamazepine, captopril, cefalosporins, cetirizine, chenodeoxycholic acid, ursodeoxycholic acid, theophylline and theophylline derivatives, trypsins, cimetidine, clarithromycin, clavulanic acid, clindamycin, clobutinol, clonidine, cotrimoxazole, codeine, caffeine, vitamin D and derivatives of vitamin D, colestyramine, cromoglicic acid, coumarin and coumarin derivatives, cysteine, cytarabine, cyclophosphamide, ciclosporin, cyproterone, cytabarine, dapiprazole, desogestrel, desonide, dihydralazine, diltiazem, ergot alkaloids, dimenhydrinate, dimethyl sulphoxide, dimeticone, domperidone and domperidan derivatives, dopamine, doxazosin, doxorubizin, doxylamine, dapiprazole, benzodiazepines, diclofenac, glycoside antibiotics, desipramine, econazole, ACE inhibitors, enalapril, ephedrine, epinephrine, epoetin and epoetin derivatives, morphinans, calcium antagonists, irinotecan, modafinil, orlistat, peptide antibiotics, phenyloin, riluzoles, risedronate, sildenafil, topiramate, macrolide antibiotics, oestrogen and oestrogen derivatives, progestogen and progestogen derivatives, testosterone and testosterone derivatives, androgen and androgen derivatives, ethenzamide, etofenamate, etofibrate, fenofibrate, etofylline, etoposide, famciclovir, famotidine, felodipine, fenofibrate, fentanyl, fenticonazole, gyrase inhibitors, fluconazole, fludarabine, fluarizine, fluorouracil, fluoxetine, flurbiprofen, ibuprofen, flutamide, fluvastatin, follitropin, formoterol, fosfomicin, furosemide, fusidic acid, gallopamil, ganciclovir, gemfibrozil, gentamicin, ginkgo, Saint John's wort, glibenclamide, urea derivatives as oral antidiabetics, glucagon, glucosamine and glucosamine derivatives, glutathione, glycerol and glycerol derivatives, hypothalamus hormones, goserelin, gyrase inhibitors, guanethidine, halofantrine, haloperidol, heparin and heparin derivatives, hyaluronic acid, hydralazine, hydrochlorothiazide and hydrochlorothiazide derivatives, salicylates, hydroxyzine, idarubicin, ifosfamide, imipramine, indometacin, indoramine, insulin, interferons, iodine and iodine derivatives, isoconazole, isoprenaline, glucitol and glucitol derivatives, itraconazole, ketoconazole, ketoprofen, ketotifen, lacidipine, lansoprazole, levodopa, levomethadone, thyroid hormones, lipoic acid and lipoic acid derivatives, lisinopril, lisuride, lofepramine, lomustine, loperamide, loratadine, maprotiline, mebendazole, mebeverine, meclozine, mefenamic acid, mefloquine, meloxicam, mepindolol, meprobamate, meropenem, mesalazine, mesuximide, metamizole, metformin, methotrexate, methylphenidate, methylprednisolone, metixene, metoclopramide, metoprolol, metronidazole, mianserin, miconazole, minocycline, minoxidil, misoprostol, mitomycin, mizolastine, moexipril, morphine and morphine derivatives, evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline and adrenaline derivatives, norfloxacin, novamine sulfone, noscapine, nystatin, ofloxacin, olanzapine, olsalazine, omeprazole, omoconazole, ondansetron, oxaceprol, oxacillin, oxiconazole, oxymetazoline, pantoprazole, paracetamol, paroxetine, penciclovir, oral penicillins, pentazocine, pentifylline, pentoxifylline, perphenazine, pethidine, plant extracts, phenazone, pheniramine, barbituric acid derivatives, phenylbutazone, phenyloin, pimozide, pindolol, piperazine, piracetam, pirenzepine, piribedil, piroxicam, pramipexole, pravastatin, prazosin, procaine, promazine, propiverine, propranolol, propyphenazone, prostaglandins, protionamide, proxyphylline, quetiapine, quinapril, quinaprilat, ramipril, ranitidine, reproterol, reserpine, ribavirin, rifampicin, risperidone, ritonavir, ropinirole, roxatidine, roxithromycin, ruscogenin, rutoside and rutoside derivatives, sabadilla, salbutamol, salmeterol, scopolamine, selegiline, sertaconazole, sertindole, sertralion, silicates, sildenafil, simvastatin, sitosterol, sotalol, spaglumic acid, sparfloxacin, spectinomycin, spiramycin, spirapril, spironolactone, stavudine, streptomycin, sucralfate, sufentanil, sulbactam, sulphonamides, sulfasalazine, sulpiride, sultamicillin, sultiam, sumatriptan, suxamethonium chloride, tacrine, tacrolimus, taliolol, tamoxifen, taurolidine, tazarotene, temazepam, teniposide, tenoxicam, terazosin, terbinafine, terbutaline, terfenadine, terlipressin, tertatolol, tetracyclins, teryzoline, theobromine, theophylline, butizine, thiamazole, phenothiazines, thiotepa, tiagabine, tiapride, propionic acid derivatives, ticlopidine, timolol, timidazole, tioconazole, tioguanine, tioxolone, tiropramide, tizanidine, tolazoline, tolbutamide, tolcapone, tolnaftate, tolperisone, topotecan, torasemide, antioestrogens, tramadol, tramazoline, trandolapril, tranylcypromine, trapidil, trazodone, triamcinolone and triamcinolone derivatives, triamterene, trifluperidol, trifluridine, trimethoprim, trimipramine, tripelennamine, triprolidine, trifosfamide, tromantadine, trometamol, tropalpin, troxerutine, tulobuterol, tyramine, tyrothricin, urapidil, ursodeoxycholic acid, chenodeoxycholic acid, valaciclovir, valproic acid, vancomycin, vecuronium chloride, Viagra, venlafaxine, verapamil, vidarabine, vigabatrin, viloazine, vinblastine, vincamine, vincristine, vindesine, vinorelbine, vinpocetine, viquidil, warfarin, xantinol nicotinate, xipamide, zafirlukast, zalcitabine, zidovudine, zolmitriptan, zolpidem, zoplicone, zotipine and the like. See, e.g., U.S. Pat. No. 6,897,205; see also U.S. Pat. No. 6,838,528; U.S. Pat. No. 6,497,729.

Examples of therapeutic agents employed in conjunction with the invention include, rapamycin, 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxy)propyl-rapamycin 4O—O-(6-Hydroxy)hexyl-rapamycin 40-O-[2-(2-Hydroxy)ethoxy]ethyl-rapamycin 4O—O-[(3S)-2,2-Dimethyldioxolan-3-yl]methyl-rapamycin, 40-O-[(2S)-2,3-Dihydroxyprop-1-yl]-rapamycin, 4O—O-(2-Acetoxy)ethyl-rapamycin 4O—O-(2-Nicotinoyloxy)ethyl-rapamycin, 4O—O-[2-(N-Morpholino)acetoxy]ethyl-rapamycin 4O—O-(2-N-Imidazolylacetoxy)ethyl-rapamycin, 4O—O-[2-(N-Methyl-N'-piperazinyl)acetoxy]ethyl-rapamycin, 39-O-Desmethyl-39, 40-O,O-ethylene-rapamycin, (26R)-26-Dihydro-40-O-(2-hydroxy)ethyl-rapamycin, 28-O-Methyl-rapamycin, 4O—O-(2-Aminoethyl)-rapamycin, 4O—O-(2-Acetaminoethyl)-rapamycin 4O—O-(2-Nicotinamidoethyl)-rapamycin, 4O—O-(2-(N-Methyl-imidazo-2'-ylcarbethoxamido)ethyl)-rapamycin, 4O—O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), and 42-[3-hydroxy-2-(hydroxymethyl)-2-methylpropanoate]rapamycin (temsirolimus).

The pharmaceutical agents may, if desired, also be used in the form of their pharmaceutically acceptable salts or derivatives (meaning salts which retain the biological effectiveness and properties of the compounds of this invention and which are not biologically or otherwise undesirable), and in the case of chiral active ingredients it is possible to employ both optically active isomers and racemates or mixtures of diastereoisomers. As well, the pharmaceutical agent may include a prodrug, a hydrate, an ester, a derivative or analogs of a compound or molecule.

A "pharmaceutically acceptable salt" may be prepared for any pharmaceutical agent having a functionality capable of forming a salt, for example an acid or base functionality. Pharmaceutically acceptable salts may be derived from organic or inorganic acids and bases. The term "pharmaceutically-acceptable salts" in these instances refers to the relatively non-toxic, inorganic and organic base addition salts of the pharmaceutical agents.

"Prodrugs" are derivative compounds derivatized by the addition of a group that endows greater solubility to the compound desired to be delivered. Once in the body, the prodrug is typically acted upon by an enzyme, e.g., an esterase, amidase, or phosphatase, to generate the active compound.

"Stability" as used herein in refers to the stability of the drug in a polymer coating deposited on a substrate in its final product form (e.g., stability of the drug in a coated stent). The term stability will define 5% or less degradation of the drug in the final product form.

"Active biological agent" as used herein refers to a substance, originally produced by living organisms, that can be used to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). It is possible that the active biological agents of the invention may also comprise two or more active biological agents or an active biological agent combined with a pharmaceutical agent, a stabilizing agent or chemical or biological entity. Although the active biological agent may have been originally produced by living organisms, those of the present invention may also have been synthetically prepared, or by methods combining biological isolation and synthetic modification. By way of a non-limiting example, a nucleic acid could be isolated form from a biological source, or prepared by traditional techniques, known to those skilled in the art of nucleic acid synthesis. Furthermore, the nucleic acid may be further modified to contain non-naturally occurring moieties. Non-limiting examples of active biological agents include peptides, proteins, enzymes, glycoproteins, nucleic acids (including deoxyribonucleotide or ribonucleotide polymers in either single or double stranded form, and unless otherwise limited, encompasses known analogues of natural nucleotides that hybridize to nucleic acids in a manner similar to naturally occurring nucleotides), antisense nucleic acids, fatty acids, antimicrobials, vitamins, hormones, steroids, lipids, polysaccharides, carbohydrates and the like. They further include, but are not limited to, anti-restenotic agents, antidiabetics, analgesics, antiinflammatory agents, antirheumatics, antihypotensive agents, antihypertensive agents, psychoactive drugs, tranquillizers, antiemetics, muscle relaxants, glucocorticoids, agents for treating ulcerative colitis or Crohn's disease, antiallergics, antibiotics, antiepileptics, anticoagulants, antimycotics, antitussives, arteriosclerosis remedies, diuretics, proteins, peptides, enzymes, enzyme inhibitors, gout remedies, hormones and inhibitors thereof, cardiac glycosides, immunotherapeutic agents and cytokines, laxatives, lipid-lowering agents, migraine remedies, mineral products, otologicals, anti parkinson agents, thyroid therapeutic agents, spasmolytics, platelet aggregation inhibitors, vitamins, cytostatics and metastasis inhibitors, phytopharmaceuticals and chemotherapeutic agents. Preferably, the active biological agent is a peptide, protein or enzyme, including derivatives and analogs of natural peptides, proteins and enzymes. The active biological agent may also be a hormone, gene therapies, RNA, siRNA, and/or cellular therapies (for non-limiting example, stem cells or T-cells).

"Active agent" as used herein refers to any pharmaceutical agent or active biological agent as described herein.

"Activity" as used herein refers to the ability of a pharmaceutical or active biological agent to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). Thus the activity of a pharmaceutical or active biological agent should be of therapeutic or prophylactic value.

"Secondary, tertiary and quaternary structure" as used herein are defined as follows. The active biological agents of the present invention will typically possess some degree of secondary, tertiary and/or quaternary structure, upon which the activity of the agent depends. As an illustrative, non-limiting example, proteins possess secondary, tertiary and quaternary structure. Secondary structure refers to the spatial arrangement of amino acid residues that are near one another in the linear sequence. The $\alpha$-helix and the $\beta$-strand are elements of secondary structure. Tertiary structure refers to the spatial arrangement of amino acid residues that are far apart in the linear sequence and to the pattern of disulfide bonds. Proteins containing more than one polypeptide chain exhibit an additional level of structural organization. Each polypeptide chain in such a protein is called a subunit. Quaternary structure refers to the spatial arrangement of subunits and the nature of their contacts. For example hemoglobin consists of two $\alpha$ and two $\beta$ chains. It is well known that protein function arises from its conformation or three dimensional arrangement of atoms (a stretched out polypeptide chain is devoid of activity). Thus one aspect of the present invention is to manipulate active biological agents, while being careful to maintain their conformation, so as not to lose their therapeutic activity.

"Polymer" as used herein, refers to a series of repeating monomeric units that have been cross-linked or polymerized. Any suitable polymer can be used to carry out the present invention. It is possible that the polymers of the invention may also comprise two, three, four or more different polymers. In some embodiments, of the invention only one polymer is used. In some preferred embodiments a combination of two polymers are used. Combinations of polymers can be in varying ratios, to provide coatings with differing properties. Those of skill in the art of polymer chemistry will be familiar with the different properties of polymeric compounds.

"Copolymer" as used herein refers to a polymer being composed of two or more different monomers. A copolymer may also and/or alternatively refer to random, block, graft, copolymers known to those of skill in the art.

"Biocompatible" as used herein, refers to any material that does not cause injury or death to the animal or induce an adverse reaction in an animal when placed in intimate contact with the animal's tissues. Adverse reactions include for example inflammation, infection, fibrotic tissue formation, cell death, or thrombosis. The terms "biocompatible" and "biocompatibility" when used herein are art-recognized and mean that the referent is neither itself toxic to a host (e.g., an animal or human), nor degrades (if it degrades) at a rate that produces byproducts (e.g., monomeric or oligomeric subunits or other byproducts) at toxic concentrations, causes inflammation or irritation, or induces an immune reaction in the host. It is not necessary that any subject composition have a purity of 100% to be deemed biocompatible. Hence, a subject composition may comprise 99%, 98%, 97%, 96%, 95%, 90% 85%, 80%, 75% or even less of biocompatible agents, e.g., including polymers and other materials and excipients described herein, and still be biocompatible.

To determine whether a polymer or other material is biocompatible, it may be necessary to conduct a toxicity analysis. Such assays are well known in the art. One example of such an assay may be performed with live carcinoma cells, such as GT3TKB tumor cells, in the following manner: the sample is degraded in 1 M NaOH at 37 degrees C. until complete degradation is observed. The solution is then neutralized with 1 M HCl. About 200 microliters of various concentrations of the degraded sample products are placed in 96-well tissue culture plates and seeded with human gastric carcinoma cells (GT3TKB) at 104/well density. The degraded sample products are incubated with the GT3TKB cells for 48 hours. The results of the assay may be plotted as % relative growth vs. concentration of degraded sample in the tissue-culture well. In addition, polymers and formulations of the present invention may also be evaluated by well-known in vivo tests, such as subcutaneous implantations in rats to confirm that they do not cause significant levels of irritation or inflammation at the subcutaneous implantation sites.

The terms "bioabsorbable," "biodegradable," "bioerodible," and "bioresorbable," are art-recognized synonyms. These terms are used herein interchangeably. Bioabsorbable polymers typically differ from non-bioabsorbable polymers in that the former may be absorbed (e.g.; degraded) during use. In certain embodiments, such use involves in vivo use, such as in vivo therapy, and in other certain embodiments, such use involves in vitro use. In general, degradation attributable to biodegradability involves the degradation of a bioabsorbable polymer into its component subunits, or digestion, e.g., by a biochemical process, of the polymer into smaller, non-polymeric subunits. In certain embodiments, biodegradation may occur by enzymatic mediation, degradation in the presence of water (hydrolysis) and/or other chemical species in the body, or both. The bioabsorbabilty of a polymer may be shown in-vitro as described herein or by methods known to one of skill in the art. An in-vitro test for bioabsorbability of a polymer does not require living cells or other biologic materials to show bioabsorption properties (e.g. degradation, digestion). Thus, resorbtion, resorption, absorption, absorbtion, erosion may also be used synonymously with the terms "bioabsorbable," "biodegradable," "bioerodible," and "bioresorbable." Mechanisms of degradation of a bioarbable polymer may include, but are not limited to, bulk degradation, surface erosion, and combinations thereof.

As used herein, the term "biodegradation" encompasses both general types of biodegradation. The degradation rate of a biodegradable polymer often depends in part on a variety of factors, including the chemical identity of the linkage responsible for any degradation, the molecular weight, crystallinity, biostability, and degree of cross-linking of such polymer, the physical characteristics (e.g., shape and size) of the implant, and the mode and location of administration. For example, the greater the molecular weight, the higher the degree of crystallinity, and/or the greater the biostability, the biodegradation of any bioabsorbable polymer is usually slower.

"Therapeutically desirable morphology" as used herein refers to the gross form and structure of the pharmaceutical agent, once deposited on the substrate, so as to provide for optimal conditions of ex vivo storage, in vivo preservation and/or in vivo release. Such optimal conditions may include, but are not limited to increased shelf life, increased in vivo stability, good biocompatibility, good bioavailability or modified release rates. Typically, for the present invention, the desired morphology of a pharmaceutical agent would be crystalline or semi-crystalline or amorphous, although this may vary widely depending on many factors including, but not limited to, the nature of the pharmaceutical agent, the disease to be treated/prevented, the intended storage conditions for the substrate prior to use or the location within the body of any biomedical implant. Preferably at least 10%, 20%, 30%, 40%, 50%, 60%, 70%, 80%, 90% or 100% of the pharmaceutical agent is in crystalline or semi-crystalline form.

"Stabilizing agent" as used herein refers to any substance that maintains or enhances the stability of the biological agent. Ideally these stabilizing agents are classified as Generally Regarded As Safe (GRAS) materials by the US Food and Drug Administration (FDA). Examples of stabilizing agents include, but are not limited to carrier proteins, such as albumin, gelatin, metals or inorganic salts. Pharmaceutically acceptable excipient that may be present can further be found in the relevant literature, for example in the Handbook of Pharmaceutical Additives An International Guide to More Than 6000 Products by Trade Name, Chemical, Function, and Manufacturer; Michael and Irene Ash (Eds.); Gower Publishing Ltd.; Aldershot, Hampshire, England, 1995.

"Compressed fluid" as used herein refers to a fluid of appreciable density (e.g., >0.2 g/cc) that is a gas at standard temperature and pressure. "Supercritical fluid", "near-critical fluid", "near-supercritical fluid", "critical fluid", "densified fluid" or "densified gas" as used herein refers to a compressed fluid under conditions wherein the temperature is at least 80% of the critical temperature of the fluid and the pressure is at least 50% of the critical pressure of the fluid, and/or a density of +50% of the critical density of the fluid.

Examples of substances that demonstrate supercritical or near critical behavior suitable for the present invention include, but are not limited to carbon dioxide, isobutylene, ammonia, water, methanol, ethanol, ethane, propane, butane, pentane, dimethyl ether, xenon, sulfur hexafluoride, halogenated and partially halogenated materials such as chlorofluorocarbons, hydrochlorofluorocarbons, hydrofluorocarbons, perfluorocarbons (such as perfluoromethane and perfluoropropane, chloroform, trichloro-fluoromethane, dichloro-difluoromethane, dichloro-tetrafluoroethane) and mixtures thereof. Preferably, the supercritical fluid is hexafluoropropane (FC-236EA), or 1,1,1,2,3,3-hexafluoropropane. Preferably, the supercritical fluid is hexafluoropropane (FC-236EA), or 1,1,1,2,3,3-hexafluoropropane for use in PLGA polymer coatings.

"Sintering" as used herein refers to the process by which parts of the polymer or the entire polymer becomes continuous (e.g., formation of a continuous polymer film). As discussed below, the sintering process is controlled to produce a fully conformal continuous polymer (complete sintering) or to produce regions or domains of continuous coating while producing voids (discontinuities) in the polymer. As well, the sintering process is controlled such that some phase separation is obtained or maintained between polymer different polymers (e.g., polymers A and B) and/or to produce phase separation between discrete polymer particles. Through the sintering process, the adhesions properties of the coating are improved to reduce flaking of detachment of the coating from the substrate during manipulation in use. As described below, in some embodiments, the sintering process is controlled to provide incomplete sintering of the polymer. In embodiments involving incomplete sintering, a polymer is formed with continuous domains, and voids, gaps, cavities, pores, channels or, interstices that provide space for sequestering a therapeutic agent which is released under controlled conditions. Depending on the nature of the polymer, the size of polymer particles and/or other polymer properties, a compressed gas, a densified gas, a near critical fluid or a super-critical fluid may be employed. In one example, carbon dioxide is used to treat a substrate that has been coated with a polymer and a drug, using dry powder and RESS electrostatic coating processes. In another example, isobutylene is employed in the sintering process. In other examples a mixture of carbon dioxide and isobutylene is employed. In another example, 1,1,2,3,3-hexafluoropropane is employed in the sintering process.

When an amorphous material is heated to a temperature above its glass transition temperature, or when a crystalline material is heated to a temperature above a phase transition temperature, the molecules comprising the material are more mobile, which in turn means that they are more active and thus more prone to reactions such as oxidation. However, when an amorphous material is maintained at a temperature below its glass transition temperature, its molecules are substantially immobilized and thus less prone to reactions. Likewise, when a crystalline material is maintained at a temperature below its phase transition temperature, its molecules are substantially immobilized and thus less prone to reactions. Accordingly, processing drug components at mild conditions, such as the deposition and sintering conditions described herein, minimizes cross-reactions and degradation of the drug component. One type of reaction that is minimized by the processes of the invention relates to the ability to avoid conventional solvents which in turn minimizes oxidation of drug, whether in amorphous, semi-crystalline, or crystalline form, by reducing exposure thereof to free radicals, residual solvents, protic materials, polar-protic materials, oxidation initiators, and autoxidation initiators.

"Rapid Expansion of Supercritical Solutions" or "RESS" as used herein involves the dissolution of a polymer into a compressed fluid, typically a supercritical fluid, followed by rapid expansion into a chamber at lower pressure, typically near atmospheric conditions. The rapid expansion of the supercritical fluid solution through a small opening, with its accompanying decrease in density, reduces the dissolution capacity of the fluid and results in the nucleation and growth of polymer particles. The atmosphere of the chamber is maintained in an electrically neutral state by maintaining an isolating "cloud" of gas in the chamber. Carbon dioxide, nitrogen, argon, helium, or other appropriate gas is employed to prevent electrical charge is transferred from the substrate to the surrounding environment.

"Bulk properties" properties of a coating including a pharmaceutical or a biological agent that can be enhanced through the methods of the invention include for example: adhesion, smoothness, conformality, thickness, and compositional mixing.

"Electrostatically charged" or "electrical potential" or "electrostatic capture" as used herein refers to the collection of the spray-produced particles upon a substrate that has a different electrostatic potential than the sprayed particles. Thus, the substrate is at an attractive electronic potential with respect to the particles exiting, which results in the capture of the particles upon the substrate. i.e. the substrate and particles are oppositely charged, and the particles transport through the gaseous medium of the capture vessel onto the surface of the substrate is enhanced via electrostatic attraction. This may be achieved by charging the particles and grounding the substrate or conversely charging the substrate and grounding the particles, by charging the particles at one potential (e.g. negative charge) and charging the substrate at an opposited potential (e.g. positive charge), or by some other process, which would be easily envisaged by one of skill in the art of electrostatic capture.

"Intimate mixture" as used herein, refers to two or more materials, compounds, or substances that are uniformly distributed or dispersed together.

"Layer" as used herein refers to a material covering a surface or forming an overlying part or segment. Two different layers may have overlapping portions whereby material from one layer may be in contact with material from another layer. Contact between materials of different layers can be measured by determining a distance between the materials. For example, Raman spectroscopy may be employed in identifying materials from two layers present in close proximity to each other.

While layers defined by uniform thickness and/or regular shape are contemplated herein, several embodiments described below relate to layers having varying thickness and/or irregular shape. Material of one layer may extend into the space largely occupied by material of another layer. For example, in a coating having three layers formed in sequence as a first polymer layer, a pharmaceutical agent layer and a second polymer layer, material from the second polymer layer which is deposited last in this sequence may extend into the space largely occupied by material of the pharmaceutical agent layer whereby material from the second polymer layer may have contact with material from the pharmaceutical layer. It is also contemplated that material from the second polymer layer may extend through the entire layer largely occupied by pharmaceutical agent and contact material from the first polymer layer.

It should be noted however that contact between material from the second polymer layer (or the first polymer layer) and material from the pharmaceutical agent layer (e.g.; a pharmaceutical agent crystal particle or a portion thereof) does not necessarily imply formation of a mixture between the material from the first or second polymer layers and material from the pharmaceutical agent layer. In some embodiments, a layer may be defined by the physical three-dimensional space occupied by crystalline particles of a pharmaceutical agent (and/or biological agent). It is contemplated that such layer may or may not be continuous as phhysical space occupied by the crystal particles of pharmaceutical agents may be interrupted, for example, by polymer material from an adjacent polymer layer. An adjacent polymer layer may be a layer that is in physical proximity to be pharmaceutical agent particles in the pharmaceutical agent layer. Similarly, an adjacent layer may be the layer formed in a process step right before or right after the process step in which pharmaceutical agent particles are deposited to form the pharmaceutical agent layer.

As described below, material deposition and layer formation provided herein are advantageous in that the pharmaceutical agent remains largely in crystalline form during the entire process. While the polymer particles and the pharmaceutical agent particles may be in contact, the layer formation process is controlled to avoid formation of a mixture between the pharmaceutical agent particles the polymer particles during formation of a coated device.

"Laminate coating" as used herein refers to a coating made up of two or more layers of material. Means for creating a laminate coating as described herein (e.g.; a laminate coating comprising bioabsorbable polymer(s) and pharmaceutical agent) may include coating the stent with drug and polymer as described herein (e-RESS, e-DPC, compressed-gas sintering). The process comprises performing multiple and sequential coating steps (with sintering steps for polymer materials) wherein different materials may be deposited in each step, thus creating a laminated structure with a multitude of layers (at least 2 layers) including polymer layers and pharmaceutical agent layers to build the final device (e.g.; laminate coated stent).

The coating methods provided herein may be calibrated to provide a coating bias whereby the mount of polymer and pharmaceutical agent deposited in the abluminal surface of the stent (exterior surface of the stent) is greater than the amount of pharmaceutical agent and amount of polymer deposited on the luminal surface of the stent (interior surface of the stent). The resulting configuration may be desirable to provide preferential elution of the drug toward the vessel wall (luminal surface of the stent) where the therapeutic effect of anti-restenosis is desired, without providing the same antiproliferative drug(s) on the abluminal surface, where they may retard healing, which in turn is suspected to be a cause of late-stage safety problems with current DESs.

As well, the methods described herein provide a device wherein the coating on the stent is biased in favor of increased coating at the ends of the stent. For example, a stent having three portions along the length of the stent (e.g.; a central portion flanked by two end portions) may have end portions coated with increased amounts of pharmaceutical agent and/or polymer compared to the central portion.

The present invention provides numerous advantages. The invention is advantageous in that it allows for employing a platform combining layer formation methods based on compressed fluid technologies; electrostatic capture and sintering methods. The platform results in drug eluting stents having enhanced therapeutic and mechanical properties. The invention is particularly advantageous in that it employs optimized laminate polymer technology. In particular, the present invention allows the formation of discrete layers of specific drug platforms. As indicated above, the shape of a discrete layer of crystal particles may be irregular, including interruptions of said layer by material from another layer (polymer layer) positioned in space between crystalline particles of pharmaceutical agent.

Conventional processes for spray coating stents require that drug and polymer be dissolved in solvent or mutual solvent before spray coating can occur. The platform provided herein the drugs and polymers are coated on the stent framework in discrete steps, which can be carried out simultaneously or alternately. This allows discrete deposition of the active agent (e.g., a drug) within a polymer thereby allowing the placement of more than one drug on a single medical device with or without an intervening polymer layer. For example, the present platform provides a dual drug eluting stent.

Some of the advantages provided by the subject invention include employing compressed fluids (e.g., supercritical fluids, for example E-RESS based methods); solvent free deposition methodology; a platform that allows processing at lower temperatures thereby preserving the qualities of the active agent and the polymer; the ability to incorporate two, three or more drugs while minimizing deleterious effects from direct interactions between the various drugs and/or their excipients during the fabrication and/or storage of the drug eluting stents; a dry deposition; enhanced adhesion and mechanical properties of the layers on the stent framework; precision deposition and rapid batch processing; and ability to form intricate structures.

In one embodiment, the present invention provides a multi-drug delivery platform which produces strong, resilient and flexible drug eluting stents including an anti-restenosis drug (e.g., a limus or taxol) and anti-thrombosis drug (e.g., heparin or an analog thereof) and well characterized bioabsorbable polymers. The drug eluting stents provided herein minimize potential for thrombosis, in part, by reducing or totally eliminating thrombogenic polymers and reducing or totally eliminating residual drugs that could inhibit healing.

The platform provides optimized delivery of multiple drug therapies for example for early stage treatment (restenosis) and late-stage (thrombosis).

The platform also provides an adherent coating which enables access through tortuous lesions without the risk of the coating being compromised.

Another advantage of the present platform is the ability to provide highly desirable eluting profiles.

Advantages of the invention include the ability to reduce or completely eliminate potentially thrombogenic polymers as well as possibly residual drugs that may inhibit long term healing. As well, the invention provides advantageous stents having optimized strength and resilience if coatings which in turn allows access to complex lesions and reduces or completely eliminates delamination. Laminated layers of bioabsorbable polymers allow controlled elution of one or more drugs.

The platform provided herein reduces or completely eliminates shortcoming that have been associated with conventional drug eluting stents. For example, the platform provided herein allows for much better tuning of the period of time for the active agent to elute and the period of time necessary for the polymer to resorb thereby minimizing thrombosis and other deleterious effects associate with poorly controlled drug release.

The present invention provides several advantages which overcome or attenuate the limitations of current technology for bioabsorbable stents. Fro example, an inherent limitation of conventional bioabsorbable polymeric materials relates to the difficulty in forming to a strong, flexible, deformable (e.g. balloon deployable) stent with low profile. The polymers generally lack the strength of high-performance metals. The present invention overcomes these limitations by creating a laminate structure in the essentially polymeric stent. Without wishing to be bound by any specific theory or analogy, the increased strength provided by the stents of the invention can be understood by comparing the strength of plywood vs. the strength of a thin sheet of wood.

Embodiments of the invention involving a thin metallic stent-framework provide advantages including the ability to overcome the inherent elasticity of most polymers. It is generally difficult to obtain a high rate (e.g., 100%) of plastic deformation in polymers (compared to elastic deformation where the materials have some 'spring back' to the original shape). Again, without wishing to be bound by any theory, the central metal stent framework (that would be too small and weak to serve as a stent itself) would act like wires inside of a plastic, deformable stent, basically overcoming any 'elastic memory' of the polymer.

Another advantage of the present invention is the ability to create a stent with a controlled (dialed-in) drug-elution profile. Via the ability to have different materials in each layer of the laminate structure and the ability to control the location of drug(s) independently in these layers, the method enables a stent that could release drugs at very specific elution profiles, programmed sequential and/or parallel elution profiles. Also, the present invention allows controlled elution of one drug without affecting the elution of a second drug (or different doses of the same drug).

Provided herein is a device comprising a stent; and a plurality of layers that form a laminate coating on said stent; wherein at least one of said layers comprises a bioabsorbable polymer and at least one of said layers comprises one or more active agents; wherein at least a portion of the active agent is in crystalline form.

Provided herein is a device comprising a stent; and a plurality of layers that form a laminate coating on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof, wherein at least a portion of the pharmaceutical agent is in crystalline form.

In some embodiments, the device has at least one pharmaceutical agent layer defined by a three-dimensional physical space occupied by crystal particles of said pharmaceutical agent and said three dimensional physical space is free of polymer. In some embodiments, at least some of the crystal particles in said three dimensional physical space defining said at least one pharmaceutical agent layer are in contact with polymer particles present in a polymer layer adjacent to said at least one pharmaceutical agent layer defined by said three-dimensional space free of polymer.

In some embodiments, the plurality of layers comprises a first polymer layer comprising a first bioabsorbable polymer and a second polymer layer comprising a second bioabsorbable polymer, wherein said at least one layer comprising said pharmaceutical agent is between said first polymer layer and said second polymer layer. In some embodiments, first and second bioabsorbable polymers are the same polymer. In some embodiments, the first and second bioabsorbable polymers are different. In some embodiments, the second polymer layer has at least one contact point with at least one particle of said pharmaceutical agent in said pharmaceutical agent layer and said second polymer layer has at least one contact point with said first polymer layer.

In some embodiments, the stent has a stent longitudinal axis; and said second polymer layer has a second polymer layer portion along said stent longitudinal wherein said second layer portion is free of contact with particles of said pharmaceutical agent. In some embodiments, the device has at least one pharmaceutical agent layer defined by a three-dimensional physical space occupied by crystal particles of said pharmaceutical agent and said three dimensional physical space is free of polymer.

The second polymer layer may have a layer portion defined along a longitudinal axis of the stent, said polymer layer portion having a thickness less than said maximum thickness of said second polymer layer; wherein said portion is free of contact with particles of said pharmaceutical agent.

The polymer layer portion may be a sub layer which, at least in part, extends along the abluminal surface of the stent along the longitudinal axis of the stent (where the longitudinal axis of the stent is the central axis of the stent along its tubular length). For example, when a coating is removed from the abluminal surface of the stent, such as when the stent is cut along its length, flattened, and the coating is removed by scraping the coating off using a scalpel, knife or other sharp tool, the coating that is removed (despite having a pattern consistent with the stent pattern) has a layer that can be shown to have the characteristics described herein. This may be shown by sampling multiple locations of the coating that is representative of the entire coating.

Alternatively, and/or additionally, since stents are generally comprised of a series of struts and voids. The methods provided herein advantageously allow for coatings extending around each strut, the layers of coating are likewise disposed around each strut. Thus, a polymer layer portion may be a layer which, at least, extends around each strut a distance from said strut (although the distance may vary where the coating thickness on the abluminal surface is different than the coating thickness on the luminal and/or sidewalls).

In some embodiments, the stent comprises at least one strut having a strut length along said stent longitudinal axis, wherein said second layer portion extends substantially along said strut length. In some embodiments, the stent has a stent length along said stent longitudinal axis and said second layer portion extends substantially along said stent length.

In some embodiments, the stent comprises at least five struts, each strut having a strut length along said stent longitudinal axis, wherein said second layer portion extends substantially along substantially the strut length of at least two struts. In some embodiments, the stent comprises at least five struts, each strut having a strut length along said stent longitudinal axis, wherein said second layer portion extends substantially along substantially the strut length of at least three struts. In some embodiments, the stent comprises at least five struts, each strut having a strut length along said stent longitudinal axis, wherein said second layer portion extends substantially along substantially the strut length of least four struts. In some embodiments, the stent comprises at least five struts, each strut having a strut length along said stent longitudinal axis, wherein said second layer portion extends substantially along substantially the strut length of all said at least five struts. In some embodiments, the stent has a stent length along said stent longitudinal axis and said second layer portion extends substantially along said stent length.

In some embodiments, the stent has a stent length along said stent longitudinal axis and said second layer portion extends along at least 50% of said stent length. In some embodiments, the stent has a stent length along said stent longitudinal axis and said second layer portion extends along at least 75% of said stent length. In some embodiments, the stent has a stent length along said stent longitudinal axis and said second layer portion extends along at least 85% of said stent length. In some embodiments, the stent has a stent length along said stent longitudinal axis and said second layer portion extends along at least 90% of said stent length. In some embodiments, the stent has a stent length along said stent longitudinal axis and said second layer portion extends along at least 99% of said stent length.

In some embodiments, the laminate coating has a total thickness and said second polymer layer portion has a thickness of from about 0.01% to about 10% of the total thickness of said laminate coating. In some embodiments, the laminate coating has a total thickness and said horizontal second polymer layer portion has a thickness of from about 1% to about 5% of the total thickness of said laminate coating. In some embodiments, the laminate coating has a total thickness of from about 5 µm to about 50 µm and said horizontal second polymer layer portion has a thickness of from about 0.001 µm to about 5 µm. In some embodiments, the laminate coating has a total thickness of from about 10 µm to about 20 µm and said second polymer layer portion has a thickness of from about 0.01 µm to about 5 µm.

In some embodiments, the laminate coating is at least 25% by volume pharmaceutical agent. In some embodiments, the laminate coating is at least 35% by volume pharmaceutical agent. In some embodiments, the laminate coating is about 50% by volume pharmaceutical agent.

In some embodiments, at least a portion of the pharmaceutical agent is present in a phase separate from one or more phases formed by said polymer.

In some embodiments, the pharmaceutical agent is at least 50% crystalline. In some embodiments, the pharmaceutical agent is at least 75% crystalline. In some embodiments, the pharmaceutical agent is at least 90% crystalline. In some embodiments, the pharmaceutical agent is at least 95% crystalline. In some embodiments, the pharmaceutical agent is at least 99% crystalline.

In some embodiments, the stent has a stent longitudinal length and the coating has a coating outer surface along said stent longitudinal length, wherein said coating comprises pharmaceutical agent in crystalline form present in the coating below said coating outer surface. In some embodiments, the stent has a stent longitudinal length and the coating has a coating outer surface along said stent longitudinal length, wherein said coating comprises pharmaceutical agent in crystalline form present in the coating up to at least 1 µm below said coating outer surface. In some embodiments, the stent has a stent longitudinal length and the coating has a coating outer surface along said stent longitudinal length, wherein said coating comprises pharmaceutical agent in crystalline form present in the coating up to at least 5 µm below said coating outer surface.

In some embodiments, the coating exhibits an X-ray spectrum showing the presence of said pharmaceutical agent in crystalline form. In some embodiments, the coating exhibits a Raman spectrum showing the presence of said pharmaceutical agent in crystalline form. In some embodiments, the coating exhibits a Differential Scanning Calorimetry (DSC) curve showing the presence of said pharmaceutical agent in crystalline form. The device of Claims 36-38, wherein said coating exhibits Wide Angle X-ray Scattering (WAXS) spectrum showing the presence of said pharmaceutical agent in crystalline form. In some embodiments, the coating exhibits a wide angle radiation scattering spectrum showing the presence of said pharmaceutical agent in crystalline form. In some embodiments, the coating exhibits an Infra Red (IR) spectrum showing the presence of said pharmaceutical agent in crystalline form.

In some embodiments, the stent has a stent longitudinal axis and a stent length along said stent longitudinal axis, wherein said coating is conformal to the stent along substantially said stent length.

In some embodiments, the stent has a stent longitudinal axis and a stent length along said stent longitudinal axis, wherein said coating is conformal to the stent along at least 75% of said stent length. In some embodiments, the stent has a stent longitudinal axis and a stent length along said stent longitudinal axis, wherein said coating is conformal to the stent along at least 85% of said stent length. In some embodiments, the stent has a stent longitudinal axis and a stent length along said stent longitudinal axis, wherein said coating is conformal to the stent along at least 90% of said stent length. In some embodiments, the stent has a stent longitudinal axis and a stent length along said stent longitudinal axis, wherein said coating is conformal to the stent along at least 95% of said stent length. In some embodiments, the stent has a stent longitudinal axis and a stent length along said stent longitudinal axis, wherein said coating is conformal to the stent along at least 99% of said stent length.

In some embodiments, the stent has a stent longitudinal axis and a plurality of struts along said stent longitudinal axis, wherein said coating is conformal to at least 50% of said struts. In some embodiments, the stent has a stent longitudinal axis and a plurality of struts along said stent longitudinal axis, wherein said coating is conformal to at least 75% of said struts. In some embodiments, the stent has a stent longitudinal axis and a plurality of struts along said stent longitudinal axis, wherein said coating is conformal to at least 90% of said struts. In some embodiments, the stent has a stent longitudinal axis and a plurality of struts along said stent longitudinal axis, wherein said coating is conformal to at least 99% of said struts. In some embodiments, the stent has a stent longitudinal axis and a stent length along said stent longitudinal axis, wherein an electron microscopy examination of the device shows said coating is conformal to said stent along at least 90% of said stent length.

In some embodiments, the stent has a stent longitudinal axis and a stent length along said stent longitudinal axis, wherein said coating has a substantially uniform thickness along substantially said stent length.

In some embodiments, the stent has a stent longitudinal axis and a stent length along said stent longitudinal axis, wherein said coating has a substantially uniform thickness along at least 75% of said stent length. In some embodiments, the stent has a stent longitudinal axis and a stent length along said stent longitudinal axis, wherein said coating has a substantially uniform thickness along at least 95% of said stent length.

In some embodiments, the stent has a stent longitudinal axis and a stent length along said stent longitudinal axis, wherein said coating has an average thickness determined by an average calculated from coating thickness values measured at a plurality of points along said stent longitudinal axis; wherein a thickness of the coating measured at any point along stent longitudinal axis is from about 75% to about 125% of said average thickness. In some embodiments, the stent has a stent longitudinal axis and a stent length along said stent longitudinal axis, wherein said coating has an average thickness determined by an average calculated from coating thickness values measured at a plurality of points along said stent longitudinal axis; wherein a thickness of the coating measured at any point along stent longitudinal axis is from about 95% to about 105% of said average thickness.

Provided herein is a device comprising: a stent; and a plurality of layers that form a laminate coating on said stent, wherein a first layer comprises a first bioabsorbable polymer, a second layer comprises a pharmaceutical agent, a third layer comprises a second bioabsorbable polymer, a fourth layer comprises the pharmaceutical agent, and a fifth layer comprises a third bioabsorbable polymer, wherein the pharmaceutical agent is selected from rapamycin, a prodrug, a derivative, an analog, a hydrate, an ester, and a salt thereof, and wherein at least a portion of the pharmaceutical agent is in crystalline form.

In some embodiments, at least two of said first bioabsorbable polymer, said second bioabsorbable polymer and said third bioabsorbable polymer are the same polymer. In some embodiments, the first bioabsorbable polymer, the second bioabsorbable polymer and the third bioabsorbable polymer are the same polymer. In some embodiments, at least two of said first bioabsorbable polymer, said second bioabsorbable polymer and said third bioabsorbable polymer are different polymers. In some embodiments, the first bioabsorbable polymer, said second bioabsorbable polymer and said third bioabsorbable polymer are different polymers.

In some embodiments, the third layer has at least one contact point with particles of said pharmaceutical agent in said second layer; and said third layer has at least one contact point with said first layer.

In some embodiments, at least two of the first polymer, the second polymer, and the third polymer are the same polymer, and wherein said same polymer comprises a PLGA copolymer. In some embodiments, the third polymer has an in vitro dissolution rate higher than the in vitro dissolution rate of the first polymer. In some embodiments, the third polymer is PLGA copolymer with a ratio of about 40:60 to about 60:40 and the first polymer is a PLGA copolymer with a ratio of about 70:30 to about 90:10. In some embodiments, the third polymer is PLGA copolymer having a molecular weight of about 10 kD and the second polymer is a PLGA copolymer having a molecular weight of about 19 kD.

In some embodiments, measuring the in vitro dissolution rate of said polymers comprises contacting the device with elution media and determining polymer weight loss at one or more selected time points. In some embodiments, measuring the in vitro dissolution rate of said polymers comprises contacting the device with elution media and determining polymer weight loss at one or more selected time points.

Provided herein is a device, comprising: a stent; and a coating on said stent comprising a first bioabsorbable polymer, a second bioabsorbable polymer; and pharmaceutical agent selected from rapamycin, a prodrug, a derivative, an analog, a hydrate, an ester, and a salt thereof wherein at least a portion of the pharmaceutical agent is in crystalline form, and wherein the first polymer has an in vitro dissolution rate higher than the in vitro dissolution rate of the second polymer.

In some embodiments, the first polymer is PLGA copolymer with a ratio of about 40:60 to about 60:40 and the second polymer is a PLGA copolymer with a ratio of about 70:30 to about 90:10. In some embodiments, the first polymer is PLGA copolymer having a molecular weight of about 10 kD and the second polymer is a PLGA copolymer having a molecular weight of about 19 kD. In some embodiments, measuring the in vitro dissolution rate of said polymers comprises contacting the device with elution media and determining polymer weight loss at one or more selected time points.

Provided herein is a device comprising a stent; and a plurality of layers that form a laminate coating on said stent; wherein at least one of said layers comprises a first bioabsorbable polymer, at least one of said layers comprises a second bioabsorbable polymer, and at least one of said layers comprises one or more active agents; wherein at least a portion of the active agent is in crystalline form, and wherein the first polymer has an in vitro dissolution rate higher than the in vitro dissolution rate of the second polymer.

Provided herein is a device comprising a stent; and a plurality of layers that form a laminate coating on said stent; wherein at least one of said layers comprises a first bioabsorbable polymer, at least one of said layers comprises a second bioabsorbable polymer, and at least one of said layers comprises a pharmaceutical agent selected from rapamycin, a prodrug, a derivative, an analog, a hydrate, an ester, and a salt thereof, wherein at least a portion of the pharmaceutical agent is in crystalline form and wherein the first polymer has an in vitro dissolution rate higher than the in vitro dissolution rate of the second polymer.

In some embodiments, the first polymer is PLGA copolymer with a ratio of about 40:60 to about 60:40 and the second polymer is a PLGA copolymer with a ratio of about 70:30 to about 90:10. In some embodiments, the first polymer is PLGA copolymer having a molecular weight of about 10 kD and the second polymer is a PLGA copolymer having a molecular weight of about 19 kD. In some embodiments, measuring the in vitro dissolution rate comprises contacting the device with elution media and determining polymer weight loss at one or more selected time points.

Provided herein is a device comprising a stent; and a plurality of layers that form a laminate coating on said stent; wherein at least one of said layers comprises a bioabsorbable polymer, at least one of said layers comprises a first active agent and at least one of said layers comprises a second active agent; wherein at least a portion of first and/or second active agents is in crystalline form.

In some embodiments, the bioabsorbable polymer is selected from the group PLGA, PGA poly(glycolide), LPLA poly(1-lactide), DLPLA poly(dl-lactide), PCL poly(e-caprolactone) PDO, poly(dioxolane) PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid). In some embodiments, the polymer comprises an intimate mixture of two or more polymers.

In some embodiments, the first and second active agents are independently selected from pharmaceutical agents and active biological agents.

In some embodiments, the stent is formed of stainless steel material. In some embodiments, the stent is formed of a material comprising a cobalt chromium alloy. In some embodiments, the stent is formed from a material comprising the following percentages by weight: about 0.05 to about 0.15 C, about 1.00 to about 2.00 Mn, about 0.04 Si, about 0.03 P, about 0.3 S, about 19.0 to about 21.0 Cr, about 9.0 to about 11.0 Ni, about 14.0 to about 16.00 W, about 3.0 Fe, and Bal. Co. In some embodiments, the stent is formed from a material comprising at most the following percentages by weight: about 0.025 C, about 0.15 Mn, aboout 0.15 Si, about 0.015 P, about 0.01 S, about 19.0 to about 21.0 Cr, about 33 to about 37 Ni, about 9.0 to about 10.5 Mo, about 1.0 Fe, about 1.0 Ti, and Bal. Co. In some embodiments, the stent is formed from a material comprising L605 alloy.

In some embodiments, the stent has a thickness of from about 50% to about 90% of a total thickness of said device. In some embodiments, the device has a thickness of from about 20 μm to about 500 μm. In some embodiments, the device has a thickness of about 90 μm or less. In some embodiments, the laminate coating has a thickness of from about 5 μm to about 50 μm. In some embodiments, the laminate coating has a thickness of from about 10 μm to about 20 μm. In some embodiments, the stent has a thickness of from about 50 μm to about 80 μm.

Provided herein is a device comprising: a stent, wherein the stent is formed from a material comprising the following percentages by weight: 0.05-0.15 C, 1.00-2.00 Mn, 0.040 Si, 0.030 P, 0.3 S, 19.00-21.00 Cr, 9.00-11.00 Ni, 14.00-16.00 W, 3.00 Fe, and Bal. Co; and a plurality of layers that form a laminate coating on said stent, wherein a first layer comprises a first bioabsorbable polymer, a second layer comprises a pharmaceutical agent, a third layer comprises a second bioabsorbable polymer, a fourth layer comprises the pharmaceutical agent, and a fifth layer comprises a third bioabsorbable polymer, wherein the pharmaceutical agent is selected from rapamycin, a prodrug, a derivative, an analog, a hydrate, an ester, and a salt thereof, wherein at least a portion of the pharmaceutical agent is in crystalline form, and wherein at least one of said first polymer, second polymer and third polymer comprises a PLGA copolymer.

In some embodiments, the device has a pharmaceutical agent content of from about 0.5 µg/mm to about 20 µg/mm. In some embodiments, the device has a pharmaceutical agent content of from about 8 µg/mm to about 12 µg/mm. In some embodiments, the device has a pharmaceutical agent content of from about 5 µg to about 500 µg. In some embodiments, the device has a pharmaceutical agent content of from about 100 µg to about 160 µg. In some embodiments, the device has a pharmaceutical agent content of from about 100 µg to about 160 µg.

Content is expressed herein in units of µg/mm, however, this may simply be converted to $µg/mm^2$ or another amount per area (e.g., $µg/cm^2$).

Provided herein is a method of preparing a device comprising a stent and a plurality of layers that form a laminate coating on said stent; said method comprising: (a) providing a stent; (b) forming a plurality of layers on said stent to form said laminate coating on said stent; wherein at least one of said layers comprises a bioabsorbable polymer and at least one of said layers comprises one or more active agents; wherein at least a portion of the active agent is in crystalline form.

Provided herein is a method of preparing a device comprising a stent and a plurality of layers that form a laminate coating on said stent; said method comprising: (a) providing a stent; (b) forming a plurality of layers to form said laminate coating on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof, wherein at least a portion of the pharmaceutical agent is in crystalline form.

Provided herein is a method of preparing a device comprising a stent and a plurality of layers that form a laminate coating on said stent; said method comprising: (a) providing a stent; (b) forming a plurality of layers to form said laminate coating on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof, wherein at least a portion of the pharmaceutical agent is in crystalline form, wherein said method comprises forming at least one pharmaceutical agent layer defined by a three-dimensional physical space occupied by crystal particles of said pharmaceutical agent and said three dimensional physical space is free of polymer.

Provided herein is a method of preparing a device comprising a stent and a plurality of layers that form a laminate coating on said stent; said method comprising: (a) providing a stent; (b) discharging at least one pharmaceutical agent and/or at least one active biological agent in dry powder form through a first orifice; (c) forming a supercritical or near supercritical fluid solution comprising at least one supercritical fluid solvent and at least one polymer and discharging said supercritical or near supercritical fluid solution through a second orifice under conditions sufficient to form solid particles of the polymer; (d) depositing the polymer and pharmaceutical agent and/or active biological agent particles onto said substrate, wherein an electrical potential is maintained between the substrate and the polymer and pharmaceutical agent and/or active biological agent particles, thereby forming said coating; and (e) sintering said polymer under conditions that do not substantially modify a morphology of said pharmaceutical agent and/or activity of said biological agent.

In some embodiments, step (b) comprises discharging a pharmaceutical agent selected from rapamycin, a prodrug, a derivative, an analog, a hydrate, an ester, and a salt thereof, wherein at least a portion of the pharmaceutical agent is in crystalline form. In some embodiments, step (c) comprises forming solid particles of a bioabsorbable polymer.

In some embodiments, step (e) comprises forming a polymer layer having a length along a horizontal axis of said device wherein said polymer layer has a layer portion along said length, wherein said layer portion is free of pharmaceutical agent.

In some embodiments, step (e) comprises contacting said polymer with a densified fluid. In some embodiments, step (e) comprises contacting said polymer with a densified fluid for a period of time at a temperature of from about 5° C. and 150° C. and a pressure of from about 10 psi to about 500 psi. In some embodiments, step (e) comprises contacting said polymer with a densified fluid for a period of time at a temperature of from about 25° C. and 95° C. and a pressure of from about 25 psi to about 100 psi. In some embodiments, step (e) comprises contacting said polymer with a densified fluid for a period of time at a temperature of from about 50° C. and 85° C. and a pressure of from about 35 psi to about 65 psi.

Provided herein is a method of preparing a device comprising a stent and a plurality of layers that form a laminate coating on said stent; said method comprising: (a) providing a stent; (b) forming a supercritical or near supercritical fluid solution comprising at least one supercritical fluid solvent and a first polymer, discharging said supercritical or near supercritical fluid solution under conditions sufficient to form solid particles of said first polymer, depositing said first polymer particles onto said stent, wherein an electrical potential is maintained between the stent and the first polymer, and sintering said first polymer; (c) depositing pharmaceutical agent particles in dry powder form onto said stent, wherein an electrical potential is maintained between the stent and said pharmaceutical agent particles; and (d) forming a supercritical or near supercritical fluid solution comprising at least one supercritical fluid solvent and a second polymer and discharging said supercritical or near supercritical fluid solution under conditions sufficient to form solid particles of said second polymer, wherein an electrical potential is maintained between the stent and the second polymer, and sintering said second polymer.

In some embodiments, step (c) and step (d) are repeated at least once. In some embodiments, steps (c) and step (d) are repeated 2 to 20 times.

In some embodiments, the pharmaceutical agent is selected from rapamycin, a prodrug, a derivative, an analog, a hydrate, an ester, and a salt thereof, wherein at least a portion of the pharmaceutical agent is in crystalline form. In some embodiments, the first and second polymers are bioabsorbable.

In some embodiments, step (d) comprises forming a polymer layer having a length along a horizontal axis of said device wherein said polymer layer has a layer portion along said length, wherein said layer portion is free of pharmaceutical agent.

In some embodiments, sintering said first and/or sintering said second polymer comprises contacting said first and/or second polymer with a densified fluid.

In some embodiments, the contacting step is carried out for a period of from about 1 minute to about 60 minutes. In some embodiments, the contacting step is carried out for a period of from about 10 minutes to about 30 minutes.

In some embodiments, maintaining said electrical potential between said polymer particles and or pharmaceutical agent particles and said stent comprises maintaining a voltage of from about 5 kvolts to about 100 kvolts. In some embodiments, maintaining said electrical potential between said polymer particles and or pharmaceutical agent particles and said stent comprises maintaining a voltage of from about 20 kvolts to about 30 kvolts.

Provided herein is a device prepared by a process comprising a method as described herein.

Provided herein is method of treating a subject comprising delivering a device as described herein in a body lumen of the subject.

Provided herein is a method of treating a subject comprising delivering in the body of the subject a device comprising: a stent, wherein the stent is formed from a material comprising the following percentages by weight: 0.05-0.15 C, 1.00-2.00 Mn, 0.040 Si, 0.030 P, 0.3 S, 19.00-21.00 Cr, 9.00-11.00 Ni, 14.00-16.00 W, 3.00 Fe, and Bal. Co; and a plurality of layers that form a laminate coating on said stent, wherein a first layer comprises a first bioabsorbable polymer, a second layer comprises a pharmaceutical agent, a third layer comprises a second bioabsorbable polymer, a fourth layer comprises the pharmaceutical agent, and a fifth layer comprises a third bioabsorbable polymer, wherein the pharmaceutical agent is selected from rapamycin, a prodrug, a derivative, an analog, a hydrate, an ester, and a salt thereof, wherein at least a portion of the pharmaceutical agent is in crystalline form, and wherein at least one of said first polymer, second polymer and third polymer comprises a PLGA copolymer.

In some embodiments, the device has a pharmaceutical agent content of from about 0.5 µg/mm to about 20 µg/mm. In some embodiments, the device has a pharmaceutical agent content of from about 8 µg/mm to about 12 µg/mm. In some embodiments, the device has a pharmaceutical agent content of from about 100 µg to about 160 µg. In some embodiments, the device has a pharmaceutical agent content of from about 120 µg to about 150 µg.

In some embodiments, the device has an initial pharmaceutical agent amount and the amount of pharmaceutical agent delivered by said device to vessel wall tissue of said subject is higher than the amount of pharmaceutical agent delivered by a conventional drug eluting stent having the same initial pharmaceutical agent content as the initial pharmaceutical agent content of said device. In some embodiments, the amount of pharmaceutical agent delivered by said device to vessel wall tissue of said subject is at least 25% more that the amount of pharmaceutical agent delivered to vessel wall tissue of said subject by said conventional drug eluting stent. In some embodiments, the method comprises treating restenosis in a blood vessel of said the subject. In some embodiments, the subject is selected from a pig, a rabbit and a human.

Figure 11:
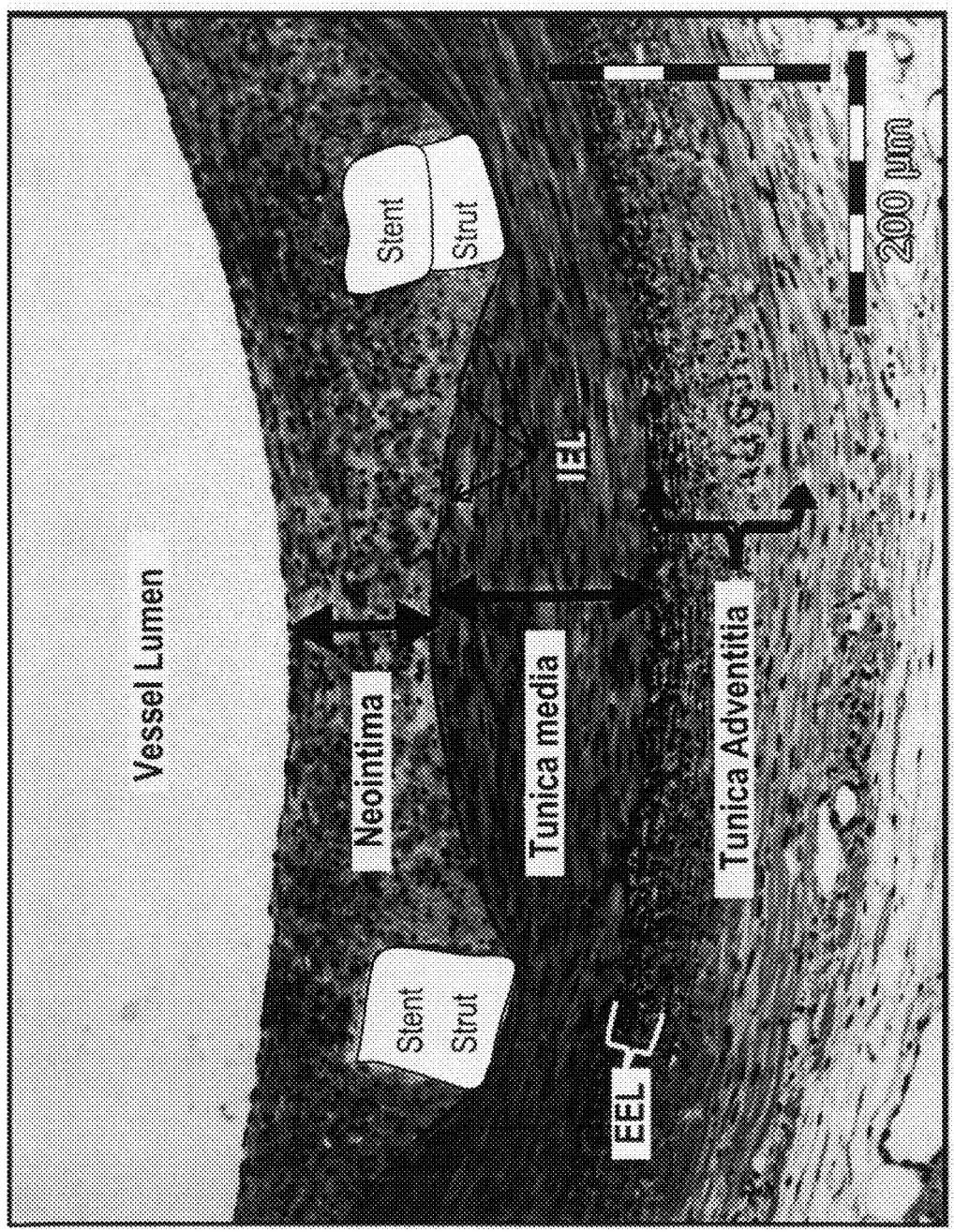
FIG. 11: Vessel wall tissue showing various elements near the lumen.

"Vessel wall tissue" as used herein is shown in FIG. 11, which depicts the tissue surrounding the lumen of a vessel, including the endothelium, neointima, tunica media, IEL (internal elastic lamina), EEL (external elastic lamina), and the tunica adventitia.

Provided herein is a device comprising: a stent; and a plurality of layers on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof, wherein said device provides an in vitro pharmaceutical agent elution profile wherein said elution profile shows about 5% to about 25% of pharmaceutical agent is eluted one day after the device is contacted with elution media; 15% to about 45% of pharmaceutical agent is eluted 7 days after the device is contacted with elution media; about 25% to about 60% of pharmaceutical agent is eluted 14 days after the device is contacted with elution media; about 35% to about 70% of pharmaceutical agent is eluted 21 days after the device is contacted with elution media; and about 40% to about 100% of pharmaceutical agent is eluted 28 days after the device is contacted with elution media.

Provided herein is a device comprising a stent; and a plurality of layers on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof, wherein said device provides an in vitro pharmaceutical agent elution profile wherein said elution profile shows about 7% to about 15% of pharmaceutical agent is eluted one day after the device is contacted with elution media; 25% to about 35% of pharmaceutical agent is eluted 7 days after the device is contacted with elution media; about 35% to about 55% of pharmaceutical agent is eluted 14 days after the device is contacted with elution media; about 45% to about 60% of pharmaceutical agent is eluted 21 days after the device is contacted with elution media; and about 50% to about 70% of pharmaceutical agent is eluted 28 days after the device is contacted with elution media.

Provided herein is a device comprising a stent; and a plurality of layers on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof, wherein said device provides an in vitro pharmaceutical agent elution profile wherein said elution profile shows at least 5% of pharmaceutical agent is eluted one day after the device is contacted with elution media; at least 15% of pharmaceutical agent is eluted 7 days after the device is contacted with elution media; at least 25% of pharmaceutical agent is eluted 14 days after the device is contacted with elution media; at least 30% of pharmaceutical agent is eluted 21 days after the device is contacted with elution media; at least 40% of pharmaceutical agent is eluted 28 days after the device is contacted with elution media.

Provided herein is a device comprising a stent; and a plurality of layers on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof, wherein said device provides an in vitro pharmaceutical agent elution profile wherein said elution profile shows about 10% of pharmaceutical agent is eluted one day after the device is contacted with elution media; about 30% of pharmaceutical agent is eluted 7 days after the device is contacted with elution media; about 45% of pharmaceutical agent is eluted 14 days after the device is contacted with elution media; about 50% of pharmaceutical agent is eluted 21 days after the device is contacted with elution media; about 60% of pharmaceutical agent is eluted 28 days after the device is contacted with elution media.

Provided herein is a device comprising a stent; and a plurality of layers on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof, wherein said device provides an in vitro pharmaceutical agent elution profile wherein said elution profile shows about 10% to about 75% of pharmaceutical agent is eluted at week 1 after the device is contacted with elution media, about 25% to about 85% of pharmaceutical agent is eluted at week 2 and about 50% to about 100% of pharmaceutical agent is eluted at week 10.

Figure 5:
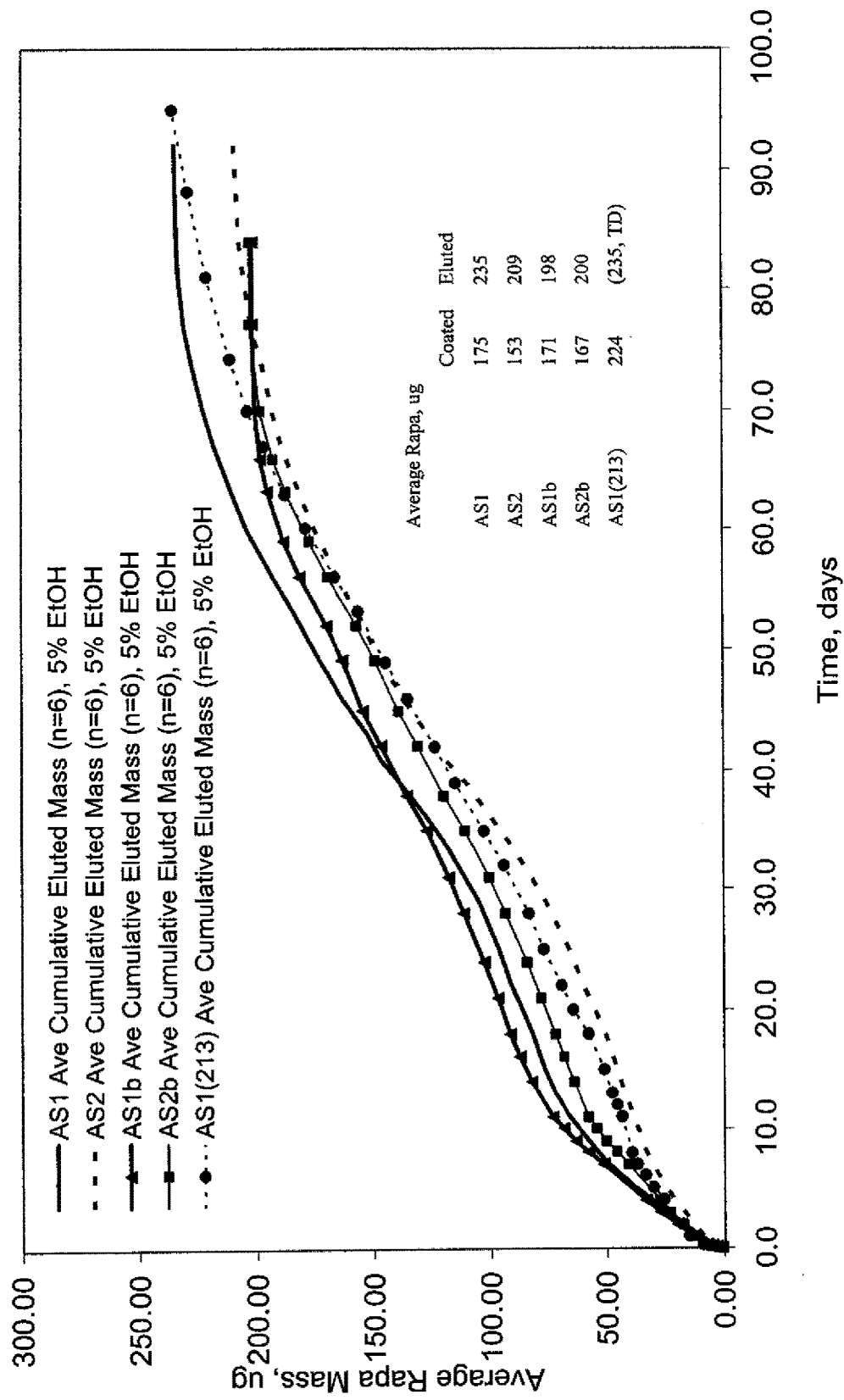
FIG. 5: Rapamycin Elution Profile of coated stents (PLGA/Rapamycin coatings) where the elution profile was determined by a static elution media of 5% EtOH/water, pH 7.4, 37° C. via UV-Vis test method as described in Example 11b of coated stents described therein.
Figure 6:
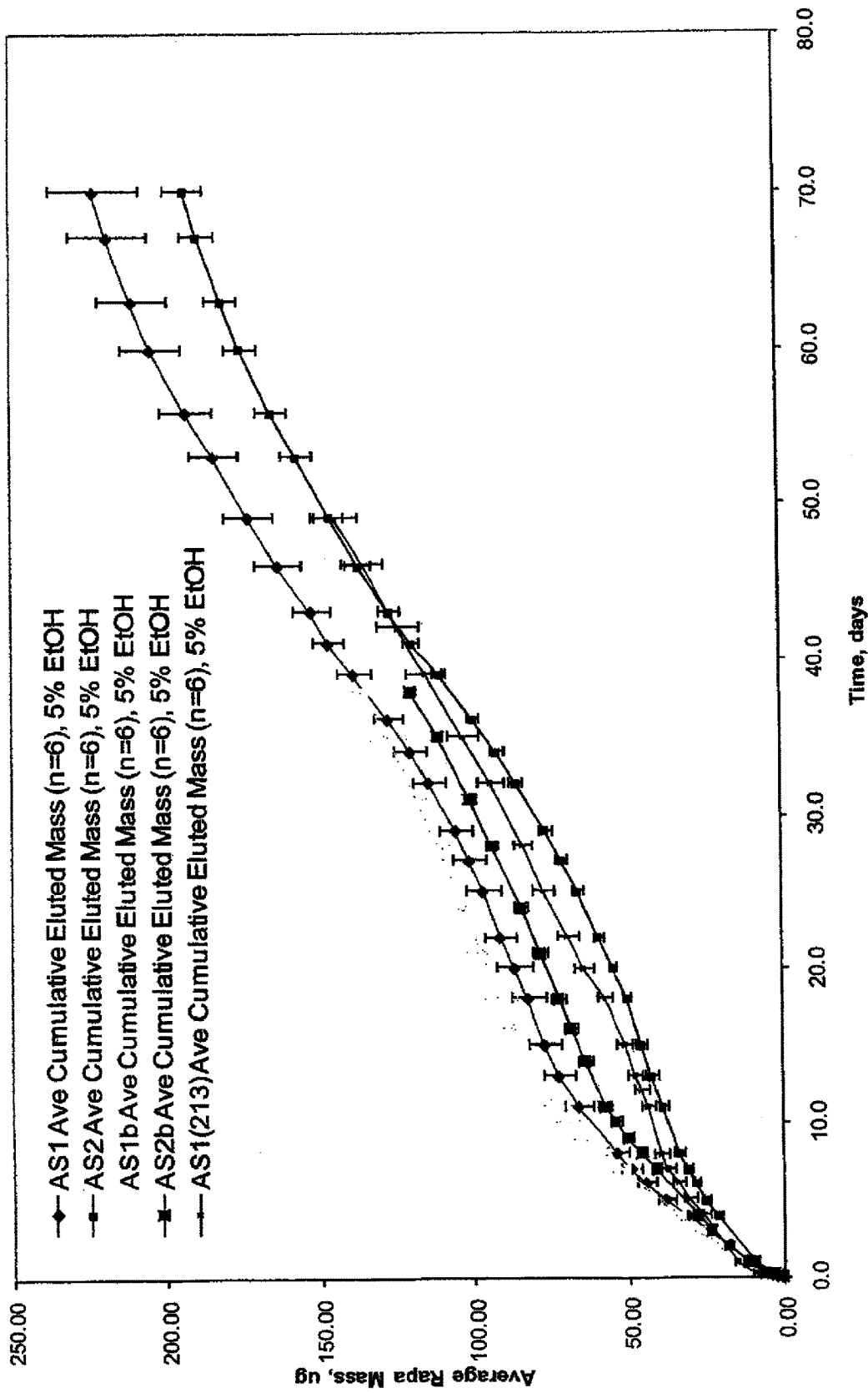
FIG. 6: Rapamycin Elution Profile of coated stents (PLGA/Rapamycin coatings) where the elution profile was determined by static elution media of 5% EtOH/water, pH 7.4, 37° C. via a UV-Vis test method as described in Example 11b of coated stents described therein.
Figure 7:
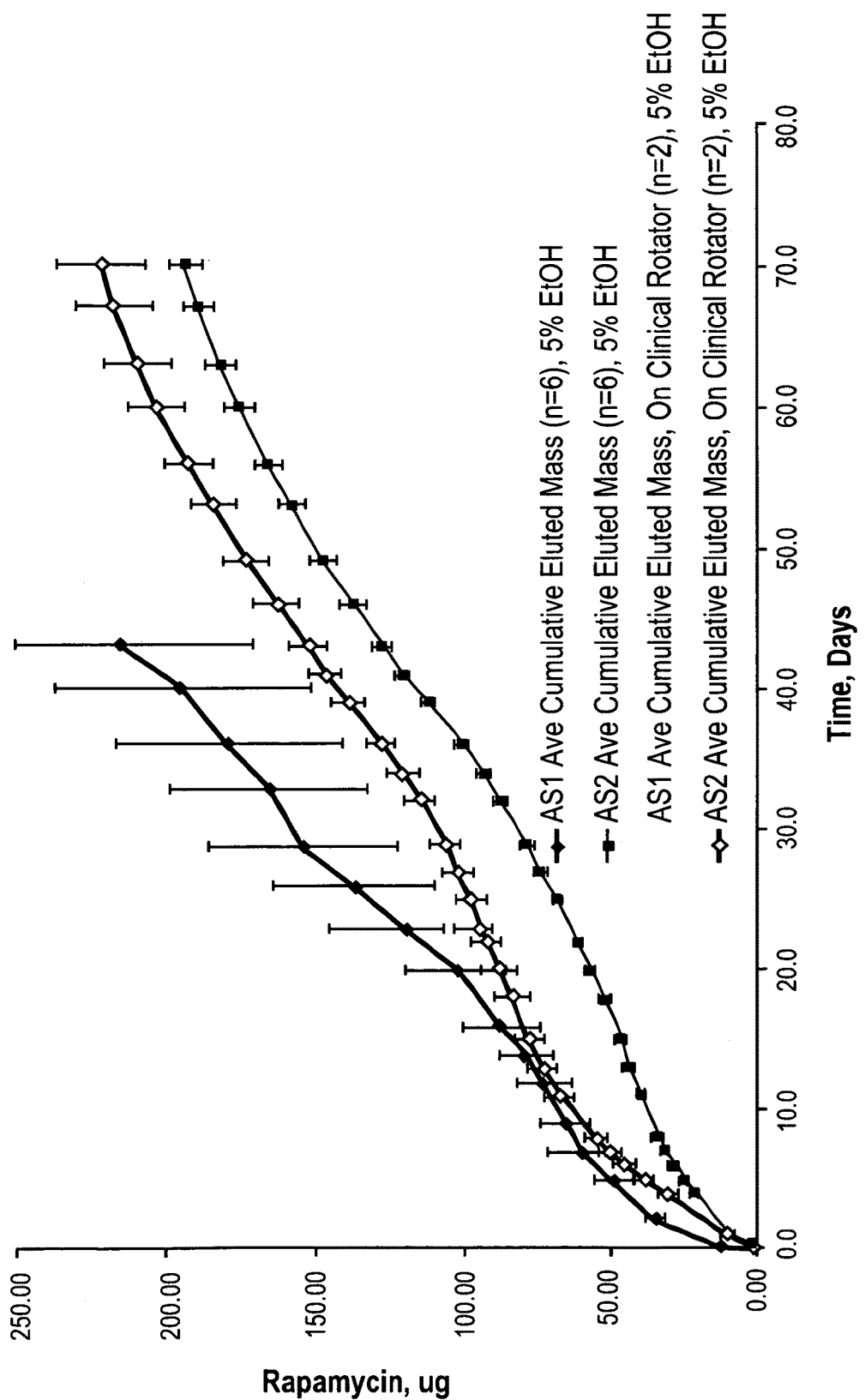
FIG. 7: Rapamycin Elution Rates of coated stents (PLGA/Rapamycin coatings) where the static elution profile was compared with agitated elution profile by an elution media of 5% EtOH/water, pH 7.4, 37° C. via a UV-Vis test method a UV-Vis test method as described in Example 11b of coated stents described therein.
Figure 8:
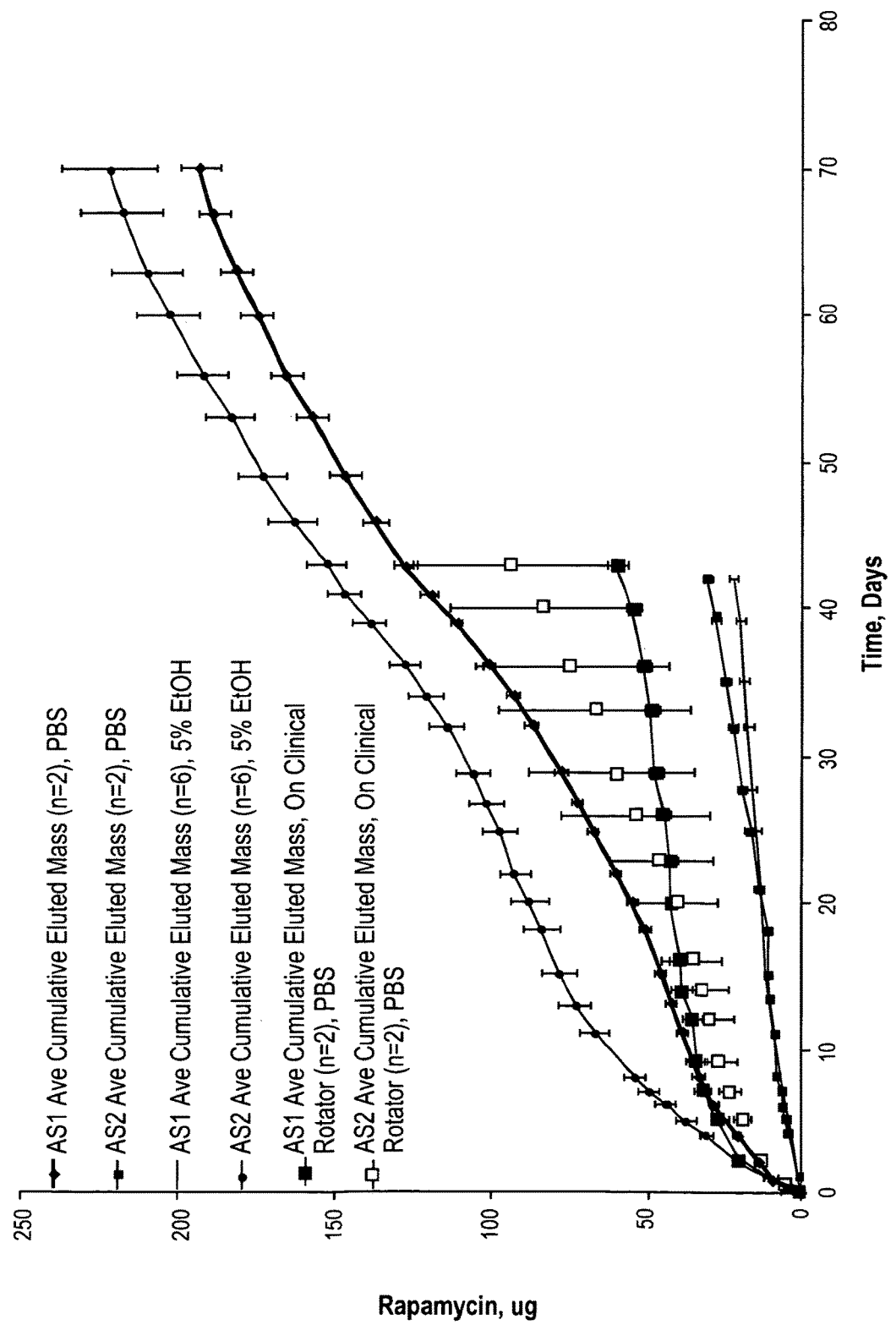
FIG. 8 Rapamycin Elution Profile of coated stents (PLGA/Rapamycin coatings) where the elution profile by 5% EtOH/water, pH 7.4, 37° C. elution buffer was compare with the elution profile using phosphate buffer saline pH 7.4, 37° C.; both profiles were determined by a UV-Vis test method as described in Example 11b of coated stents described therein.

Provided herein is a device comprising: a stent; and a plurality of layers on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof, wherein said device provides an in vitro pharmaceutical agent elution profile shown in FIG. 5.

In some embodiments, the in vitro pharmaceutical agent elution profile is determined by a procedure comprising: (i) contacting the device with an elution media comprising 5% ethanol by volume wherein the pH of the media is about 7.4 and wherein the device is contacted with the elution media at a temperature of about 37° C.; (ii) optionally agitating the elution media during the contacting step in (i); (iii) removing the elution media at designated time points; and (iv) assaying the removed elution media to determine pharmaceutical agent content.

In some embodiments, the in vitro pharmaceutical agent elution profile is determined by a procedure comprising: (i) contacting the device with an elution media comprising 5% ethanol by volume, wherein the pH of the media is about 7.4 and wherein the device is contacted with the elution media at a temperature of about 37° C.; (ii) optionally agitating the elution media during the contacting step in (i); (iii) removing said device from the elution media at designated time points; and (iv) assaying the elution media to determine pharmaceutical agent content.

In some embodiments, the in vitro pharmaceutical agent elution profile is determined in the absence of agitation.

In some embodiments, the procedure further comprises: (v) determining polymer weight loss by comparing the weight of the device before and after the contacting step and adjusting for the amount of pharmaceutical agent eluted into the elution media as determined in step (iv). In some embodiments, step (v) shows at least 50% of polymer is released into the media after the device is contacted with the media for 90 days or more. In some embodiments, step (v) shows at least 75% of polymer is released into the media after the device is contacted with the media for 90 days or more.

In some embodiments, step (v) shows at least 85% of polymer is released into the media after the device is contacted with the media for 90 days or more. In some embodiments, step (v) shows at least 50% of polymer is released into the media after the device is contacted with the media for about 90 days. In some embodiments, step (v) shows at least 75% of polymer is released into the media after the device is contacted with the media for about 90 days. In some embodiments, step (v) shows at least 85% of polymer is released into the media after the device is contacted with the media for about 90 days. In some embodiments, step (v) shows at least 95% of polymer is released into the media after the device is contacted with the media for about 90 days. In some embodiments, step (v) shows up to 100% of polymer is released into the media after the device is contacted with the media for about 90 days.

Provided herein is a device comprising: a stent; and a plurality of layers on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof, wherein said device provides an in vitro pharmaceutical agent elution profile wherein said elution profile shows about 1% to about 35% of pharmaceutical agent is eluted one hour after the device is contacted with elution media; 5% to about 45% of pharmaceutical agent is eluted 3 hours after the device is contacted with elution media; about 30% to about 70% of pharmaceutical agent is eluted 1 day after the device is contacted with elution media; about 40% to about 80% of pharmaceutical agent is eluted 3 days after the device is contacted with elution media; about 50% to about 90% of pharmaceutical agent is eluted 10 days after the device is contacted with elution media about 55% to about 95% of pharmaceutical agent is eluted 15 days after the device is contacted with elution media; and about 60% to about 100% of pharmaceutical agent is eluted 20 days after the device is contacted with elution media.

Provided herein is a device comprising: a stent; and a plurality of layers on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof, wherein said device provides an in vitro pharmaceutical agent elution profile wherein said elution profile shows about 5% to about 25% of pharmaceutical agent is eluted one hour after the device is contacted with elution media; 5% to about 35% of pharmaceutical agent is eluted 3 hours after the device is contacted with elution media; about 30% to about 65% of pharmaceutical agent is eluted 1 day after the device is contacted with elution media; about 45% to about 70% of pharmaceutical agent is eluted 3 days after the device is contacted with elution media; about 55% to about 85% of pharmaceutical agent is eluted 10 days after the device is contacted with elution media about 65% to about 85% of pharmaceutical agent is eluted 15 days after the device is contacted with elution media; and about 75% to about 100% of pharmaceutical agent is eluted 20 days after the device is contacted with elution media.

Figure 9:
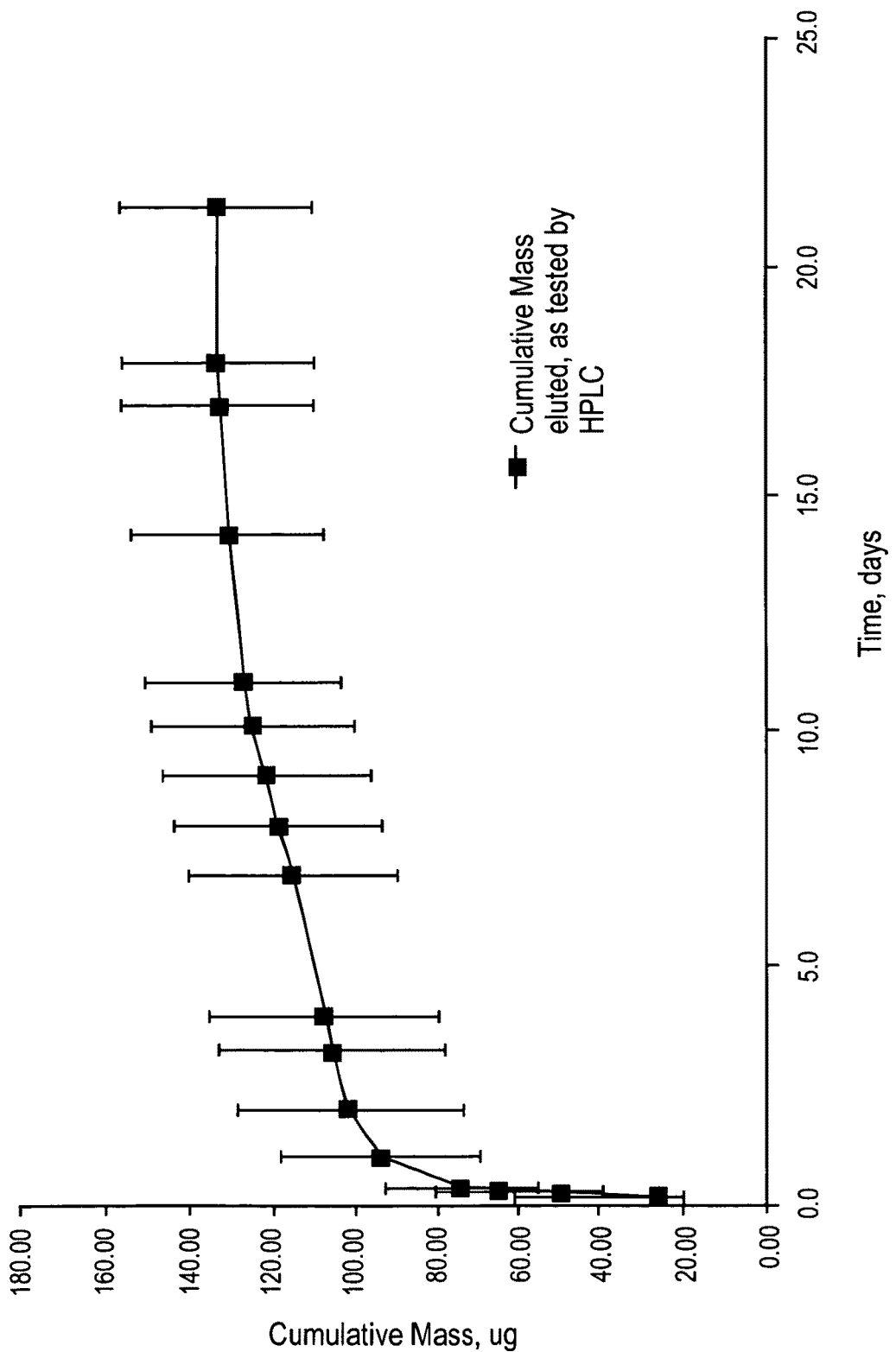
FIG. 9: Rapamycin Elution Profile of coated stents (PLGA/Rapamycin coatings) where the elution profile was determined by a 20% EtOH/phosphate buffered saline, pH 7.4, 37° C. elution buffer and a HPLC test method as described in Example 11c described therein, wherein the elution time (x-axis) is expressed linearly.

Provided herein is a device comprising: a stent; and a plurality of layers on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof, wherein said device provides an in vitro pharmaceutical agent elution profile shown in FIG. 9.

In some embodiments, the in vitro pharmaceutical agent elution profile is determined by a procedure comprising: (i) contacting the device with an elution media comprising ethanol and phosphate buffered saline wherein the pH of the media is about 7.4 and wherein the device is contacted with the elution media at a temperature of about 37° C.; (ii) optionally agitating the elution media during the contacting step in (i); (iii) removing the elution media at designated time points; and (iv) assaying the removed elution media to determine pharmaceutical agent content.

In some embodiments, the in vitro pharmaceutical agent elution profile is determined by a procedure comprising: (i) contacting the device with an elution media comprising ethanol and phosphate buffered saline wherein the pH of the media is about 7.4 and wherein the device is contacted with the elution media at a temperature of about 37° C.; (ii) optionally agitating the elution media during the contacting step in (i); (iii) removing said device from the elution media at designated time points; and (iv) assaying the elution media to determine pharmaceutical agent content.

In some embodiments, the in vitro pharmaceutical agent elution profile is determined in the absence of agitation.

In some embodiments, the procedure further comprises: (v) determining polymer weight loss by comparing the weight of the device before and after the contacting step and adjusting for the amount of pharmaceutical agent eluted into the elution media as determined in step iv. The device of claim 160 wherein step v shows at least 50% of polymer is released into the media after the device is contacted with the media for 90 days or more.

In some embodiments, step (v) shows at least 75% of polymer is released into the media after the device is contacted with the media for 90 days or more. In some embodiments, step (v) shows at least 85% of polymer is released into the media after the device is contacted with the media for 90 days or more. In some embodiments, step (v) shows at least 50% of polymer is released into the media after the device is contacted with the media for about 90 days. In some embodiments, step (v) shows at least 75% of polymer is released into the media after the device is contacted with the media for about 90 days. In some embodiments, step (v) shows at least 85% of polymer is released into the media after the device is contacted with the media for about 90 days. In some embodiments, step (v) shows at least 95% of polymer is released into the media after the device is contacted with the media for about 90 days.

Provided herein is a device comprising: a stent; and a coating comprising a pharmaceutical agent selected from rapamycin, a prodrug, a derivative, ester and a salt thereof and a polymer wherein the coating has an initial pharmaceutical agent amount; wherein when said device is delivered in a body lumen of a subject the pharmaceutical agent is delivered in vessel wall tissue of the subject as follows: from about 0.1% to about 35% of the initial pharmaceutical agent amount is delivered in the subject's vessel wall tissue one week after the device is delivered in the subject's body; and from about 0.5% to about 50% of the initial pharmaceutical agent amount is delivered in the subject's vessel wall tissue two weeks after the device is delivered in the subject's body.

In some embodiments, the amount delivered to the subject's lumen is obtained by adding pharmaceutical agent present alone in said subject's vessel wall tissue and pharmaceutical agent delivered together with said polymer. In some embodiments, the subject is a human.

In some embodiments, subject is a pig and the amount of pharmaceutical agent delivered in the subject's vessel wall tissue is determined as follows: delivering the device in the pig's blood vessel lumen; euthanizing the pig at predetermined period of time after the device is delivered in the pig's blood vessel lumen and explanting the device; measuring the amount of pharmaceutical agent delivered in the vessel wall tissue.

Provided herein, a device comprising: a stent; and a coating comprising a pharmaceutical agent selected from rapamycin, a prodrug, a derivative, an analog, a hydrate, an ester, and a salt thereof and a bioabsorbable polymer wherein the coating has an initial pharmaceutical agent content of about 1 µg/mm to about 15 µg/mm; wherein said device provides an area under a curve (AUC) for content of pharmaceutical agent delivered in the vessel wall tissue of a subject over time as follows: from about 0.05 (µg/mm)*day to about 1 (µg/mm)*day when AUC is calculated from the time the device is delivered in a subject's body to one day after the device is delivered in the subject's body; from about 5 (µg/mm)*day to about 10 (µg/mm)*day when AUC is calculated starting after the first week the device is delivered in the subject's body through the second week after the device is delivered in the subject's body; from about 10 (µg/mm)*day to about 20 (µg/mm)*day when AUC is calculated starting after the second week the device is delivered in the subject's body through the fourth week after the device is delivered in the subject's body; and an AUC last of from about 40 (µg/mm)*day to about 60 (µg/mm)*day.

Provided herein is a device comprising: a stent; and a coating comprising a pharmaceutical agent selected from rapamycin, a prodrug, a derivative, an analog, a hydrate, an ester, and a salt thereof and a bioabsorbable polymer wherein the coating has an initial polymer amount; wherein when said device is delivered in a body lumen of a subject about 75% of polymer is released from the device 90 days or more after the device is delivered in the body lumen of the subject.

Provided herein is a device comprising: a stent; and a coating comprising a pharmaceutical agent selected from rapamycin, a prodrug, a derivative, an analog, a hydrate, an ester, and a salt thereof and a bioabsorbable polymer wherein the coating has an initial polymer amount; wherein when said device is delivered in a body lumen of a subject about 85% of polymer is released from the device about 90 days after the device is delivered in the body lumen of the subject.

Provided herein is a device comprising: a stent; and a coating comprising a pharmaceutical agent selected from rapamycin, a prodrug, a derivative, an analog, a hydrate, an ester, and a salt thereof and a bioabsorbable polymer wherein the coating has an initial polymer amount; wherein when said device is delivered in a body lumen of a subject at least about 75% of polymer is released from the device about 90 days after the device is delivered in the body lumen of the subject.

Provided herein is a device comprising: a stent; and a coating comprising a pharmaceutical agent selected from rapamycin, a prodrug, a derivative, an analog, a hydrate, an ester, and a salt thereof and a bioabsorbable polymer wherein the coating has an initial polymer amount; wherein when said device is delivered in a body lumen of a subject about 100% of polymer is released from the device about 90 days after the device is delivered in the body lumen of the subject.

In some embodiments, the subject is a human. In some embodiments, the subject is a pig and the amount of polymer released from the device is determined as follows: delivering the device in the pig's blood vessel lumen; euthanizing the pig at predetermined period of time after the device is delivered in the pig's blood vessel lumen and explanting the device; and measuring the amount of polymer released from the device.

In some embodiments, measuring the amount of polymer released from the device comprises LC/MS/MS measurements. In some embodiments, measuring the amount released from the device comprises weight loss measurement. In some embodiments, weight loss measurement comprises measuring an amount of polymer remaining in the device and subtracting said remaining amount from the initial amount present in the device prior to delivering the device to the pig's blood vessel lumen.

Provided herein is a device comprising a stent; and a plurality of layers on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof, wherein the device has an initial pharmaceutical agent content of about 1 µg/mm to about 15

μg/mm; wherein when said device is delivered in a body lumen of a subject said device provides a blood concentration within 60 minutes from delivery of said device to the subject's body lumen that is from about 1% to about 50% of the blood concentration provided by a conventional drug eluting stent delivered to the subject under similar conditions.

Provided herein is a device comprising a stent; and a plurality of layers on said stent; wherein at least one of said layers comprises a bioabsorbable polymer and at least one of said layers comprises a pharmaceutical agent selected from rapamycin, a prodrug, a derivative, an analog, a hydrate, an ester, and a salt thereof, wherein the device has an initial pharmaceutical agent content of about 1 μg/mm to about 15 μg/mm; wherein when said device is delivered in a body lumen of a subject said device provides a blood concentration within 60 minutes from delivery of said device to the subject's body lumen that is from about 11% to about 20% of the blood concentration provided by a conventional drug eluting stent delivered to the subject under similar conditions.

Provided herein is a device comprising a stent; and coating on said stent; wherein said coating comprises a bioabsorbable polymer and a pharmaceutical agent selected from rapamycin, a prodrug, a derivative, an analog, a hydrate, an ester, and a salt thereof, wherein the device has an initial pharmaceutical agent content of about 1 μg/mm to about 15 μg/mm; wherein when said device is delivered in a body lumen of a subject said device provides about the same blood concentration over the first 72 hours from delivery of said device to the subject's body lumen.

In some embodiments, the blood concentration during the first 72 hours from delivery of said device to the subject's body lumen remains between 75% and 125% of an average blood concentration calculated over the first 72 hours from delivery of said device to the subject's body lumen. In some embodiments, the average blood concentration is from about 0.05 ng/mL to about 0.5 ng/mL. In some embodiments, the device provides an AUC for blood concentration over a period of 72 hours after the device is delivered to the subject's body lumen of from about 2 (ng/mL)*hour to about 20 (ng/mL)*hour.

In some embodiments, the device provides an AUC for blood concentration over a period of 72 hours after the device is delivered to the subject's body lumen of from about 4 (ng/mL)*hour to about 10 (ng/mL)*hour. In some embodiments, at least part of pharmaceutical agent is in crystalline form. In some embodiments, the pharmaceutical agent is provided at a reduced dose compared to a conventional drug eluting stent. In some embodiments, at least one of said layers comprises a PLGA bioabsorbable polymer.

In some embodiments, the pharmaceutical agent in said device has a shelf stability of at least 12 months.

In some embodiments, the device provides an in vitro pharmaceutical agent elution profile comparable to first order kinetics.

In some embodiments, the device provides pharmaceutical agent tissue concentration of at least twice the tissue concentration provided by a conventional stent. In some embodiments, the device provides a pharmaceutical agent tissue concentration of at least 5 times greater than the tissue concentration provided by a conventional stent. In some embodiments, the device provides a pharmaceutical agent tissue concentration of at least 25 times greater than the tissue concentration provided by a conventional stent. In some embodiments, the device provides a pharmaceutical agent tissue concentration of at least 100 times greater than the tissue concentration provided by a conventional stent.

In some embodiments, about 50% of said polymer is resorbed within 45-90 days after an angioplasty procedure wherein said device is delivered in a subject's body. In some embodiments, about 75% of said polymer is resorbed within 45-90 days after an angioplasty procedure wherein said device is delivered in a subject's body. In some embodiments, about 95% of said polymer is resorbed within 45-90 days after an angioplasty procedure wherein said device is delivered in a subject's body.

In some embodiments, 99% of said polymer is resorbed within 45-90 days after an angioplasty procedure wherein said device is delivered in a subject's body.

In some embodiments, the device provides reduced inflammation over the course of polymer resorbtion compared to a conventional stent.

Provided herein is a method of treating a subject comprising delivering a device as described herein in a body lumen.

Provided herein, is a method of treating a subject comprising delivering in the body of the subject a device comprising: a stent; and a coating comprising a pharmaceutical agent selected from rapamycin, a prodrug, a derivative, an analog, a hydrate, an ester, and a salt thereof and a polymer wherein the coating has an initial pharmaceutical agent amount; wherein said device is delivered in a body lumen of the subject and the pharmaceutical agent is delivered in vessel wall tissue of the subject as follows: i. from about 0.05% to about 35% of the initial pharmaceutical agent amount is delivered in the subject's vessel wall tissue one week after the device is delivered in the subject's body; and ii. from about 0.5% to about 50% of the initial pharmaceutical agent amount is delivered in the subject's vessel wall tissue two weeks after the device is delivered in the subject's body.

In some embodiments, the device provides reduced inflammation over the course of polymer resorbtion.

In some embodiments, the presence of crystallinity is shown by at least one of XRD, Raman Spectroscopy, Infrared analytical methods, and DSC.

In some embodiments, the coating on an abluminal surface of said stent has a greater thickness than coating on a luminal surface of said stent. In some embodiments, the ratio of coating on the abluminal surface to coating on the luminal surface of the device is 80:20. In some embodiments, the ratio of coating on the abluminal surface to coating on the luminal surface of the device is 75:25. In some embodiments, the ratio of coating on the abluminal surface to coating on the luminal surface of the device is 70:30. In some embodiments, the ratio of coating on the abluminal surface to coating on the luminal surface of the device is 60:40.

In some embodiments, the stent is a coronary stent, a vascular stent, a peripheral stent, billiarty stent, and intercranial stent.

EXAMPLES

The following examples are provided to illustrate selected embodiments. They should not be considered as limiting the scope of the invention, but merely as being illustrative and representative thereof. For each example listed below, multiple analytical techniques may be provided. Any single technique of the multiple techniques listed may be sufficient to show the parameter and/or characteristic being tested, or any combination of techniques may be used to show such parameter and/or characteristic. Those skilled in the art will be familiar with a wide range of analytical techniques for the characterization of drug/polymer coatings. Techniques presented here, but not limited to, may be used to additionally and/or alternatively characterize specific properties of the coatings with variations and adjustments employed which would be obvious to those skilled in the art.

Sample Preparation

Generally speaking, coatings on stents, on coupons, or samples prepared for in-vivo models are prepared as below. Nevertheless, modifications for a given analytical method are presented within the examples shown, and/or would be obvious to one having skill in the art. Thus, numerous variations, changes, and substitutions will now occur to those skilled in the art without departing from the invention. It should be understood that various alternatives to the embodiments of the invention described herein and examples provided may be employed in practicing the invention and showing the parameters and/or characteristics described.

Coatings on Stents

Coated stents as described herein and/or made by a method disclosed herein are prepared. In some examples, the coated stents have a targeted thickness of ~15 microns (~5 microns of active agent). In some examples, the coating process is PDPDP (Polymer, sinter, Drug, Polymer, sinter, Drug, Polymer, sinter) using deposition of drug in dry powder form and deposition of polymer particles by RESS methods and equipment described herein. In the illustrations below, resulting coated stents may have a 3-layer coating comprising polymer (for example, PLGA) in the first layer, drug (for example, rapamycin) in a second layer and polymer in the third layer, where a portion of the third layer is substantially drug free (e.g. a sub-layer within the third layer having a thickness equal to a fraction of the thickness of the third layer). As described layer, the middle layer (or drug layer) may be overlapping with one or both first (polymer) and third (polymer) layer. The overlap between the drug layer and the polymer layers is defined by extension of polymer material into physical space largely occupied by the drug. The overlap between the drug and polymer layers may relate to partial packing of the drug particles during the formation of the drug layer. When crystal drug particles are deposited on top of the first polymer layer, voids and or gaps may remain between dry crystal particles. The voids and gaps are available to be occupied by particles deposited during the formation of the third (polymer) layer. Some of the particles from the third (polymer) layer may rest in the vicinity of drug particles in the second (drug) layer. When the sintering step is completed for the third (polymer) layer, the third polymer layer particles fuse to form a continuous film that forms the third (polymer) layer. In some embodiments, the third (polymer) layer however will have a portion along the longitudinal axis of the stent whereby the portion is free of contacts between polymer material and drug particles. The portion of the third layer that is substantially of contact with drug particles can be as thin as 1 nanometer.

Polymer-coated stents having coatings comprising polymer but no drug are made by a method disclosed herein and are prepared having a targeted thickness of, for example, 5 microns. An example coating process is PPP(PLGA, sinter, PLGA, sinter, PLGA, sinter) using RESS methods and equipment described herein. These polymer-coated stents may be used as control samples in some of the examples, infra.

In some examples, the stents are made of a cobalt-chromium alloy and are 5 to 50 mm in length, preferably 10-20 mm in length, with struts of thickness between 20 and 100 microns, preferably 50-70 microns, measuring from an abluminal surface to a luminal surface, or measuring from a side wall to a side wall. In some examples, the stent may be cut lengthwise and opened to lay flat be visualized and/or assayed using the particular analytical technique provided.

The coating may be removed (for example, for analysis of a coating band and/or coating on a strut, and/or coating on the abluminal surface of a flattened stent) by scraping the coating off using a scalpel, knife or other sharp tool. This coating may be sliced into sections which may be turned 90 degrees and visualized using the surface composition techniques presented herein or other techniques known in the art for surface composition analysis (or other characteristics, such as crystallinity, for example). In this way, what was an analysis of coating composition through a depth when the coating was on the stent or as removed from the stent (i.e. a depth from the abluminal surface of the coating to the surface of the removed coating that once contacted the strut or a portion thereof), becomes a surface analysis of the coating which can, for example, show the layers in the slice of coating, at much higher resolution. Coating removed from the stent may be treated the same way, and assayed, visualized, and/or characterized as presented herein using the techniques described and/or other techniques known to a person of skill in the art.

Coatings on Coupons

In some examples, samples comprise coupons of glass, metal, e.g. cobalt-chromium, or another substance that are prepared with coatings as described herein, with a plurality of layers as described herein, and/or made by a method disclosed herein. In some examples, the coatings comprise polymer. In some examples, the coatings comprise polymer and active agent. In some examples, the coated coupons are prepared having a targeted thickness of ~10 microns (with 5 microns of active agent), and have coating layers as described for the coated stent samples, infra.

Sample Preparation for In-Vivo Models

Devices comprising stents having coatings disclosed herein are implanted in the porcine coronary arteries of pigs (domestic swine, juvenile farm pigs, or Yucatan miniature swine). Porcine coronary stenting is exploited herein since such model yields results that are comparable to other investigations assaying neointimal hyperplasia in human subjects. The stents are expanded to a 1:1.1 balloon:artery ratio. At multiple time points, animals are euthanized (e.g. t=1 day, 7 days, 14 days, 21 days, and 28 days), the stents are explanted, and assayed.

Devices comprising stents having coatings disclosed herein alternatively are implanted in the common iliac arteries of New Zealand white rabbits. The stents are expanded to a 1:1.1 balloon:artery ratio. At multiple time points, animals are euthanized (e.g., t=1 day, 7 days, 14 days, 21 days, and 28 days), the stents are explanted, and assayed.

Example 1

This example illustrates embodiments that provide a coated coronary stent, comprising: a stent framework and a rapamycin-polymer coating wherein at least part of rapamycin is in crystalline form and the rapamycin-polymer coating comprises one or more resorbable polymers.

In these experiments two different polymers were employed:
Polymer A: ~50:50 PLGA-Ester End Group, MW~19 kD, degradation rate ~1-2 months Polymer B: ~50:50 PLGA-Carboxylate End Group, MW~10 kD, degradation rate ~28 days Metal stents were coated as follows:

AS1: Polymer A/Rapamycin/Polymer A/Rapamycin/Polymer A

AS2: Polymer A/Rapamycin/Polymer A/Rapamycin/Polymer B

AS1 (B) or AS1(213): Polymer B/Rapamycin/Polymer B/Rapamycin/Polymer B

AS1b: Polymer A/Rapamycin/Polymer A/Rapamycin/Polymer A

AS2b: Polymer A/Rapamycin/Polymer A/Rapamycin/Polymer B

Example 2: Crystallinity

The presence and or quantification of the Active agent crystallinity can be determined from a number of characterization methods known in the art, but not limited to, XRPD, vibrational spectroscopy (FTIR, NIR, Raman), polarized optical microscopy, calorimetry, thermal analysis and solid-state NMR.

X-Ray Diffraction to Determine the Presence and/or Quantification of Active Agent Crystallinity Active agent and polymer coated proxy substrates are prepared using 316L stainless steel coupons for X-ray powder diffraction (XRPD) measurements to determine the presence of crystallinity of the active agent. The coating on the coupons is equivalent to the coating on the stents described herein. Coupons of other materials described herein, such as cobalt-chromium alloys, may be similarly prepared and tested. Likewise, substrates such as stents, or other medical devices described herein may be prepared and tested. Where a coated stent is tested, the stent may be cut lengthwise and opened to lay flat in a sample holder.

For example XRPD analyses are performed using an X-ray powder diffractometer (for example, a Bruker D8 Advance X-ray diffractometer) using Cu Kα radiation. Diffractograms are typically collected between 2 and 40 degrees 2 theta. Where required low background XRPD sample holders are employed to minimize background noise.

The diffractograms of the deposited active agent are compared with diffractograms of known crystallized active agents, for example micronized crystalline sirolimus in powder form. XRPD patterns of crystalline forms show strong diffraction peaks whereas amorphous show diffuse and non-distinct patterns. Crystallinity is shown in arbitrary Intensity units.

A related analytical technique which may also be used to provide crystallinity detection is wide angle scattering of radiation (e.g.; Wide Anle X-ray Scattering or WAXS), for example, as described in F. Unger, et al., "Poly(ethylene carbonate): A thermoelastic and biodegradable biomaterial for drug eluting stent coatings?" *Journal of Controlled Release*, Volume 117, Issue 3, 312-321 (2007) for which the technique and variations of the technique specific to a particular sample would be obvious to one of skill in the art.

Raman Spectroscopy

Raman spectroscopy, a vibrational spectroscopy technique, can be useful, for example, in chemical identification, characterization of molecular structures, effects of bonding, identification of solid state form, environment and stress on a sample. Raman spectra can be collected from a very small volume (<1 μm$^3$); these spectra allow the identification of species present in that volume. Spatially resolved chemical information, by mapping or imaging, terms often used interchangeably, can be achieved by Raman microscopy.

Raman spectroscopy and other analytical techniques such as described in Balss, et al., "Quantitative spatial distribution of sirolimus and polymers in drug-eluting stents using confocal Raman microscopy" *J. of Biomedical Materials Research Part A,* 258-270 (2007), incorporated in its entirety herein by reference, and/or described in Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference may be used.

For example, to test a sample using Raman microscopy and in particular confocal Raman microscopy, it is understood that to get appropriate Raman high resolution spectra sufficient acquisition time, laser power, laser wavelength, sample step size and microscope objective need to be optimized. For example a sample (a coated stent) is prepared as described herein. Alternatively, a coated coupon could be tested in this method. Maps are taken on the coating using Raman microscopy. A WITec CRM 200 scanning confocal Raman microscope using a Nd:YAG laser at 532 nm is applied in the Raman imaging mode. The laser light is focused upon the sample using a 10× dry objective (numerical aperture 0.90), and the finely focused laser spot is scanned into the sample. As the laser scans the sample, over each 0.33 micron interval a Raman spectrum with high signal to noise is collected using 0.3 seconds of integration time. Each confocal cross-sectional image of the coatings displays a region 70 μm wide by 10 μm deep, and results from the gathering of 6300 spectra with a total imaging time of 32 min.

Multivariate analysis using reference spectra from samples of rapamycin (amorphous and crystalline) and polymer are used to deconvolve the spectral data sets, to provide chemical maps of the distribution.

Infrared (IR) Spectroscopy for In-Vitro Testing

Infrared (IR) Spectroscopy such as FTIR and ATR-IR are well utilized techniques that can be applied to show, for example, the quantitative drug content, the distribution of the drug in the sample coating, the quantitative polymer content in the coating, and the distribution of polymer in the coating. Infrared (IR) Spectroscopy such as FTIR and ATR-IR can similarly be used to show, for example, drug crystallinity. The following table (Table 1) lists the typical IR materials for various applications. These IR materials are used for IR windows, diluents or ATR crystals.

TABLE 1

| | MATERIAL | | | | | | |
|---|---|---|---|---|---|---|---|
| | NACL | KBR | CSI | AGCL | GE | ZNSE | DIAMOND |
| Transmission range (cm−1) | 40,000~625 | 40,000~400 | 40,000~200 | 25,000~360 | 5,500~625 | 20,000~454 | 40,000~2,500 & 1667-33 |
| Water sol (g/100 g, 25 C.) | 35.7 | 53.5 | 44.4 | Insol. | Insol. | Insol. | Insol. |

TABLE 1-continued

| | MATERIAL | | | | | | |
|---|---|---|---|---|---|---|---|
| | NACL | KBR | CSI | AGCL | GE | ZNSE | DIAMOND |
| Attacking materials | Wet Solvents | Wet Solvents | Wet Solvents | Ammonium Salts | H2SO4, aqua regin | Acids, strong alkalies, chlorinated solvents | K2Cr2Os, conc. H2SO4 |

In one test, a coupon of crystalline ZnSe is coated by the processes described herein, creating a PDPDP (Polymer, Drug, Polymer, Drug, Polymer) layered coating that is about 10 microns thick. The coated coupon is analyzed using FTIR. The resulting spectrum shows crystalline drug as determined by comparison to the spectrum obtained for the crystalline form of a drug standard (i.e. a reference spectrum).

Differential Scanning Calorimetry (DSC)

DSC can provide qualitative evidence of the crystallinity of the drug (e.g. rapamycin) using standard DSC techniques obvious to one of skilled in the art. Crystalline melt can be shown using this analytical method (e.g. rapamycin crystalline melting—at about 185 decrees C to 200 degrees C., and having a heat of fusion at or about 46.8 J/g). The heat of fusion decreases with the percent crystallinity. Thus, the degree of crystallinity could be determined relative to a pure sample, or versus a calibration curve created from a sample of amorphous drug spiked and tested by DSC with known amounts of crystalline drug. Presence (at least) of crystalline drug on a stent could be measured by removing (scraping or stripping) some drug from the stent and testing the coating using the DSC equipment for determining the melting temperature and the heat of fusion of the sample as compared to a known standard and/or standard curve.

Example 3: Determination of Bioabsorbability/Bioresorbability/Dissolution Rate of a Polymer Coating a Device Gel Permeation Chromatography In-vivo Weight Loss Determination Standard methods known in the art can be applied to determine polymer weight loss, for example gel permeation chromatography and other analytical techniques such as described in jackson et al., "Characterization of perivascular poly(lactic-co-glycolic acid) films containing paclitaxel" *Int. J. of Pharmaceutics,* 283:97-109 (2004), incorporated in its entirety herein by reference.

For example rabbit in vivo models as described above are euthanized at multiple time points (t=1 day, 2 days, 4 days, 7 days, 14 days, 21 days, 28 days, 35 days n=5 per time point). Alternatively, pig in vivo models as described above are euthanized at multiple time points (t=1 day, 2 days, 4 days, 7 days, 14 days, 21 days, 28 days, 35 days n=5 per time point). The stents are explanted, and dried down at 30° C. under a stream of gas to complete dryness. A stent that has not been implanted in the animal is used as a control for no loss of polymer.

The remaining polymer on the explanted stents is removed using a solubilizing solvent (for example chloroform). The solutions containing the released polymers for each time point are filtered. Subsequent GPC analysis is used for quantification of the amount of polymer remaining in the stent at each explant time point. The system, for example, comprises a Shimadzu LC-10 AD HPLC pump, a Shimadzu RID-6A refractive index detector coupled to a 50 Å Hewlett Packard Pl-Gel column. The polymer components are detected by refractive index detection and the peak areas are used to determine the amount of polymer remaining in the stents at the explant time point. A calibration graph of log molecular weight versus retention time is established for the 50 A Pl-Gel column using polystyrene standards with molecular weights of 300, 600, 1.4 k, 9 k, 20 k, and 30 k g/mol. The decreases in the polymer peak areas on the subsequent time points of the study are expressed as weight percentages relative to the 0 day stent.

Gel Permeation Chromatography In-Vitro testing

Gel Permeation Chromatography (GPC) can also be used to quantify the bioabsorbability/bioresorbability, dissolution rate, and/or biodegrability of the polymer coating. The in vitro assay is a degradation test where the concentration and molecular weights of the polymers can be assessed when released from the stents in an aqueous solution that mimics physiological surroundings. See for example, Jackson et al., "Characterization of perivascular poly(lactic-co-glycolic acid) films containing paclitaxel" *Int. J. of Pharmaceutics,* 283:97-109 (2004), incorporated in its entirety herein by reference.

For example Stents (n=15) described herein are expanded and then placed in a solution of 1.5 ml solution of phosphate buffered saline (pH=7.4) with 0.05% wt of Tween20, or in the alternative 10 mM Tris, 0.4 wt. % SDS, pH 7.4, in a 37° C. bath with bath rotation at 70 rpm. Alternatively, a coated coupon could be tested in this method. The solution is then collected at the following time points: 0 min., 15 min., 30 min., 1 hr, 2 hr, 4 hr, 6 hr, 8 hr, 12 hr, 16 hr, 20 hr, 24 hr, 30 hr, 36 hr, 48 hr, and daily up to 70 days, for example. The solution is replaced at least at each time point, and/or periodically (e.g. every four hours, daily, weekly, or longer for later time points) to prevent saturation, the removed solution is collected, saved, and assayed. The solutions containing the released polymers for each time point are filtered to reduce clogging the GPC system. For time points over 4 hours, the multiple collected solutions are pooled together for liquid extraction.

1 ml Chloroform is added to the phosphate buffered saline solutions and shaken to extract the released polymers from the aqueous phase. The chloroform phase is then collected for assay via GPC.

The system comprises a Shimadzu LC-10 AD HPLC pump, a Shimadzu RID-6A refractive index (RI) detector coupled to a 50 Å Hewlett Packard Pl-Gel column. The mobile phase is chloroform with a flow rate of 1 mL/min. The injection volume of the polymer sample is 100 μL of a polymer concentration. The samples are run for 20 minutes at an ambient temperature.

For determination of the released polymer concentrations at each time point, quantitative calibration graphs are first made using solutions containing known concentrations of each polymer in chloroform. Stock solutions containing each polymer in 0-5 mg/ml concentration range are first analyzed by GPC and peak areas are used to create separate calibration curves for each polymer.

For polymer degradation studies, a calibration graph of log molecular weight versus retention time is established for a 50 Å Pl-Gel column (Hewlett Packard) using polystyrene standards with molecular weights of 300, 600, 1.4 k, 9 k, 20 k, and 30 k g/mol. In the alternative, a Multi angle light scattering (MALS) detector may be fitted to directly assess the molecular weight of the polymers without the need of polystyrene standards.

To perform an accelerated in-vitro dissolution of the bioresorbable polymers, a protocol is adapted from ISO Standard 13781 "Poly(L-lactide) resides and fabricated an accelerated froms for surgical implants—in vitro degradation testing" (1997), incorporated in its entirety herein by reference. Briefly, elution buffer comprising 18% v/v of a stock solution of 0.067 mol/L $KH_2PO_4$ and 82% v/v of a stock solution of 0.067 mol/L $Na_2HPO_4$ with a pH of 7.4 is used. Stents described herein are expanded and then placed in 1.5 ml solution of this accelerated elution in a 70° C. bath with rotation at 70 rpm. The solutions are then collected at the following time points: 0 min., 15 min., 30 min., 1 hr, 2 hr, 4 hr, 6 hr, 8 hr, 12 hr, 16 hr, 20 hr, 24 hr, 30 hr, 36 hr and 48 hr. Fresh accelerated elution buffer are added periodically every two hours to replace the incubated buffers that are collected and saved in order to prevent saturation. The solutions containing the released polymers for each time point are filtered to reduce clogging the GPC system. For time points over 2 hours, the multiple collected solutions are pooled together for liquid extraction by chloroform. Chloroform extraction and GPC analysis is performed in the manner described above.

Scanning Electron Microscopy (SEM) with Focused Ion Beam (FIB) Milling In-Vitro Testing Focused ion beam FIB is a tool that allows precise site-specific sectioning, milling and depositing of materials. FIB can be used in conjunction with SEM, at ambient or cryo conditions, to produce in-situ sectioning followed by high-resolution imaging. FIB-SEM can produce a cross-sectional image of the polymer layers on the stent. The image can be used to quantitate the thickness of the layers to reveal rate of bioresorbability of single or multiple polymers as well as show whether there is uniformity of the layer thickness at manufacture and at time points after stenting (or after in-vitro elution at various time points).

For example, testing is performed at multiple time points. Stents are removed from the elution media and dried, the dried stent is visualized using FIB-SEM for changes in the coating. Alternatively, a coated coupon could be tested in this method.

Stents (n=15) described herein are expanded and then placed in 1.5 ml solution of phosphate buffered saline (pH=7.4) with 0.05% wt of Tween20 in a 37° C. bath with bath rotation at 70 rpm. Alternatively, a coated coupon could be tested in this method. The phosphate buffered saline solution is periodically replaced with fresh solution at each time point and/or every four hours to prevent saturation. The stents are collected at the following time points: 30 min, 1 hr, 2 hr, 4 hr, 6 hr, 8, hr, 12 hr, 16 hr, 20 hr, 24 hr, 30 hr, 36 hr, 48 hr, 60 h and 72 h. The stents are dried down at 30° C. under a stream of gas to complete dryness. A stent that not been subjected to these conditions is used as a t=0 control.

A FEI Dual Beam Strata 235 FIB/SEM system is a combination of a finely focused Ga ion beam (FIB) accelerated by 30 kV with a field emission electron beam in a scanning electron microscope instrument and is used for imaging and sectioning the stents. Both beams focus at the same point of the sample with a probe diameter less than 10 nm. The FIB can also produce thinned down sections for TEM analysis.

To prevent damaging the surface of the stent with incident ions, a Pt coating is first deposited via electron beam assisted deposition and ion beam deposition prior to FIB sectioning. For FIB sectioning, the Ga ion beam is accelerated to 30 kV and the sectioning process is about 2 h in duration. Completion of the FIB sectioning allows one to observe and quantify by SEM the thickness of the polymer layers that are left on the stent as they are absorbed.

Raman Spectroscopy In-Vitro Testing

As discussed in example 2, Raman spectroscopy can be applied to characterize the chemical structure and relative concentrations of drug and polymer coatings. This can also be applied to characterize in-vitro tested polymer coatings on stents or other substrates.

For example, confocal Raman Spectroscopy/microscopy can be used to characterize the relative drug to polymer ratio at the outer 1 μm of the coated surface as a function of time exposed to elution media. In addition confocal Raman x-z or z (maps or line scans) microscopy can be applied to characterize the relative drug to polymer ratio as a function of depth at time t after exposure to elution media.

For example a sample (a coated stent) is prepared as described herein and placed in elution media (e.g., 10 mM tris(hydroxymethyl)aminomethane (Tris), 0.4 wt. % Sodium dodecyl sulphate (SDS), pH 7.4 or 1.5 ml solution of phosphate buffered saline (pH=7.4) with 0.05% wt of Tween20) in a 37° C. bath with bath rotation at 70 rpm. Confocal Raman Images are taken on the coating before elution. At least four elution time points within a 48 day interval, (e.g. 0 min., 15 min., 30 min., 1 hr, 2 hr, 4 hr, 6 hr, 8, hr, 12 hr, 16 hr, 20 hr, 24 hr, 30 hr, 36 hr and 48 hr) the sample is removed from the elution, and dried (for example, in a stream of nitrogen). The dried stent is visualized using Raman Spectroscopy for changes in coating. Alternatively, a coated coupon could be tested in this method. After analysis, each is returned to the buffer for further elution.

Raman spectroscopy and other analytical techniques such as described in Balss, et al., "Quantitative spatial distribution of sirolimus and polymers in drug-eluting stents using confocal Raman microscopy" *J. of Biomedical Materials Research Part A*, 258-270 (2007), incorporated in its entirety herein by reference, and/or described in Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference may be used.

For example a WITec CRM 200 scanning confocal Raman microscope using a Nd:YAG laser at 532 nm is applied in the Raman imaging mode to generate an x-z map. The sample is placed upon a piezoelectrically driven table, the laser light is focused upon the sample using a 10× dry objective (numerical aperture 0.90), and the finely focused laser spot is scanned into the sample. As the laser scans the sample, over each 0.33 micron interval a Raman spectrum with high signal to noise is collected using 0.3 Seconds of integration time. Each confocal cross-sectional image of the coatings displays a region 70 μm wide by 10 μm deep, and results from the gathering of 6300 spectra with a total imaging time of 32 min.

SEM-In-Vitro Testing

Testing is performed at multiple time points (e.g. 0 min., 15 min., 30 min., 1 hr, 2 hr, 4 hr, 6 hr, 8, hr, 12 hr, 16 hr, 20 hr, 24 hr, 30 hr, 36 hr and 48 hr). Stents are removed from the elution media (described supra) and dried at these time points. The dried stent is visualized using SEM for changes in coating.

For example the samples are observed by SEM using a Hitachi S-4800 with an accelerating voltage of 800V. Various magnifications are used to evaluate the coating integrity, especially at high strain regions. Change in coating over time is evaluated to visualize the bioabsorption of the polymer over time.

X-ray photoelectron spectroscopy (XPS)—In-Vitro Testing

XPS can be used to quantitatively determine elemental species and chemical bonding environments at the outer 5-10 nm of sample surface. The technique can be operated in spectroscopy or imaging mode. When combined with a sputtering source, XPS can be utilized to give depth profiling chemical characterization.

XPS testing can be used to characterize the drug to polymer ratio at the very surface of the coating of a sample. Additionally XPS testing can be run in time lapse to detect changes in composition. Thus, in one test, samples are tested using XPS at multiple time points (e.g. 0 min., 15 min., 30 min., 1 hr, 2 hr, 4 hr, 6 hr, 8, hr, 12 hr, 16 hr, 20 hr, 24 hr, 30 hr, 36 hr and 48 hr). Stents are removed from the elution media (e.g., 10 mM Tris, 0.4 wt. % SDS, pH 7.4 or 1.5 ml solution of phosphate buffered saline (pH=7.4) with 0.05% wt of Tween20) in a 37° C. bath with rotation at 70 rpm and dried at these time points.

XPS (ESCA) and other analytical techniques such as described in Belu et al, "Three-Dimensional Compositional Analysis of Drug Eluting Stent Coatings Using Cluster Secondary Ion Mass Spectroscopy" Anal. Chem. 80: 624-632 (2008) incorporated herein in its entirety by reference may be used.

For example, XPS analysis is performed using a Physical Electronics Quantum 2000 Scanning ESCA. The monochromatic Al Kα source is operated at 15 kV with a power of 4.5 W. The analysis is performed at a 45° take off angle. Three measurements are taken along the length of each stent with the analysis area 20 microns in diameter. Low energy electron and $Ar^+$ ion floods are used for charge compensation.

Time of Flight Secondary Ion Mass Spectrometery (TOF-SIMS)

TOF-SIMS can be used to determine molecular species at the outer 1-2 nm of sample surface when operated under static conditions. The technique can be operated in spectroscopy or imaging mode at high spatial resolution. When operated under dynamic experimental conditions, known in the art, depth profiling chemical characterization can be achieved.

TOF-SIMS testing can be used to characterize the presence of polymer and or drug at uppermost surface of the coating of a sample. Additionally TOF-SIMS testing can be run in time lapse to detect changes in composition. Thus, in one test, samples are tested using TOF-SIMS at multiple time points (e.g., 0 min., 15 min., 30 min., 1 hr, 2 hr, 4 hr, 6 hr, 8, hr, 12 hr, 16 hr, 20 hr, 24 hr, 30 hr, 36 hr and 48 hr). Stents are removed from the elution media (e.g. 10 mM Tris, 0.4 wt. % SDS, pH 7.4 or 1.5 ml solution of phosphate buffered saline (pH=7.4) with 0.05% wt of Tween20) in a 37° C. bath with rotation at 70 rpm and dried at these time points.

For example, to analyze the uppermost surface only, static conditions (for example a ToF-SIMS IV (IonToF, Munster)) using a 25 Kv $Bi^{++}$ primary ion source maintained below $10^{12}$ ions per $cm^2$ is used. Where necessary a low energy electron flood gun (0.6 nA DC) is used to charge compensate insulating samples.

Cluster Secondary Ion Mass Spectrometry, may be employed for depth profiling as described Belu et al., "Three-Dimensional Compositional Analysis of Drug Eluting Stent Coatings Using Cluster Secondary Ion Mass Spectroscopy" Anal. Chem. 80: 624-632 (2008) incorporated herein in its entirety by reference.

For example, a stent as described herein is obtained. The stent is prepared for SIMS analysis by cutting it longitudinally and opening it up with tweezers. The stent is then pressed into multiple layers of indium foil with the outer diameter facing outward.

TOF-SIMS depth profiling experiments are performed using an Ion-TOF IV instrument equipped with both Bi and SF5+ primary ion beam cluster sources. Sputter depth profiling is performed in the dual-beam mode, while preserving the chemical integrity of the sample. For example, the analysis source is a pulsed, 25-keV bismuth cluster ion source, which bombarded the surface at an incident angle of 45° to the surface normal. The target current is maintained at ~0.3 pÅ (+10%) pulsed current with a raster size of 200 micron×200 micron for all experiments. Both positive and negative secondary ions are extracted from the sample into a reflectron-type time-of-flight mass spectrometer. The secondary ions are then detected by a microchannel plate detector with a post-acceleration energy of 10 kV. A low-energy electron flood gun is utilized for charge neutralization in the analysis mode.

The sputter source used is a 5-keV SF5+ cluster source also operated at an incident angle of 45° to the surface normal. For thin model samples on Si, the SF5+ current is maintained at ~2.7 nÅ with a 750 micron×750 micron raster. For the thick samples on coupons and for the samples on stents, the current is maintained at 6 nA with a 500 micron× 500 micron raster. All primary beam currents are measured with a Faraday cup both prior to and after depth profiling.

All depth profiles are acquired in the noninterlaced mode with a 5-ms pause between sputtering and analysis. Each spectrum is averaged over a 7.37 second time period. The analysis is immediately followed by 15 seconds of $SF_5^+$ sputtering. For depth profiles of the surface and subsurface regions only, the sputtering time was decreased to 1 second for the 5% active agent sample and 2 seconds for both the 25% and 50% active agent samples. Temperature-controlled depth profiles are obtained using a variable-temperature stage with Eurotherm Controls temperature controller and IPSG V3.08 software. Samples are first placed into the analysis chamber at room temperature. The samples are brought to the desired temperature under ultra high-vacuum conditions and are allowed to stabilize for 1 minute prior to analysis. All depth profiling experiments are performed at −100 degrees C. and 25 degrees C.

Infrared (IR) Spectroscopy for In-Vitro Testing

Infrared (IR) Spectroscopy such as, but not limited to, FTIR, ATR-IR and micro ATR-IR are well utilized techniques that can be applied to show the quantitative polymer content in the coating, and the distribution of polymer in the coating.

For example using FTIR, a coupon of crystalline ZnSe is coated by the processes described herein, creating a PDPDP (Polymer, Drug, Polymer, Drug, Polymer) layered coating that is about 10 microns thick. At time=0 and at least four elution time points within a 48 day interval (e.g., 0 min., 15 min., 30 min., 1 hr, 2 hr, 4 hr, 6 hr, 8, hr, 12 hr, 16 hr, 20 hr, 24 hr, 30 hr, 36 hr and 48 hr), the sample (coated crystal) was tested by FTIR for polymer content. The sample was placed in an elution media (e.g. 10 mM Tris, 0.4 wt. % SDS, pH 7.4 or 1.5 ml solution of phosphate buffered saline (pH=7.4) with 0.05% wt of Tween20) in a 37° C. bath with bath rotation at 70 rpm and at each time point, the sample is removed from the elution media and dried (e.g. in a stream of nitrogen). FTIR spectrometry was used to quantify the polymer on the sample. After analysis, each is returned to the buffer for further elution.

In another example using FTIR, sample elution media at each time point was tested for polymer content. In this example, a coated stent was prepared that was coated by the processes described herein, creating a PDPDP (Polymer, Drug, Polymer, Drug, Polymer) layered coating that is about 10 microns thick. The coated stent was placed in an elution media (e.g. 10 mM Tris, 0.4 wt. % SDS, pH 7.4 or 1.5 ml solution of phosphate buffered saline (pH=7.4) with 0.05% wt of Tween20) in a 37° C. bath with rotation at 70 rpm. and at each time point (e.g., 0 min., 15 min., 30 min., 1 hr, 2 hr, 4 hr, 6 hr, 8, hr, 12 hr, 16 hr, 20 hr, 24 hr, 30 hr, 36 hr and 48 hr), a sample of the elution media is removed and dried onto a crystalline ZnSe window (e.g. in a stream of nitrogen). At each elution time point, the sample elution media was tested by FTIR for polymer content.

Atomic Force Microscopy (AFM)

AFM is a high resolution surface characterization technique. AFM is used in the art to provide topographical imaging, in addition when employed in Tapping Mode™ can image material and or chemical properties of the surface. The technique can be used under ambient, solution, humidified or temperature controlled conditions. Other modes of operation are well known and can be readily employed here by those skilled in the art. The AFM topography images can be run in time-lapse to characterize the surface as a function of elution time. Three-dimensionally rendered images show the surface of a coated stent, which can show holes or voids of the coating which may occur as the polymer is absorbed and the drug is eluted over time.

A stent as described herein is obtained. AFM is used to determine the drug polymer distribution. AFM may be employed as described in Ranade et al., "Physical characterization of controlled release of paclitaxel from the TAXUS Express2 drug-eluting stent" *J. Biomed. Mater. Res.* 71(4):625-634 (2004) incorporated herein in its entirety by reference.

For example a multi-mode AFM (Digital Instruments/Veeco Metrology, Santa Barbara, Calif.) controlled with Nanoscope IIIa and NanoScope Extender electronics is used. Samples are examined in the dry state using AFM before elution of the drug (e.g. rapamycin). Samples are also examined at select time points through a elution period (e.g. 48 hours) by using an AFM probe-tip and flow-through stage built to permit analysis of wet samples. The wet samples are examined in the presence of the same elution medium used for in-vitro kinetic drug release analysis (e.g. PBS-Tween20, or 10 mM Tris, 0.4 wt. % SDS, pH 7.4). Saturation of the solution is prevented by frequent exchanges of the release medium with several volumes of fresh medium. TappingMode™ AFM imaging may be used to show topography (a real-space projection of the coating surface microstructure) and phase-angle changes of the AFM over the sample area to contrast differences in the material and physical structure.

Nano X-Ray Computer Tomography

Another technique that may be used to view the physical structure of a device in 3-D is Nano X-Ray Computer Tomography (e.g. such as made by SkyScan), which could be used in an elution test and/or bioabsorbability test, as described herein to show the physical structure of the coating remaining on stents at each time point, as compared to a scan prior to elution/bioabsorbtion.

pH Testing

The bioabsorbability of PLGA of a coated stent can be shown by testing the pH of an elution media (EtOH/PBS, for example) in which the coated stent is placed. Over time, a bioabsorbable PLGA coated stent (with or without the drug) will show a decreased pH until the PLGA is fully bioabsorbed by the elution media.

Figure 2:
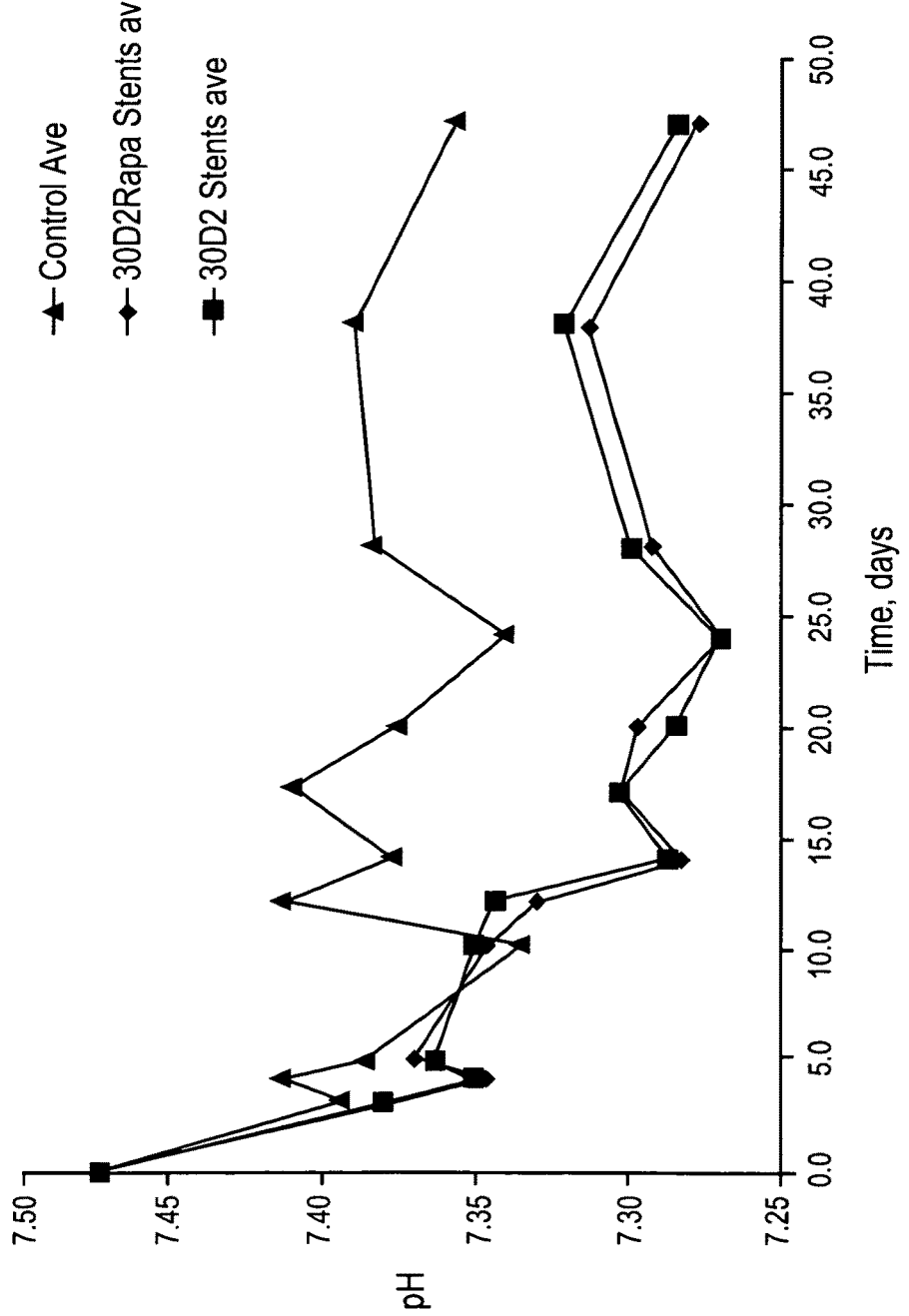
FIG. 2: Bioabsorbability testing of 50:50 PLGA-carboxylate end group (MW 10 kD) PLGA polymer coating formulations on stents by determination of pH Changes with Polymer Film Degradation in 20% Ethanol/Phosphate Buffered Saline as set forth in Example 3 described herein.
Figure 3:
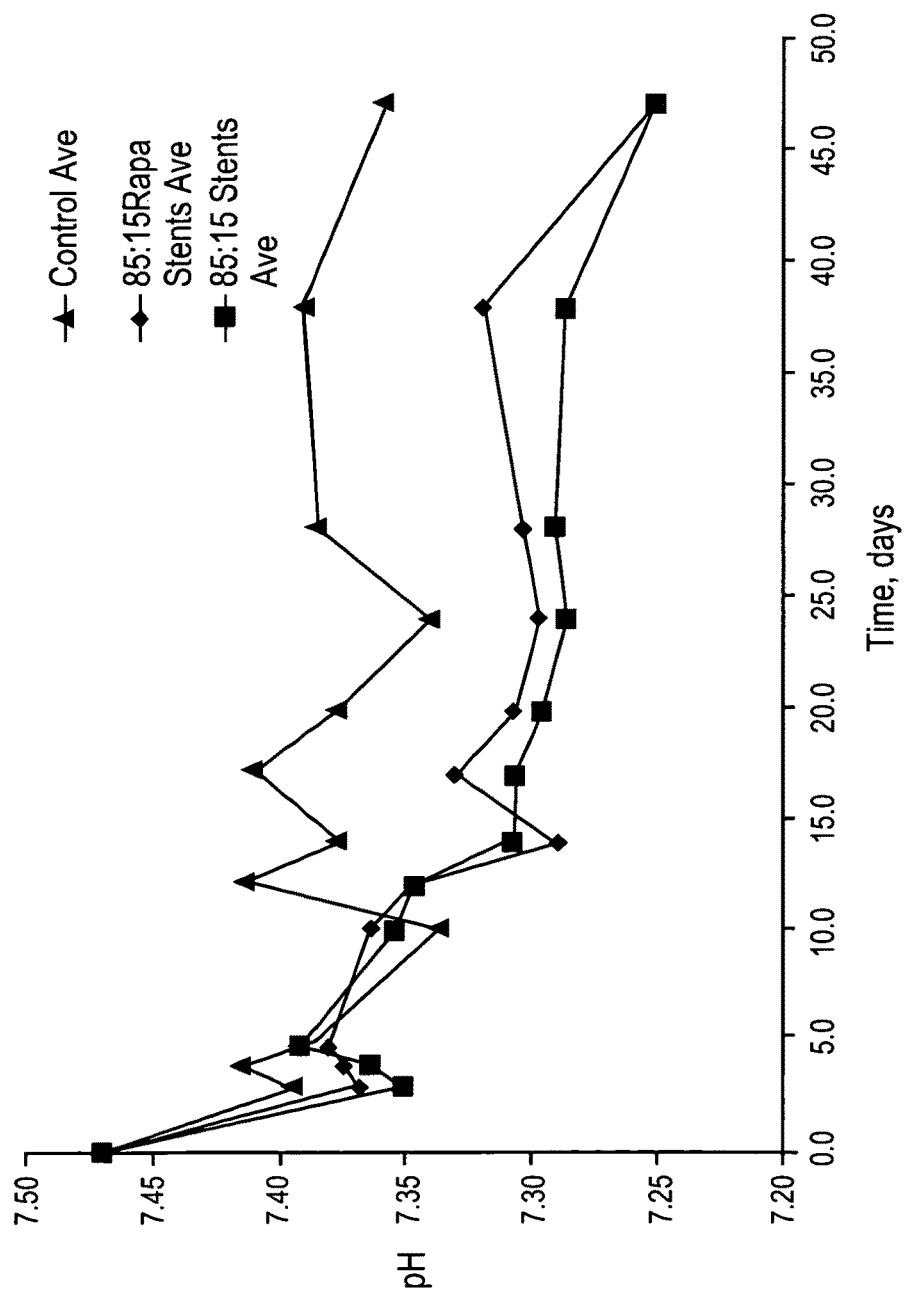
FIG. 3: Bioabsorbability testing of 85:15 (85% lactic acid, 15% glycolic acid) PLGA polymer coating formulations on stents by determination of pH Changes with Polymer Film Degradation in 20% Ethanol/Phosphate Buffered Saline as set forth in Example 3 described herein.
Figure 4:
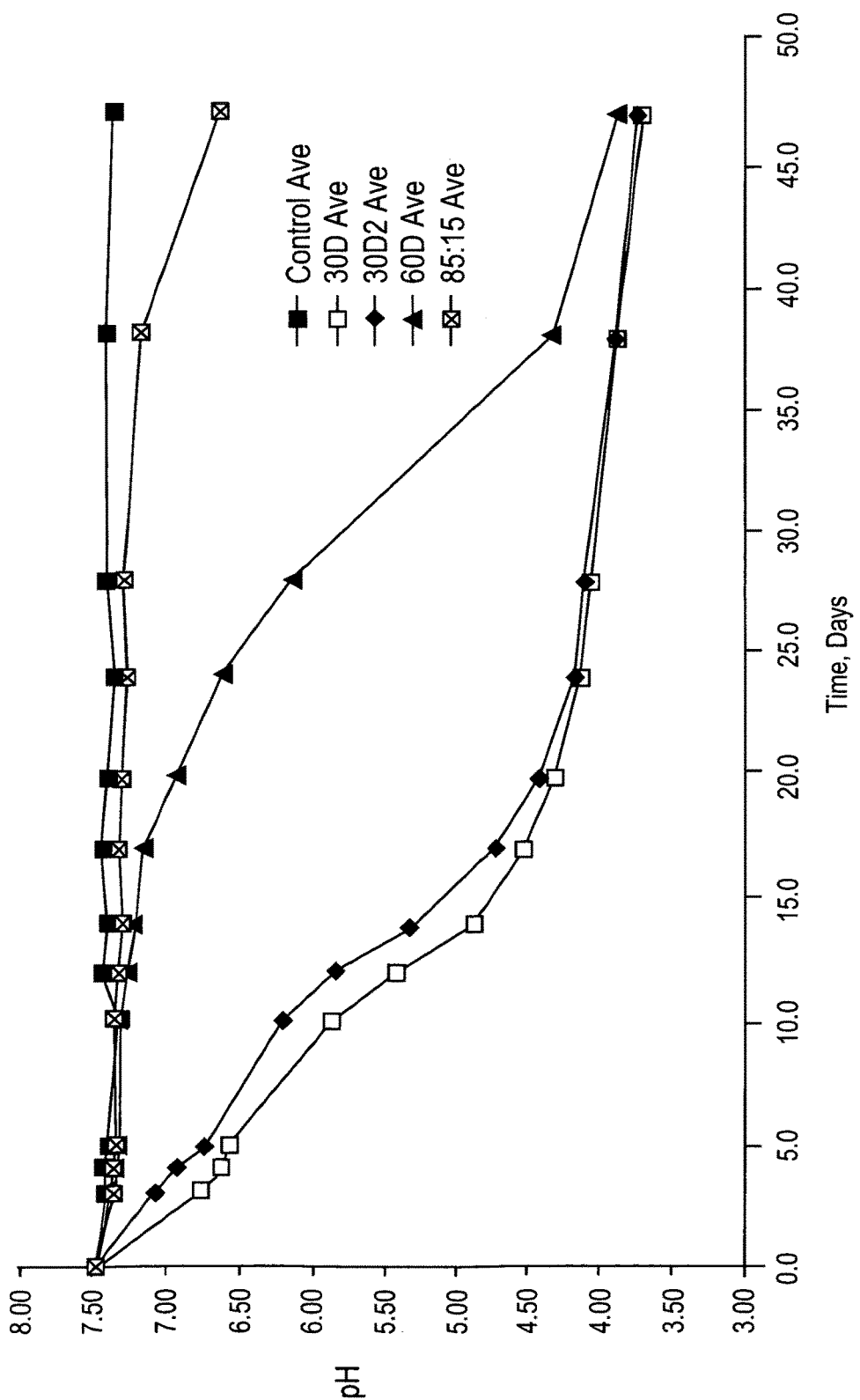
FIG. 4: Bioabsorbability testing of various PLGA polymer coating film formulations by determination of pH Changes with Polymer Film Degradation in 20% Ethanol/Phosphate Buffered Saline as set forth in Example 3 described herein.

A test was performed using stents coated with PLGA alone, stents coated with PLGA and rapamycin, PLGA films, and PLGA films containing rapamycin. The samples were put in elution media of 20% EtOH/PBS at 37° C. The elution media was tested at multiple intervals from 0 to 48 days. In FIGS. 1, 2 and 3, stents having coatings as provided herein were tested for pH over time according to this method. FIG. 4 shows results of the PLGA films (with and without rapamycin) tested according to this method. Control elution media was run in triplicate alongside the samples, and the results of this pH testing was averaged and is presented as "Control AVE" in each of the FIGS. 1-4.

In FIG. 2, the "30D2Rapa Stents ave" line represents a stent having coating according to AS1(213) of Example 1 (PDPDP) with Polymer B (50:50 PLGA-Carboxylate end group, MW ~10 kD) and rapamycin, where the coating was removed from the stent and tested in triplicate for pH changes over time in the elution media, the average of which is presented. The "30D2 Stents ave" line represents a stent having coating of only Polymer B (50:50 PLGA-Carboxylate end group, MW ~10 kD) (no rapamycin), where the coating was removed from the stent and tested in triplicate for pH changes over time in the elution media, the average of which is presented.

In FIG. 1, the "60DRapa Stents ave" line represents a stent having coating according to AS1 of Example 1 (PDPDP) with Polymer A (50:50 PLGA-Ester end group, MW ~19 kD) and rapamycin, where the coating was removed from the stent and tested in triplicate for pH changes over time in the elution media, the average of which is presented.

The "60D Stents ave" line represents a stent having coating of only Polymer A (50:50 PLGA-Ester end group, MW ~19 kD) (no rapamycin), where the coating was removed from the stent and tested in triplicate for pH changes over time in the elution media, the average of which is presented.

In FIG. 3, the "85:15 Rapa Stents ave" line represents a stent having coating according to PDPDP with a PLGA comprising 85% lactic acid, 15% glycolic acid, and rapamycin, where the coating was removed from the stent and tested in triplicate for pH changes over time in the elution media, the average of which is presented. The "85:15 Stents ave" line represents a stent having coating of only PLGA comprising 85% lactic acid, 15% glycolic acid (no rapamycin), where the coating was removed from the stent and tested in triplicate for pH changes over time in the elution media, the average of which is presented.

In FIG. 4, the "30D Ave" line represents a polymer film comprising Polymer B (50:50 PLGA-Carboxylate end group, MW ~10 kD) (no rapamycin), where the film was tested in triplicate for pH changes over time in the elution media, the average of which is presented. The "30D2 Ave" line also represents a polymer film comprising Polymer B (50:50 PLGA-Carboxylate end group, MW ~10 kD) (no rapamycin), where the film was tested in triplicate for pH changes over time in the elution media, the average of which is presented. The "60D Ave" line represents a polymer film comprising Polymer A (50:50 PLGA-Ester end group, MW ~19 kD) (no rapamycin), where the film was tested in triplicate for pH changes over time in the elution media, the average of which is presented. The "85:15 Ave" line represents a polymer film comprising PLGA comprising 85% lactic acid, 15% glycolic acid (no rapamycin), where the film was tested in triplicate for pH changes over time in the elution media, the average of which is presented. To create the polymer films in FIG. 4, the polymers were dissolved in methylene chloride, THF, and ethyl acetate. The films that were tested had the following average thicknesses and masses, 30D-152.4 um, 12.0 mg; 30D2-127.0 um, 11.9 mg; 60D-50.8 um, 12.4 mg; 85:15-127 um, 12.5 mg.

Example 4: Visualization of Polymer/Active Agent Layers Coating a Device

Raman Spectroscopy

As discussed in example 2, Raman spectroscopy can be applied to characterize the chemical structure and relative concentrations of drug and polymer coatings. For example, confocal Raman Spectroscopy/microscopy can be used to characterize the relative drug to polymer ratio at the outer ~1 μm of the coated surface. In addition confocal Raman x-z or z (maps or line scans) microscopy can be applied to characterize the relative drug to polymer ratio as a function of depth. Additionally cross-sectioned samples can be analysed. Raman spectroscopy and other analytical techniques such as described in Balss, et al., "Quantitative spatial distribution of sirolimus and polymers in drug-eluting stents using confocal Raman microscopy" *J. of Biomedical Materials Research Part A,* 258-270 (2007), incorporated in its entirety herein by reference, and/or described in Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference may be used.

A sample (a coated stent) is prepared as described herein. Images are taken on the coating using Raman Spectroscopy. Alternatively, a coated coupon could be tested in this method. To test a sample using Raman microscopy and in particular confocal Raman microscopy, it is understood that to get appropriate Raman high resolution spectra sufficient acquisition time, laser power, laser wavelength, sample step size and microscope objective need to be optimized.

For example a WITec CRM 200 scanning confocal Raman microscope using a Nd:YAG laser at 532 nm is applied in the Raman imaging mode to give x-z maps. The sample is placed upon a piezoelectrically driven table, the laser light is focused upon the sample using a 100× dry objective (numerical aperture 0.90), and the finely focused laser spot is scanned into the sample. As the laser scans the sample, over each 0.33 micron interval a Raman spectrum with high signal to noise is collected using 0.3 Seconds of integration time. Each confocal cross-sectional image of the coatings displays a region 70 μm wide by 10 μm deep, and results from the gathering of 6300 spectra with a total imaging time of 32 min. Multivariate analysis using reference spectra from samples of rapamycin and polymer are used to deconvolve the spectral data sets, to provide chemical maps of the distribution.

In another test, spectral depth profiles (x-z maps) of samples are performed with a CRM200 microscope system from WITec Instruments Corporation (Savoy, Ill.). The instrument is equipped with a Nd:YAG frequency doubled laser (532 excitation), a single monochromator (Acton) employing a 600 groove/mm grating and a thermoelectrically cooled 1024 by 128 pixel array CCD camera (Andor Technology). The microscope is equipped with appropriate collection optics that include a holographic laser bandpass rejection filter (Kaiser Optical Systems Inc.) to minimize Rayleigh scatter into the monochromator. The Raman scattered light are collected with a 50 micron optical fiber. Using the "Raman Spectral Imaging" mode of the instrument, spectral images are obtained by scanning the sample in the x, z direction with a piezo driven xyz scan stage and collecting a spectrum at every pixel. Typical integration times are 0.3 s per pixel. The spectral images are 4800 total spectra corresponding to a physical scan dimension of 40 by 20 microns. For presentation of the confocal Raman data, images are generated based on unique properties of the spectra (i.e. integration of a Raman band, band height intensity, or band width). The microscope stage is modified with a custom-built sample holder that positioned and rotated the stents around their primary axis. The x direction is defined as the direction running parallel to the length of the stent and the z direction refers to the direction penetrating through the coating from the air-coating to the coating-metal interface. Typical laser power is <10 mW on the sample stage. All experiments can be conducted with a plan a chromat objective, 100×$N_A$=0.9 (Nikon).

Samples (n=5) comprising stents made of L605 (0.05-0.15% C, 1.00-2.00% Mn, maximum 0.040% Si, maximum 0.030% P, maximum 0.3% S, 19.00-21.00% Cr, 9.00-11.00% Ni, 14.00-16.00% W, 3.00% Fe, and Bal. Co) and having coatings as described herein and/or produced by methods described herein can be analyzed. For each sample, three locations are selected along the stent length. The three locations are located within one-third portions of the stents so that the entire length of the stent are represented in the data. The stent is then rotated 180 degrees around the circumference and an additional three locations are sampled along the length. In each case, the data is collected from the strut portion of the stent. Six random spatial locations are also profiled on coated coupon samples made of L605 and having coatings as described herein and/or produced by methods described herein. The Raman spectra of each individual component present in the coatings are also collected for comparison and reference. Using the instrument software, the average spectra from the spectral image data are calculated by selecting the spectral image pixels that are exclusive to each layer. The average spectra are then exported into GRAMS/AI v. 7.02 software (Thermo Galactic) and the appropriate Raman bands are fit to a Voigt function. The band areas and shift positions are recorded.

The pure component spectrum for each component of the coating (e.g. drug, polymer) are also collected at 532 and 785 nm excitation. The 785 nm excitation spectra are collected with a confocal Raman microscope (WITec Instruments Corp. Savoy, Ill.) equipped with a 785 nm diode laser, appropriate collection optics, and a back-illuminated thermoelectriaclly cooled 1024×128 pixel array CCD camera optimized for visible and infrared wavelengths (Andor Technology).

X-Ray Photoelectron Spectroscopy (XPS)

XPS can be used to quantitatively determine elemental species and chemical bonding environments at the outer 5-10 nm of sample surface. The technique can be operated in spectroscopy or imaging mode. When combined with a sputtering source XPS can be utilized to give depth profiling chemical characterization. XPS (ESCA) and other analytical techniques such as described in Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference may be used.

For example, in one test, a sample comprising a stent coated by methods described herein and/or a device as described herein is obtained. XPS analysis is performed on a sample using a Physical Electronics Quantum 2000 Scanning ESCA. The monochromatic Al Kα source is operated at 15 kV with a power of 4.5 W. The analysis is done at a 45° take off angle. Three measurements are taken along the length of each sample with the analysis area 20 microns in diameter. Low energy electron and Ar$^+$ ion floods are used for charge compensation.

Time of Flight Secondary Ion Mass Spectrometery (TOF-SIMS)

TOF-SIMS can be used to determine molecular species (drug and polymer) at the outer 1-2 nm of sample surface when operated under static conditions. The technique can be operated in spectroscopy or imaging mode at high spatial resolution. Additionally cross-sectioned samples can be analysed. When operated under dynamic experimental conditions, known in the art, depth profiling chemical characterization can be achieved.

For example, to analyze the uppermost surface only, static conditions (for example a ToF-SIMS IV (IonToF, Munster)) using a 25 Kv Bi$^{++}$ primary ion source maintained below $10^{12}$ ions per cm$^2$ is used. Where necessary a low energy electron flood gun (0.6 nA DC) is used to charge compensate insulating samples.

Cluster Secondary Ion Mass Spectrometry, may be employed for depth profiling as described Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference.

For example, a stent as described herein is obtained. The stent is prepared for SIMS analysis by cutting it longitudinally and opening it up with tweezers. The stent is then pressed into multiple layers of indium foil with the outer diameter facing outward.

TOF-SIMS depth profiling experiments are performed using an Ion-TOF IV instrument equipped with both Bi and SF5+ primary ion beam cluster sources. Sputter depth profiling is performed in the dual-beam mode, whilst preserving the chemical integrity of the sample. The analysis source is a pulsed, 25-keV bismuth cluster ion source, which bombarded the surface at an incident angle of 45° to the surface normal. The target current is maintained at 0.3 pA (+10%) pulsed current with a raster size of 200 um×200 um for all experiments. Both positive and negative secondary ions are extracted from the sample into a reflectron-type time-of-flight mass spectrometer. The secondary ions are then detected by a microchannel plate detector with a post-acceleration energy of 10 kV. A low-energy electron flood gun is utilized for charge neutralization in the analysis mode.

The sputter source used is a 5-keV SF5+ cluster source also operated at an incident angle of 45° to the surface normal. For thin model samples on Si, the SF5+ current is maintained at ~2.7 nA with a 750 um×750 um raster. For the thick samples on coupons and for the samples on stents, the current is maintained at 6 nA with a 500 um×500 um raster.

All primary beam currents are measured with a Faraday cup both prior to and after depth profiling.

All depth profiles are acquired in the noninterlaced mode with a 5-ms pause between sputtering and analysis. Each spectrum is averaged over a 7.37 second time period. The analysis is immediately followed by 15 seconds of SF$_5^+$ sputtering. For depth profiles of the surface and subsurface regions only, the sputtering time was decreased to 1 second for the 5% active agent sample and 2 seconds for both the 25% and 50% active agent samples. Temperature-controlled depth profiles are obtained using a variable-temperature stage with Eurotherm Controls temperature controller and IPSG V3.08 software. samples are first placed into the analysis chamber at room temperature. The samples are brought to the desired temperature under ultra high-vacuum conditions and are allowed to stabilize for 1 minute prior to analysis. All depth profiling experiments are performed at –100 C and 25 C.

Atomic Force Microscopy (AFM)

AFM is a high resolution surface characterization technique. AFM is used in the art to provide topographical imaging, in addition when employed in Tapping Mode™ can image material and or chemical properties of the surface. Additionally cross-sectioned samples can be analyzed. The technique can be used under ambient, solution, humidified or temperature controlled conditions. Other modes of operation are well known and can be readily employed here by those skilled in the art.

A stent as described herein is obtained. AFM is used to determine the structure of the drug polymer layers. AFM may be employed as described in Ranade et al., "Physical characterization of controlled release of paclitaxel from the TAXUS Express2 drug-eluting stent" *J. Biomed. Mater. Res.* 71(4):625-634 (2004) incorporated herein in its entirety by reference.

Polymer and drug morphologies, coating composition, at least may be determined using atomic force microscopy (AFM) analysis. A multi-mode AFM (Digital Instruments/Veeco Metrology, Santa Barbara, Calif.) controlled with Nanoscope IIIa and NanoScope Extender electronics is used. Samples are examined in the dry state using AFM before elution of the drug (e.g. rapamycin). Samples are also examined at select time points through a elution period (e.g. 48 hours) by using an AFM probe-tip and flow-through stage built to permit analysis of wet samples. The wet samples are examined in the presence of the same elution medium used for in-vitro kinetic drug release analysis (e.g. PBS-Tween20, or mM Tris, 0.4 wt. % SDS, pH 7.4). Saturation of the solution is prevented by frequent exchanges of the release medium with several volumes of fresh medium. Tapping-Mode™ AFM imaging may be used to show topography (a real-space projection of the coating surface microstructure) and phase-angle changes of the AFM over the sample area to contrast differences in the materials properties. The AFM topography images can be three-dimensionally rendered to show the surface of a coated stent, which can show holes or voids of the coating which may occur as the polymer is absorbed and the drug is eluted over time, for example.

Scanning Electron Microscopy (SEM) with Focused Ion Beam (FIB) Milling Stents as described herein, and or produced by methods described herein are visualized using SEM-FIB. Alternatively, a coated coupon could be tested in this method. Focused ion beam FIB is a tool that allows precise site-specific sectioning, milling and depositing of materials. FIB can be used in conjunction with SEM, at ambient or cryo conditions, to produce in-situ sectioning followed by high-resolution imaging. FIB-SEM can produce a cross-sectional image of the polymer and drug layers on the stent. The image can be used to quantitate the thickness of the layers and uniformity of the layer thickness at manufacture and at time points after stenting (or after in-vitro elution at various time points).

A FEI Dual Beam Strata 235 FIB/SEM system is a combination of a finely focused Ga ion beam (FIB) accelerated by 30 kV with a field emission electron beam in a scanning electron microscope instrument and is used for imaging and sectioning the stents. Both beams focus at the same point of the sample with a probe diameter less than 10 nm. The FIB can also produce thinned down sections for TEM analysis.

To prevent damaging the surface of the stent with incident ions, a Pt coating is first deposited via electron beam assisted deposition and ion beam deposition prior to FIB sectioning. For FIB sectioning, the Ga ion beam is accelerated to 30 kV and the sectioning process is about 2 h in duration. Completion of the FIB sectioning allows one to observe and quantify by SEM the thickness of the polymer layers that are, for example, left on the stent as they are absorbed.

Example 5: Analysis of the Thickness of a Device Coating

Analysis can be determined by either in-situ analysis or from cross-sectioned samples.

X-Ray Photoelectron Spectroscopy (XPS)

XPS can be used to quantitatively determine the presence of elemental species and chemical bonding environments at the outer 5-10 nm of sample surface. The technique can be operated in spectroscopy or imaging mode. When combined with a sputtering source XPS can be utilized to give depth profiling chemical characterization. XPS (ESCA) and other analytical techniques such as described in Belu et al., "Three-Dimensional Compositional Analysis of Drug Eluting Stent Coatings Using Cluster Secondary Ion Mass Spectroscopy" *Anal Chem.* 80: 624-632 (2008) incorporated herein in its entirety by reference may be used.

Thus, in one test, a sample comprising a stent coated by methods described herein and/or a device as described herein is obtained. XPS analysis is done on a sample using a Physical Electronics Quantum 2000 Scanning ESCA. The monochromatic Al Kα source is operated at 15 kV with a power of 4.5 W. The analysis is done at a 45° take off angle. Three measurements are taken along the length of each sample with the analysis area 20 microns in diameter. Low energy electron and $Ar^+$ ion floods are used for charge compensation.

Time of Flight Secondary Ion Mass Spectrometery

TOF-SIMS can be used to determine molecular species (drug and polymer) at the outer 1-2 nm of sample surface when operated under static conditions. The technique can be operated in spectroscopy or imaging mode at high spatial resolution. Additionally cross-sectioned samples can be analysed. When operated under dynamic experimental conditions, known in the art, depth profiling chemical characterization can be achieved. For example, under static conditions (for example a ToF-SIMS IV (IonToF, Munster)) using a 25 Kv $Bi^{++}$ primary ion source maintained below $10^{12}$ ions per $cm^2$ is used. Where necessary a low energy electron flood gun (0.6 nA DC) is used to charge compensate insulating samples.

Cluster Secondary Ion Mass Spectrometry, may be employed for depth profiling as described Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference.

A stent as described herein is obtained. The stent is prepared for SIMS analysis by cutting it longitudinally and opening it up with tweezers. The stent is then pressed into multiple layers of iridium foil with the outer diameter facing outward.

TOF-SIMS experiments are performed on an Ion-TOF IV instrument equipped with both Bi and SF5+ primary ion beam cluster sources. Sputter depth profiling is performed in the dual-beam mode. The analysis source is a pulsed, 25-keV bismuth cluster ion source, which bombarded the surface at an incident angle of 45° to the surface normal. The target current is maintained at ~0.3 pÅ (+10%) pulsed current with a raster size of 200 um×200 um for all experiments. Both positive and negative secondary ions are extracted from the sample into a reflectron-type time-of-flight mass spectrometer. The secondary ions are then detected by a microchannel plate detector with a post-acceleration energy of 10 kV. A low-energy electron flood gun is utilized for charge neutralization in the analysis mode.

The sputter source used is a 5-keV SF5+ cluster source also operated at an incident angle of 45° to the surface normal. For thin model samples on Si, the SF5+ current is maintained at ~2.7 nÅ with a 750 um×750 um raster. For the thick samples on coupons and for the samples on stents, the current is maintained at 6 nA with a 500 um×500 um raster.

All primary beam currents are measured with a Faraday cup both prior to and after depth profiling.

All depth profiles are acquired in the noninterlaced mode with a 5-ms pause between sputtering and analysis. Each spectrum is averaged over a 7.37 second time period. The analysis is immediately followed by 15 seconds of $SF_5+$ sputtering. For depth profiles of the surface and subsurface regions only, the sputtering time was decreased to 1 second for the 5% active agent sample and 2 seconds for both the 25% and 50% active agent samples. Temperature-controlled depth profiles are obtained using a variable-temperature stage with Eurotherm Controls temperature controller and IPSG V3.08 software. samples are first placed into the analysis chamber at room temperature. The samples are brought to the desired temperature under ultra high-vacuum conditions and are allowed to stabilize for 1 minute prior to analysis. All depth profiling experiments are performed at −100 C and 25 C.

Atomic Force Microscopy (AFM)

AFM is a high resolution surface characterization technique. AFM is used in the art to provide topographical imaging, in addition when employed in Tapping Mode™ can image material and or chemical properties of the surface. Additionally cross-sectioned samples can be analyzed.

A stent as described herein is obtained. AFM may be alternatively be employed as described in Ranade et al., "Physical characterization of controlled release of paclitaxel from the TAXUS Express2 drug-eluting stent" *J. Biomed. Mater. Res.* 71(4):625-634 (2004) incorporated herein in its entirety by reference.

Polymer and drug morphologies, coating composition, and cross-sectional thickness at least may be determined using atomic force microscopy (AFM) analysis. A multi-mode AFM (Digital Instruments/Veeco Metrology, Santa Barbara, Calif.) controlled with Nanoscope IIIa and NanoScope Extender electronics is used TappingMode™ AFM imaging may be used to show topography (a real-space projection of the coating surface microstructure) and phase-angle changes of the AFM over the sample area to contrast differences in the materials properties. The AFM topography images can be three-dimensionally rendered to show the surface of a coated stent or cross-section. *Scanning Electron Microscopy* (*SEM*) *with Focused Ion Beam* (*FIB*) Stents as described herein, and or produced by methods described herein are visualized using SEM-FIB analysis. Alternatively, a coated coupon could be tested in this method. Focused ion beam FIB is a tool that allows precise site-specific sectioning, milling and depositing of materials. FIB can be used in conjunction with SEM, at ambient or cryo conditions, to produce in-situ sectioning followed by high-resolution imaging. FIB-SEM can produce a cross-sectional image of the polymer layers on the stent. The image can be used to quantitate the thickness of the layers as well as show whether there is uniformity of the layer thickness at manufacture and at time points after stenting (or after in-vitro elution at various time points).

A FEI Dual Beam Strata 235 FIB/SEM system is a combination of a finely focused Ga ion beam (FIB) accelerated by 30 kV with a field emission electron beam in a scanning electron microscope instrument and is used for imaging and sectioning the stents. Both beams focus at the same point of the sample with a probe diameter less than 10 nm. The FIB can also produce thinned down sections for TEM analysis.

To prevent damaging the surface of the stent with incident ions, a Pt coating is first deposited via electron beam assisted deposition and ion beam deposition prior to FIB sectioning. For FIB sectioning, the Ga ion beam is accelerated to 30 kV and the sectioning process is about 2 h in duration. Completion of the FIB sectioning allows one to observe and quantify by SEM the thickness of the polymer layers that are, for example, left on the stent as they are absorbed.

Interferometry

Interferometry may additionally and/or alternatively used to determine the thickness of the coating as noted in Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference may be used.

Ellipsometry

Ellipsometry is sensitive measurement technique for coating analysis on a coupon. It uses polarized light to probe the dielectric properties of a sample. Through an analysis of the state of polarization of the light that is reflected from the sample the technique allows the accurate characterization of the layer thickness and uniformity. Thickness determinations ranging from a few angstroms to tens of microns are possible for single layers or multilayer systems. See, for example, Jewell, et al., "Release of Plasmid DNA from Intravascular Stents Coated with Ultrathin Mulyikayered Polyelectrolyte Films" *Biomacromolecules.* 7: 2483-2491 (2006) incorporated herein in its entirety by reference.

Example 6: Analysis of the Thickness of a Device

Scanning Electron Microscopy (SEM)

A sample coated stent described herein is obtained. Thickness of the device can be assessed using this analytical technique. The thickness of multiple struts were taken to ensure reproducibility and to characterize the coating and stent. The thickness of the coating was observed by SEM using a Hitachi S-4800 with an accelerating voltage of 800V. Various magnifications are used. SEM can provide top-down and cross-section images at various magnifications.

Nano X-Ray Computer Tomography

Another technique that may be used to view the physical structure of a device in 3-D is Nano X-Ray Computer Tomography (e.g. such as made by SkyScan).

Example 7: Determination of the Type or Composition of a Polymer Coating a Device Nuclear Magnetic Resonance (NMR)

Composition of the polymer samples before and after elution can be determined by $^1$H NMR spectrometry as described in Xu et al., "Biodegradation of poly(1-lactide-co-glycolide tube stents in bile" *Polymer Degradation and Stability.* 93:811-817 (2008) incorporated herein in its entirety by reference. Compositions of polymer samples are determined for example using a 300M Bruker spectrometer with d-chloroform as solvent at room temperature.

Raman Spectroscopy

FT-Raman or confocal raman microscopy can be employed to determine composition.

For example, a sample (a coated stent) is prepared as described herein. Images are taken on the coating using Raman Spectroscopy. Alternatively, a coated coupon could be tested in this method. To test a sample using Raman microscopy and in particular confocal Raman microscopy, it is understood that to get appropriate Raman high resolution spectra sufficient acquisition time, laser power, laser wavelength, sample step size and microscope objective need to be optimized. Raman spectroscopy and other analytical techniques such as described in Balss, et al., "Quantitative spatial distribution of sirolimus and polymers in drug-eluting stents using confocal Raman microscopy" *J. of Biomedical Materials Research Part A,* 258-270 (2007), incorporated in its entirety herein by reference, and/or described in Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference may be used.

For example a WITec CRM 200 scanning confocal Raman microscope using a Nd:YAG laser at 532 nm is applied in the Raman imaging mode. The sample is placed upon a piezoelectrically driven table, the laser light is focused upon the sample using a 10× dry objective (numerical aperture 0.90), and the finely focused laser spot is scanned into the sample. As the laser scans the sample, over each 0.33 micron interval a Raman spectrum with high signal to noise is collected using 0.3 Seconds of integration time. Each confocal cross-sectional image of the coatings displays a region 70 μm wide by 10 μm deep, and results from the gathering of 6300 spectra with a total imaging time of 32 min. Multivariate analysis using reference spectra from samples of rapamycin (amorphous and crystalline) and polymer references are used to deconvolve the spectral data sets, to provide chemical maps of the distribution.

In another test, spectral depth profiles of samples are performed with a CRM200 microscope system from WITec Instruments Corporation (Savoy, Ill.). The instrument is equipped with a NdYAG frequency doubled laser (532 excitation), a single monochromator (Acton) employing a 600 groove/mm grating and a thermoelectrically cooled 1024 by 128 pixel array CCD camera (Andor Technology). The microscope is equipped with appropriate collection optics that include a holographic laser bandpass rejection filter (Kaiser Optical Systems Inc.) to minimize Rayleigh scatter into the monochromator. The Raman scattered light are collected with a 50 micron optical fiber. Using the "Raman Spectral Imaging" mode of the instrument, spectral images are obtained by scanning the sample in the x, z direction with a piezo driven xyz scan stage and collecting a spectrum at every pixel. Typical integration times are 0.3 s per pixel. The spectral images are 4800 total spectra corresponding to a physical scan dimension of 40 by 20 microns. For presentation of the confocal Raman data, images are generated base don unique properties of the spectra (i.e. integration of a Raman band, band height intensity, or band width). The microscope stage is modified with a custom-built sample holder that positioned and rotated the stents around their primary axis. The x direction is defined as the direction running parallel to the length of the stent and the z direction refers to the direction penetrating through the coating from the air-coating to the coating-metal interface. Typical laser power is <10 mW on the sample stage. All experiments can be conducted with a plan achromat objective, 100×$N_A$=0.9 (Nikon).

Samples (n=5) comprising stents made of L605 and having coatings as described herein and/or produced by methods described herein can be analyzed. For each sample, three locations are selected along the stent length. The three locations are located within one-third portions of the stents so that the entire length of the stent are represented in the data. The stent is then rotated 180 degrees around the circumference and an additional three locations are sampled along the length. In each case, the data is collected from the strut portion of the stetn. Six random spatial locations are also profiled on coated coupon samples made of L605 and having coatings as described herein and/or produced by methods described herein. The Raman spectra of each individual component present in the coatings are also collected for comparison and reference. Using the instrument software, the average spectra from the spectral image data are calculated by selecting the spectral image pixels that are exclusive to each layer. The average spectra are then exported into GRAMS/AI v. 7.02 software (Thermo Galactic) and the appropriate Raman bands are fit to a Voigt function. The band areas and shift positions are recorded.

The pure component spectrum for each component of the coating (e.g. drug, polymer) are also collected at 532 and 785 nm excitation. The 785 nm excitation spectra are collected with a confocal Raman microscope (WITec Instruments Corp. Savoy, Ill.) equipped with a 785 nm diode laser, appropriate collection optics, and a back-illuminated thermoelectriaclly cooled 1024×128 pixel array CCD camera optimized for visible and infrared wavelengths (Andor Technology).

Time of Flight Secondary Ion Mass Spectrometery

TOF-SIMS can be used to determine molecular species (drug and polymer) at the outer 1-2 nm of sample surface when operated under static conditions. The technique can be operated in spectroscopy or imaging mode at high spatial resolution. Additionally cross-sectioned samples can be analysed. When operated under dynamic experimental conditions, known in the art, depth profiling chemical characterization can be achieved.

For example, under static conditions (for example a ToF-SIMS IV (IonToF, Munster)) using a 25 Kv $Bi^{++}$ primary ion source maintained below $10^{12}$ ions per $cm^2$ is used. Where necessary a low energy electron flood gun (0.6 nA DC) is used to charge compensate insulating samples.

Cluster Secondary Ion Mass Spectrometry, may be employed as described Belu et al, "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference.

A stent as described herein is obtained. The stent is prepared for SIMS analysis by cutting it longitudinally and opening it up with tweezers. The stent is then pressed into multiple layers of iridium foil with the outer diameter facing outward.

TOF-SIMS experiments are performed on an Ion-TOF IV instrument equipped with both Bi and SF5+ primary ion beam cluster sources. Sputter depth profiling is performed in the dual-beam mode. The analysis source is a pulsed, 25-keV bismuth cluster ion source, which bombarded the surface at an incident angle of 45° to the surface normal. The target current is maintained at ~0.3 pÅ (+10%) pulsed current with a raster size of 200 um×200 um for all experiments. Both positive and negative secondary ions are extracted from the sample into a reflectron-type time-of-flight mass spectrometer. The secondary ions are then detected by a microchannel plate detector with a post-acceleration energy of 10 kV. A low-energy electron flood gun is utilized for charge neutralization in the analysis mode.

The sputter source used is a 5-keV SF5+ cluster source also operated at an incident angle of 45° to the surface normal. For thin model samples on Si, the SF5+ current is maintained at ~2.7 nÅ with a 750 um×750 um raster. For the thick samples on coupons and for the samples on stents, the current is maintained at 6 nA with a 500 um×500 um raster. All primary beam currents are measured with a Faraday cup both prior to and after depth profiling.

All depth profiles are acquired in the noninterlaced mode with a 5-ms pause between sputtering and analysis. Each spectrum is averaged over a 7.37 second time period. The analysis is immediately followed by 15 seconds of $SF_5^+$ sputtering. For depth profiles of the surface and subsurface regions only, the sputtering time was decreased to 1 second for the 5% active agent sample and 2 seconds for both the 25% and 50% active agent samples. Temperature-controlled depth profiles are obtained using a variable-temperature stage with Eurotherm Controls temperature controller and IPSG V3.08 software. samples are first placed into the analysis chamber at room temperature. The samples are brought to the desired temperature under ultra high-vacuum conditions and are allowed to stabilize for 1 minute prior to analysis. All depth profiling experiments are performed at −100 C and 25 C.

Atomic Force Microscopy (AFM)

AFM is a high resolution surface characterization technique. AFM is used in the art to provide topographical imaging, in addition when employed in Tapping Mode™ can image material and or chemical properties of the surface. Additionally cross-sectioned samples can be analyzed. Coating composition may be determined using Tapping Mode™ atomic force microscopy (AFM) analysis. Other modes of operation are well known and can be employed here by those skilled in the art.

A stent as described herein is obtained. AFM may be employed as described in Ranade et al., "Physical characterization of controlled release of paclitaxel from the TAXUS Express2 drug-eluting stent" *J. Biomed. Mater. Res.* 71(4):625-634 (2004) incorporated herein in its entirety by reference.

Polymer and drug morphologies, coating composition, at least may be determined using atomic force microscopy (AFM) analysis. A multi-mode AFM (Digital Instruments/Veeco Metrology, Santa Barbara, Calif.) controlled with Nanoscope IIIa and NanoScope Extender electronics is used. TappingMode™ AFM imaging may be used to show topography (a real-space projection of the coating surface microstructure) and phase-angle changes of the AFM over the sample area to contrast differences in the materials properties.

Infrared (IR) Spectroscopy for In-Vitro Testing

Infrared (IR) Spectroscopy using FTIR, ATR-IR or micro ATR-IR can be used to identify polymer composition by comparison to standard polymer reference spectra.

Example 8: Determination of the Bioabsorbability of a Device

In some embodiments of the device the substrate coated itself is made of a bioabsorbable material, such as the bioabsorbable polymers presented herein, or another bioabsorbable material such as magnesium and, thus, the entire device is bioabsorbable. Techniques presented with respect to showing Bioabsorbability of a polymer coating may be used to additionally and/or alternatively show the bioabsorbability of a device, for example, by GPC In-Vivo testing, HPLC In-Vivo Testing, GPC In-Vitro testing, HPLC In-Vitro Testing, SEM-FIB Testing, Raman Spectroscopy, SEM, and XPS as described herein with variations and adjustments which would be obvious to those skilled in the art. Another technique to view the physical structure of a device in 3-D is Nano X-Ray Computer Tomography (e.g. such as made by SkyScan), which could be used in an elution test and/or bioabsorbability test, as described herein to show the physical structure of the coating remaining on stents at each time point, as compared to a scan prior to elution/bioabsorbtion.

Example 9: Determination of Secondary Structures Presence of a Biological Agent

Raman Spectroscopy

FT-Raman or confocal raman microscopy can be employed to determine secondary structure of a biological Agent. For example fitting of the Amide I, II, or III regions of the Raman spectrum can elucidate secondary structures (e.g. alpha-helices, beta-sheets). See, for example, Iconomidou, et al., "Secondary Structure of Chorion Proteins of the Teleosetan Fish Dentex dentex by ATR FR-IR and FT-Raman Spectroscopy" *J. of Structural Biology*, 132, 112-122 (2000); Griebenow, et al., "On Protein Denaturation in Aqueous-Organic Mixtures but Not in Pure Organic Solvents" *J. Am. Chem. Soc.*, Vol 118, No. 47, 11695-11700 (1996).

Infrared (IR) Spectroscopy for In-Vitro Testing

Infrared spectroscopy, for example FTIR, ATR-IR and micro ATR-IR can be employed to determine secondary structure of a biological Agent. For example fitting of the Amide I, II, of III regions of the infrared spectrum can elucidate secondary structures (e.g. alpha-helices, beta-sheets).

Example 10: Determination of the Microstructure of a Coating on a Medical Device Atomic Force Microscopy (AFM)

AFM is a high resolution surface characterization technique. AFM is used in the art to provide topographical imaging, in addition when employed in Tapping Mode™ can image material and or chemical properties of the surface. Additionally cross-sectioned samples can be analyzed. The technique can be used under ambient, solution, humidified or temperature controlled conditions. Other modes of operation are well known and can be readily employed here by those skilled in the art.

A stent as described herein is obtained. AFM is used to determine the microstructure of the coating. A stent as described herein is obtained. AFM may be employed as described in Ranade et al., "Physical characterization of controlled release of paclitaxel from the TAXUS Express2 drug-eluting stent" *J. Biomed. Mater. Res.* 71(4):625-634 (2004) incorporated herein in its entirety by reference.

For example, polymer and drug morphologies, coating composition, and physical structure may be determined using atomic force microscopy (AFM) analysis. A multi-mode AFM (Digital Instruments/Veeco Metrology, Santa Barbara, Calif.) controlled with Nanoscope IIIa and Nano-Scope Extender electronics is used. Samples are examined in the dry state using AFM before elution of the drug (e.g. rapamycin). Samples are also examined at select time points through a elution period (e.g. 48 hours) by using an AFM probe-tip and flow-through stage built to permit analysis of wet samples. The wet samples are examined in the presence of the same elution medium used for in-vitro kinetic drug release analysis (e.g. PBS-Tween20, or 10 mM Tris, 0.4 wt. % SDS, pH 7.4). Saturation of the solution is prevented by frequent exchanges of the release medium with sever volumes of fresh medium. TappingMode™ AFM imaging may be used to show topography (a real-space projection of the coating surface microstructure) and phase-angle changes of the AFM over the sample area to contrast differences in the materials properties. The AFM topography images can be three-dimensionally rendered to show the surface of a coated stent, which can show holes or voids of the coating which may occur as the polymer is absorbed and the drug is released from the polymer over time, for example.

Nano X-Ray Computer Tomography

Another technique that may be used to view the physical structure of a device in 3-D is Nano X-Ray Computer Tomography (e.g. such as made by SkyScan), which could be used in an elution test and/or bioabsorbability test, as described herein to show the physical structure of the coating remaining on stents at each time point, as compared to a scan prior to elution/bioabsorbtion.

Example 11: Determination of an Elution Profile

In Vitro

Example 11a

In one method, a stent described herein is obtained. The elution profile is determined as follows: stents are placed in 16 mL test tubes and 15 mL of 10 mM PBS (pH 7.4) is pipetted on top. The tubes are capped and incubated at 37 C with end-over-end rotation at 8 rpm. Solutions are then collected at the designated time points (e.g. 1d, 7d, 14d, 21d, and 28d) (e.g. 1 week, 2 weeks, and 10 weeks) and replenished with fresh 1.5 ml solutions at each time point to prevent saturation. One mL of DCM is added to the collected sample of buffer and the tubes are capped and shaken for one minute and then centrifuged at 200×G for 2 minutes. The supernatant is discarded and the DCM phase is evaporated to dryness under gentle heat (40° C.) and nitrogen gas. The dried DCM is reconstituted in 1 mL of 60:40 acetonitrile: water (v/v) and analyzed by HPLC. HPLC analysis is performed using Waters HPLC system (mobile phase 58:37:5 acetonitrile:water:methanol 1 mL/min, 20 uL injection, C18 Novapak Waters column with detection at 232 nm).

Example 11b

In another method, the in vitro pharmaceutical agent elution profile is determined by a procedure comprising contacting the device with an elution media comprising ethanol (5%) wherein the pH of the media is about 7.4 and wherein the device is contacted with the elution media at a temperature of about 37° C. The elution media containing the device is optionally agitating the elution media during the contacting step. The device is removed (and/or the elution media is removed) at least at designated time points (e.g. 1 h, 3 h, 5 h, 7 h, 1d, and daily up to 28d) (e.g. 1 week, 2 weeks, and 10 weeks). The elution media is then assayed using a UV-Vis for determination of the pharmaceutical agent content. The elution media is replaced at each time point with fresh elution media to avoid saturation of the elution media. Calibration standards containing known amounts of drug were also held in elution media for the same durations as the samples and used at each time point to determine the amount of drug eluted at that time (in absolute amount and as a cumulative amount eluted).

In one test, devices were coated tested using this method. In these experiments two different polymers were employed: Polymer A: ~50:50 PLGA-Ester End Group, MW ~19 kD, degradation rate 70 days; Polymer B: ~50:50 PLGA-Carboxylate End Group, MW~10 kD, degradation rate 28 days. Metal stents were coated as follows: AS1: (n=6) Polymer A/Rapamycin/Polymer A/Rapamycin/Polymer A; AS2: (n=6) Polymer A/Rapamycin/Polymer A/Rapamycin/Polymer B; AS1 (213): (n=6) Polymer B/Rapamycin/Polymer B/Rapamycin/Polymer B; AS1b: (n=6) Polymer A/Rapamycin/Polymer A/Rapamycin/Polymer A; AS2b: (n=6) Polymer A/Rapamycin/Polymer A/Rapamycin/Polymer B. The in vitro pharmaceutical agent elution profile was determined by contacting each device with an elution media comprising ethanol (5%) wherein the pH of the media is about 7.4 and wherein the device was contacted with the elution media at a temperature of about 37° C. The elution media was removed from device contact at least at 1 h, 3 h, 5 h, 7 h, 1d, and at additional time points up to 70 days (See FIGS. 5-8). The elution media was then assayed using a UV-Vis for determination of the pharmaceutical agent content (in absolute amount and cumulative amount eluted). The elution media was replaced at each time point with fresh elution media to avoid saturation of the elution media. Calibration standards containing known amounts of drug were also held in elution media for the same durations as the samples and assayed by UV-Vis at each time point to determine the amount of drug eluted at that time (in absolute amount and as a cumulative amount eluted), compared to a blank comprising Spectroscopic grade ethanol. Elution profiles as shown in FIGS. 5-8, showing the average amount of rapamycin eluted at each time point (average of all stents tested) in micrograms. Table 2 shows for each set of stents (n=6) in each group (AS1, AS2, AS(213), AS1b, AS2b), the average amount of rapamycin in ug loaded on the stents, the average amount of polymer in ug loaded on the stents, and the total amount of rapamycin and polymer in ug loaded on the stents.

TABLE 2

| Stent Coating | Ave. Rapa, ug | Ave. Poly, ug | Ave. Total Mass, ug |
|---|---|---|---|
| AS1 | 175 | 603 | 778 |
| AS2 | 153 | 717 | 870 |
| AS1(213) | 224 | 737 | 961 |
| AS1b | 171 | 322 | 493 |
| AS2b | 167 | 380 | 547 |

Example 11c

In another method, the in vitro pharmaceutical agent elution profile is determined by a procedure comprising contacting the device with an elution media comprising ethanol (20%) and phosphate buffered saline (80%) wherein the pH of the media is about 7.4 and wherein the device is contacted with the elution media at a temperature of about 37° C. The elution media containing the device is optionally agitating the elution media during the contacting step. The device is removed (and/or the elution media is removed) at least at designated time points (e.g. 1 h, 3 h, 5 h, 7 h, 1d, and daily up to 28d) (e.g. 1 week, 2 weeks, and 10 weeks). The elution media is replaced periodically (at least at each time point, and/or daily between later time points) to prevent saturation; the collected media are pooled together for each time point. The elution media is then assayed for determination of the pharmaceutical agent content using HPLC. The elution media is replaced at each time point with fresh elution media to avoid saturation of the elution media. Calibration standards containing known amounts of drug are also held in elution media for the same durations as the samples and used at each time point to determine the amount of drug eluted at that time (in absolute amount and as a cumulative amount eluted). Where the elution method changes the drug over time, resulting in multiple peaks present for the drug when tested, the use of these calibration standards will also show this change, and allows for adding all the peaks to give the amount of drug eluted at that time period (in absolute amount and as a cumulative amount eluted).

In one test, devices (n=9, laminate coated stents) as described herein were coated and tested using this method. In these experiments a single polymer was employed: Polymer A: 50:50 PLGA-Ester End Group, MW~19 kD. The metal (stainless steel) stents were coated as follows: Polymer A/Rapamycin/Polymer A/Rapamycin/Polymer A, and the average amount of rapamycin on each stent was 162 ug (stdev 27 ug). The coated stents were contacted with an elution media (5.00 mL) comprising ethanol (20%) and phosphate buffered saline wherein the pH of the media is about 7.4 (adjusted with potassiume carbonate solution—1 g/100 mL distilled water) and wherein the device is contacted with the elution media at a temperature of about 37° C.+/−0.2° C. The elution media containing the device was agitated in the elution media during the contacting step. The elution media was removed at least at time points of 1 h, 3 h, 5 h, 7 h, 1d, and daily up to 28d. The elution media was assayed for determination of the pharmaceutical agent (rapamycin) content using HPLC. The elution media was replaced at each time point with fresh elution media to avoid saturation of the elution media. Calibration standards containing known amounts of drug were also held in elution media for the same durations as the samples and assayed at each time point to determine the amount of drug eluted at that time (in absolute amount and as a cumulative amount eluted). The multiple peaks present for the rapamycin (also present in the calibration standards) were added to give the amount of drug eluted at that time period (in absolute amount and as a cumulative amount eluted). HPLC analysis is performed using Waters HPLC system, set up and run on each sample as provided in the Table 3 below using an injection volume of 100 uL.

TABLE 3

| Time point (minutes) | % Acetonitrile | % Ammonium Acetate (0.5%), pH 7.4 | Flow Rate (mL/min) |
|---|---|---|---|
| 0.00 | 10 | 90 | 1.2 |
| 1.00 | 10 | 90 | 1.2 |
| 12.5 | 95 | 5 | 1.2 |
| 13.5 | 100 | 0 | 1.2 |
| 14.0 | 100 | 0 | 3 |
| 16.0 | 100 | 0 | 3 |
| 17.0 | 10 | 90 | 2 |
| 20.0 | 10 | 90 | 0 |

Figure 10:
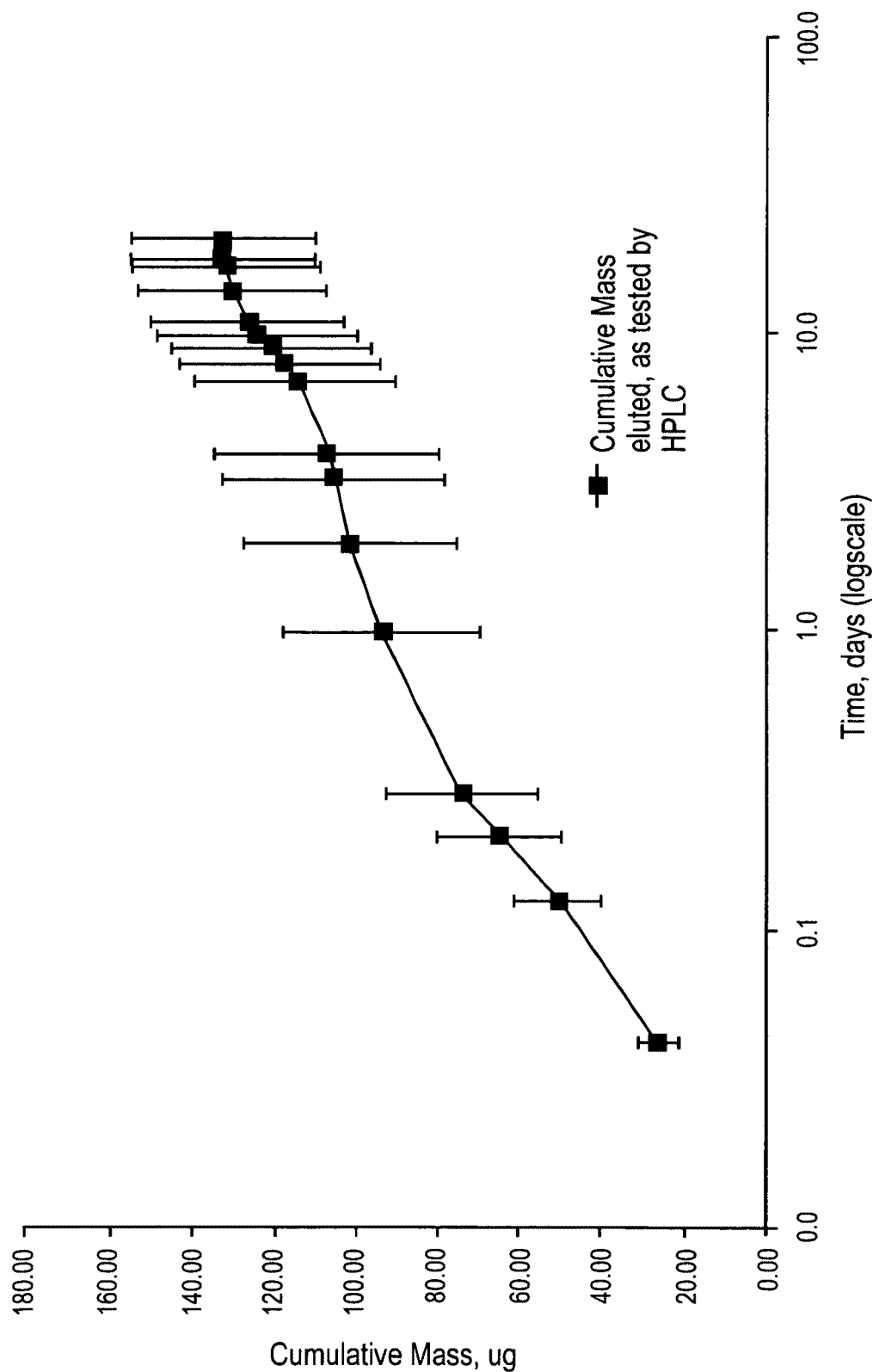
FIG. 10: Rapamycin Elution Profile of coated stents (PLGA/Rapamycin coatings) where the elution profile was determined by a 20% EtOH/phosphate buffered saline, pH 7.4, 37° C. elution buffer and a HPLC test method as described in Example 11c of described therein, wherein the elution time (x-axis) is expressed in logarithmic scale (i.e., log(time)).

FIG. 9 elution profiles resulted, showing the average cumulative amount of rapamycin eluted at each time point (average of n=9 stents tested) in micrograms. FIG. 10 also expresses the same elution profile, graphed on a logarithmic scale (x-axis is log(time)).

Example 11d

To obtain an accelerated in-vitro elution profile, an accelerated elution buffer comprising 18% v/v of a stock solution of 0.067 mol/L KH2PO4 and 82% v/v of a stock solution of 0.067 mol/L Na2HPO4 with a pH of 7.4 is used. Stents described herein are expanded and then placed in 1.5 ml solution of this accelerated elution in a 70° C. bath with rotation at 70 rpm. The solutions are then collected at the following time points: 0 min., 15 min., 30 min., 1 hr, 2 hr, 4 hr, 6 hr, 8 hr, 12 hr, 16 hr, 20 hr, 24 hr, 30 hr, 36 hr and 48 hr. Fresh accelerated elution buffer are added periodically at least at each time point to replace the incubated buffers that are collected and saved in order to prevent saturation. For time points where multiple elution media are used (refreshed between time points), the multiple collected solutions are pooled together for liquid extraction by dichloromethane. Dichloromethane extraction and HPLC analysis is performed in the manner described previously.

In Vivo

Example 11e

Rabbit in vivo models as described above are euthanized at multiple time points. Stents are explanted from the rabbits. The explanted stents are placed in 16 mL test tubes and 15 mL of 10 mM PBS (pH 7.4) is pipette on top. One mL of DCM is added to the buffer and the tubes are capped and shaken for one minute and then centrifuged at 200×G for 2 minutes. The supernatant is discarded and the DCM phase is evaporated to dryness under gentle heat (40° C.) and nitrogen gas. The dried DCM is reconstituted in 1 mL of 60:40 acetonitrile:water (v/v) and analyzed by HPLC. HPLC analysis is performed using Waters HPLC system (mobile phase 58:37:5 acetonitrile:water:methanol 1 mL/min, 20 uL injection, C18 Novapak Waters column with detection at 232 nm).

Example 12: Determination of the Conformability (Conformality) of a Device Coating The ability to uniformly coat arterial stents with controlled composition and thickness using electrostatic capture in a rapid expansion of supercritical solution (RESS) experimental series has been demonstrated.

Scanning Electron Microscopy (SEM)

Stents are observed by SEM using a Hitachi S-4800 with an accelerating voltage of 800V. Various magnifications are used to evaluate the integrity, especially at high strain regions. SEM can provide top-down and cross-section images at various magnifications. Coating uniformity and thickness can also be assessed using this analytical technique. Pre- and post-expansions stents are observed by SEM using a Hitachi S-4800 with an accelerating voltage of 800V. Various magnifications are used to evaluate the integrity of the layers, especially at high strain regions.

Scanning Electron Microscopy (SEM) with Focused Ion Beam (FIB) Stents as described herein, and or produced by methods described herein are visualized using SEM-FIB analysis. Alternatively, a coated coupon could be tested in this method. Focused ion beam FIB is a tool that allows precise site-specific sectioning, milling and depositing of materials. FIB can be used in conjunction with SEM, at ambient or cryo conditions, to produce in-situ sectioning followed by high-resolution imaging. Cross-sectional FIB images may be acquired, for example, at 7000× and/or at 20000× magnification. An even coating of consistent thickness is visible.

Optical Microscopy

An Optical microscope may be used to create and inspect the stents and to empirically survey the coating of the substrate (e.g. coating uniformity). Nanoparticles of the drug and/or the polymer can be seen on the surfaces of the substrate using this analytical method. Following sintering, the coatings can be see using this method to view the coating conformably and for evidence of crystallinity of the drug.

Example 13: Determination of the Total Content of the Active Agent

Determination of the total content of the active agent in a coated stent may be tested using techniques described herein as well as other techniques obvious to one of skill in the art, for example using GPC and HPLC techniques to extract the drug from the coated stent and determine the total content of drug in the sample.

UV-VIS can be used to quantitatively determine the mass of rapamycin coated onto the stents. A UV-Vis spectrum of Rapamycin can be shown and a Rapamycin calibration curve can be obtained, (e.g. λ@277 nm in ethanol). Rapamycin is then dissolved from the coated stent in ethanol, and the drug concentration and mass calculated.

In one test, the total amount of rapamycin present in units of micrograms per stent is determined by reverse phase high performance liquid chromatography with UV detection (RP-HPLC-UV). The analysis is performed with modifications of literature-based HPLC methods for rapamycin that would be obvious to a person of skill in the art. The average drug content of samples (n=10) from devices comprising stents and coatings as described herein, and/or methods described herein are tested.

Example 14: Determination of the Extent of Aggregation of an Active Agent

Raman Spectroscopy

Confocal Raman microscopy can be used to characterize the drug aggregation by mapping in the x-y or x-z direction. Additionally cross-sectioned samples can be analysed. Raman spectroscopy and other analytical techniques such as described in Balss, et al., "Quantitative spatial distribution of sirolimus and polymers in drug-eluting stents using confocal Raman microscopy" *J. of Biomedical Materials Research Part A,* 258-270 (2007), incorporated in its entirety herein by reference, and/or described in Belu et al., "Three- Dimensional Compositional Analysis of Drug Eluting Stent Coatings Using Cluster Secondary Ion Mass Spectroscopy" *Anal. Chem.* 80: 624-632 (2008) incorporated herein in its entirety by reference may be used.

A sample (a coated stent) is prepared as described herein. Images are taken on the coating using Raman Spectroscopy. Alternatively, a coated coupon could be tested in this method. A WITec CRM 200 scanning confocal Raman microscope using a NiYAG laser at 532 nm is applied in the Raman imaging mode. The sample is place upon a piezo-electrically driven table, the laser light is focused upon the sample using a 100× dry objective (numerical aperture 0.90), and the finely focused laser spot is scanned into the sample. As the laser scans the sample, over each 0.33 micron interval a Raman spectrum with high signal to noise is collected using 0.3 Seconds of integration time. Each confocal cross-sectional image of the coatings displays a region 70 μm wide by 10 μm deep, and results from the gathering of 6300 spectra with a total imaging time of 32 min. To deconvolute the spectra and obtain separate images of the active agent and the polymer, all the spectral data (6300 spectra over the entire spectral region 500-3500 cm−1) are processed using an augmented classical least squares algorithm (Eigenvector Research, Wenatchee Wash.) using basis spectra obtained from samples of rapamycin (amorphous and crystalline) and polymer. For each sample, several areas are measured by Raman to ensure that results are reproducible, and to show layering of drug and polymer through the coating. Confocal Raman Spectroscopy can profile down micron by micron, can show the composition of the coating through the thickness of the coating.

Time of Flight Secondary Ion Mass Spectrometery

TOF-SIMS can be used to determine drug aggregation at the outer 1-2 nm of sample surface when operated under static conditions. The technique can be operated in spectroscopy or imaging mode at high spatial resolution. Additionally cross-sectioned samples can be analysed. When operated under dynamic experimental conditions, known in the art, depth profiling chemical characterization can be achieved.

For example, under static conditions (for example a ToF-SIMS IV (IonToF, Munster)) using a 25 Kv Bi$^{++}$ primary ion source maintained below $10^{12}$ ions per cm$^2$ is used. Where necessary a low energy electron flood gun (0.6 nA DC) is used to charge compensate insulating samples.

Cluster Secondary Ion Mass Spectrometry, may be employed as described in Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference.

A stent as described herein is obtained. The stent is prepared for SIMS analysis by cutting it longitudinally and opening it up with tweezers. The stent is then pressed into multiple layers of iridium foil with the outer diameter facing outward.

For example TOF-SIMS experiments are performed on an Ion-TOF IV instrument equipped with both Bi and SF5+ primary ion beam cluster sources. Sputter depth profiling is performed in the dual-beam mode. The analysis source is a pulsed, 25-keV bismuth cluster ion source, which bombarded the surface at an incident angle of 45° to the surface normal. The target current is maintained at ~0.3 pA (+10%) pulsed current with a raster size of 200 um×200 um for all experiments. Both positive and negative secondary ions are extracted from the sample into a reflectron-type time-of-flight mass spectrometer. The secondary ions are then detected by a microchannel plate detector with a post-acceleration energy of 10 kV. A low-energy electron flood gun is utilized for charge neutralization in the analysis mode.

The sputter source used is a 5-keV SF5+ cluster source also operated at an incident angle of 45° to the surface normal. For thin model samples on Si, the SF5+ current is maintained at ~2.7 nA with a 750 um×750 um raster. For the thick samples on coupons and for the samples on stents, the current is maintained at 6 nA with a 500 um×500 um raster. All primary beam currents are measured with a Faraday cup both prior to and after depth profiling.

All depth profiles are acquired in the noninterlaced mode with a 5-ms pause between sputtering and analysis. Each spectrum is averaged over a 7.37 second time period. The analysis is immediately followed by 15 seconds of SF5+ sputtering. For depth profiles of the surface and subsurface regions only, the sputtering time was decreased to 1 second for the 5% active agent sample and 2 seconds for both the 25% and 50% active agent samples.

Temperature-controlled depth profiles are obtained using a variable-temperature stage with Eurotherm Controls temperature controller and IPSG V3.08 software. samples are first placed into the analysis chamber at room temperature. The samples are brought to the desired temperature under ultra high-vacuum conditions and are allowed to stabilize for 1 minute prior to analysis. All depth profiling experiments are performed at −100 C and 25 C.

Atomic Force Microscopy (AFM)

AFM is a high resolution surface characterization technique. AFM is used in the art to provide topographical imaging, in addition when employed in Tapping Mode™ can image material and or chemical properties for example imaging drug in an aggregated state. Additionally cross-sectioned samples can be analyzed.

A stent as described herein is obtained. AFM may be employed as described in Ranade et al., "Physical characterization of controlled release of paclitaxel from the TAXUS Express2 drug-eluting stent" *J. Biomed. Mater. Res.* 71(4):625-634 (2004) incorporated herein in its entirety by reference.

Polymer and drug morphologies, coating composition, at least may be determined using atomic force microscopy (AFM) analysis. A multi-mode AFM (Digital Instruments/Veeco Metrology, Santa Barbara, Calif.) controlled with Nanoscope IIIa and NanoScope Extender electronics is used. TappingMode™ AFM imaging may be used to show topography (a real-space projection of the coating surface microstructure) and phase-angle changes of the AFM over the sample area to contrast differences in the materials properties.

Example 15: Determination of the Blood Concentration of an Active Agent

This assay can be used to demonstrate the relative efficacy of a therapeutic compound delivered from a device of the invention to not enter the blood stream and may be used in conjunction with a drug penetration assay (such as is described in PCT/US2006/010700, incorporated in its entirety herein by reference). At predetermined time points (e.g. 1d, 7d, 14d, 21d, and 28d, or e.g. 6 hrs, 12 hrs, 24 hrs, 36 hrs, 2d, 3d, 5d, 7d, 8d, 14d, 28d, 30d, and 60d), blood samples from the subjects that have devices that have been implanted are collected by any art-accepted method, including venipuncture. Blood concentrations of the loaded therapeutic compounds are determined using any art-accepted method of detection, including immunoassay, chromatography (including liquid/liquid extraction HPLC tandem mass spectrometric method (LC-MS/MS), and activity assays. See, for example, Ji, et al., "96-Well liquid-liquid extraction liquid chromatography-tandem mass spectrometry method for the quantitative determination of ABT-578 in human blood samples" *Journal of Chromatography B.* 805:67-75 (2004) incorporated in its entirety herein by reference.

In one test, blood samples are collected by venipuncture into evacuated collection tubes containing editic acid (EDTA) (n=4). Blood concentrations of the active agent (e.g. rapamycin) are determined using a validated liquid/liquid extraction HPLC tandem pass mass spectormetric method (LC-MS/MS) (Ji et al., et al., 2004). The data are averaged, and plotted with time on the x-axis and blood concetration of the drug is represented on the y-axis in ng/ml.

Example 16: Preparation of Supercritical Solution Comprising Poly(Lactic-Co-Glycolic Acid) (PLGA) in Hexafluoropropane A view cell at room temperature (with no applied heat) is pressurized with filtered 1,1,1,2,3,3-Hexafluoropropane until it is full and the pressure reaches 4500 psi. Poly(lactic-co-glycolic acid) (PLGA) is added to the cell for a final concentration of 2 mg/ml. The polymer is stirred to dissolve for one hour. The polymer is fully dissolved when the solution is clear and there are no solids on the walls or windows of the cell.

Example 17: Dry Powder Rapamycin Coating on an Electrically Charged L605 Cobalt Chromium Metal Coupon A 1 cm×2 cm L605 cobalt chromium metal coupon serving as a target substrate for rapamycin coating is placed in a vessel and attached to a high voltage electrode. Alternatively, the substrate may be a stent or another biomedical device as described herein, for example. The vessel (V), of approximately 1500 $cm^3$ volume, is equipped with two separate nozzles through which rapamycin or polymers could be selectively introduced into the vessel. Both nozzles are grounded. Additionally, the vessel (V) is equipped with a separate port was available for purging the vessel. Upstream of one nozzle (D) is a small pressure vessel (PV) approximately 5 $cm^3$ in volume with three ports to be used as inlets and outlets. Each port is equipped with a valve which could be actuated opened or closed. One port, port (1) used as an inlet, is an addition port for the dry powdered rapamycin. Port (2), also an inlet is used to feed pressurized gas, liquid, or supercritical fluid into PV. Port (3), used as an outlet, is used to connect the pressure vessel (PV) with nozzle (D) contained in the primary vessel (V) with the target coupon.

Dry powdered Rapamycin obtained from LC Laboratories in a predominantly crystalline solid state, 50 mg milled to an average particle size of approximately 3 microns, is loaded into (PV) through port (1) then port (1) is actuated to the closed position. The metal coupon is then charged to +7.5 kV using a Glassman Series EL high-voltage power source. The drug nozzle on port has a voltage setting of −7.5 kV. After approximately 60-seconds, the drug is injected and the voltage is eliminated. Upon visual inspection of the coupon using an optical microscope, the entire surface area of the coupon is examined for relatively even distribution of powdered material. X-ray diffraction (XRD) is performed as described herein to confirm that the powdered material is largely crystalline in nature as deposited on the metal coupon. UV-Vis and FTIR spectroscopy is performed as describe herein to confirm that the material deposited on the coupon is rapamycin.

Example 18: Polymer Coating on an Electrically Charged L605 Coupon Using Rapid Expansion from a Liquefied Gas A coating apparatus as described in example 17 above is used in the foregoing example. In this example the second nozzle, nozzle (P), is used to feed precipitated polymer particles into vessel (V) to coat a L605 coupon. Alternatively, the substrate may be a stent or another biomedical device as described herein, for example. Nozzle (P) is equipped with a heater and controller to minimize heat loss due to the expansion of liquefied gases. Upstream of nozzle (P) is a pressure vessel, (PV2), with approximately 25-$cm^3$ internal volume. The pressure vessel (PV2) is equipped with multiple ports to be used for inlets, outlets, thermocouples, and pressure transducers. Additionally, (PV2) is equipped with a heater and a temperature controller. Each port is connected to the appropriate valves, metering valves, pressure regulators, or plugs to ensure adequate control of material into and out of the pressure vessel (PV2). One outlet from (PV2) is connected to a metering valve through pressure rated tubing which was then connected to nozzle (P) located in vessel (V). In the experiment, 150 mg of poly(lactic-co-glycolic acid) (PLGA) is added to pressure vessel (PV2). 1,1,1,2,3,3-hexafluoropropane is added to the pressure vessel (PV2) through a valve and inlet. Pressure vessel (PV2) is set at room temperature with no applied heat and the pressure is 4500 psi. Nozzle (P) is heated to 150° C. A 1-cm×2-cm L605 coupon is placed into vessel (V), attached to an electrical lead and heated via a heat block 110° C. Nozzle (P) is attached to ground. The voltage is set on the polymer spray nozzle and an emitter=pair beaker to a achieve a current greater than or equal to 0.02 mAmps using a Glassman high-voltage power source at which point the metering valve is opened between (PV2) and nozzle (P) in pressure vessel (PV). Polymer dissolved in liquefied gas and is fed at a constant pressure of 200 psig into vessel (V) maintained at atmospheric pressure through nozzle (P) at an approximate rate of 3.0 $cm^3$/min. After approximately 5 seconds, the metering valve is closed discontinuing the polymer-solvent feed. Vessel (V) is Nitrogen gas for 30 seconds to displace the fluorocarbon. After approximately 30 seconds, the metering valve is again opened for a period of approximately 5 seconds and then closed. This cycle is repeated about 4 times. After an additional 1-minute the applied voltage to the coupon was discontinued and the coupon was removed from pressure vessel (V). Upon inspection by optical microscope, a polymer coating is examined for even distribution on all non-masked surfaces of the coupon.

Example 19: Dual Coating of a Metal Coupon with Crystalline Rapamycin and poly(lactic-co-glycolic acid) (PLGA)

An apparatus described in example 17 and further described in example 18 is used in the foregoing example. In preparation for the coating experiment, 25 mg of crystalline powdered rapamycin with an average particle size of 3-microns is added to (PV) through port (1), then port (1) was closed. Next, 150 mg of poly(lactic-co-glycolic acid) (PLGA) is added to pressure vessel (PV2). 1,1,1,2,3,3-hexafluoropropane is added to the pressure vessel (PV2)

through a valve and inlet. Pressure vessel (PV2) is kept at room temperature with no applied heat with the pressure inside the isolated vessel (PV2) approximately 4500 psi. Nozzle (P) is heated to 15° C. A 1-cm×2-cm L605 coupon is added to vessel (V) and connected to a high-voltage power lead. Both nozzles (D) and (P) are grounded. To begin, the coupon is charged to +7.5 kV after which port (3) connecting (PV) containing rapamycin to nozzle (D) charged at −7.5 kV is opened allowing ejection of rapamycin into vessel (V) maintained at ambient pressure. Alternatively, the substrate may be a stent or another biomedical device as described herein, for example. After closing port (3) and approximately 60-seconds, the metering valve connecting (PV2) with nozzle (P) inside vessel (V) is opened allowing for expansion of liquefied gas to a gas phase and introduction of precipitated polymer particles into vessel (V) while maintaining vessel (V) at ambient pressure. After approximately 15 seconds at a feed rate of approximately 3 cm$^3$/min., the metering valve s closed while the coupon remained charged. The sequential addition of drug followed by polymer as described above is optionally repeated to increase the number of drug-polymer layers after which the applied potential is removed from the coupon and the coupon was removed from the vessel. The coupon is then examined using an optical microscope to to determine whether a consistent coating is visible on all surfaces of the coupon except where the coupon was masked by the electrical lead.

Example 20: Dual Coating of a Metal Coupon with Crystalline Rapamycin and poly(lactic-co-glycolic acid) (PLGA) Followed by Supercritical Hexafluoropropane Sintering After inspection of the coupon created in example 19, the coated coupon (or other coated substrate, e.g. coated stent) is carefully placed in a sintering vessel that is at a temperature of 75° C. 1,1,1,2,3,3-hexafluoropropane in a separate vessel at 75 psi is slowly added to the sintering chamber to achieve a pressure of 23 to 27 psi. This hexafluoropropane sintering process is done to enhance the physical properties of the film on the coupon. The coupon remains in the vessel under these conditions for approximately 10 min after which the supercritical hexafluoropropane is slowly vented from the pressure vessel and then the coupon was removed and reexamined under an optical microscope. The coating is observed in conformal, consistent, and semi-transparent properties as opposed to the coating observed and reported in example 19 without dense hexafluoropropane treatment. The coated coupon is then submitted for x-ray diffraction (XRD) analysis, for example, as described herein to confirm the presence of crystalline rapamycin in the polymer.

Example 21: Coating of a Metal Cardiovascular Stent with Crystalline Rapamycin and Poly(Lactic-Co-Glycolic Acid) (PLGA)

The apparatus described in examples 17, 18 and 20 is used in the foregoing example. The metal stent used is made from cobalt chromium alloy of a nominal size of 18 mm in length with struts of 63 microns in thickness measuring from an abluminal surface to a luminal surface, or measuring from a side wall to a side wall. The stent is coated in an alternating fashion whereby the first coating layer of drug is followed by a layer of polymer. These two steps, called a drug/polymer cycle, are repeated twice so there are six layers in an orientation of drug-polymer-drug-polymer-drug-polymer. After completion of each polymer coating step and prior the application of the next drug coating step, the stent is first removed from the vessel (V) and placed in a small pressure vessel where it is exposed to supercritical hexafluoropropane as described above in example 20.

Example 22: Layered Coating of a Cardiovascular Stent with an Anti-Restenosis Therapeutic and Polymer in Layers to Control Drug Elution Characteristics A cardiovascular stent is coated using the methods described in examples 10 and 11 above. The stent is coated in such as way that the drug and polymer are in alternating layers. The first application to the bare stent is a thin layer of a non-resorbing polymer, approximately 2-microns thick. The second layer is a therapeutic agent with anti-restenosis indication. Approximately 35 micrograms are added in this second layer. A third layer of polymer is added at approximately 2-microns thick, followed by a fourth drug layer which is composed of about 25 micrograms of the anti-restenosis agent. A fifth polymer layer, approximately 1-micron thick is added to stent, followed by the sixth layer that includes the therapeutic agent of approximately 15-micrograms. Finally, a last polymer layer is added to a thickness of about 2-microns. After the coating procedure, the stent is annealed using carbon dioxide as described in example 16 above. In this example a drug eluting stent (DES) is described with low initial drug "burst" properties by virtue of a "sequestered drug layering" process, not possible in conventional solvent-based coating processes. Additionally, by virtue of a higher concentration of drug at the stent 'inter-layer' the elution profile is expected to reach as sustained therapeutic release over a longer period of time.

Example 23: Layered Coating of a Cardiovascular Stent with an Anti-Restenosis Therapeutic and an Anti-Thrombotic Therapeutic in a Polymer A cardiovascular stent is coated as described in example 11 above. In this example, after a first polymer layer of approximately 2-microns thick, a drug with anti-thrombotic indication is added in a layer of less than 2-microns in thickness. A third layer consisting of the non-resorbing polymer is added to a thickness of about 4-microns. Next another drug layer is added, a different therapeutic, with an anti-restenosis indication. This layer contains approximately 100 micrograms of the anti-restenosis agent. Finally, a polymer layer approximately 2-microns in thickness is added to the stent. After coating the stent is treated as described in example 20 to sinter the coating using hexafluoropropane.

Example 24: Coating of Stent with Rapamycin and Poly(Lactic-Co-Glycolic Acid) (PLGA)

Micronized Rapamycin is purchased from LC Laboratories. 50:50 PLGA (Mw=~90) are purchased from Aldrich Chemicals. Eurocor CoCr (7 cell) stents are used. The stents are coated by dry electrostatic capture followed by supercritical fluid sintering, using 3 stents/coating run and 3 runs/data set. Analysis of the coated stents is performed by multiple techniques on both stents and coupons with relevant control experiments described herein.

In this example, PLGA is dissolved in 1,1,1,2,3,3-Hexafluoropropane with the following conditions: a) room temperature, with no applied heat; b) 4500 psi; and c) at 2 mg/ml concentration. The spray line is set at 4500 psi, 150°

C. and nozzle temperature at 150° C. The solvent (Hexafluoropropane) is rapidly vaporized when coming out of the nozzle (at 150° C.). A negative voltage is set on the polymer spray nozzle to achieve a current of greater than or equal to 0.02 mAmps. The stent is loaded and polymer is sprayed for 15 seconds to create a first polymer coating.

The stent is then transferred to a sintering chamber that is at 75° C. The solvent, in this example 1, 1,2,3,3-hexafluoropropane, slowly enters the sintering chamber to create a pressure at 23 to 27 psi. Stents are sintered at this pressure for 10 minutes.

11.5 mg Rapamycin is loaded into the Drug injection port. The injection pressure is set at 280 psi with +7.5 kV for the stent holder and −7.5 kV for the drug injection nozzle. After the voltage is set for 60 s, the drug is injected into the chamber to create a first drug coating.

A second polymer coating is applied with two 15 second sprays of dissolved polymer with the above first polymer coating conditions. The second coating is also subsequently sintered in the same manner.

A second drug coating is applied with the same parameters as the first drug coating. Lastly, the outer polymer layer is applied with three 15 second sprays of dissolved polymer with the above polymer coating conditions and subsequently sintered.

Example 25: Histology of In Vivo Stented Porcine Models and Preparation for Pharmacokinetics Studies Coronary stenting was applied to porcine animal models as described previously. An angiography was perform on each animal prior to euthanasia. After prenecropsy angiography, each animal was euthanized via an overdose of euthanasia solution or potassium chloride solution, IV in accordance to the Test Facility's Standard Operating Procedure and was performed in accordance with accepted American Veterinary Medical Association's "AVMA Guidelines on Euthanasia" (June 2007; accessed at http://www.avma.org/issues/animal-welfare/euthansia.pdf). A limited necropsy consisting of examination of the heart was performed on all animals. Observations of macroscopic findings were recorded. Any evidence of macroscopic findings, were processed for histological examination. Regardless, all hearts were collected for histologic processing and assessment.

The hearts were perfusion fixed at ~100 mmHg with Lactated Ringer's Solution until cleared of blood followed by 10% neutral buffered formalin (NBF). The fixed hearts were placed in a NBF filled container and labeled as appropriate.

Whole heart radiographs were taken to document stent location and morphology in situ. In addition, each explanted stent was radiographed in two views (perpendicular or orthogonal incidences) along its longitudinal plane to assist in the assessment of expansion morphology, damage and/or areas of stent discontinuity (eg, strut fractures).

Fixed stented vessels were carefully dissected from the myocardium, leaving sufficient vessel both proximal and distal to the stented portion. Unless otherwise stated or required, all tissues/sections were processed according to the CBSET standard operating procedures. In particular, transverse sections of unstented vessel were obtained within approximately 1-3 mm of the proximal and distal ends of the stent (i.e., unstented vessel) and from the proximal, middle and distal regions of the stented vessel. All vessel sections were stained with hematoxylin and eosin and a tissue elastin stain (e.g., Verhoeff's).

The remaining myocardium was then transversely sectioned (i.e., "bread-loafed") from apex to base (~1 cm apart) to further assess for evidence of adverse reactions (e.g., infarction). If gross findings were present they were collected and processed for light microscopy. Remaining myocardial tissue were stored until finalization of the study at which time, it was disposed of according to Test Facility standard operating procedures, shipped to Sponsor, or archived at Sponsor's request and expense.

Quantitative morphometric analysis was performed on the histological sections from each stented artery. For each histological section, the parameters listed in Table 4 were directly measured using standard light microscopy and computer-assisted image measurement systems.

TABLE 4

Morphometry Parameters

| Parameter | Abbreviation | Calculation | Unit |
|---|---|---|---|
| Lumen Area | $L_a$ | directly measured | $mm^2$ |
| Internal Elastic Layer (IEL) Bounded Area | $IEL_a$ | directly measured | $mm^2$ |
| Stent Area | $S_a$ | directly measured | $mm^2$ |
| External Elastic Layer (EEL) Bounded Area | $EEL_a$ | directly measured | $mm^2$ |

From these direct measurements, all other histomorphological parameters were calculated. Measured and calculated parameters, formulae, and units of measure are given in Table 5.

TABLE 5

Calculated Morphometry Parameters and Units of Measure

| Parameter | Abbreviation | Calculation | Unit |
|---|---|---|---|
| Area Measurements | | | |
| Neointimal Area | $N_a$ | $IEL_a - L_a$ | $mm^2$ |
| Medial Area | $M_a$ | $EEL_a - IEL_a$ | $mm^2$ |
| Artery Area | $A_a$ | $L_a + N_a + M_a$ | $mm^2$ |
| Length Measurements | | | |
| Lumen Diameter | $L_d$ | $2 \times \sqrt{(L_a/\pi)}$ | mm |
| IEL Diameter | $IEL_d$ | $2 \times \sqrt{(L_a + N_a)/\pi}$ | mm |
| Stent Diameter | $S_d$ | $2 \times \sqrt{(S_a/\pi)}$ | mm |
| Arterial Diameter | $A_d$ | $2 \times \sqrt{(A_a/\pi)}$ | mm |
| Ratios | | | |
| Lumen/Artery Areas | L:A | $L_a/A_a$ | NA* |
| Neointima/Media Areas | N:M | $N_a/M_a$ | NA |
| EEL/IEL Areas | $EEL_a:IEL_a$ | $A_a/(L_a + N_a)$ | NA |
| IEL/Stent Areas | $IEL_a:S_a$ | $IEL_a/S_a$ | NA |
| Restenosis Parameters | | | |
| % Area Occlusions) | % AO | $N_a/(N_a + L_a) \times 100\%$ | % |
| Neointima Thickness | $N_{\mu m}$ | $N_{mm} \times 1000 (\mu m/mm)$ | μm |
| Neointima Thickness | $N_{mm}$ | $(IEL_d - L_d)/2$ | mm |

Histopathology—Stented & Adjacent Non-Stented Vessels

Histopathological scoring via light microscopy was also used to grade various parameters that reflect the degree and extent of the host response/repair process to treatment. These parameters included, but were not limited to, injury, inflammation, endothelialization, and fibrin deposition. When a microscopic endpoint listed below is not present/observed, the score 0 was given.

The scoring of the arterial cross-sections was carried out as follows:

Injury score for stented arterial segments is dependent on that portion of the arterial wall which is disrupted by the stent and/or associated tissue response. Injury was scored on a per-strut basis and the median and average calculated per plane (i.e., proximal, middle, distal) and stent. The scoring polymer for injury at each strut is listed in Table 6.

TABLE 6

Injury Score Polymer

| Score | Value |
|---|---|
| 0 | IEL intact |
| 1 | Disruption of IEL |
| 2 | Disruption of tunica media |
| 3 | Disruption of tunica adventitia |

Inflammation score depends on the degree of inflammation and extent of inflammation on a per-strut basis as outlined in Table 7. Inflammation was scored on a per strut basis and the average was calculated per plane and stent.

TABLE 7

Inflammation Score Polymer

| Score | Value |
|---|---|
| 0 | Absent |
| 1 | Scattered cellular infiltrates associated with strut |
| 2 | Notable cellular infiltrates associated with strut |
| 3 | Cellular infiltrates circumscribing strut |

Neointimal fibrin score depends on the degree of fibrin deposition in the neointima as outlined in Table 8.

TABLE 8

Neointimal Fibrin Score Polymer

| Score | Value |
|---|---|
| 0 | Absent |
| 1 | Infrequent spotting of fibrin |
| 2 | Heavier deposition of fibrin |
| 3 | Heavy deposition of fibrin that spans between struts |

Endothelialization score depends on the extent of the circumference of the artery lumen showing coverage with endothelial cells as outlined in Table 9.

TABLE 9

Endothelialization Score Polymer

| Score | Value |
|---|---|
| 0 | Absent |
| 1 | <25% |
| 2 | 25% to 75% |
| 3 | >75% |
| 4 | 100%, confluent |

Adventitial fibrosis score depends on the severity of response and circumference of artery affected as outlined in Table 10.

TABLE 10

Adventitial Fibrosis Score Polymer

| Score | Observation |
|---|---|
| 0 | Absent |
| 1 | Minimal presence of fibrous tissue |
| 2 | Notable fibrous tissue in 25%-50% of artery circumference |
| 3 | Notable fibrous tissue in ≥50% of artery circumference |

Neointimal maturation depends on the cellularity and organization of the neointima as outlined in Table 11.

TABLE 11

Neointimal Maturation Score Polymer

| Score | Observation |
|---|---|
| 0 | Absent |
| 1 | Immature, predominantly fibrino-vascular tissue |
| 2 | Transitional, predominantly organizing smooth muscle |
| 3 | Mature, generalized organized smooth muscle |

The histologic section of the artery was also examined for other histologic parameters including, but not limited to, hemorrhage, necrosis, medial fibrosis, type and relative amounts of inflammatory cell infiltrates (eg, neutrophils, histiocytes, lymphocytes, multinucleated giant cells), mineralization, strut malapposition, thrombosis and/or neointimal vascularity, or others as deemed appropriate by the pathologist. Unless otherwise stated in the pathology data/report, additional findings were graded as follow: 0=Absent; 1=Present, but minimal feature; 2=Notable feature; 3=Overwhelming feature.

Sections of the non-stented proximal and distal portions of the stented arteries, were similarly assessed and scored for histologic parameters as above (excluding neointimal fibrin) but were assessed for histomorphometry.

One histology study according to the description above was performed using the groups and coated stents (test articles) as noted in Table 12 which were coated according to the methods provided herein, and/or devices having coatings as described herein (for example, at AS1, AS2, or another coating combination as described herein) as compared to a control bare metal stent (BMS, AS3) The animals were Yucatan pigs, which were given an anticoagulation regimen of Day 1: ASA 650 mg+Plavix 300 mg, maintenance of: ASA 81 mg+Plavix75, and Procedural: ACT ~250 sec. Oversizing was 10-20%.

TABLE 12

| Group | Test Article | Number of Test Devices | Necropsy Time Point |
|---|---|---|---|
| 1 | AS1 | N = 6 | Day 28 |
|  |  | N = 6 | Day 90 |
| 2 | AS2 | N = 6 | Day 28 |
|  |  | N = 6 | Day 90 |
| 3 | AS3 (Bare metal Stent) | N = 6 | Day 28 |
|  |  | N = 6 | Day 90 |

A second histology study also according to the description above was performed and compared with a CYPHER stent control. In these studies, AS21, AS23, and AS24 were tested along with the CYPHER stent. AS21, AS23, and AS24 were designed with coatings comprising Polymer B as described above, with about half the polymer load of AS1. AS23 and AS24 had about half the amount of rapamycin as AS1, while AS21 was designed with a target rapamycin load that was about the same as AS1, as described previously.

Figure 12:
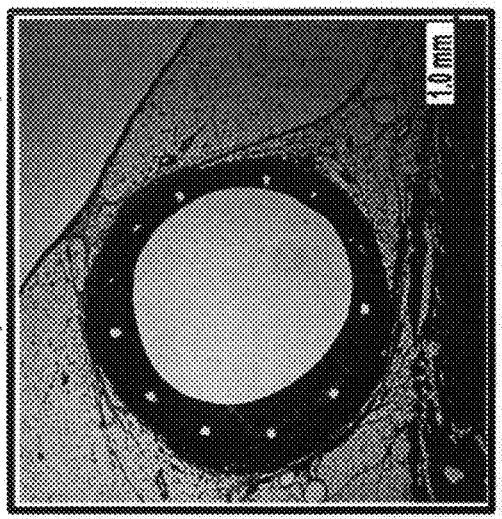
FIG. 12: Low-magnification cross-sections of porcine coronary artery stent implants (AS1, AS2 and Bare-metal stent control) at 28 days post-implantation as described in Example 25.
Figure 12:
Figure 12:
Figure 13:
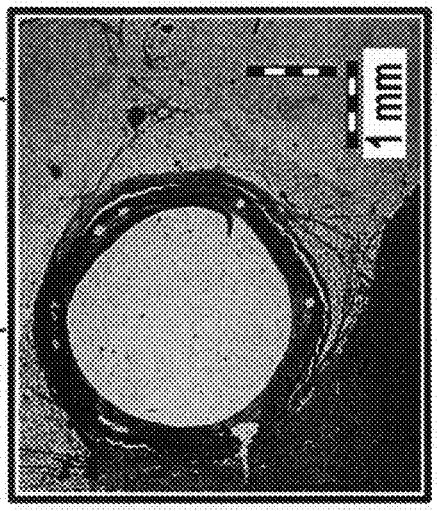
FIG. 13: Low-magnification cross-sections of porcine coronary artery stent implants (AS1, AS2 and Bare-metal stent control) at 90 days post-implantation as described in Example 25.
Figure 13:
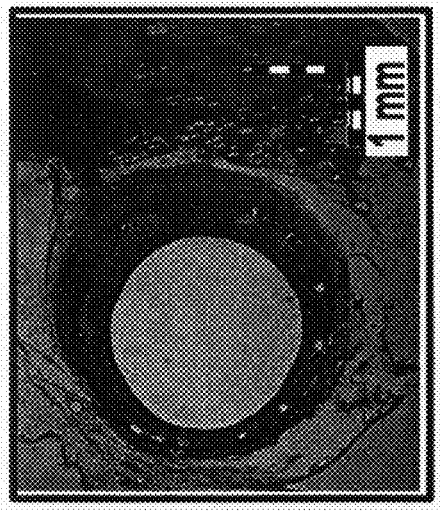
Figure 13:
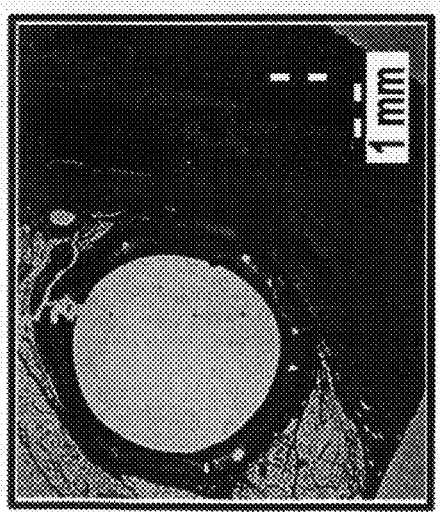
Figure 14:
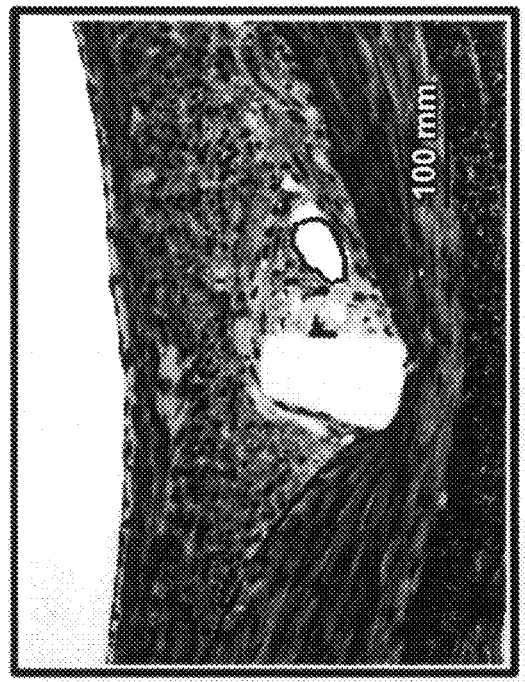
FIG. 14: Low-magnification cross-sections of porcine coronary artery stent implants depicting AS1 and AS2 drug depots as described in Example 25.
Figure 14:
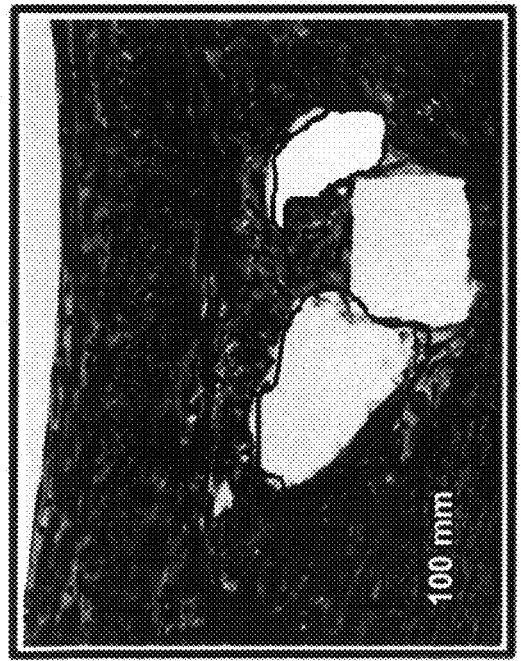
Figure 15:
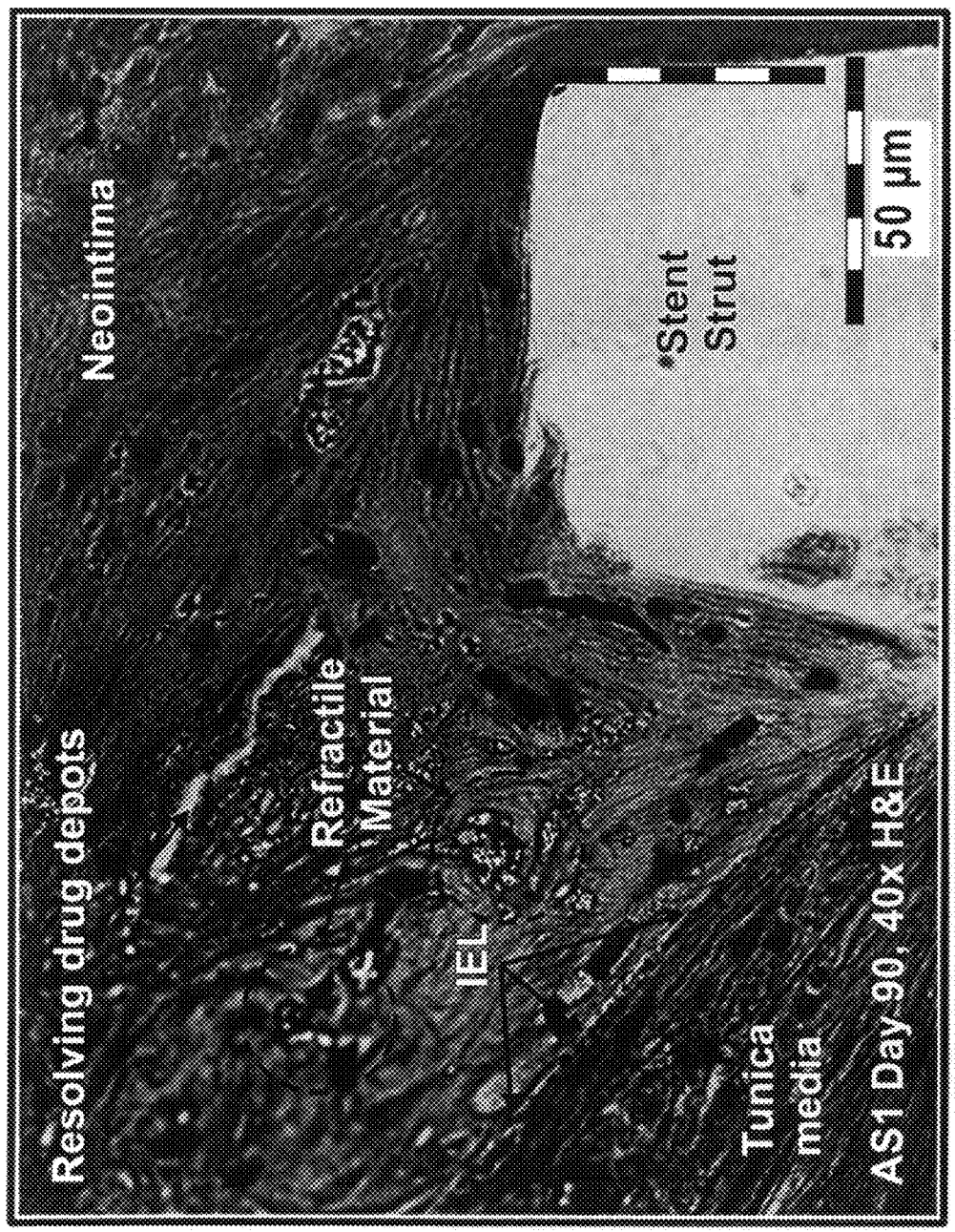
FIG. 15: Low-magnification cross-sections of porcine coronary artery AS1 stent implants at 90 days depicting drug depots as described in Example 25.
Figure 16:
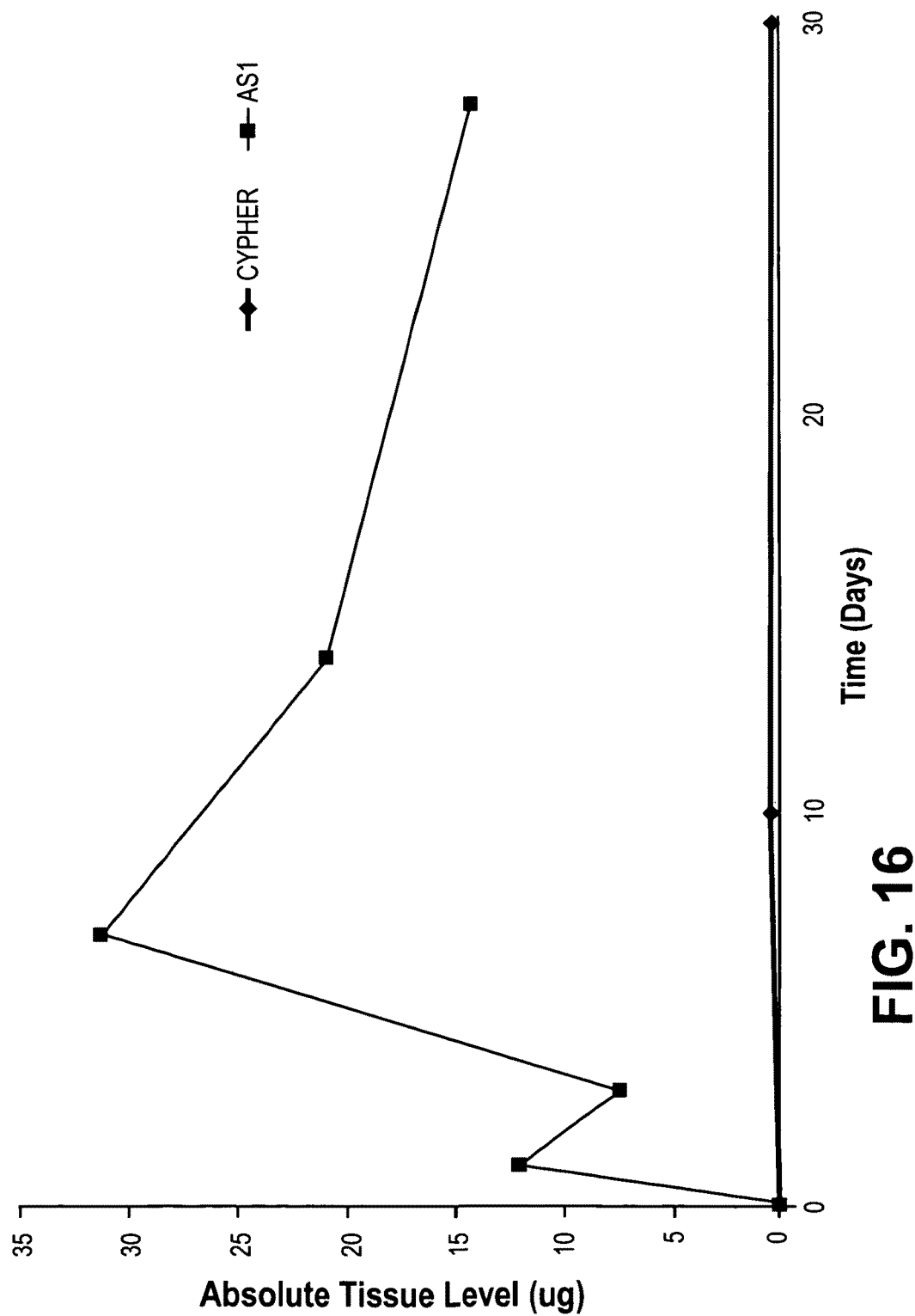
FIG. 16: Mean (n=3) Sirolimus Levels in Arterial Tissue Following AS1 and Cypher Stent Implantations in Swine Coronary Arteries expressed as absolute tissue level (y-axis) versus time (x-axis) following testing as described in Example 25. The results for AS1 presented in FIG. 16 were taken from a separate study as the results for the Cypher Stents presented in FIG. 16. Both studies were performed as described in Example 25, and data was collected similarly, however, data from the two studies were combined in this Figure to show the relative results of AS1 to the Cypher stents.
Figure 17:
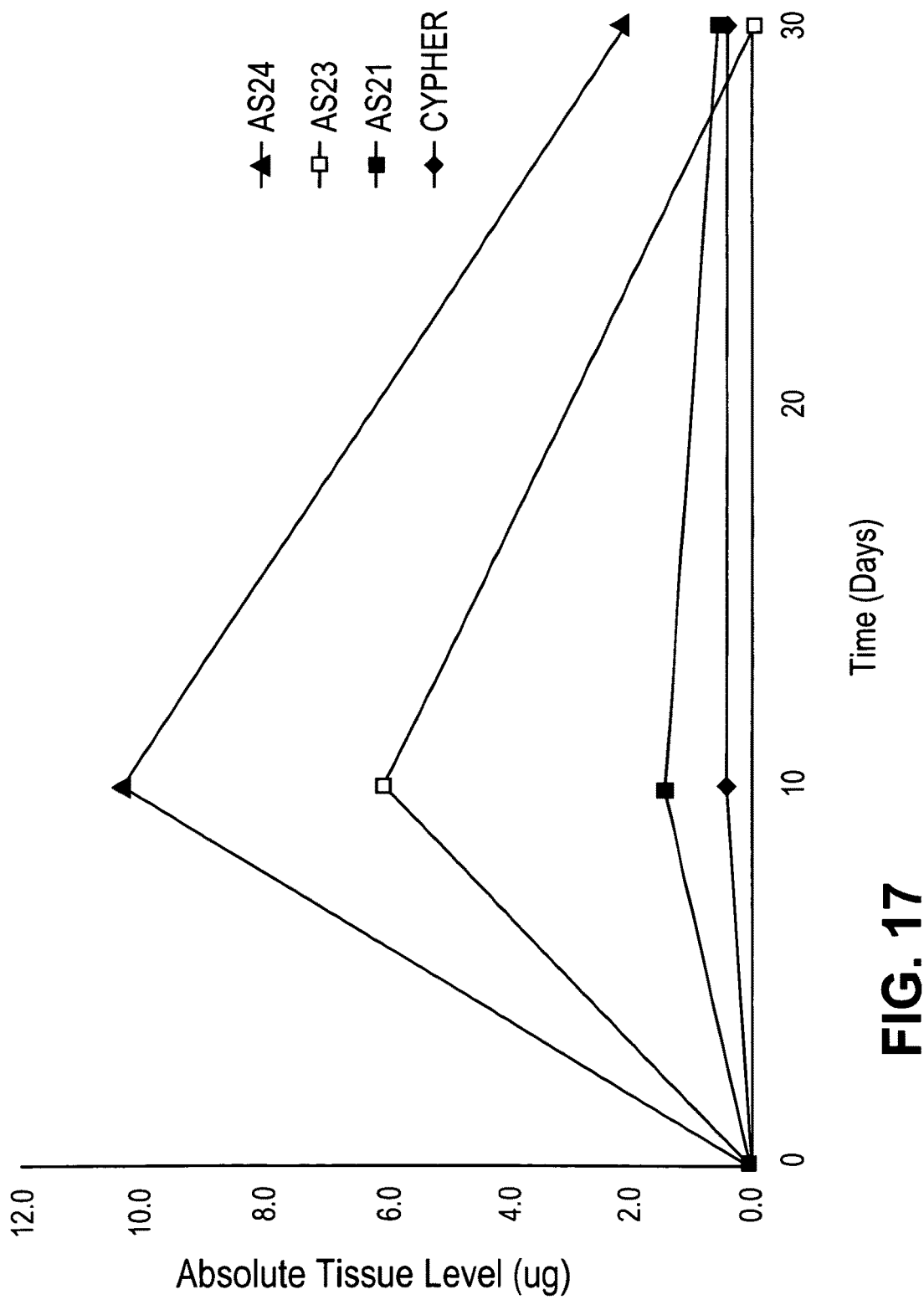
FIG. 17: Mean (n=3) Sirolimus Levels in Arterial Tissue Following Various Stent Implantations in Swine Coronary Arteries expressed as absolute tissue level (y-axis) versus time (x-axis) following testing as described in Example 25.
Figure 18:
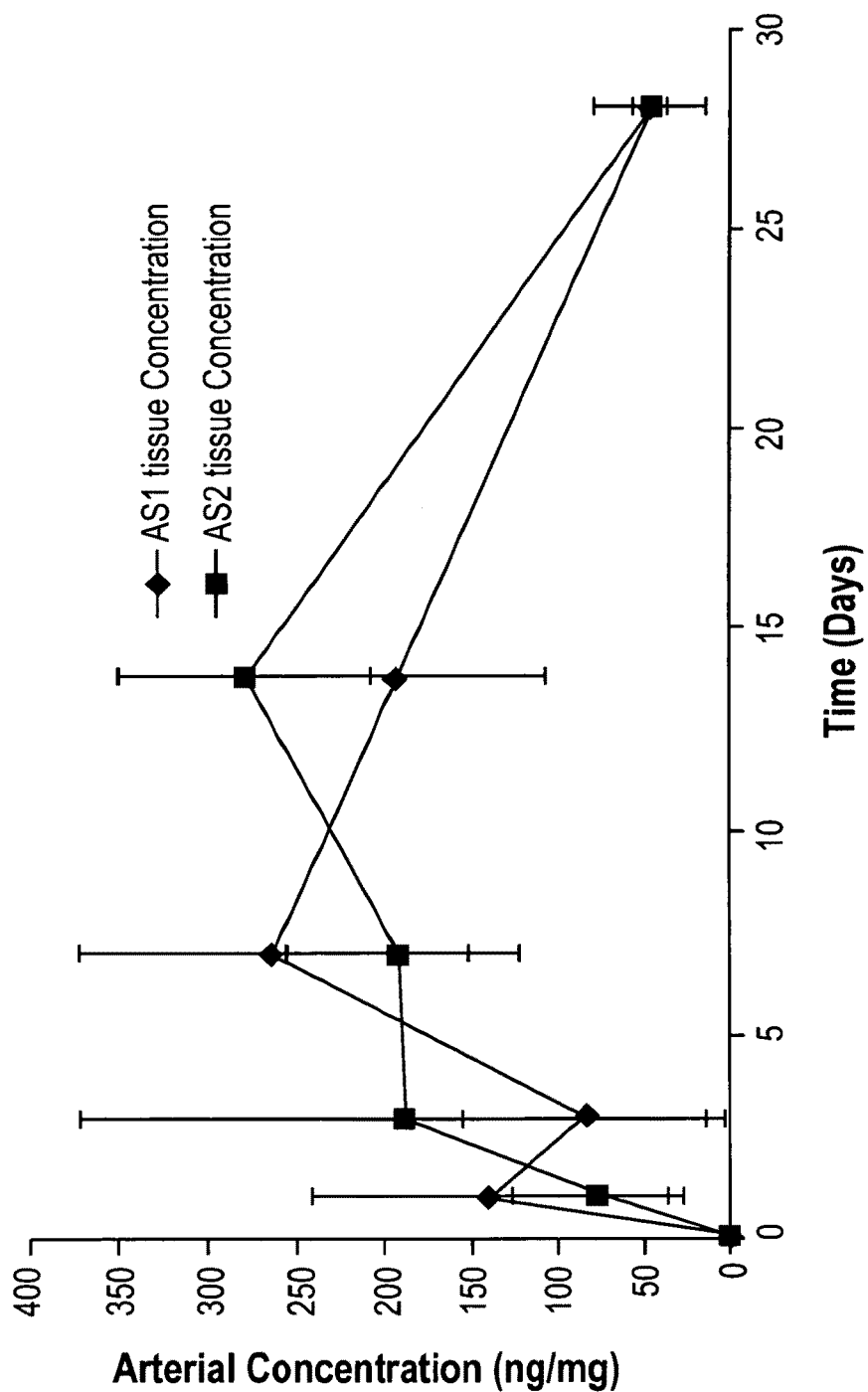
FIG. 18: Arterial Tissue Concentrations (y-axis) versus time (x-axis) for AS1 and AS2 stents following testing as described in Example 25.
Figure 19:
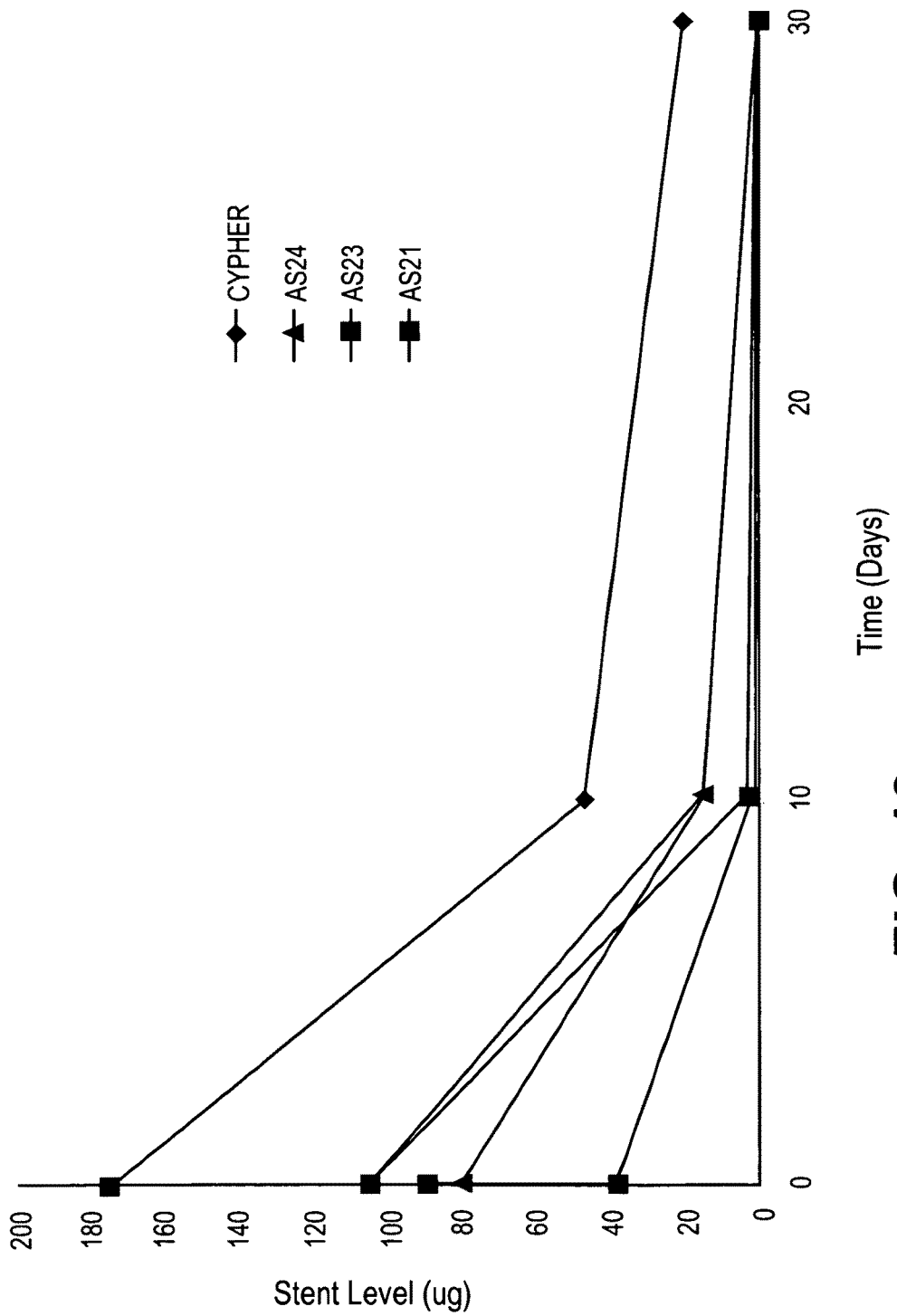
FIG. 19: Mean (n=3) Sirolimus Levels in Arterial Tissue Following Various Stent Implantations in Swine Coronary Arteries expressed as stent level (y-axis) versus time (x-axis) following testing as described in Example 25.
Figure 20:
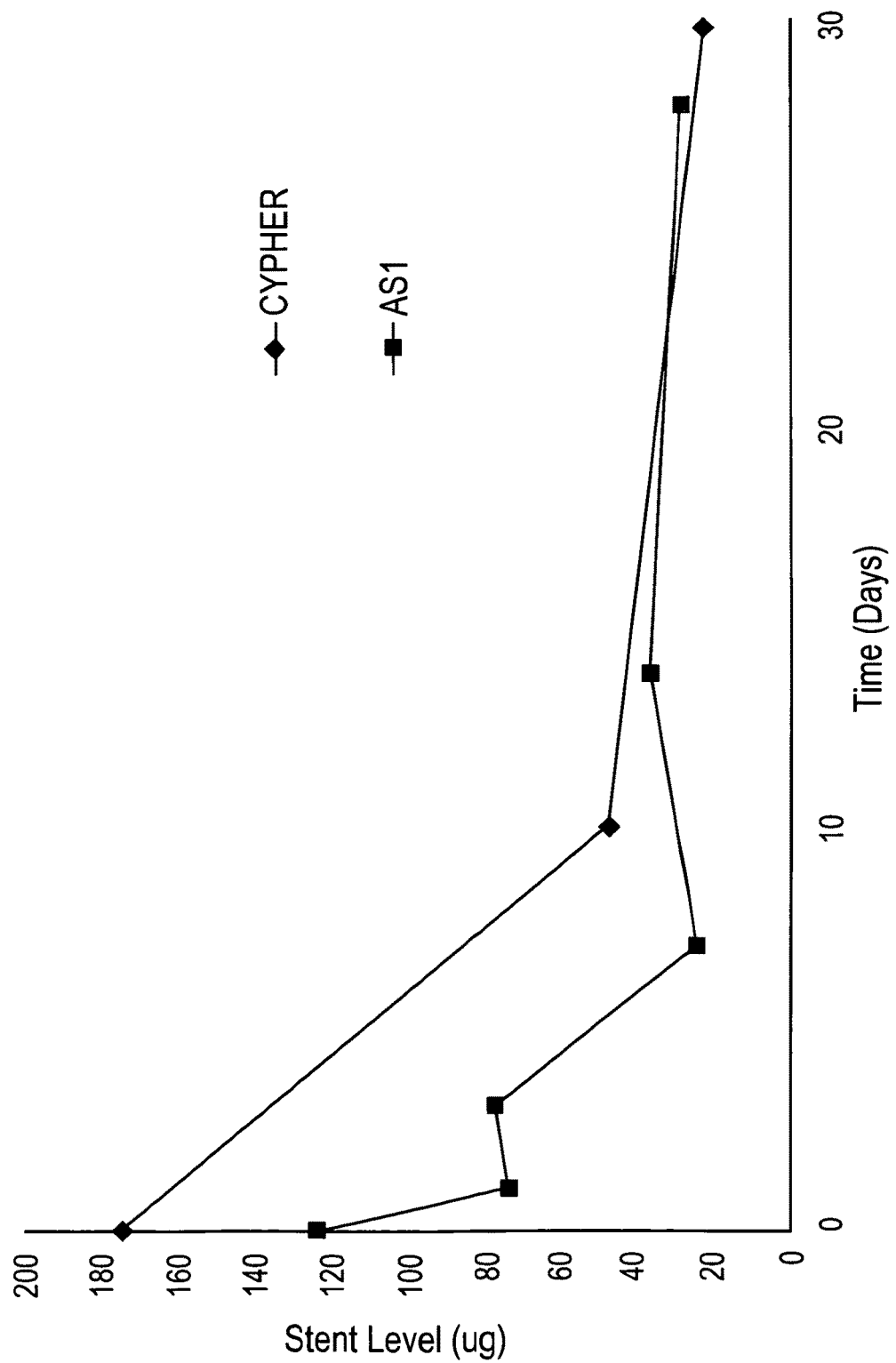
FIG. 20: Mean (n=3) Sirolimus Levels remaining on stents in Following AS1 and Cypher Stent Implantations in Swine Coronary Arteries expressed as stent level (y-axis) versus time (x-axis) following testing as described in Example 25. The results for AS1 presented in FIG. 20 were taken from a separate study as the results for the Cypher Stents presented in FIG. 20. Both studies were performed as described in Example 25, and data was collected similarly, however, data from the two studies were combined in this Figure to show the relative results of AS1 to the Cypher stents.
Figure 21:
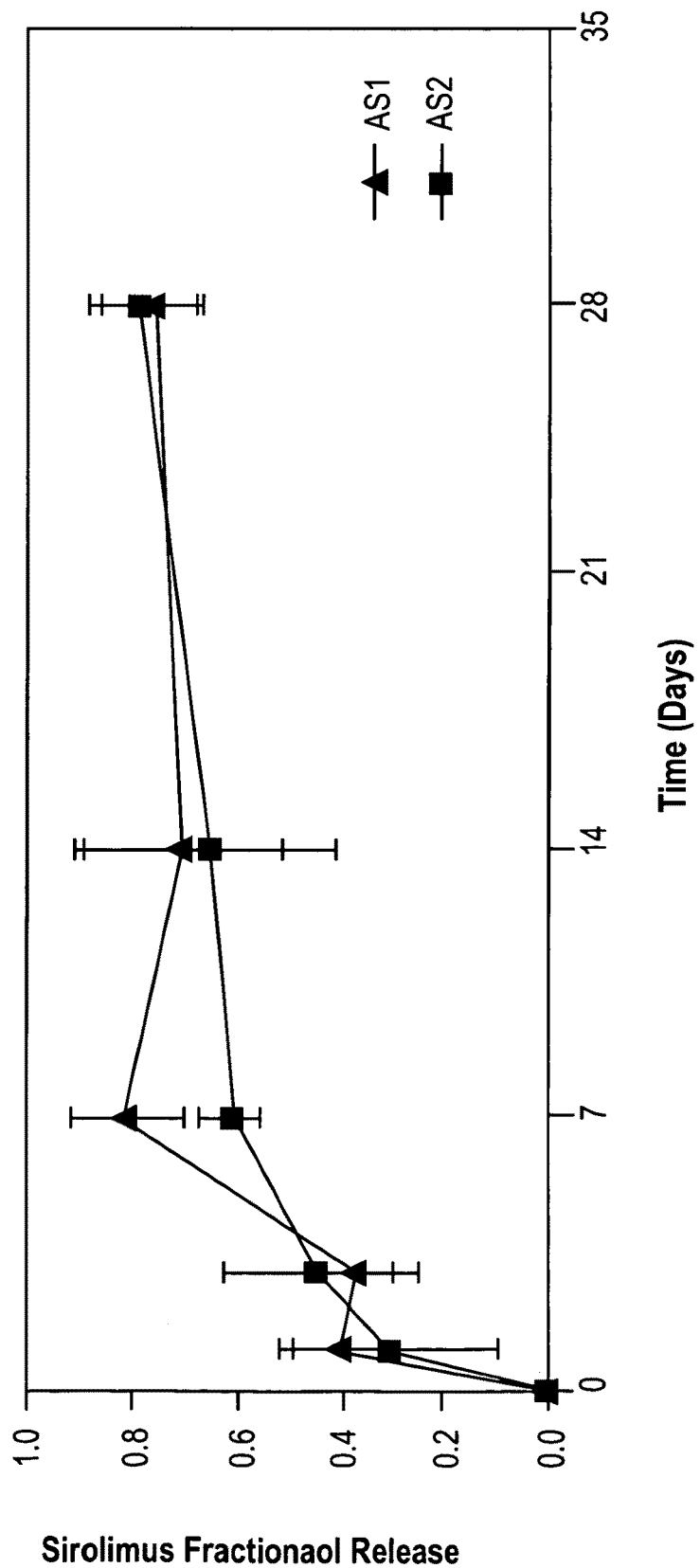
FIG. 21: Fractional Sirolimus Release (y-axis) versus time (x-axis) in Arterial Tissue for AS1 and AS2 Stents following testing as described in Example 25.
Figure 22:
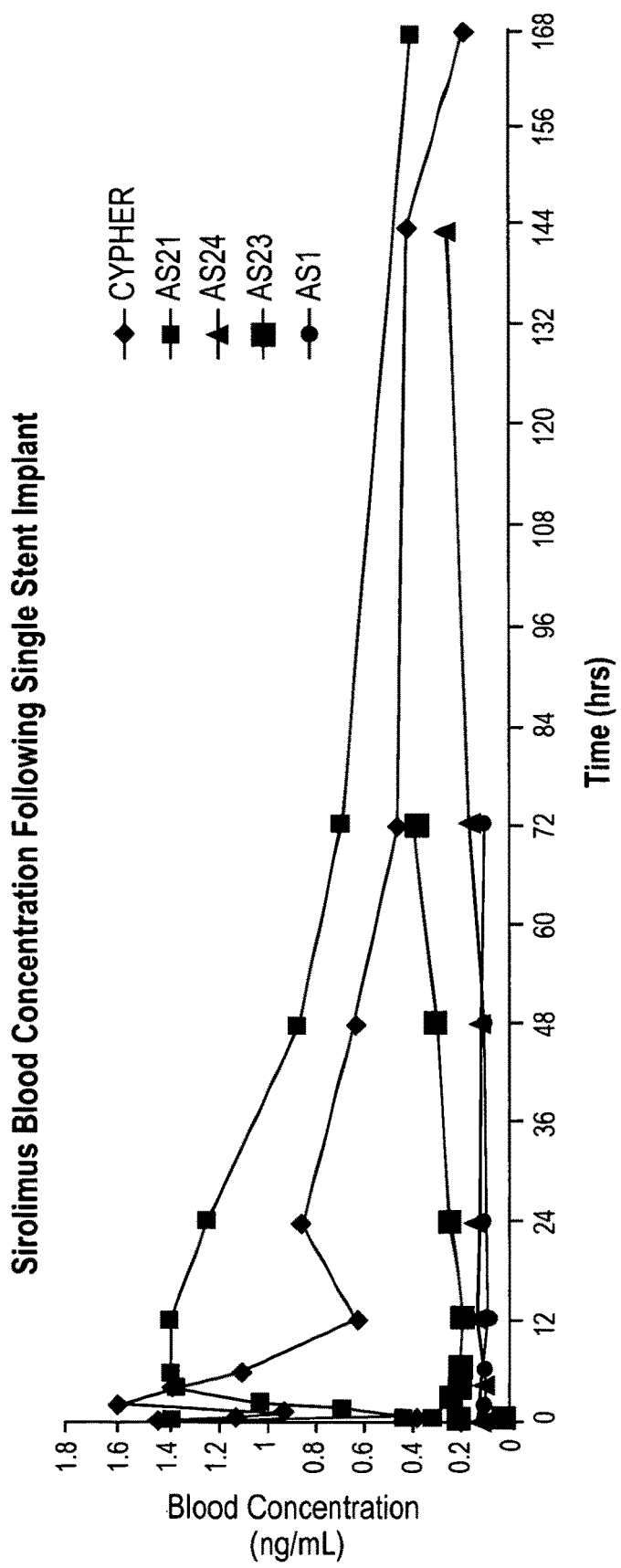
FIG. 22: Sirolimus Blood Concentration following Single Stent Implant expressed in Blood Concentration (ng/mL) (y-axis) versus time (x-axis) following testing as described in Example 25.
Figure 23:
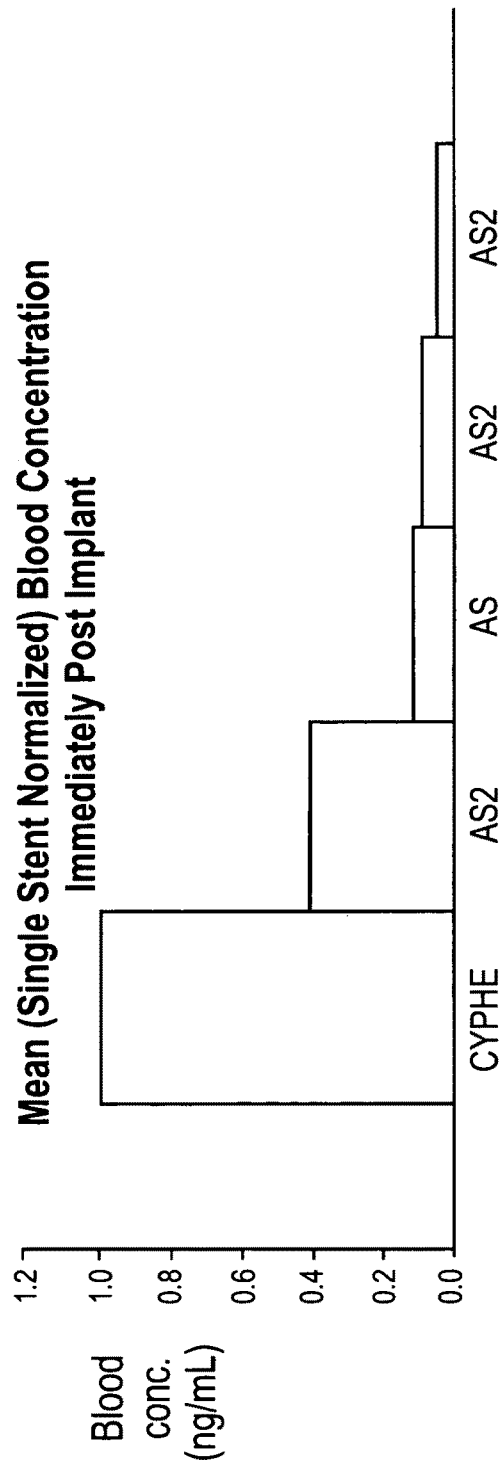
FIG. 23: Mean (Single stent normalized) Blood Concentration Immediately post implant (between 15 minutes and 1 hour, typically 30 minutes) expressed as Blood Concentrations (ng/mL) (y-axis) for a Cypher stent, and stents having coatings as described herein (AS21, AS1, AS23, AS24 are devices comprising coatings as described herein) following testing as described in Example 25.

Results of histology studies performed according to the methods described above are presented in FIGS. 12-23. FIGS. 12 and 13 depict low-magnification cross-sections of porcine coronary artery stent implants (AS1, AS2 and Bare-metal stent control) at 28 days and 90 days post-implantation. FIGS. 14 and 15 show drug depots in low-magnification cross-sections of porcine coronary artery stent implants. FIG. 16 shows mean (n=3) sirolimus levels in arterial tissue following AS1 and Cypher stent implantation. The results for AS1 presented in FIG. 16 were taken from a separate study as the results for the Cypher Stents presented in FIG. 16. Both studies were performed as described above, and data was collected similarly, however, data from the two studies were combined in this Figure to illustrate a comparison for results obtained for AS1 stent to results obtained for Cypher stent in a separate, but similar study. FIG. 17 shows mean sirolimus levels in arterial tissue following various stent implantations. FIG. 18 shows arterial tissue concentrations (y-axis) versus time (x-axis) for AS1 and AS2 stents implantations in swine coronary arteries expressed as absolute tissue level (y-axis) versus time (x-axis). FIG. 19 depicts mean (n=3) sirolimus levels in remaining on stent following various stent implantations in swine coronary arteries expressed as stent level (y-axis) versus time (x-axis). FIG. 20 depicts mean (n=3) sirolimus levels remaining on stent following AS1 and Cypher stent implantations in swine coronary arteries expressed as stent level (y-axis) versus time (x-axis). The results for AS1 presented in FIG. 20 were taken from a separate study as the results for the Cypher Stents presented in FIG. 20. Both studies were performed as described above, and data was collected similarly, however, data from the two studies were combined in this Figure to show a comparison of results obtained for AS1 stent and results obtained for the Cypher stent in a separate, but similar study. FIG. 21 is Fractional Sirolimus Release (y-axis) versus time (x-axis) in Arterial Tissue for AS1 and AS2 Stents. FIG. 22 is sirolimus blood concentration following single stent implant expressed in blood concentration (ng/ml) (y-axis) versus time (x-axis). Pigs were implanted with coated stents as described above. Blood was drawn at predetermined times and assayed to determine rapamycin concentration. The assays were based on technology known to one of ordinary skill in the art. FIG. 23 shows mean (single stent normalized) blood concentration immediately post implant expressed as blood concentrations (ng/ml) (y-axis) for a Cypher stent, and stents having coatings as described herein (AS21, AS1, AS23, AS24 are devices comprising coatings as described herein).

The foregoing is illustrative of the present invention, and is not to be construed as limiting thereof. While embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A device comprising:
   a. a stent consisting essentially of layers of polymer and layers of pharmaceutical agent;
   b. a plurality of layers deposited directly on said stent; wherein at least one of said polymer layers comprises a bioabsorbable polymer and at least one of said pharmaceutical agent layers comprises a pharmaceutical agent selected from rapamycin, a prodrug, a derivative, an analog, a hydrate, an ester, and a salt thereof in intimate contact with said bioabsorbable polymer, wherein at least a portion of the pharmaceutical agent is in crystalline form, wherein said device provides an in vitro elution profile in which 5% to 25% of the pharmaceutical agent is eluted one day after the device is contacted with elution media.

2. The device of claim 1, wherein said device has a pharmaceutical agent content of about 1 µg/mm to about 15 µm/mm.

3. The device of claim 1, wherein said at least one of said polymer layers comprises a plurality of layers comprising a first polymer layer comprising a first bioabsorbable polymer and a second polymer layer comprising a second bioabsorbable polymer, wherein said at least one of said pharmaceutical agent layers is between said first polymer layer and said second polymer layer.

4. The device of claim 3, wherein said first and second bioabsorbable polymers are the same polymer.

5. The device of claim 3, wherein said first and second bioabsorbable polymers are different polymers.

6. The device of claim 3, wherein said second polymer layer has at least one contact point with at least one particle of said pharmaceutical agent in said pharmaceutical agent layer and said second polymer layer has at least one contact point with said first polymer layer.

7. The device of claim 3, wherein said stent has a stent longitudinal axis; and said second polymer layer has a second polymer layer portion along said stent longitudinal axis wherein said second polymer layer portion is free of contact with particles of said pharmaceutical agent.

8. The device of claim 7, wherein said device has at least one pharmaceutical agent layer defined by a three-dimensional physical space occupied by crystal particles of said pharmaceutical agent and said three dimensional physical space is free of polymer.

9. The device of claim 7, wherein said stent comprises at least one strut having a strut length along said stent longitudinal axis, wherein said second polymer layer portion extends substantially along said strut length.

10. The device of claim 7, wherein said stent has a stent length along said stent longitudinal axis and said second polymer layer portion extends substantially along said stent length.

11. The device of claim 7, wherein said stent comprises at least five struts, each strut having a strut length along said stent longitudinal axis, wherein said second polymer layer portion extends substantially along the strut length of at least two struts.

12. The device of claim 7, wherein said stent comprises at least five struts, each strut having a strut length along said stent longitudinal axis, wherein said second polymer layer portion extends substantially along the strut length of at least three struts.

13. The device of claim 7, wherein said stent comprises at least five struts, each strut having a strut length along said stent longitudinal axis, wherein said second polymer layer portion extends substantially along the strut length of least four struts.

14. The device of claim 7, wherein said stent comprises at least five struts, each strut having a strut length along said stent longitudinal axis, wherein said second polymer layer portion extends substantially along the strut length of all said at least five struts.

15. The device of claim 7, wherein said stent has a stent length along said stent longitudinal axis and said second polymer layer portion extends along at least 50% of said stent length.

16. The device of claim 7, wherein said stent has a stent length along said stent longitudinal axis and said second polymer layer portion extends along at least 75% of said stent length.

17. A device comprising:
   a. a stent consisting essentially of layers of polymer and layers of pharmaceutical agent;
   b. a plurality of layers deposited directly on said stent, wherein a first layer comprises a first bioabsorbable polymer, a second layer comprises a layer of a first pharmaceutical agent, a third layer comprises a second bioabsorbable polymer, a fourth layer comprises a layer of said first pharmaceutical agent, and a fifth layer comprises a third bioabsorbable polymer,
   wherein the first pharmaceutical agent is selected from rapamycin, a prodrug, a derivative, an analog, a hydrate, an ester, and a salt thereof, and wherein said device has a first pharmaceutical agent content of about 1 µg/mm to about 15 µg/mm, and
   wherein at least a portion of the first pharmaceutical agent is in crystalline form.

18. The device of claim 1, wherein 5% to 25% of the first pharmaceutical agent is eluted one day after the device is contacted with elution media.

19. The device of claim 1, wherein 15% to 45% of the first pharmaceutical agent is eluted 7 days after the device is contacted with elution media.

20. The device of claim 1, wherein 25% to 60% of the first pharmaceutical agent is eluted 14 days after the device is contacted with elution media.

21. The device of claim 1, wherein 35% to 70% of the first pharmaceutical agent is eluted 21 days after the device is contacted with elution media.

22. A device comprising:
   a. a stent consisting essentially of layers of polymer and layers of pharmaceutical agent;
   b. a plurality of layers on said stent; wherein at least one of said polymer layers comprises a solvent free bioabsorbable polymer and at least one of said pharmaceutical agent layers comprises a pharmaceutical agent selected from rapamycin, a prodrug, a derivative, an analog, a hydrate, an ester, and a salt thereof in intimate contact with said solvent free bioabsorbable polymer, wherein at least a portion of the pharmaceutical agent is in crystalline form,
   wherein said device provides an in vitro elution profile in which
   5% to 25% of the pharmaceutical agent is eluted one day after the device is contacted with elution media;
   15% to 45% of the pharmaceutical agent is eluted 7 days after the device is contacted with elution media;
   25% to 60% of the pharmaceutical agent is eluted 14 days after the device is contacted with elution media;
   35% to 70% of the pharmaceutical agent is eluted 21 days after the device is contacted with elution media; and
   40% to 100% of the pharmaceutical agent is eluted 28 days after the device is contacted with elution media.

* * * * *